United States Patent
Katoh et al.

(10) Patent No.: US 10,611,731 B2
(45) Date of Patent: Apr. 7, 2020

(54) 5-METHYL-6-PHENYL-4,5-DIHYDRO-2H-PYRIDAZIN-3-ONE DERIVATIVE

(71) Applicant: OTSUKA PHARMACEUTICAL CO., LTD., Tokyo (JP)

(72) Inventors: Takahiro Katoh, Osaka (JP); Masatoshi Iida, Osaka (JP); Yuki Terauchi, Osaka (JP); Kazuya Yamaguchi, Osaka (JP); Toshiyuki Hirose, Osaka (JP); Fumiharu Yokoyama, Osaka (JP); Hikaru Nishimori, Osaka (JP); Yutaka Obuchi, Osaka (JP); Hiroshi Nabeshima, Osaka (JP); Emiri Takaki, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/081,260

(22) PCT Filed: Mar. 2, 2017

(86) PCT No.: PCT/JP2017/008246
§ 371 (c)(1),
(2) Date: Aug. 30, 2018

(87) PCT Pub. No.: WO2017/150654
PCT Pub. Date: Sep. 8, 2017

(65) Prior Publication Data
US 2019/0023662 A1  Jan. 24, 2019

(30) Foreign Application Priority Data
Mar. 4, 2016  (JP) .................. 2016-042535

(51) Int. Cl.
| C07D 237/04 | (2006.01) |
| A61K 31/50 | (2006.01) |
| C07D 237/14 | (2006.01) |
| C07D 237/02 | (2006.01) |
| A61P 35/00 | (2006.01) |

(52) U.S. Cl.
CPC ............ *C07D 237/04* (2013.01); *A61P 35/00* (2018.01); *C07D 237/02* (2013.01); *C07D 237/14* (2013.01)

(58) Field of Classification Search
CPC .................................................... C07D 237/04
See application file for complete search history.

(56) References Cited

U.S. PATENT DOCUMENTS

| 5,100,892 A | 3/1992 | Wheeler et al. |
| 2010/0160335 A1 | 6/2010 | Kohno et al. |
| 2011/0112061 A1 | 5/2011 | Hu et al. |

FOREIGN PATENT DOCUMENTS

| EP | 2 253 625 A1 | 11/2010 |
| JP | S63-145272 A | 6/1988 |
| WO | 2008/156094 A1 | 12/2008 |
| WO | 2009/114993 A1 | 9/2009 |
| WO | 2014/164704 A2 | 10/2014 |

OTHER PUBLICATIONS

English translation of International Search Report, dated May 11, 2017, in corresponding International Application No. PCT/JP2017/008246, 3 pages in English.
English translation of International Preliminary Report on Patentability, dated Sep. 4, 2018, in corresponding International Application No. PCT/JP2017/008246, 6 pages in English.

*Primary Examiner* — Emily A Bernhardt
(74) *Attorney, Agent, or Firm* — Sughrue Mion, PLLC

(57) ABSTRACT

The present invention provides an agent for treating malignant tumor, comprising a compound of formula (1):

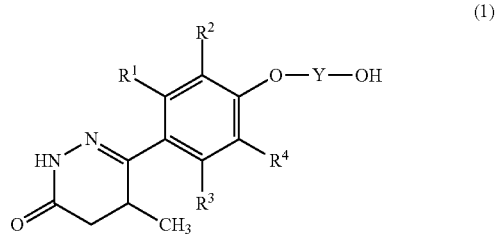

wherein $R^1$ to $R^4$ are hydrogen atom, halogen, or etc., Y is optionally-substituted alkylene group or etc.

58 Claims, No Drawings

5-METHYL-6-PHENYL-4,5-DIHYDRO-2H-PYRIDAZIN-3-ONE DERIVATIVE

CROSS REFERENCE TO RELATED APPLICATIONS

This application is a National Stage of International Application No. PCT/JP2017/008246 filed on Mar. 2, 2017, which claims priority from Japanese Patent Application No. 2016-042535 filed on Mar. 4, 2016.

TECHNICAL FIELD

The present invention may relate to a 5-methyl-6-phenyl-4,5-dihydro-2H-pyridazin-3-one derivative having antitumor activity, in particular, antitumor activity in brain.

BACKGROUND ART

Since nitrogen mustard was clinically used as an antineoplastic drug in the 1940s for the first time in the world, many antitumor drugs have been developed until now. Many of these antitumor drugs, however, can also exhibit cytotoxic action to normal cells, and thereby can show severe side-effects such as gastrointestinal dysfunction, myelosuppression, and hair loss. Therefore, most of these antitumor drugs are limited to the usage, and often show partial and short-term effects. Along with the recent developments in molecular biology, it has been tried to identify more highly tumor-selective molecular targets to improve the effect and side-effect, and such trials have attained some progress. However, the positive effects are not so expected in tumors which have low express/contribution of molecular targets, and the side-effects are not low as desired. Thus, it has been desired to develop novel drugs.

Some antitumor drugs having a phenyldihydropyridazinone moiety which the present invention comprises are known, but all those structures are different from that of the present invention (Patent Literature 1 and Patent Literature 2).

CITATION LIST

Patent Literature

[PL 1] WO 2009/114993
[PL 2] WO 2014/164704

SUMMARY OF INVENTION

Technical Problem

The main purpose of the present invention is to provide a compound having a potent anticancer effect, low side-effects, which is expected to have good water-solubility.

Solution to Problem

The present inventors have extensively studied and then have found that a novel compound represented by the following formula (1) has a potent antitumor activity, particularly antitumor activity in brain. Based upon the new findings, the present invention has been completed. The present invention provides 5-methyl-6-phenyl-4,5-dihydro-2H-pyridazin-3-one derivative represented by the following formula (1) or a pharmaceutically acceptable salt thereof (hereinafter, sometimes referred to as "the present compound"). The present invention mainly is mentioned below.

(Item 1) A compound of formula (1):

[Chem.1]

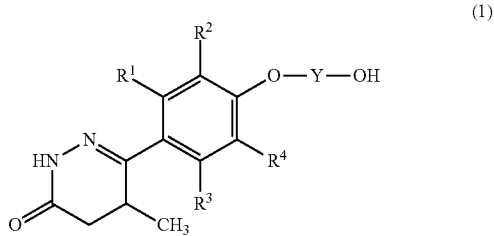

(1)

or a pharmaceutically acceptable salt thereof
wherein
R1 to R4 are independently hydrogen atom, halogen, OH, CN, $C_{1-6}$ alkyl group, halogenated $C_{1-6}$ alkyl group, $C_{2-6}$ alkenyl group, $C_{1-6}$ alkoxy group, or halogenated C alkoxy group provided that one or two of $R^1$ to $R^4$ are hydrogen atoms, but it is not that all of three or four thereof are hydrogen atoms, and
Y is $C_{1-6}$ alkylene or $C_{2-6}$ alkenylene group, wherein the alkylene or alkenylene group may be substituted with one or more substituents selected independently from the group consisting of $C_{1-6}$ alkyl group, halogen, and halogenated $C_{1-6}$ alkyl group, further wherein a substitutable carbon atom in the substituent bonding to the alkylene or alkenylene group and another substitutable carbon atom in the alkylene or alkenylene group, or two substitutable carbon atoms in the substituent bonding to the alkylene or alkenylene group may be combined together to form a 3- to 6-membered carbon ring.

(Item 2) The compound of Item 1 or a pharmaceutically acceptable salt thereof, wherein any two of $R^1$ to $R^4$ are hydrogen atoms.

(Item 3) The compound of Item 1 or 2 or a pharmaceutically acceptable salt thereof, wherein $R^1$ to $R^4$ are independently hydrogen atom, halogen, OH, CN, $C_{1-6}$ alkyl group, halogenated $C_{1-6}$ alkyl group, $C_{2-6}$ alkenyl group, $C_{1-6}$ alkoxy group, or halogenated $C_{1-6}$ alkoxy group.

(Item 4) The compound of Item 1 or 2 or a pharmaceutically acceptable salt thereof, wherein $R^1$ to $R^4$ are independently hydrogen atom, fluorine atom, chlorine atom, OH, CN, $C_{1-4}$ alkyl group, vinyl group, or $C_{1-4}$ alkoxy group.

(Item 5) The compound of any one of Terms Items 1 to 4 or a pharmaceutically acceptable salt thereof, wherein the alkylene or alkenylene group in Y is substituted with one or more substituents selected independently from the group consisting of C, 4 alkyl group, halogen, and halogenated C, 4 alkyl group, further wherein a substitutable carbon atom in the substituent bonding to the alkylene or alkenylene group and another substitutable carbon atom in the alkylene or alkenylene group, or two substitutable carbon atoms in the substituent bonding to the alkylene or alkenylene group may be combined together to form a 3- to 6-membered carbon ring.

(Item 6) The compound of any one of Items 1 to 4 or a pharmaceutically acceptable salt thereof, wherein a carbon atom of the alkylene or alkenylene group in Y is substituted with one or two substituents selected independently from the group consisting of $C_{1-4}$ alkyl group and halogenated $C_{1-4}$ alkyl group, further when the carbon atom is substituted with two substituents, each substitutable carbon atom in the two substituents may be combined together to form a 3- to 6-membered carbon ring.

(Item 7) The compound of any one of Items 1 to 4 or a pharmaceutically acceptable salt thereof, wherein the alkylene or alkenylene group in Y has no substituent.

(Item 8) The compound of any one of Items 1 to 7 or a pharmaceutically acceptable salt thereof, wherein the compound of formula (1) is represented in the following formula.

[Chem.2]

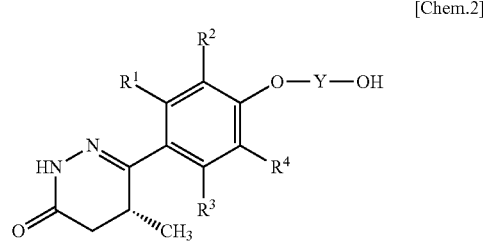

(Item 9) The compound of Item 1 or a pharmaceutically acceptable salt thereof, which is selected from the following compounds:

Example 1

6-[3-bromo-5-chloro-4-(2-hydroxy-2-methylpropoxy)phenyl]-5-methyl-4,5-dihydro-2H-pyridazin-3-one, Example 2

6-[3,5-dichloro-4-(2-hydroxy-2-methylpropoxy)phenyl]-5-methyl-4,5-dihydro-2H-pyridazin-3-one, Example 7

6-[3-chloro-5-fluoro-4-(3-hydroxy-2,2-dimethylpropoxy)phenyl]-5-methyl-4,5-dihydro-2H-pyridazin-3-one, Example 12

6-[3-bromo-2-fluoro-4-(3-hydroxypropoxy)phenyl]-5-methyl-4,5-dihydro-2H-pyridazin-3-one, Example 19

6-[3-chloro-2-fluoro-4-(3-hydroxypropoxy)phenyl]-5-methyl-4,5-dihydro-2H-pyridazin-3-one, Example 22

6-[3-chloro-2-fluoro-4-(3-hydroxypropoxy)-5-methylphenyl]-5-methyl-4,5-dihydro-2H-pyridazin-3-one, Example 24

6-[3-bromo-2-fluoro-4-(2-hydroxy-2-methylpropoxy)phenyl]-5-methyl-4,5-dihydro-2H-pyridazin-3-one, Example 26

6-[3-bromo-5-fluoro-4-(2-hydroxy-2-methylpropoxy)phenyl]-5-methyl-4,5-dihydro-2H-pyridazin-3-one, Example 31

6-[3-chloro-4-(2-hydroxy-2-methylpropoxy)-5-methylphenyl]-5-methyl-4,5-dihydro-2H-pyridazin-3-one, Example 36

6-[3-chloro-2-fluoro-4-(2-hydroxy-2-methylpropoxy)-5-methylphenyl]-5-methyl-4,5-dihydro-2H-pyridazin-3-one, Example 40

6-{3-chloro-4-[(2R)-2-hydroxypropoxy]-5-methylphenyl}-5-methyl-4,5-dihydro-2H-pyridazin-3-one, Example 44

6-{3-chloro-4-[(1-hydroxycyclopropyl)methoxy]-5-methylphenyl}-5-methyl-4,5-dihydro-2H-pyridazin-3-one, Example 47

6-{3-chloro-2-fluoro-4-[(1-hydroxycyclopropyl)methoxy]phenyl}-5-methyl-4,5-dihydro-2H-pyridazin-3-one, Example 48

6-[3-bromo-2-fluoro-4-(2-hydroxypropoxy)phenyl]-5-methyl-4,5-dihydro-2H-pyridazin-3-one, Example 53

6-[3,5-dichloro-4-(2-hydroxypropoxy)phenyl]-5-methyl-4,5-dihydro-2H-pyridazin-3-one, Example 54

6-[3-chloro-2-fluoro-4-(2-hydroxypropoxy)phenyl]-5-methyl-4,5-dihydro-2H-pyridazin-3-one, Example 55

6-[3-chloro-4-(2-hydroxypropoxy)-5-methylphenyl]-5-methyl-4,5-dihydro-2H-pyridazin-3-one, Example 57

6-[3-bromo-5-chloro-4-(2-hydroxypropoxy)phenyl]-5-methyl-4,5-dihydro-2H-pyridazin-3-one, Example 59

6-[2-fluoro-4-(2-hydroxypropoxy)-3-vinylphenyl]-5-methyl-4,5-dihydro-2H-pyridazin-3-one, Example 64

6-[3-chloro-2-fluoro-4-(2-hydroxybutoxy)phenyl]-5-methyl-4,5-dihydro-2H-pyridazin-3-one, Example 69

6-[3-bromo-5-fluoro-4-(3-hydroxy-2,2-dimethylpropoxy)phenyl]-5-methyl-4,5-dihydro-2H-pyridazin-3-one,

Example 72

6-[3-chloro-4-(3-hydroxy-2,2-dimethylpropoxy)-5-methyl-phenyl]-5-methyl-4,5-dihydro-2H-pyridazin-3-one,

Example 99

6-[3-chloro-5-fluoro-4-(4-hydroxy-2,2-dimethylbutoxy)phenyl]-5-methyl-4,5-dihydro-2H-pyridazin-3-one,

Example 100

6-[3,5-dichloro-4-(4-hydroxy-2,2-dimethylbutoxy)phenyl]-5-methyl-4,5-dihydro-2H-pyridazin-3-one,

Example 109

6-[3,5-dichloro-4-(2,2-difluoro-3-hydroxypropoxy)phenyl]-5-methyl-4,5-dihydro-2H-pyridazin-3-one,

Example 112

6-[3-bromo-4-(2,2-difluoro-3-hydroxypropoxy)-2-fluorophenyl]-5-methyl-4,5-dihydro-2H-pyridazin-3-one,

Example 113

6-[3-chloro-4-(2,2-difluoro-3-hydroxypropoxy)-5-methyl-phenyl]-5-methyl-4,5-dihydro-2H-pyridazin-3-one,

Example 118

(5R)-(−)-6-[3-chloro-2-fluoro-4-(2-hydroxy-2-methyl-propoxy)phenyl]-5-methyl-4,5-dihydro-2H-pyridazin-3-one,

Example 120

(5R)-(−)-6-[4-(2,2-difluoro-3-hydroxypropoxy)-2-fluoro-3-methylphenyl]-5-methyl-4,5-dihydro-2H-pyridazin-3-one,

Example 124

(5R)-(−)-6-[2,3-difluoro-4-(2-hydroxy-2-methylpropoxy)phenyl]-5-methyl-4,5-dihydro-2H-pyridazin-3-one,

Example 125

(5R)-(−)-6-[3-fluoro-4-(3-hydroxy-2,2-dimethylpropoxy)-5-methylphenyl]-5-methyl-4,5-dihydro-2H-pyridazin-3-one,

Example 127

(5R)-(−)-6-[3-bromo-5-chloro-4-(3-hydroxy-2,2-dimethylpropoxy)phenyl]-5-methyl-4,5-dihydro-2H-pyridazin-3-one,

Example 131

6-[3-chloro-2,5-difluoro-4-(2-hydroxy-2-methylpropoxy)phenyl]-5-methyl-4,5-dihydro-2H-pyridazin-3-one,

Example 137

6-[3-chloro-2-fluoro-4-(3-hydroxy-2,2-dimethylpropoxy)-5-methylphenyl]-5-methyl-4,5-dihydro-2H-pyridazin-3-one,

Example 140

6-[3-chloro-2,5-difluoro-4-(3-hydroxypropoxy)phenyl]-5-methyl-4,5-dihydro-2H-pyridazin-3-one,

Example 142

6-[3-chloro-4-(3-hydroxy-2-methylpropoxy)-5-methylphenyl]-5-methyl-4,5-dihydro-2H-pyridazin-3-one,

Example 148

6-[3-chloro-2-fluoro-4-(2-hydroxypropoxy)-5-methylphenyl]-5-methyl-4,5-dihydro-2H-pyridazin-3-one,

Example 151

6-{3-chloro-2-fluoro-4-[(Z)-4-hydroxy-2-butenyloxy]-5-methylphenyl}-5-methyl-4,5-dihydro-2H-pyridazin-3-one,

Example 155

6-(3-chloro-4-{[(1S*,2R*)-2-(hydroxymethyl)cyclopropyl]methoxy}-5-methylphenyl)-5-methyl-4,5-dihydro-2H-pyridazin-3-one,

Example 159

6-[3-chloro-4-(2,2-difluoro-3-hydroxypropoxy)-2-fluoro-5-methylphenyl]-5-methyl-4,5-dihydro-2H-pyridazin-3-one,

Example 160

6-[4-(2,2-difluoro-3-hydroxypropoxy)-2-fluoro-3,5-dimethylphenyl]-5-methyl-4,5-dihydro-2H-pyridazin-3-one,

Example 167

6-{3-chloro-2-fluoro-4-[(1-hydroxycyclopropyl)methoxy]-5-methylphenyl}-5-methyl-4,5-dihydro-2H-pyridazin-3-one,

Example 168

6-{3-bromo-2-fluoro-4-[(1-hydroxycyclopropyl)methoxy]phenyl}-5-methyl-4,5-dihydro-2H-pyridazin-3-one,

Example 170

6-{3,5-dichloro-4-[(1-hydroxycyclopropyl)methoxy]phenyl}-5-methyl-4,5-dihydro-2H-pyridazin-3-one, and

Example 184

6-[2-fluoro-4-(2-hydroxy-2-methylpropoxy)-3-(trifluoromethyl)phenyl]-5-methyl-4,5-dihydro-2H-pyridazin-3-one.

(Item 10) A pharmaceutical composition comprising the compound of any one of Items 1 to 9 or a pharmaceutically acceptable salt thereof.

(Item 11) An agent for treating malignant tumor, comprising the compound of any one of Items 1 to 9 or a pharmaceutically acceptable salt thereof.

(Item 12) A method for treating or preventing malignant tumor, comprising administering a therapeutically effective amount of the compound of any one of Items 1 to 9 or a pharmaceutically acceptable salt thereof to a patient in need thereof.

(Item 13) The pharmaceutical composition of Item 10 for use in treating or preventing malignant tumor.

(Item 14) Use of the compound of any one of Items 1 to 9 or a pharmaceutically acceptable salt thereof in the manufacture of an agent for treating malignant tumor.

Preferably, the malignant tumor defined in the above Items 11 to 14 is particularly brain tumor.

Effect of Invention

The compound of the present invention can be a useful agent for treating tumor, particularly malignant tumor, in more detail, the compound is useful as a novel agent for treating childhood brain tumor selected from the group consisting of astrocytoma, malignant medulloblastoma, germ cell tumor, craniopharyngioma, and ependymoma; adult brain tumor selected from the group consisting of glioma, meningioma, pituitary adenoma, and nerve sheath tumor; head and neck cancer selected from the group consisting of maxillary sinus cancer, pharyngeal cancer (e.g. nasopharyngeal cancer, oropharyngeal cancer, hypopharyngeal cancer), laryngeal cancer, oral cancer (e.g. lip cancer, tongue cancer), and salivary gland cancer (e.g. parotid gland cancer); thoracic cancer and tumor selected from the group consisting of small cell lung cancer, non-small-cell lung cancer, thymoma, and mesothelioma; gastrointestinal cancer and tumor selected from the group consisting of esophageal cancer, liver cancer, primary liver cancer, gallbladder cancer, bile duct cancer, gastric cancer, colorectal cancer (e.g. rectal cancer, anal cancer), pancreatic cancer, and pancreatic endocrine tumor; urologic cancer and tumor selected from the group consisting of penile cancer, renal pelvic/ureter cancer, renal cell cancer, testicular tumor (also referred to as testicular neoplasm), prostate cancer, bladder cancer, Wilms' tumor, and urothelial carcinoma; gynecologic cancer and tumor selected from the group consisting of vulvar cancer, cervical cancer, uterine body cancer, endometrial cancer, uterine sarcoma, choriocarcinoma, vaginal cancer, breast cancer, ovarian cancer, and ovarian germ cell tumor; adult and childhood soft tissue sarcoma; bone tumor selected from the group consisting of osteosarcoma and Ewing's tumor; endocrine tissue cancer and tumor selected from the group consisting of adrenocortical carcinoma and thyroid cancer; malignant lymphoma and leukemia selected from the group consisting of malignant lymphoma, non-Hodgkin's lymphoma, Hodgkin's disease, multiple myeloma, plasma cell neoplasm, acute myeloid leukemia, acute lymphoblastic leukemia, adult T-cell leukemia-lymphoma, chronic myeloid leukemia, and chronic lymphocytic leukemia; or skin cancer and tumor selected from the group consisting of chronic myeloproliferative disorder, malignant melanoma, squamous cell carcinoma, basal cell carcinoma, and mycosis fungoides. In particular, the compound of the present invention is expected to have a high safety, for example, because the compound has no myelosuppressive action or the like that is a frequently-occurring side-effect in using a conventional anti-malignant tumor agent. In addition, the compound has a good water-solubility, thus it is expected to be used in the treatment via various administration ways.

DESCRIPTION OF EMBODIMENTS

The compound of the present invention may be in the form of hydrate and/or solvate, and hence the present compound also encompasses hydrate and/or solvate thereof.

The compound of the present invention may have one chiral carbon atom or optionally more chiral carbon atoms. Unless otherwise indicated, the present compound also encompasses all stereoisomers thereof.

The compound of formula (1) may have a chiral carbon at 5th position of its 4,5-dihydro-2H-pyridazin-3-one moiety. Unless otherwise indicated here, the compound of formula (1) may encompass all stereoisomers, preferably a stereoisomer having R configuration at 5th position.

In addition, the compound of formula (1) (deuterium form) in which any one or more $^1$H atoms are replaced by $^2$H(D) atoms is within the scope of the present invention.

There may exist a polymorphism in a crystal of the compound of formula (1) or a pharmaceutically acceptable salt thereof, and hence such crystal polymorphism is also within the scope of the present invention.

Each term used herein is explained below.

The term "halogen" herein means fluorine atom, chlorine atom, bromine atom or iodine atom. Preferably, it is fluorine atom or chlorine atom.

The term "alkyl group" herein means a saturated straight or branched chain hydrocarbon group. For example, the "$C_{1-4}$ alkyl" or "$C_{1-6}$ alkyl" means an alkyl having 1-4 or 1-6 carbon atoms, respectively. The "$C_{1-4}$ alkyl" includes, for example, methyl, ethyl, propyl, isopropyl, butyl, isobutyl, sec-butyl, and tert-butyl. The "$C_{1-6}$ alkyl" includes pentyl, isopentyl, neopentyl, and hexyl, besides the above $C_{1-4}$ alkyl.

The term "halogenated alkyl group" means an alkyl group in which one or more replaceable hydrogen atoms are replaced by the same or different and one or more halogen atoms. For example, the term "halogenated $C_{1-6}$ alkyl group" means an alkyl group having 1-6 carbon atoms, in which one or more replaceable hydrogen atoms are replaced by the same or different and one or more halogen atoms, and it includes, for example, trifluoromethyl, pentafluoroethyl, 2-chloroethyl, 2-bromoethyl, heptafluoropropyl, 3-bromopropyl, nonafluorobutyl, tridecafluorohexyl, 2,2,2-trifluoroethyl, 1,1-difluoroethyl, 1,1-difluoropropyl, 1,1,2,2-tetrafluoropropyl, 3,3,3-trifluoropropyl, and 2,2,3,3,3-pentafluoropropyl, and it is preferably trifluoromethyl.

The term "$C_{2-6}$ alkenyl group" means an unsaturated straight or branched chain $C_{2-6}$ hydrocarbon group having 1-3 carbon-carbon double bonds. Preferably, it is "$C_{2-4}$ alkenyl group". The "$C_{2-6}$ alkenyl group" includes, for example, ethenyl (i.e., vinyl group), propenyl, butenyl, pentenyl, and hexenyl.

The term "alkoxy group" means "alkyl-O— group". For example, the "$C_{1-6}$ alkoxy group" means "$C_{1-6}$ alkyl-O— group", wherein the part "$C_{1-6}$ alkyl" is as defined in the above-defined "$C_{1-6}$ alkyl". Preferably, it is "$C_{1-4}$ alkoxy group". The "$C_{1-6}$ alkoxy group" includes, for example, methoxy, ethoxy, propoxy, isopropoxy, butoxy, isobutoxy, sec-butoxy, and tert-butoxy.

The term "alkylene group" means a saturated straight or branched chain divalent hydrocarbon group. For example, the "$C_{1-6}$ alkylene group" means an alkylene group having 1-6 carbon atoms. The "$C_{1-6}$ alkylene group" includes, for example, methylene, ethylene, propylene, butylene, 1-methylpropylene, 2-methylpropylene, pentylene, 1-methylbutylene, 2-methylbutylene, hexylene, 2-ethylbutylene, and 1,3-dimethylbutylene.

The term "alkenylene group" means an unsaturated straight or branched chain divalent hydrocarbon group having 1 or more carbon-carbon double bonds. For example, the "$C_{2-6}$ alkenylene group" means a $C_{2-6}$ alkylene group having 1-3 carbon-carbon double bonds. The "$C_{2-6}$ alkenylene group" includes, for example, ethynylene group, propynylene group, butynylene group, pentynylene group, and hexynylene group.

In the phrase "a substitutable carbon atom in the substituent bonding to the alkylene or alkenylene group and another substitutable carbon atom in the alkylene or alkenylene group, or two substitutable carbon atoms in the substituent bonding to the alkylene or alkenylene group may be combined together to form a 3- to 6-membered carbon ring" in Y, the term "substitutable carbon atom in the substituent bonding to the alkylene or alkenylene group" means a substitutable carbon atom in the $C_{1-6}$ alkyl group or the halogenated $C_{1-6}$ alkyl group which is selected as a substituent of the alkylene or alkenylene group in Y, and the term "3- to 6-membered carbon ring" includes, for example, cyclopropyl, cyclobutyl, cyclopentyl, cyclohexyl, cyclobutenyl, cyclopentenyl, cyclohexenyl, and a halogenated product thereof.

The term "pharmaceutically acceptable salt" includes, as an acid addition salt, an inorganic acid salt such as hydrochloride, hydrobromide, hydroiodide, sulfate, per-chlorate, and phosphate, an organic acid salt such as oxalate, malonate, maleate, fumarate, lactate, malate, citrate, tartrate, benzoate, trifluoroacetate, acetate, methanesulfonate, p-toluenesulfonate, and trifluoromethanesulfonate, and an amino acid salt such as glutamate and aspartate; and as a basic salt, an alkali metal salt such as sodium salt and potassium salt, an alkaline-earth metal salt such as calcium salt, and ammonium salt.

General Process to Prepare the Present Compound

The above 4,5-dihydro-2H-pyridazin-3-one compound of formula (1) or a salt thereof can be prepared in a general manner of organic synthesis, for example, in the manner below, but the present invention should not be limited thereto. Material compounds used herein may be obtained from commercially available products or prepared in a conventional manner as appropriate.

Scheme 1

[Chem.3]

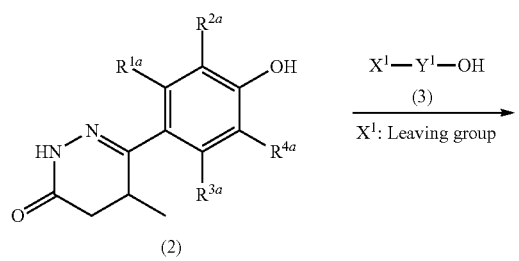

(2)    $X^1$—$Y^1$—OH
       (3)
       $X^1$: Leaving group

-continued

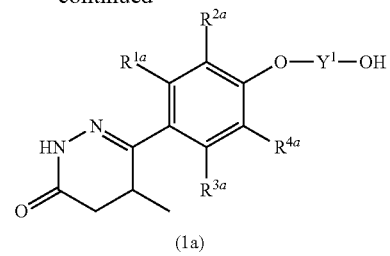

(1a)

Wherein $R^{1a}$ to $R^{4a}$ are independently hydrogen atom, halogen, CN, $C_{1-6}$ alkyl group, halogenated $C_{1-6}$ alkyl group, $C_{2-6}$ alkenyl group, $C_{1-6}$ alkoxy group, or halogenated $C_{1-6}$ alkoxy group, provided that one or two of $R^{1a}$ to $R^{4a}$ are hydrogen atoms, but it is not that all of three or four thereof are hydrogen atoms. $X^1$ denotes a leaving group. $Y^1$ is $C_{1-6}$ alkylene or $C_{2-6}$ alkenylene group, wherein the alkylene or alkenylene group may be substituted with one or more substituents selected independently from the group consisting of $C_{1-6}$ alkyl group, fluorine group, and fluorinated $C_{1-6}$ alkyl group, further wherein a substitutable carbon atom in the substituent bonding to the alkylene or alkenylene group and another substitutable carbon atom in the alkylene or alkenylene group, or two substitutable carbon atoms in the substituent bonding to the alkylene or alkenylene group may be combined together to form a 3- to 6-membered carbon ring.

According to the method shown in Scheme 1, Compound (1a) can be prepared by reacting Compound (2) and Compound (3), in an appropriate solvent or without a solvent, in the presence or absence of a basic compound.

The leaving group $X^1$ used herein includes halogen group such as fluorine, chlorine, bromine, and iodine; substituted sulfonyloxy group such as $C_{1-6}$ alkylsulfonyloxy group (e.g. methanesulfonyloxy, ethanesulfonyloxy), $C_{6-14}$ arylsulfonyloxy group (e.g. benzenesulfonyloxy, p-toluenesulfonyloxy), and $C_{7-16}$ aralkylsulfonyloxy group (e.g. benzylsulfonyloxy); acyloxy group such as acetoxy and benzoyloxy; oxy group substituted with heterocyclyl or aryl such as succinimide, benzotriazole, quinoline, and 4-nitrophenyl; and heterocyclyl such as imidazole.

The solvent used herein can be broadly chosen from known solvents unless it negatively affects the reaction. The solvent used herein includes, for example, water; ethers such as dioxane, tetrahydrofuran (THF), diethyl ether, diethylene glycol dimethyl ether (diglyme), and ethylene glycol dimethyl ether; aromatic hydrocarbons such as benzene, toluene, and xylene; halogenated hydrocarbons such as dichloromethane, dichloroethane, chloroform, and carbon tetrachloride; alcohols such as methanol, ethanol, and 2-propanol; ketones such as acetone and methyl ethyl ketone; polar solvents such as N,N-dimethylformamide (DMF), dimethylsulfoxide (DMSO), hexamethylphosphate triamide, and acetonitrile; and a mixture thereof.

The basic compound used herein can be broadly chosen from known basic compounds, which includes, for example, an alkali metal hydroxides such as sodium hydroxide, potassium hydroxide, cesium hydroxide, and lithium hydroxide; an alkali metal carbonates such as sodium carbonate, potassium carbonate, cesium carbonate, lithium carbonate, lithium hydrogen carbonate, sodium hydrogen carbonate, and potassium hydrogen carbonate; an acetates such as sodium acetate and potassium acetate; an alkali metals such as sodium and potassium; inorganic salts such as sodium amide, sodium hydride, and potassium hydride; an alkali metal lower alkoxides such as sodium methoxide, sodium ethoxide, and potassium tert-butoxide; an organic bases such as triethylamine, diisopropylethylamine, tripropylamine, pyridine, quinoline, 1,5-diazabicyclo[4.3.0]non-5-ene (DBN), 1,8-diazabicyclo[5.4.0]undec-7-ene (DBU), and 1,4-diazabicyclo[2.2.2]octane (DABCO). These basic compounds may be used as a single ingredient or in a combination of two or more ingredients.

If necessary, in the reaction, alkali metal iodide such as potassium iodide and sodium iodide can be used as a reaction accelerator.

The amount of Compound (3) used herein is generally at least about 0.5 mole, preferably about 0.5 to 10 moles per one mole of Compound (2). The amount of the basic compound used herein is generally about 0.5 to 10 moles, preferably about 0.5 to 6 moles per one mole of Compound (2). The above reaction is carried out generally at 0° C. to 250° C., preferably at 0° C. to 200° C., under ordinary pressure or increased pressure, and the reaction is completed in about 1 to 80 hours. In addition, the reaction can be carried out under microwave irradiation.

Scheme 2

[Chem.4]

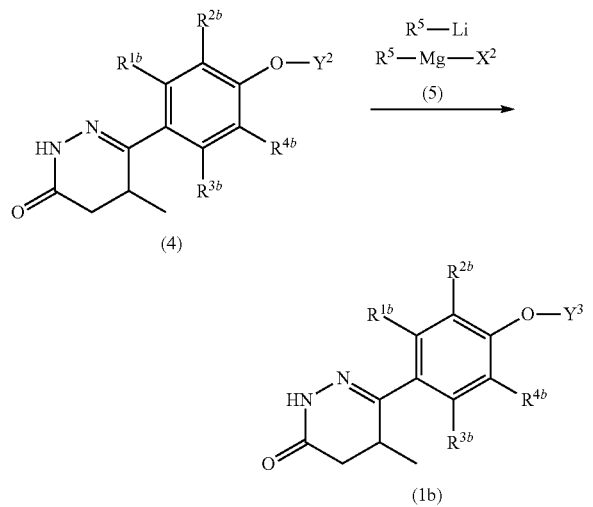

Wherein $R^{1b}$ to $R^{4b}$ are independently hydrogen atom, halogen, $C_{1-6}$ alkyl group, halogenated $C_{1-6}$ alkyl group, $C_{2-6}$ alkenyl group, $C_{1-6}$ alkoxy group, or halogenated C, 6 alkoxy group, provided that one or two of $R^{1b}$ to $R^{4b}$ are hydrogen atoms, but it is not that all of three or four thereof are hydrogen atoms. $Y^2$ is $C_1$ alkyl or $C_m$ alkenyl group which has oxo group, wherein the alkyl or alkenyl group may be substituted with one or more substituents selected independently from the group consisting of $C_{1-6}$ alkyl group, halogen, and halogenated $C_{1-6}$ alkyl group, further wherein a substitutable carbon atom in the substituent bonding to the alkyl or alkenyl group and another substitutable carbon atom in the alkyl or alkenyl group, or two substitutable carbon atoms in the substituent bonding to the alkyl or alkenyl group may be combined together to form a 3- to 6-membered carbon ring, provided that the carbon atom to which the oxo group binds is not next to the halogen atom or the oxygen atom between the benzene ring and $Y^2$, and the oxo group is not bound to the olefin carbon. $R^5$ is $C_n$ alkyl group. $X^2$ is halogen atom. $Y^3$ is $C_{36}$ alkyl or $C_{46}$ alkenyl group which has hydroxy group, wherein the alkyl or alkenyl group may be substituted with one or more substituents selected independently from the group consisting of $C_{1-6}$ alkyl group, halogen, and halogenated $C_{1-6}$ alkyl group, further wherein a substitutable carbon atom in the substituent bonding to the alkyl or alkenyl group and another substitutable carbon atom in the alkyl or alkenyl group, or two substitutable carbon atoms in the substituent bonding to the alkyl or alkenyl group may be combined together to form a 3- to 6-membered carbon ring, provided that the carbon atom to which the hydroxy group binds is not next to the halogen atom or the oxygen atom between the benzene ring and $Y^3$, and the hydroxy group is not bound to the olefin carbon, and the hydroxy group is not primary alcohol. l is an integer of 2 to 5, m is an integer of 3 to 5, and n is an integer of 1 to 4, provided that l+n≤6, and m+n≤6.

According to the method shown in Scheme 2, Compound (1b) having hydroxy group in $Y^3$ can be prepared by reacting Compound (4) having oxo group in $Y^2$ with Grignard reagent ($R^5MgX^2$) or lithium reagent ($R^5Li$) in an appropriate inert solvent such as diethyl ether and THF.

The amount of the Grignard reagent ($R^5MgX^2$) or lithium reagent ($R^5Li$) of formula (5) used herein is generally at least about 0.5 mole, preferably about 3 to 10 moles per one mole of Compound (4). The above reaction is carried out generally at −78° C. to room temperature, preferably at 0° C. to room temperature, and the reaction is completed in about 1 to 24 hours.

Scheme 3

[Chem.5]

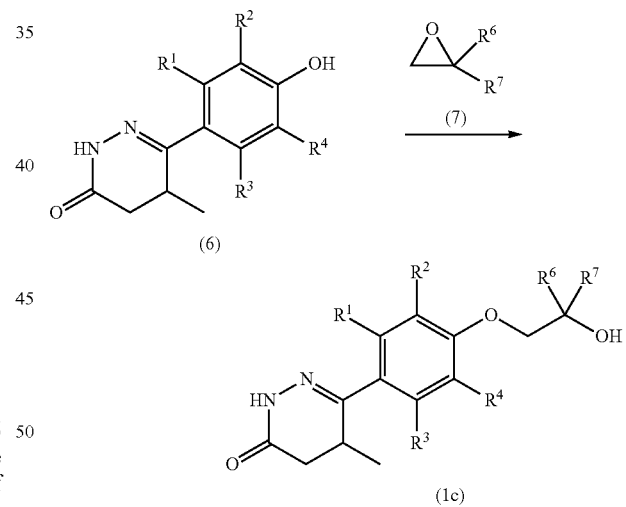

Wherein $R^1$ to $R^4$ are as defined above. $R^6$ and $R^7$ are independently hydrogen atom, $C_{1-6}$ alkyl group, or halogenated $C_{1-6}$ alkyl group. $R^6$ and $R^7$ may be combined together at each substitutable carbon atom in $R^6$ and $R^7$ to form a 3- to 6-membered carbon ring.

According to the method shown in Scheme 3, Compound (1c) can be prepared by reacting Compound (6) and Compound (7), in an appropriate solvent, in the presence of a basic compound.

The solvent used herein can be broadly chosen from known solvents unless it negatively affects the reaction. The solvent used herein includes, for example, polar solvents such as DMF, DMSO, and acetonitrile; ketones such as acetone and methyl ethyl ketone; hydrocarbons such as benzene, toluene, xylene, tetralin, and liquid paraffin; alcohols such as methanol, ethanol, 2-propanol, n-butanol, and tert-butanol; ethers such as THF, dioxane, dipropyl ether, diethyl ether, and diglyme; esters such as methyl acetate, ethyl acetate, isopropyl acetate, and tert-butyl acetate; and a mixture thereof.

The basic compound used herein can be broadly chosen from known basic compounds, which includes, for example the basic compounds listed in Scheme 1.

The amount of Compound (7) used herein is generally about 0.5 to 5 moles, preferably about 0.5 to 3 moles per one mole of Compound (6). The amount of the basic compound used herein is generally about 0.1 to 5 moles, preferably about 1 to 2 moles, per one mole of Compound (6).

The above reaction can be carried out, for example, as follows: Compound (6) is dissolved in a reaction solvent, a basic compound is added to the stirred solution under ice-cold or at room temperature, the reaction mixture is stirred at room temperature to 80° C. for 30 minutes to 1 hour, Compound (7) is added thereto, and then the reaction mixture is stirred at generally room temperature to 100° C., preferably at 50 to 80° C., for 30 minutes to 60 hours, preferably 1 to 50 hours.

Scheme 4

[Chem.6]

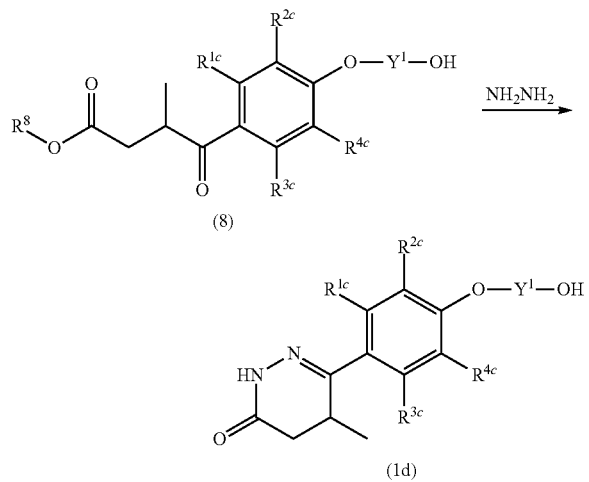

(8)

(1d)

Wherein $R^{1c}$ to $R^{4c}$ are independently hydrogen atom, halogen, OH, CN, $C_{1-6}$ alkyl group, fluorinated $C_{1-6}$ alkyl group, $C_{2-6}$ alkenyl group, $C_{1-6}$ alkoxy group, or fluorinated $C_{1-6}$ alkoxy group, provided that one or two of $R^{1c}$ to $R^{4c}$ are hydrogen atoms, but it is not that all of three or four thereof are hydrogen atoms. $R^8$ is $C_{1-6}$ alkyl group. $Y^1$ is as defined above.

According to the method shown in Scheme 4, Compound (1d) can be prepared by reacting Compound (8) and hydrazine, in an appropriate solvent, in the presence or absence of an acidic compound.

The solvent used herein is an inert solvent, which includes, for example, alcohols such as methanol, ethanol and 2-propanol; acetic acid; and water; preferably ethanol.

The hydrazine used herein is generally a hydrate thereof or a mineral acid salt thereof such as hydrochloride and sulfate. The amount of hydrazine used herein is generally about one or more moles, preferably about 1 to 3 moles per one mole of Compound (8).

The reaction temperature is not limited in specific, which includes a temperature from room temperature to reflux temperature of the used solvent, and it is preferable to heat the reaction media to promote the reaction. The reaction time is generally 0.1 to 100 hours.

Scheme 5

[Chem.7]

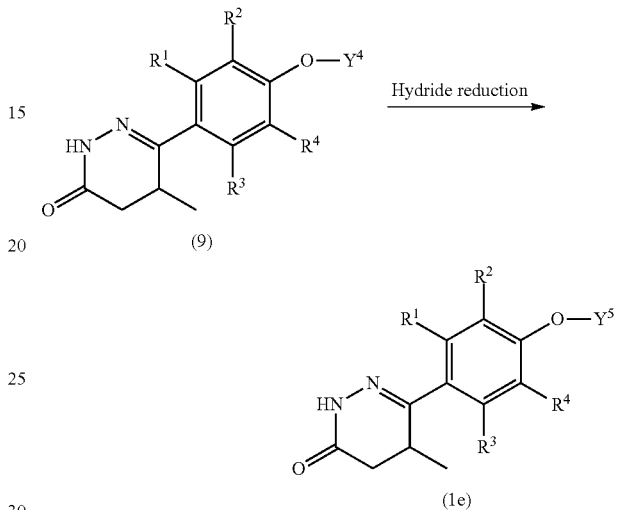

(9)

(1e)

Wherein $R^1$ to $R^4$ are as defined above. $Y^4$ is $C_{1-6}$ alkyl or $C_{2-6}$ alkenyl group which has oxo group, wherein the alkyl or alkenyl group may be substituted with one or more substituents selected independently from the group consisting of $C_{1-6}$ alkyl group, halogen, and halogenated $C_{1-6}$ alkyl group, further wherein a substitutable carbon atom in the substituent bonding to the alkyl or alkenyl group and another substitutable carbon atom in the alkyl or alkenyl group, or two substitutable carbon atoms in the substituent bonding to the alkyl or alkenyl group may be combined together to form a 3- to 6-membered carbon ring, provided that the carbon atom to which the oxo group binds is not next to the halogen atom or the oxygen atom between the benzene ring and $Y^4$, and the oxo group is not bound to the olefin carbon. $Y^5$ represents a substituent in which the oxo group moiety of $Y^4$ is reduced to a hydroxyl group.

According to the method shown in Scheme 5, Compound (1e) having hydroxy group in $Y^5$ can be prepared by reacting Compound (9) having oxo group in $Y^4$ with a hydride reductant in an appropriate solvent.

The hydride reductant used herein includes, for example, sodium borohydride, zinc borohydride, and these hydride reductants may be used as a single ingredient or in a combination of two or more ingredients. The reduction with a hydride reductant may be generally carried out in a solvent. The solvent used herein includes, for example, water; alcohols such as methanol and 2-propanol; and ethers such as THF, diethyl ether, diisopropyl ether, and diglyme. These solvents may be used as a single solvent or in a combination of two or more solvents.

The reaction temperature is not limited in specific, which is generally at −60 to 150° C., preferably at −30 to 100° C. The reaction time is generally 10 minutes to 15 hours.

Scheme 6

[Chem.8]

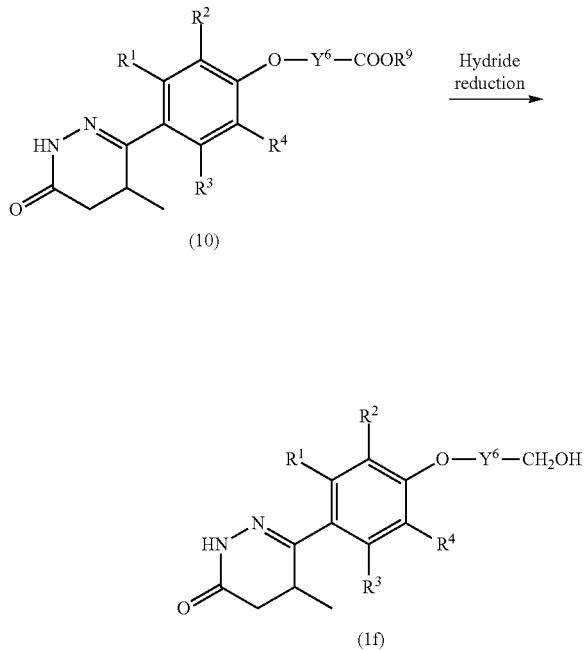

(10) → Hydride reduction → (1f)

Wherein $R^1$ to $R^4$ are as defined above. $Y^6$ is $C_{1-5}$ alkylene or $C_{2-5}$ alkenylene group, wherein the alkylene or alkenylene group may be substituted with one or more substituents selected independently from the group consisting of $C_{1-6}$ alkyl group, halogen, and halogenated $C_{1-6}$ alkyl group, further wherein a substitutable carbon atom in the substituent bonding to the alkylene or alkenylene group and another substitutable carbon atom in the alkylene or alkenylene group, or two substitutable carbon atoms in the substituent bonding to the alkylene or alkenylene group may be combined together to form a 3- to 6-membered carbon ring. $R^9$ is $C_{1-6}$ alkyl group.

According to the method shown in Scheme 6, Compound (1f) can be prepared by reacting Compound (10) with a hydride reductant in an appropriate solvent.

The hydride reductant used herein includes, for example, diisobutylaluminum hydride, sodium borohydride, and lithium borohydride-trimethoxyborane. These reductants may be used as a single ingredient or in a combination of two or more ingredients. The amount of the hydride reductant used herein is generally at least equimolar to Compound (1f), preferably in the range of equimolar to 15 times molar.

The reduction reaction may be carried out in a suitable solvent, for example, water; alcohols such as methanol, ethanol, and 2-propanol; ethers such as THF, diethyl ether, diisopropyl ether, and diglyme; halogenated hydrocarbons such as dichloromethane, chloroform, and carbon tetrachloride; or a mixture thereof, at about −60° C. to 150° C., preferably −30° C. to 100° C., generally for about 10 minutes to 40 hours.

Scheme 7

[Chem.9]

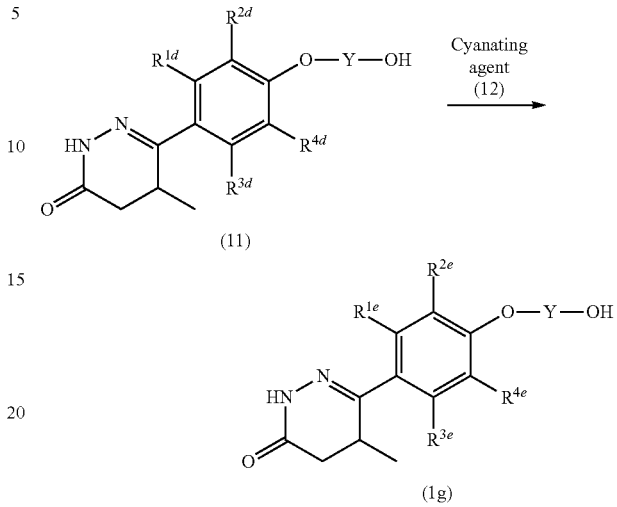

(11) → Cyanating agent (12) → (1g)

Wherein $R^{1d}$ to $R^{4d}$ are independently a leaving group, hydrogen atom, halogen, OH, CN, $C_{1-6}$ alkyl group, halogenated $C_{1-6}$ alkyl group, $C_{2-6}$ alkenyl group, $C_{1-6}$ alkoxy group, or halogenated $C_{1-6}$ alkoxy group, provided that at least one of $R^{1d}$ to $R^{4d}$ is a leaving group, one or two thereof are hydrogen atoms, but it is not that all of three or four thereof are hydrogen atoms. The leaving group includes chlorine, bromine, iodine, and a substituted sulfonyloxy group. Y is as defined above. $R^{1e}$ to $R^{4e}$ are independently hydrogen atom, halogen, OH, CN, $C_{1-6}$ alkyl group, halogenated $C_{1-6}$ alkyl group, $C_{2-6}$ alkenyl group, $C_{1-6}$ alkoxy group, or halogenated $C_{1-6}$ alkoxy group, provided that at least one of $R^{1e}$ to $R^{4e}$ is CN, one or two thereof are hydrogen atoms, but it is not that all of three or four thereof are hydrogen atoms. The leaving group in Compound (11) is replaced by CN at the same position in Compound (1g).

According to the method shown in Scheme 7, Compound (1g) can be prepared by reacting Compound (11) and a cyanating agent, in an appropriate solvent, in the presence of a palladium compound.

The solvent used herein includes, for example, ethers such as THF, ethylene glycol dimethyl ether, tert-butyl methyl ether, and 1,4-dioxane; aliphatic hydrocarbons such as hexane, heptane, and octane; aromatic hydrocarbons such as toluene and xylene; alcohols such as methanol and ethanol; acid amides such as DMF and N-methyl-2-pyrrolidone (NMP); sulfoxides such as DMSO; and a mixture thereof, preferably DMF.

The cyanating agent used herein includes, for example, zinc cyanide, and the palladium compound used herein include, for example, tetrakis(triphenylphosphine)palladium. The amount of cyanating agent used herein is generally 1 to 5 moles per one mole of Compound (11), and the amount of palladium compound used herein is generally 0.01 to 0.5 moles per one mole of Compound (11).

The reaction temperature is generally in the range of 50 to 200° C. The reaction time is generally in the range of 0.5 to 24 hours. In addition, the reaction can be carried out under microwave irradiation.

Scheme 8

[Chem.10]

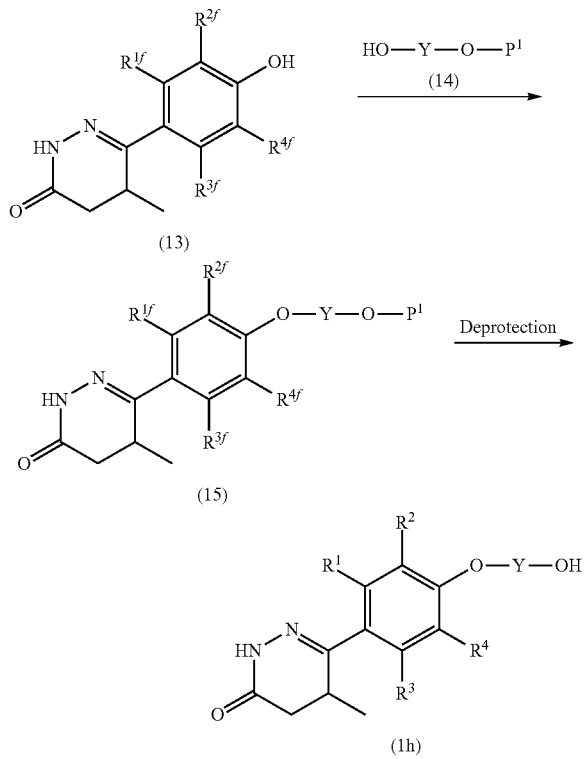

Wherein $R^{1f}$ to $R^{4f}$ are independently hydrogen atom, halogen, OH, hydroxy group protected with a protecting group for hydroxy group (hereinafter, this is abbreviated as "protected hydroxy group"), CN, $C_{1-6}$ alkyl group, halogenated $C_{1-6}$ alkyl group, $C_{2-6}$ alkenyl group, $C_{1-6}$ alkoxy group, or halogenated $C_{1-6}$ alkoxy group, provided that one or two of $R^{1f}$ to $R^{4f}$ are hydrogen atoms, but it is not that all of three or four thereof are hydrogen atoms. $P^1$ is a protecting group for hydroxy group. When one or more of $R^{1f}$ to $R^{4f}$ are protected hydroxy group, the protecting group can be removed at the same time of the deprotection of $P^1$. $R^1$ to $R^4$, and Y are as defined above.

The protecting group for hydroxy group used herein is not limited unless it negatively affects the reaction. The protecting group includes, for example, a silyl protecting group (e.g. trimethylsilyl, tert-butyldimethylsilyl, triisopropylsilyl, tert-butyldiphenylsilyl), an acetal protecting group (e.g. tetrahydropyranyl (THP), methoxymethyl (MOM), methylthiomethyl, ethoxyethyl, benzyloxymethyl), and an acyl protecting group (e.g. acetyl, propionyl, pivaloyl, tert-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl or 4-nitrobenzoyl).

According to the method shown in Scheme 8, Compound (15) can be prepared by reacting Compound (13) and Compound (14), in an appropriate solvent, in the presence of the Mitsunobu reagent and a phosphine.

The Mitsunobu reagent includes, for example, diethyl azodicarboxylate and bis(2-methoxyethyl) azodicarboxylate. The amount of Mitsunobu reagent used herein is 1 to 10 moles, preferably 1 to 5 moles per one mole of Compound (13) shown in Scheme 8. The amount of Compound (14) used herein is 1 to 10 moles, preferably 1 to 5 moles per one mole of Compound (13) shown in Scheme 8. The phosphine reagent used herein includes, for example, triphenylphosphine and tributylphosphine. The amount of phosphine reagent used herein is 1 to 10 moles, preferably 1 to 5 moles per one mole of Compound (13) shown in Scheme 8.

The solvent used herein is not limited unless it negatively affects the reaction. The preferred solvent used herein includes, for example, toluene, benzene, THF, 1,4-dioxane, DMF, N,N-dimethylacetamide, NMP, DMSO, and a mixture thereof.

The reaction temperature is generally at −78 to 200° C., preferably at 0 to 50° C. The reaction time is generally 5 minutes to 3 days, preferably 10 minutes to 10 hours.

According to the method shown in Scheme 8, Compound (1h) can be prepared by de-protecting Compound (15).

When the protecting group for hydroxy group is a silyl-type protecting group, the deprotection can be carried out by hydrolysis under an acidic condition or by using a fluoride ion. For example, in case of tert-butyldimethylsilyl group selected as the silyl protecting group, the deprotection reaction is carried out with a fluoride ion. Suitable fluoride ion sources include, for example, tetrabutylammonium fluoride and hydrogen fluoride-pyridine, preferably tetrabutylammonium fluoride. The amount of the fluorine compound used herein is 1 to 10 moles, preferably 1 to 5 moles per one mole of Compound (15) shown in Scheme 8.

The solvent used herein is not limited unless it negatively affects the reaction. The solvent used herein includes, for example, THF, acetonitrile, and methylene chloride.

The deprotection reaction can be carried out at 0° C. to a reflux temperature of the used reaction solvent, preferably 0° C. to room temperature. The reaction time is generally 5 minutes to 3 days, preferably 10 minutes to 10 hours.

When the protecting group for hydroxy group is an acetal protecting group such as a methoxymethyl group, the deprotection can be generally carried out by using an acid hydrolysis condition. The "acid" used in the acid hydrolysis includes, for example, acetic acid, hydrochloric acid and phosphoric acid, preferably hydrochloric acid. The amount of the acid is in the range of suitably 1 to 1000 moles, preferably 1 to 10 moles per one mole of Compound (15) shown in Scheme 8.

The solvent used herein is not limited unless it negatively affects the reaction. The solvent used herein includes, for example, dichloromethane, methanol, and water.

The reaction time may vary depending on a material compound used herein, reaction temperature, or other factors, but it is suitably in the range of 0.5 hour to 24 hours.

When the protecting group for hydroxy group is an acyl-type protecting group, the deprotection can be generally carried out by using a basic hydrolysis condition. The solvent used herein includes, for example, water; alcohols such as methanol, ethanol, 2-propanol, and tert-butanol; ketones such as acetone and methyl ethyl ketone; ethers such as diethyl ether, dioxane, THF, monoglyme, and diglyme; esters such as methyl acetate and ethyl acetate; halogenated hydrocarbons such as chloroform, dichloromethane, dichloroethane, and carbon tetrachloride; DMSO; DMF; hexamethylphosphate triamide; and a mixture thereof. The basic compound used herein includes, for example, carbonates such as sodium carbonate, potassium carbonate, sodium hydrogen carbonate, and potassium hydrogen carbonate; and metal hydroxides such as sodium hydroxide, potassium hydroxide, calcium hydroxide, and lithium hydroxide. These basic compounds may be used as a single ingredient or in a combination of two or more ingredients.

The hydrolysis reaction can proceed generally at at 0 to 200° C., preferably at 0 to 150° C., and the reaction is completed generally in about 10 minutes to 50 hours.

When there are plural protecting groups for hydroxy group in $R^{1f}$ to $R^{4f}$ and $P^1$, the protecting groups may be the same or different. If the protecting groups are different, the deprotection reaction can be carried out by combining plural deprotection conditions suitable for each protecting group.

Scheme 9

[Chem.11]

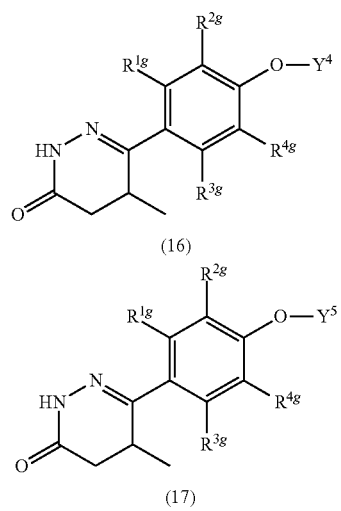

Scheme 10

[Chem.12]

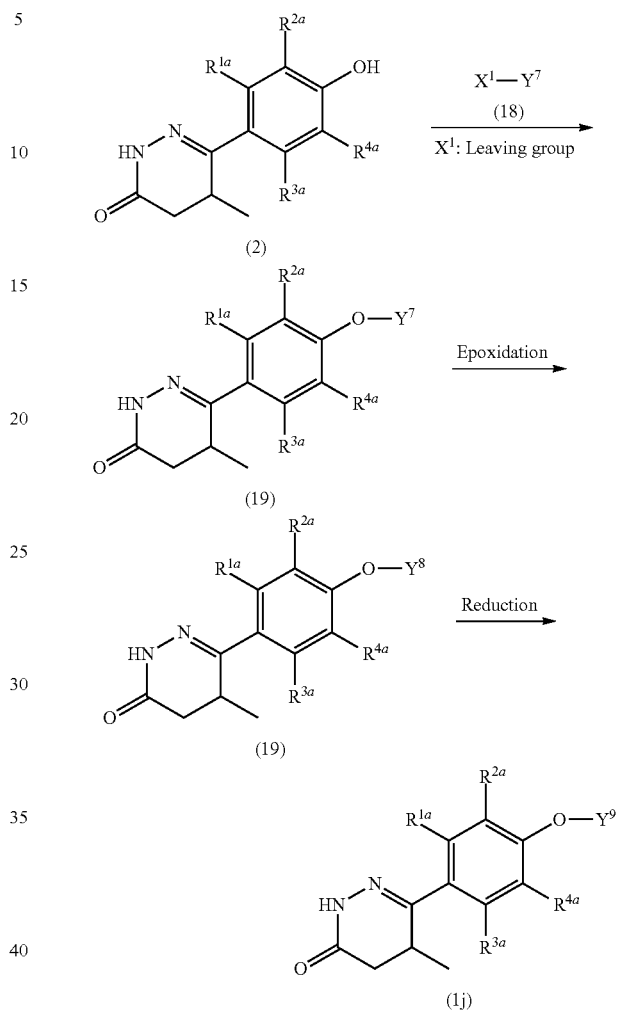

Wherein $R^{1g}$ to $R^{4g}$ are independently hydrogen atom, halogen, protected hydroxy group, CN, $C_{1-6}$ alkyl group, halogenated $C_{1-6}$ alkyl group, $C_{2-6}$ alkenyl group, $C_{1-6}$ alkoxy group, or halogenated $C_{1-6}$ alkoxy group, provided that at least one of $R^{1g}$ to $R^{4g}$ is protected hydroxy group, one or two thereof are hydrogen atoms, but it is not that all of three or four thereof are hydrogen atoms. $R^{1h}$ to $R^{4h}$ are independently hydrogen atom, halogen, OH, CN, $C_{1-6}$ alkyl group, halogenated $C_{1-6}$ alkyl group, $C_{2-6}$ alkenyl group, $C_{1-6}$ alkoxy group, or halogenated $C_{1-6}$ alkoxy group, provided that at least one of $R^{1h}$ to $R^{4h}$ is hydroxy group, one or two thereof are hydrogen atoms, but it is not that all of three or four thereof are hydrogen atoms. Protected hydroxy group in Compound (17) is deprotected to OH at the same position in Compound (1i). $Y^4$ and $Y^5$ are as defined above.

The reaction of Compound (16) and a hydride reductant can be carried out in a reaction condition similar to the reaction of Scheme 5.

The deprotection of Compound (17) can be carried out in a reaction condition similar to the reaction of Scheme 8.

Wherein $R^{1a}$ to $R^{4a}$, and $X^1$ are as defined above. $Y^7$ is $C_{2-6}$ alkenyl group, wherein the alkenyl group may be substituted with one or more substituents selected independently from the group consisting of $C_{1-6}$ alkyl group, halogen, and halogenated $C_{1-6}$ alkyl group, further wherein a substitutable carbon atom in the substituent bonding to the alkenyl group and another substitutable carbon atom in the alkenyl group, or two substitutable carbon atoms in the substituent bonding to the alkenyl group may be combined together to form a 3- to 6-membered carbon ring. $Y^8$ represents a group in which the double bond in the alkenyl group of $Y^7$ is converted to an epoxy group $Y^9$ represents a group in which the epoxy group of $Y^8$ is ring-opened.

The reaction of Compound (2) and Compound (18) can be carried out in a reaction condition similar to the reaction of Scheme 1.

According to the method shown in Scheme 10, Compound (20) can be prepared by reacting Compound (19) and an oxidant in an appropriate solvent or without a solvent. The oxidant used herein includes, for example, m-chloroperbenzoic acid, peracetic acid, oxone, and hydrogen peroxide. The solvent used herein can be broadly chosen from known solvents unless it negatively affects the reaction. The solvent used herein includes, for example, aromatic hydrocarbons such as benzene, toluene, and xylene; aliphatic hydrocarbons such as hexane and heptane; alcohols such as methanol and ethanol; halogenated solvents such as chloroform, dichloromethane, and dichloroethane; nitriles such as acetonitrile and butyronitrile; esters such as ethyl acetate, butyl acetate, and methyl formate; amides such as DMF and N,N-dimethylacetamide; and a mixture thereof.

The amount of the oxidant used herein is generally about 1 to 5 moles per one mole of Compound (19). The above reaction is carried out generally at 0° C. to 100° C., preferably at 0° C. to room temperature, and the reaction is generally completed in about 0.5 to 24 hours.

According to the method shown in Scheme 10, Compound (1j) can be prepared by ring-opening Compound (20) under the hydrogenation condition, in an appropriate solvent, in the presence of a palladium compound.

The reductant used herein includes, for example, hydrogen and ammonium formate and these reductants may be used as a single ingredient or in a combination of two ingredients.

The palladium compound used herein include, for example, palladium-carbon (10% w/w). The amount of palladium compound used herein is generally 0.01 to 0.5 moles per one mole of Compound (20).

The solvent used herein can be broadly chosen from known solvents unless it negatively affects the reaction. The solvent used herein includes, for example, ethers such as dioxane, THF, diethyl ether, diglyme, and ethylene glycol dimethyl ether; halogenated hydrocarbons such as dichloromethane, dichloroethane, chloroform, and carbon tetrachloride; alcohols such as methanol, ethanol, and 2-propanol; polar solvents such as DMF, DMSO and acetonitrile; and a mixture thereof.

The above reaction is carried out generally at 0° C. to 70° C., preferably at 0° C. to room temperature, and the reaction is generally completed in about 0.5 to 24 hours.

Wherein $R^1$ to $R^4$, Y, and $P^1$ are as defined above.

The reaction of Compound (21) and hydrazine can be carried out in a reaction condition similar to the reaction of Scheme 4. The deprotection of Compound (22) can be carried out in a reaction condition similar to the reaction of Scheme 8.

The present compound of formula (1) can be prepared according to the above synthetic processes, and it can be also prepared based on the synthetic processes described in the reference examples and examples herein, considering the prior art known at the time of the filing date.

If necessary, the starting materials and intermediates shown in the above schemes can be protected with a suitable protecting group before starting the reaction, and then the protecting group can be removed in a known manner after the reaction.

Each product prepared according to the above schemes can be purified from each reaction mixture as follows, for example, the reaction mixture is cooled, the reaction mixture is treated in an isolation procedure such as filtration, concentration, and ex-traction to isolate the crude product, and the crude product is purified in a conventional manner of purification such as column chromatography and recrystallization.

The starting materials and products shown in each scheme also include a solvate thereof as an additional form, for example, a hydrate and ethanolate.

The starting materials and products shown in each scheme may be used in a preferred salt form. Each product in each step can be used in its next step without isolation.

The present compound (1), intermediates prepared in the above schemes, and starting materials thereof may include geometric isomer, stereoisomer, tautomer and optical isomer thereof.

Each isomer can be isolated by a conventional manner. For example, racemic compounds can be divided by a general optical resolution such as crystallization and chro- Scheme 11

[Chem.13]

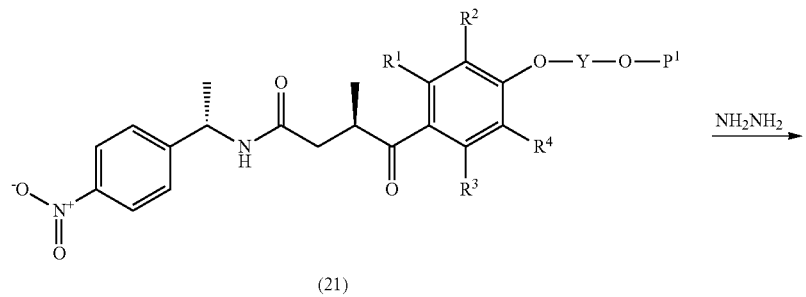

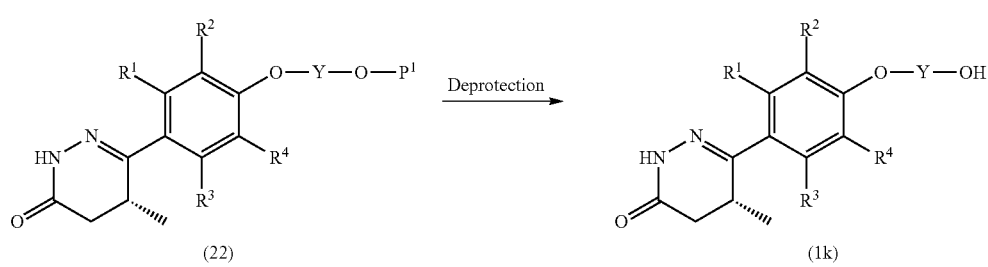

matography to optically pure isomers thereof. In addition, an optically pure compound can be also prepared from an appropriate material.

The compound of the present invention can be a useful agent for treating tumor, particularly malignant tumor, in more detail, the compound can be a novel agent for treating and/or preventing childhood brain tumor selected from the group consisting of astrocytoma, malignant medulloblastoma, germ cell tumor, craniopharyngioma, and ependymoma; adult brain tumor selected from the group consisting of glioma, meningioma, pituitary adenoma, and nerve sheath tumor; head and neck cancer selected from the group consisting of maxillary sinus cancer, pharyngeal cancer (e.g. nasopharyngeal cancer, oropharyngeal cancer, hypopharyngeal cancer), laryngeal cancer, oral cancer (e.g. lip cancer, tongue cancer), and salivary gland cancer (e.g. parotid gland cancer); thoracic cancer and tumor selected from the group consisting of small cell lung cancer, non-small-cell lung cancer, thymoma, and mesothelioma; gastrointestinal cancer and tumor selected from the group consisting of esophageal cancer, liver cancer, primary liver cancer, gallbladder cancer, bile duct cancer, gastric cancer, colorectal cancer (e.g. rectal cancer, anal cancer), pancreatic cancer, and pancreatic endocrine tumor; urologic cancer and tumor selected from the group consisting of penile cancer, renal pelvic/ureter cancer, renal cell cancer, testicular tumor (also referred to as testicular neoplasm), prostate cancer, bladder cancer, Wilms' tumor, and urothelial carcinoma; gynecologic cancer and tumor selected from the group consisting of vulvar cancer, cervical cancer, uterine body cancer, endometrial cancer, uterine sarcoma, choriocarcinoma, vaginal cancer, breast cancer, ovarian cancer, and ovarian germ cell tumor; adult and childhood soft tissue sarcoma; bone tumor selected from the group consisting of osteosarcoma and Ewing's tumor; endocrine tissue cancer and tumor selected from the group consisting of adrenocortical carcinoma and thyroid cancer; malignant lymphoma and leukemia selected from the group consisting of malignant lymphoma, non-Hodgkin's lymphoma, Hodgkin's disease, multiple myeloma, plasma cell neoplasm, acute myeloid leukemia, acute lymphoblastic leukemia, adult T-cell leukemia-lymphoma, chronic myeloid leukemia, and chronic lymphocytic leukemia; or skin cancer and tumor selected from the group consisting of chronic myeloproliferative disorder, malignant melanoma, squamous cell carcinoma, basal cell carcinoma, and mycosis fungoides. The administration route of the present compound may be selected from oral administration, parenteral administration or rectal administration, and the daily dosage may vary depending on the compound structure, the administration route, the condition/age of patients, etc. For example, in case of oral administration, the present compound may be administered to a human being or a mammal in a dosage of generally about 0.01 μg-10 mg, preferably about 1 μg-5 mg, per kg of its body weight, in one to several divided doses. For example, in case of parenteral administration such as intravenous injection, the present compound may be administered to a human being or a mammal in a dosage of generally about 0.01 μg-10 mg, preferably about 1 μg-5 mg, per kg of its body weight.

The dosage form in the present invention includes tablet, capsule, granule, powder, syrup, suspension, injection, suppository, eyedrop, ointment, liniment, patch, and inhalant. These dosage forms can be prepared in a conventional manner. If the dosage form is a liquid one, it may be a formulation to prepare a solution or suspension in use by mixing it with water, appropriate water-solution, or other appropriate solvent. The tablet and the granule may be coated in a well-known manner. Furthermore, these dosage forms may comprise another therapeutically-useful ingredient.

In case that the present compound is formulated into a single dosage form, the dosage form may include the present compound in 0.1-70% (w/w) per the whole composition, but the present invention is not limited thereto. Preferably, it is 5-40% (w/w) per the whole composition.

EXAMPLES

The present invention is explained in more detail in the following by referring to Reference examples, Examples and Test, however, the present invention should not be limited thereto.

Reference Example 1

Production of (4-bromo-2-chloro-6-methylphenoxy)-tert-butyldimethylsilane

[Chem.14]

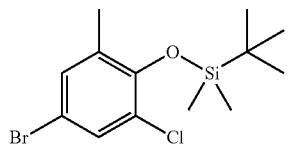

To a mixture of 4-bromo-2-chloro-6-methylphenol (13.3 g) in DMF (120 mL) were added imidazole (6.1 g) and tert-butylchlorodimethylsilane (10.9 g), and the mixture was stirred at room temperature overnight. The solvent was removed, and water was added to the residue. The mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=100:0 to 99:1) to afford the title compound as a colorless oil (20.0 g).

$^1$H-NMR (CDCl$_3$) δ: 0.24 (6H, s), 1.03 (9H, s), 2.22 (3H, s), 7.14-7.17 (1H, m), 7.30-7.33 (1H, m).

Reference Example 2

Production of methyl 2-(4-bromo-2-chloro-6-fluorophenoxy)acetate

[Chem.15]

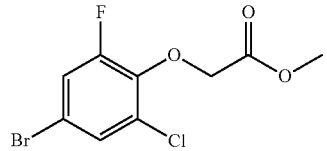

To a mixture of 4-bromo-2-chloro-6-fluorophenol (2.0 g) and potassium carbonate (1.47 g) in DMF (15 mL) was added methyl bromoacetate (0.924 mL), and the mixture was stirred at room temperature for 2 hours. To the reaction mixture was added water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=80:20 to 60:40) to afford the title compound as a colorless oil (2.53 g).

$^1$H-NMR (CDCl$_3$) δ: 3.81 (3H, s), 4.73 (2H, s), 7.20 (1H, dd, J=10.4, 2.3 Hz), 7.33-7.37 (1H, m).

The following compounds were prepared from each appropriate starting material in a similar manner to Reference example 2.

Reference Example 3

Methyl 2-(4-bromo-2-fluoro-6-methylphenoxy)acetate

[Chem.16]

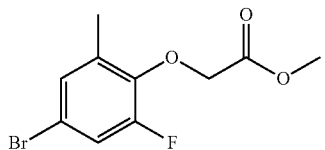

$^1$H-NMR (CDCl$_3$) δ: 2.33 (3H, s), 3.79 (3H, s), 4.69 (2H, d, J=1.0 Hz), 7.06-7.11 (2H, m).

Reference Example 4

Methyl 2-(4-bromo-3-fluoro-2-methylphenoxy)acetate

[Chem.17]

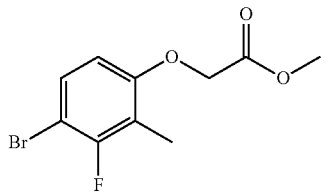

$^1$H-NMR (CDCl$_3$) δ: 2.24 (3H, d, J=2.3 Hz), 3.80 (3H, s), 4.65 (2H, s), 6.42 (1H, dd, J=8.9, 1.2 Hz), 7.28 (1H, t, J=8.9 Hz).

Reference Example 5

Production of methyl 2-(4-bromo-2-chloro-3-fluorophenoxy)acetate

[Chem.18]

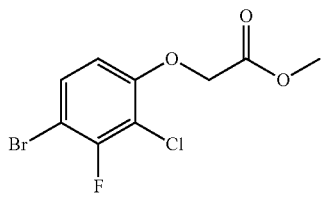

To a mixture of 2-chloro-3-fluorophenol (2.6 g) in acetic acid (30 mL) was added pyridinium bromide perbromide (6.0 g), and the mixture was stirred at room temperature for 4.5 hours. To the reaction mixture was added aqueous sodium thiosulfate, and the mixture was extracted with toluene. The organic layer was washed with water and brine, dried over anhydrous sodium sulfate, and filtrated, and the solvent was removed to afford a yellow oil (3.4 g). This oil was dissolved in DMF (30 mL), and potassium carbonate (4.9 g) and methyl bromoacetate (2.0 mL) were added to the mixture. The mixture was stirred at room temperature for 30 minutes. To the reaction mixture was added water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=100:0 to 84:16) to afford the title compound as a colorless oil (2.3 g).

$^1$H-NMR (CDCl$_3$) δ: 3.81 (3H, s), 4.73 (2H, s), 6.56 (1H, dd, J=9.0, 1.8 Hz), 7.37 (1H, dd, J=9.0, 7.4 Hz).

Reference Example 6

Production of 1-[(4-bromo-2-chloro-6-fluorophenoxy)methyl]cyclopropan-1-ol

[Chem.19]

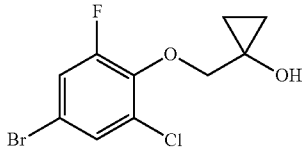

Under an argon atmosphere, to a mixture of methyl 2-(4-bromo-2-chloro-6-fluorophenoxy)acetate (Reference example 2, 2.53 g) in THF (30 mL) was added tetraisopropyl orthotitanate (2.49 mL) at 0° C. Ethylmagnesium bromide (3.0 M diethyl ether solution, 7.65 mL) was slowly added thereto at 0° C., and the reaction mixture was stirred at room temperature for one hour. To the reaction mixture was added 1 M hydrochloric acid at 0° C., and the mixture was extracted with ethyl acetate. The organic layer was washed with brine, dried over anhydrous sodium sulfate, and filtrated, and the solvent was removed. The obtained crude product was purified by silica gel column chromatography (heptane:ethyl acetate=100:0 to 80:20) and then by amino silica gel column chromatography (methylene chloride:methanol=100:0 to 90:10) to afford the title compound as a colorless oil (1.15 g).

$^1$H-NMR (CDCl$_3$) δ: 0.60-0.66 (2H, m), 0.89-0.95 (2H, m), 2.95 (1H, s), 4.14 (2H, s), 7.21 (1H, dd, J=9.8, 2.2 Hz), 7.33-7.37 (1H, m).

The following compounds were prepared from each appropriate starting material in a similar manner to Reference example 6.

Reference Example 7

1-[(2,3-Difluorophenoxy)methyl]cyclopropan-1-ol

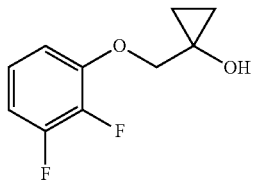
[Chem.20]

$^1$H-NMR (CDCl$_3$) δ: 0.68-0.74 (2H, m), 0.95-1.00 (2H, m), 2.78 (1H, s), 4.08 (2H, s), 6.71-6.84 (2H, m), 6.93-7.02 (1H, m).

Reference Example 8

1-[(4-Bromo-2,6-dimethylphenoxy)methyl]cyclopropan-1-ol

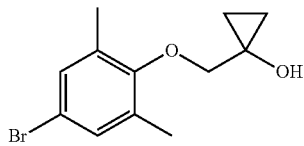
[Chem.21]

$^1$H-NMR (CDCl$_3$) δ: 0.66-0.71 (2H, m), 0.93-0.98 (2H, m), 2.26-2.28 (6H, m), 2.77 (1H, s), 3.78 (2H, s), 7.13-7.16 (2H, m).

Reference Example 9

1-[(4-Bromo-2-chloro-6-methylphenoxy)methyl]cyclopropan-1-ol

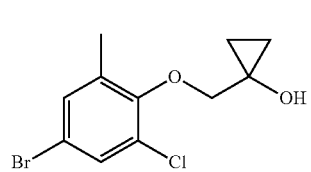
[Chem.22]

$^1$H-NMR (CDCl$_3$) δ: 0.66-0.73 (2H, m), 0.92-0.98 (2H, m), 2.32 (3H, s), 2.90 (1H, s), 3.95 (2H, s), 7.23 (1H, dd, J=2.4, 0.6 Hz), 7.37 (1H, d, J=2.4 Hz).

Reference Example 10

1-[(4-Bromo-2-fluoro-6-methylphenoxy)methyl]cyclopropan-1-ol

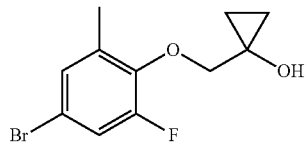
[Chem.23]

$^1$H-NMR (CDCl$_3$) δ: 0.62-0.68 (2H, m), 0.90-0.95 (2H, m), 2.30 (3H, s), 2.76 (1H, d, J=1.0 Hz), 4.02 (2H, s), 7.07-7.13 (2H, m).

Reference Example 11

1-[(4-Bromo-3-fluoro-2-methylphenoxy)methyl]cyclopropan-1-ol

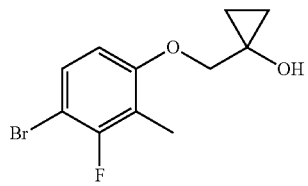
[Chem.24]

$^1$H-NMR (CDCl$_3$) δ: 0.69-0.75 (2H, m), 0.95-1.00 (2H, m), 2.22 (3H, d, J=2.3 Hz), 2.59 (1H, s), 4.00 (2H, s), 6.53 (1H, dd, J=8.9, 1.3 Hz), 7.25-7.32 (1H, m).

Reference Example 12

1-[(4-Bromo-2-chloro-3-fluorophenoxy)methyl]cyclopropan-1-ol

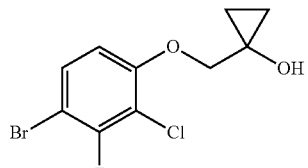
[Chem.25]

$^1$H-NMR (CDCl$_3$) δ: 0.70-0.76 (2H, m), 0.96-1.03 (2H, m), 2.81 (1H, s), 4.07 (2H, s), 6.65 (1H, dd, J=9.0, 1.8 Hz), 7.38 (1H, dd, J=9.0, 7.5 Hz).

Reference Example 13

Production of {1-[(4-bromo-2-chloro-6-fluorophenoxy)methyl]cyclopropyloxy}triethylsilane

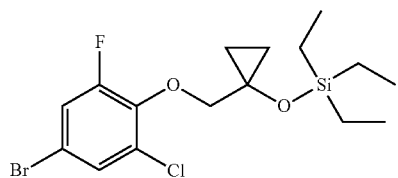
[Chem.26]

To a mixture of 1-[(4-bromo-2-chloro-6-fluorophenoxy)methyl]cyclopropan-1-ol (Reference example 6, 1.15 g) in methylene chloride (15 mL) were added 2,6-lutidine (0.544 mL) and triethylsilyl trifluoromethanesulfonate (0.968 mL) at 0° C. The reaction mixture was stirred at room temperature overnight. To the reaction mixture was added water, and then the mixture was extracted with methylene chloride. The organic layer was washed with brine, dried over anhydrous sodium sulfate, and filtrated, and the solvent was removed. The obtained crude product was purified by silica gel column chromatography (heptane:ethyl acetate=100:0 to 85:15) to afford the title compound as a colorless oil (1.08 g).

$^1$H-NMR (CDCl$_3$) δ: 0.64 (6H, q, J=7.8 Hz), 0.77-0.84 (2H, m), 0.84-0.91 (2H, m), 0.95 (9H, t, J=7.8 Hz), 4.05 (2H, s), 7.17 (1H, dd, J=10.0, 2.4 Hz), 7.30-7.33 (1H, m).

The following compounds were prepared from each appropriate starting material in a similar manner to Reference example 13.

Reference Example 14

{1-[(2,3-Difluorophenoxy)methyl]cyclopropyloxy}triethylsilane

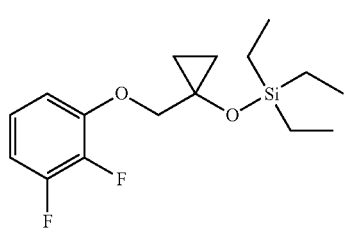
[Chem.27]

$^1$H-NMR (CDCl$_3$) δ: 0.62-0.70 (6H, m), 0.73-0.78 (2H, m), 0.86-0.99 (11H, m), 4.02 (2H, s), 6.67-6.81 (2H, m), 6.91-7.00 (1H, m).

Reference Example 15

{1-[(4-Bromo-2,6-dimethylphenoxy)methyl]cyclopropyloxy}triethylsilane

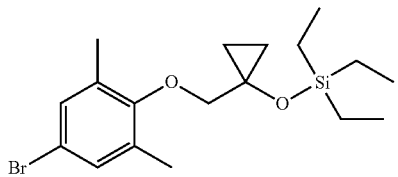
[Chem.28]

$^1$H-NMR (CDCl$_3$) δ: 0.64 (6H, q, J=7.9 Hz), 0.74-0.79 (2H, m), 0.87-0.92 (2H, m), 0.96 (9H, t, J=7.9 Hz), 2.25 (6H, s), 3.73 (2H, s), 7.12 (2H, s).

Reference Example 16

{1-[(4-Bromo-2-chloro-6-methylphenoxy)methyl]cyclopropyloxy}triethylsilane

[Chem.29]

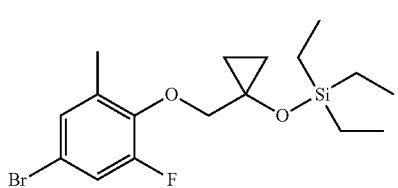

$^1$H-NMR (CDCl$_3$) δ: 0.60-0.68 (6H, m), 0.77-0.81 (2H, m), 0.86-0.91 (2H, m), 0.92-0.98 (9H, m), 2.32 (3H, s), 3.90 (2H, s), 7.21 (1H, dd, J=2.4, 0.7 Hz), 7.33 (1H, dd, J=2.4, 0.5 Hz).

Reference Example 17

{1-[(4-Bromo-2-fluoro-6-methylphenoxy)methyl]cyclopropyloxy}triethylsilane

[Chem.30]

$^1$H-NMR (CDCl$_3$) δ: 0.62 (6H, q, J=8.0 Hz), 0.68-0.74 (2H, m), 0.83-0.89 (2H, m), 0.94 (9H, t, J=8.0 Hz), 2.30 (3H, s), 3.98 (2H, s), 7.04-7.09 (2H, m).

Reference Example 18

{1-[(4-Bromo-3-fluoro-2-methylphenoxy)methyl]cyclopropyloxy}triethylsilane

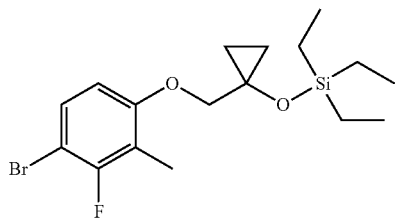

[Chem.31]

¹H-NMR (CDCl₃) δ: 0.59-0.68 (6H, m), 0.73-0.78 (2H, m), 0.85-0.90 (2H, m), 0.93 (9H, t, J=7.9 Hz), 2.20 (3H, d, J=2.3 Hz), 3.96 (2H, s), 6.50 (1H, dd, J=8.9, 1.3 Hz), 7.24-7.30 (1H, m).

Reference Example 19

{1-[(4-Bromo-2-chloro-3-fluorophenoxy)methyl]cyclopropyloxy}triethylsilane

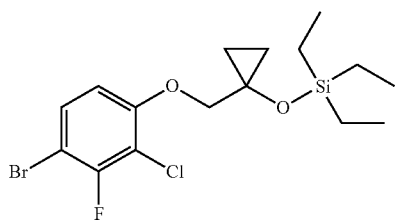

[Chem.32]

¹H-NMR (CDCl₃) δ: 0.61-0.71 (6H, m), 0.75-0.98 (13H, m), 4.03 (2H, s), 6.63 (1H, dd, J=9.0, 1.7 Hz), 7.36 (1H, dd, J=9.0, 7.6 Hz).

Reference Example 20

Production of 3-chloro-5-fluoro-4-{[1-(triethylsilyloxy)cyclopropyl]methoxy}benzaldehyde

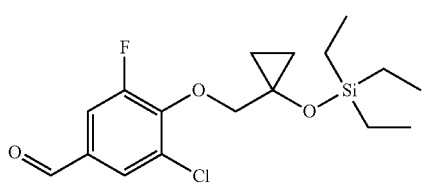

[Chem.33]

Under an argon atmosphere, to a mixture of {1-[(4-bromo-2-chloro-6-fluorophenoxy)methyl]cyclopropyloxy}triethylsilane (Reference example 13, 1.08 g) in THF (10 mL) at −78° C. was added n-butyl lithium (1.6 M n-hexane solution, 1.73 mL), and under the same condition, the reaction mixture was stirred for 30 minutes. At −78° C., DMF (0.224 mL) was added to the reaction mixture, and the reaction mixture was stirred at −78° C. for 30 minutes and then at room temperature for 30 minutes. To the reaction mixture was added aqueous ammonium chloride, and the mixture was extracted with ethyl acetate. The organic layer was washed with brine, dried over anhydrous sodium sulfate, and filtrated, and the solvent was removed. The obtained crude product was purified by silica gel column chromatography (heptane:ethyl acetate=100:0 to 90:10) to afford the title compound as a colorless oil (873 mg).

¹H-NMR (CDCl₃) δ: 0.63 (6H, q, J=7.9 Hz), 0.78-0.85 (2H, m), 0.86-0.99 (2H, m), 0.94 (9H, t, J=7.9 Hz), 4.23 (2H, s), 7.53 (1H, dd, J=10.7, 2.0 Hz), 7.69-7.72 (1H, m), 9.84 (1H, d, J=2.0 Hz).

The following compounds were prepared from each appropriate starting material in a similar manner to Reference example 20.

Reference Example 21

3,5-Dimethyl-4-{[1-(triethylsilyloxy)cyclopropyl]methoxy}benzaldehyde

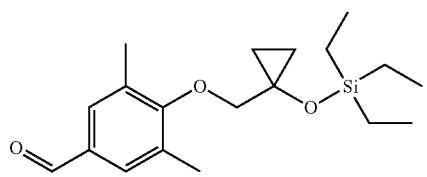

[Chem.34]

¹H-NMR (CDCl₃) δ: 0.64 (6H, q, J=7.9 Hz), 0.76-0.80 (2H, m), 0.86-0.92 (2H, m), 0.96 (9H, t, J=7.9 Hz), 2.36 (6H, s), 3.83 (2H, s), 7.55 (2H, s), 9.87 (1H, s).

Reference Example 22

3-Chloro-5-methyl-4-{[1-(triethylsilyloxy)cyclopropyl]methoxy}benzaldehyde

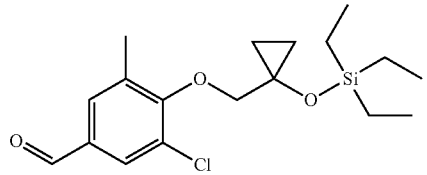

[Chem.35]

¹H-NMR (CDCl₃) δ: 0.59-0.70 (6H, m), 0.76-1.01 (13H, m), 2.43 (3H, s), 4.02 (2H, s), 7.61 (1H, d, J=1.6 Hz), 7.73 (1H, d, J=1.6 Hz), 9.86 (1H, s).

Reference Example 23

2-Fluoro-3-methyl-4-{[1-(triethylsilyloxy)cyclopropyl]methoxy}benzaldehyde

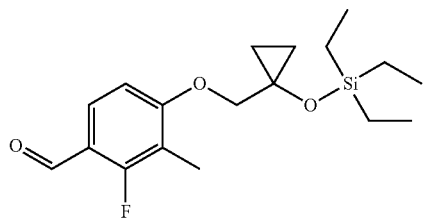

[Chem.36]

¹H-NMR (CDCl₃) δ: 0.63 (6H, q, J=7.9 Hz), 0.75-0.80 (2H, m), 0.87-0.98 (11H, m), 2.20 (3H, d, J=2.1 Hz), 4.08 (2H, s), 6.70 (1H, d, J=8.8 Hz), 7.70 (1H, t, J=8.8 Hz), 10.22 (1H, s).

Reference Example 24

3-Fluoro-5-methyl-4-{[1-(triethylsilyloxy)cyclopropyl]methoxy}benzaldehyde

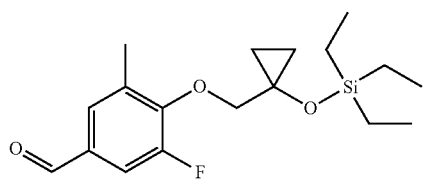

[Chem.37]

¹H-NMR (CDCl₃) δ: 0.61 (6H, q, J=7.9 Hz), 0.71-0.76 (2H, m), 0.85-0.90 (2H, m), 0.93 (9H, t, J=7.9 Hz), 2.39 (3H, s), 4.18 (2H, s), 7.44 (1H, dd, J=11.4, 1.9 Hz), 7.47-7.50 (1H, m), 9.84 (1H, d, J=2.0 Hz).

Reference Example 25

3-Chloro-2-fluoro-4-{[1-(triethylsilyloxy)cyclopropyl]methoxy}benzaldehyde

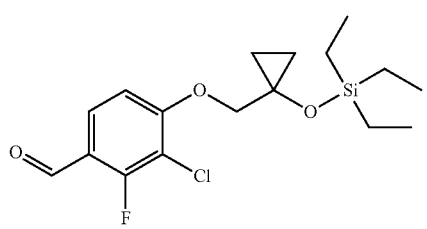

[Chem.38]

¹H-NMR (CDCl₃) δ: 0.66 (6H, q, J=7.9 Hz), 0.78-0.84 (2H, m), 0.89-0.98 (11H, m), 4.14 (2H, s), 6.82 (1H, d, J=9.0 Hz), 7.77 (1H, dd, J=9.0, 7.7 Hz), 10.22 (1H, s).

Reference Example 26

Production of 2,3-difluoro-4-{[1-(triethylsilyloxy)cyclopropyl]methoxy}benzaldehyde

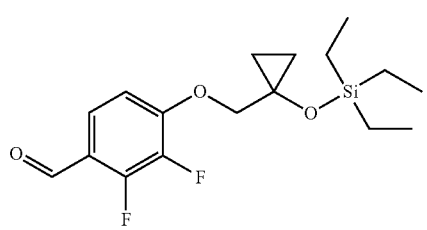

[Chem.39]

Under an argon atmosphere, to a mixture of {1-[(2,3-difluorophenoxy)methyl]cyclopropyloxy}triethylsilane (Reference example 14, 1.4 g) and 2,2,6,6-tetramethylpiperidine (0.8 mL) in THF (10 mL) at −78° C. was added n-butyl lithium (1.6 M n-hexane solution, 2.9 mL). The mixture was stirred at −78° C. for 30 minutes, and then DMF (0.4 mL) was added thereto. The reaction mixture was stirred at −78° C. for 30 minutes, and then at room temperature for 30 minutes. To the reaction mixture was added aqueous ammonium chloride at 0° C., and the mixture was extracted with ethyl acetate. The organic layer was washed with brine, dried over anhydrous sodium sulfate, and filtrated, and the solvent was removed. The obtained crude product was purified by silica gel column chromatography (heptane:ethyl acetate=94:6 to 76:24) to afford the title compound as a colorless oil (1.3 g).

¹H-NMR (CDCl₃) δ: 0.60-0.69 (6H, m), 0.74-0.79 (2H, m), 0.86-0.96 (11H, m), 4.11 (2H, s), 6.79-6.86 (1H, m), 7.57-7.64 (1H, m), 10.20 (1H, s).

Reference Example 27

Production of 3-bromo-2-fluoro-4-methoxybenzaldehyde

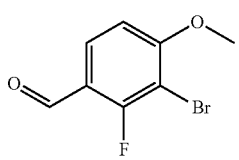

[Chem.40]

A mixture of 2-bromo-3-fluoroanisole (25 g), hexamethylenetetramine (34.2 g), and trifluoroacetic acid (150 mL) was stirred at 90° C. for 27 hours. The reaction mixture was allowed to cool to room temperature, and then 1 M hydrochloric acid was added to the reaction mixture. The reaction mixture was extracted with ethyl acetate, and then the organic layer was concentrated to about half of its volume. To the concentrated organic layer was added aqueous sodium hydroxide, and then the organic layer was separated from the mixture and washed with brine. The organic layer was dried over anhydrous sodium sulfate, and filtrated, and the solvent was removed. The obtained crude product was purified by silica gel column chromatography (heptane:ethyl acetate=94:6 to 73:27) to afford the title compound as a white solid (22.3 g).

$^1$H-NMR (CDCl$_3$) δ: 4.01 (3H, s), 6.82 (1H, d, J=8.8 Hz), 7.85 (1H, dd, J=8.8, 7.7 Hz), 10.22 (1H, d, J=0.7 Hz).

Reference Example 28

Production of 2-fluoro-4-methoxy-3-methylbenzaldehyde

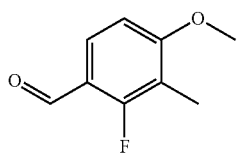

[Chem.41]

To a mixture of 3-bromo-2-fluoro-4-methoxybenzaldehyde (Reference example 27, 6.0 g) in 1,2-dimethoxyethane (90 mL) were added methyl boronate (4.6 g), tripotassium phosphate (16.4 g) and [1,1'-bis(diphenylphosphino)ferrocene]palladium dichloride complex with methylene chloride (1.1 g). The reaction mixture was refluxed for 24 hours under an argon atmosphere. The reaction mixture was allowed to cool to room temperature, and then ethyl acetate was added thereto. The mixture was filtered through a Celite pad, and then aqueous ammonium chloride was added to the filtrate. The organic layer was separated from the mixture, washed with brine, dried over anhydrous sodium sulfate, and filtrated, and the solvent was removed. The obtained crude product was purified by silica gel column chromatography (heptane:ethyl acetate=100:0 to 73:27) to afford the title compound as a white solid (3.8 g).

$^1$H-NMR (CDCl$_3$) δ: 2.15 (3H, d, J=2.2 Hz), 3.92 (3H, s), 6.74 (1H, d, J=8.7 Hz), 7.73 (1H, t, J=8.7 Hz), 10.22 (1H, s).

Reference Example 29

Production of 3-chloro-2-fluoro-4-hydroxy-5-methylbenzaldehyde

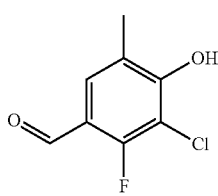

[Chem.42]

To a mixture of 2-fluoro-4-hydroxy-5-methylbenzaldehyde (2.7 g) in acetic acid (5 mL) was added sulfuryl chloride (2.8 mL), and the mixture was stirred at room temperature for 3 hours. Sulfuryl chloride (0.7 mL) was added thereto, and the reaction mixture was stirred at room temperature further for one hour. To the reaction mixture was added ice in water at 0° C., and the obtained precipitates were collected on a filter. The collected precipitates were dissolved in ethyl acetate, the mixture was dried over anhydrous sodium sulfate and filtrated, and the solvent was removed. The obtained crude product was purified by silica gel column chromatography (heptane:ethyl acetate=88:12 to 67:33) to afford the title compound as a white solid (1.3 g).

$^1$H-NMR (DMSO-d6) δ: 2.23 (3H, s), 7.56 (1H, dd, J=7.9, 0.7 Hz), 10.02 (1H, s), 10.98 (1H, brs).

Reference Example 30

Production of 5-chloro-2-fluoro-4-methoxy-3-methylbenzaldehyde

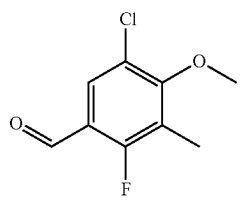

[Chem.43]

Under an argon atmosphere, to a mixture of 1-chloro-4-fluoro-2-methoxy-3-methylbenzene (2.6 g) in methylene chloride (30 mL) were added titanium tetrachloride (8.1 mL) and dichloromethyl methyl ether (2.7 mL) at 0° C. The reaction mixture was stirred at 0° C. for 1.5 hours, and then poured into ice in water. The mixture was stirred at room temperature for one hour, and then extracted with ethyl acetate. The organic layer was washed with brine, dried over anhydrous sodium sulfate, and filtrated, and the solvent was removed. The obtained crude product was purified by silica gel column chromatography (heptane:ethyl acetate=100:0 to 90:10) to afford the title compound as a white solid (2.6 g).

$^1$H-NMR (CDCl$_3$) δ: 2.28 (3H, d, J=2.4 Hz), 3.91 (3H, s), 7.75 (1H, d, J=7.3 Hz), 10.24 (1H, s).

Reference Example 31

Production of 3-chloro-2,4-dimethoxybenzaldehyde

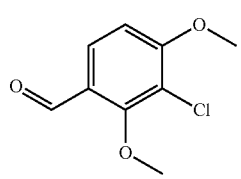

[Chem.44]

A suspension of 3-chloro-2,4-dihydroxybenzaldehyde (3.35 g), methyl iodide (12.1 mL), and potassium carbonate (26.8 g) in acetone (70 mL) was stirred at 40° C. overnight. The reaction mixture was filtered through a Celite pad, and the filtrate was concentrated. The obtained crude product was purified by silica gel column chromatography (heptane:ethyl acetate=85:15) to afford the title compound as a pale yellow solid (2.57 g).

$^1$H-NMR (CDCl$_3$) δ: 3.99 (3H, s), 4.01 (3H, s), 6.84 (1H, d, J=9.0 Hz), 7.79-7.82 (1H, m), 10.24 (1H, s).

Reference Example 32

Production of 3-bromo-5-chloro-4-(methoxymethyloxy)benzaldehyde

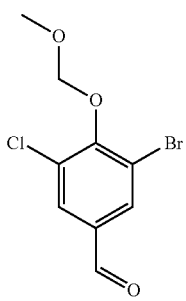

To a mixture of 3-Bromo-5-chloro-4-hydroxybenzaldehyde (1.00 g) in dichloroethane (20 mL) were added N,N-diisopropylethylamine (2.23 mL) and chloromethyl methyl ether (0.645 mL), and the mixture was refluxed overnight. The reaction mixture was concentrated, water was added to the residue, and then the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=83:17 to 67:33) to afford the title compound as a white solid (920 mg).

$^1$H-NMR (CDCl$_3$) δ 3.72 (3H, s), 5.29 (2H, s), 7.87 (1H, d, J=2.0 Hz), 8.00 (1H, d, J=2.0 Hz), 9.87 (1H, s).

The following compounds were prepared from each appropriate starting material in a similar manner to Reference example 32.

Reference Example 33

3-Bromo-5-fluoro-4-(methoxymethyloxy)benzaldehyde

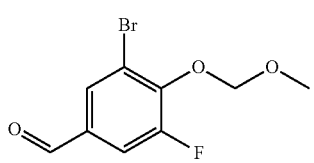

$^1$H-NMR (CDCl$_3$) δ: 3.63 (3H, s), 5.34 (2H, d, J=1.0 Hz), 7.59 (1H, dd, J=10.6, 1.9 Hz), 7.89 (1H, dd, J=1.9, 1.3 Hz), 9.86 (1H, d, J=2.1 Hz).

Reference Example 34

3,5-Dichloro-4-(methoxymethyloxy)benzaldehyde

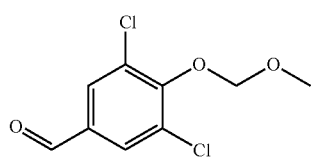

$^1$H-NMR (CDCl$_3$) δ: 3.70 (3H, s), 5.29 (2H, s), 7.84 (2H, s), 9.87 (1H, s).

Reference Example 35

4-Benzyloxy-3-chloro-2-(methoxymethyloxy)benzaldehyde

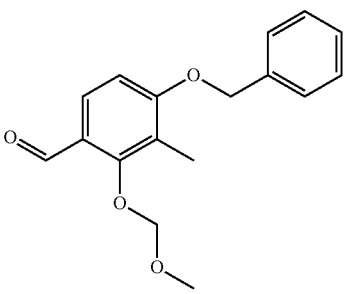

$^1$H-NMR (CDCl$_3$) δ: 3.63 (3H, s), 5.24 (2H, s), 5.25 (2H, s), 6.90 (1H, d, J=8.8 Hz), 7.32-7.48 (5H, m), 7.77 (1H, d, J=8.8 Hz), 10.23 (1H, s).

Reference Example 36

4-Benzyloxy-2-(methoxymethyloxy)-3-methylbenzaldehyde $^1$H-NMR (CDCl$_3$) δ: 2.24 (3H, s), 3.61 (3H, s), 5.08 (2H, s), 5.16 (2H, s), 6.83 (1H, d, J=8.5 Hz), 7.32-7.46 (5H, m), 7.72 (1H, d, J=8.8 Hz), 10.19 (1H, s).

Reference Example 37

3-Chloro-2-fluoro-4-(methoxymethyloxy)-5-methyl-benzaldehyde

[Chem.50]

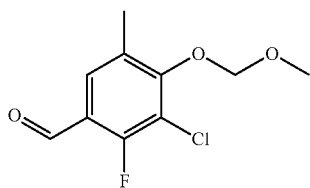

$^1$H-NMR (CDCl$_3$) δ: 2.34-2.36 (3H, m), 3.65 (3H, s), 5.20 (2H, s), 7.62 (1H, dd, J=7.6, 0.7 Hz), 10.26 (1H, s).

Reference Example 38

Production of 1-[4-(tert-butyldimethylsilyloxy)-3-chloro-5-methylphenyl]propan-1-one

[Chem.51]

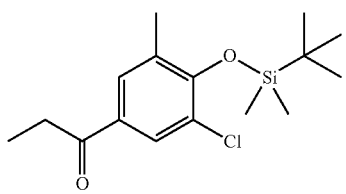

Under an argon atmosphere, to a mixture of (4-bromo-2-chloro-6-methylphenoxy)-tert-butyldimethylsilane (Reference example 1, 10.0 g) in THF (100 mL) at −78° C. was added dropwise n-butyl lithium (2.65 M n-hexane solution, 11.8 mL). The reaction mixture was stirred at the same temperature for 30 minutes, and then N,N-dimethylpropanamide (3.9 mL) was added thereto. The reaction mixture was stirred at the same temperature for 30 minutes and then at room temperature for 2 hours. To the reaction mixture at −78° C. was added aqueous ammonium chloride to quench the reaction. The mixture was extracted with ethyl acetate, and the organic layer was washed with brine, dried over anhydrous sodium sulfate, and filtrated, and the solvent was removed. The obtained crude product was purified by silica gel column chromatography (heptane:ethyl acetate=100:0 to 91:9) to afford the title compound as a pale yellow oil (6.3 g).

$^1$H-NMR (CDCl$_3$) δ: 0.28 (6H, s), 1.04 (9H, s), 1.20 (3H, t, J=7.3 Hz), 2.29 (3H, s), 2.92 (2H, q, J=7.3 Hz), 7.67 (1H, d, J=2.1 Hz), 7.81 (1H, d, J=2.1 Hz).

Reference Example 39

Production of methyl 4-[4-(tert-butyldimethylsilyloxy)-3-chloro-5-methylphenyl]-3-methyl-4-oxobutanoate

[Chem.52]

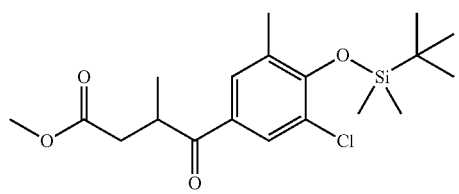

Under an argon atmosphere, to a mixture of 1-[4-(tert-butyldimethylsilyloxy)-3-chloro-5-methylphenyl]propan-1-one (Reference example 38, 6.3 g) in THF (100 mL) at −78° C. was added dropwise lithium diisopropylamide (2.0 M, a mixed solution of THF/heptane/ethylbenzene, 15.0 mL). The mixture was stirred at the same temperature for one hour, and then methyl bromoacetate (2.9 mL) was added thereto. The reaction mixture was stirred at −78° C. for 15 minutes, and then at room temperature overnight. The reaction mixture was cooled on ice-methanol bath, and then aqueous ammonium chloride was added thereto. The mixture was extracted with ethyl acetate, and the organic layer was washed with brine, dried over anhydrous sodium sulfate, and filtrated, and the solvent was removed. The obtained crude product was purified by silica gel column chromatography (heptane:ethyl acetate=100:0 to 82:18) to afford the title compound as a pale yellow oil (2.7 g).

$^1$H-NMR (CDCl$_3$) δ: 0.28 (6H, s), 1.04 (9H, s), 1.21 (3H, d, J=7.1 Hz), 2.30 (3H, s), 2.44 (1H, dd, J=16.8, 5.7 Hz), 2.94 (1H, dd, J=16.8, 8.5 Hz), 3.65 (3H, s), 3.80-3.90 (1H, m), 7.70 (1H, d, J=2.3 Hz), 7.85 (1H, d, J=2.3 Hz).

The following compound was prepared from the appropriate starting material in a similar manner to Reference example 39.

Reference Example 40

Methyl 4-(3,5-difluoro-4-methoxyphenyl)-3-methyl-4-oxobutanoate

[Chem.53]

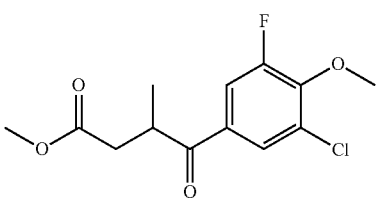

$^1$H-NMR (CDCl$_3$) δ: 1.21 (3H, d, J=7.2 Hz), 2.46 (1H, dd, J=17.0, 5.3 Hz), 2.96 (1H, dd, J=17.0, 9.0 Hz), 3.65 (3H, s), 3.73-3.85 (1H, m), 4.11 (3H, t, J=1.6 Hz), 7.52-7.60 (2H, m).

Reference Example 41

Production of methyl 4-[3-bromo-5-chloro-4-(methoxymethyloxy)phenyl]-3-methyl-4-oxobutanoate

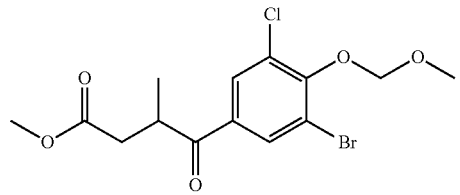

[Chem.54]

Under an argon atmosphere, to 3-bromo-5-chloro-4-(methoxymethyloxy)benzaldehyde (Reference example 32, 885 mg) were added lithium chloride (7 mg) and trimethylsilyl cyanide (0.509 mL), and the mixture was stirred at 50° C. for 2 hours. THF (30 mL) was added to the mixture to dissolve the mixture, and then the reaction mixture was cooled to −78° C. To the mixture was slowly added lithium diisopropylamide (2.0 M, a mixed solution of THF/heptane/ethylbenzene, 1.90 mL), and the mixture was stirred at −78° C. for 30 minutes. Methyl crotonate (0.369 mL) was added to the reaction mixture, and then the mixture was stirred at the same temperature for 2 hours. To the reaction mixture was added water, and the mixture was extracted with ethyl acetate. The organic layer was washed with water and brine, dried over anhydrous sodium sulfate, and filtrated, and the solvent was removed. The residue was purified by silica gel column chromatography (heptane:ethyl acetate=83:17 to 67:33) to afford the title compound as a pale yellow oil (1.15 g).

$^1$H-NMR (CDCl$_3$) δ: 1.21 (3H, d, J=7.1 Hz), 2.46 (1H, dd, J=17.1, 5.1 Hz), 2.96 (1H, dd, J=17.1, 9.0 Hz), 3.65 (3H, s), 3.71 (3H, s), 3.74-3.87 (1H, m), 5.26 (2H, s), 7.97 (1H, d, J=2.0 Hz), 8.10 (1H, d, J=2.0 Hz).

The following compounds were prepared from each appropriate starting material in a similar manner to Reference example 41.

Reference Example 42

Methyl 4-(3-chloro-5-fluoro-4-methoxyphenyl)-3-methyl-4-oxobutanoate

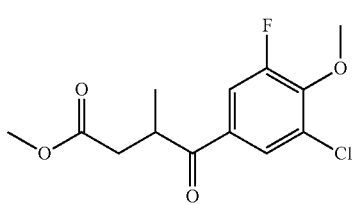

[Chem.55]

$^1$H-NMR (CDCl$_3$) δ: 1.21 (3H, d, J=7.2 Hz), 2.47 (1H, dd, J=17.0, 5.2 Hz), 2.97 (1H, dd, J=17.0, 8.9 Hz), 3.65 (3H, s), 3.75-3.86 (1H, m), 4.08 (3H, d, J=2.7 Hz), 7.66 (1H, dd, J=11.8, 2.1 Hz), 7.80-7.83 (1H, m).

Reference Example 43

Methyl 4-(3-chloro-2-fluoro-4-methoxyphenyl)-3-methyl-4-oxobutanoate

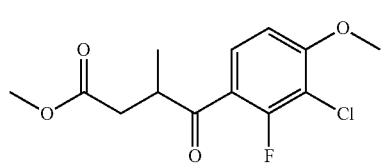

[Chem.56]

$^1$H-NMR (CDCl$_3$) δ: 1.22 (3H, dd, J=7.1, 1.0 Hz), 2.44 (1H, dd, J=16.8, 5.3 Hz), 2.96 (1H, ddd, J=16.8, 8.8, 1.8 Hz), 3.65 (3H, s), 3.73-3.83 (1H, m), 3.98 (3H, s), 6.83 (1H, dd, J=9.0, 1.3 Hz), 7.82 (1H, dd, J=9.0, 8.1 Hz).

Reference Example 44

Methyl 4-(2,4-dimethoxy-3-methylphenyl)-3-methyl-4-oxobutanoate

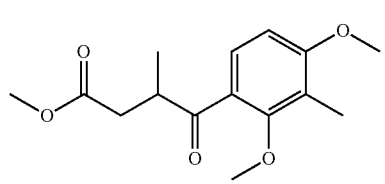

[Chem.57]

$^1$H-NMR (CDCl$_3$) δ: 1.14 (3H, d, J=7.3 Hz), 2.17 (3H, s), 2.38 (1H, dd, J=16.6, 5.7 Hz), 2.89 (1H, dd, J=16.6, 8.3 Hz), 3.67 (3H, s), 3.77 (3H, s), 3.87 (3H, s), 3.88-3.98 (1H, m), 6.68 (1H, d, J=8.5 Hz), 7.53 (1H, d, J=8.5 Hz).

Reference Example 45

Methyl 4-(3-chloro-2,4-dimethoxyphenyl)-3-methyl-4-oxobutanoate

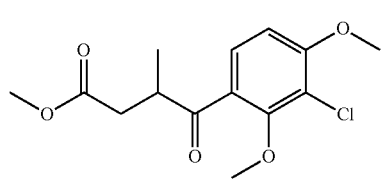

[Chem.58]

$^1$H-NMR (CDCl$_3$) δ: 1.15 (3H, d, J=7.1 Hz), 2.40 (1H, dd, J=16.9, 5.4 Hz), 2.91 (1H, dd, J=16.9, 8.8 Hz), 3.67 (3H, s), 3.84-3.95 (1H, m), 3.94 (3H, s), 3.95 (3H, s), 6.79 (1H, d, J=8.8 Hz), 7.61 (1H, d, J=8.8 Hz).

Reference Example 46

Methyl 4-[3-bromo-5-fluoro-4-(methoxymethyloxy)phenyl]-3-methyl-4-oxobutanoate

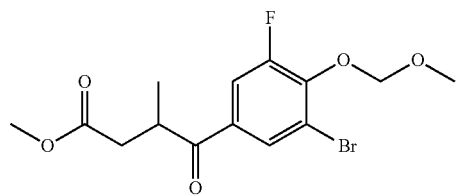

[Chem.59]

$^1$H-NMR (CDCl$_3$) δ: 1.22 (3H, d, J=7.2 Hz), 2.47 (1H, dd, J=17.0, 5.3 Hz), 2.97 (1H, dd, J=17.0, 9.0 Hz), 3.63 (3H, s), 3.65 (3H, s), 3.75-3.86 (1H, m), 5.31 (2H, d, J=0.6 Hz), 7.70 (1H, dd, J=11.5, 2.1 Hz), 8.00 (1H, t, J=2.1 Hz).

Reference Example 47

Methyl 4-(3-bromo-2-fluoro-4-methoxyphenyl)-3-methyl-4-oxobutanoate

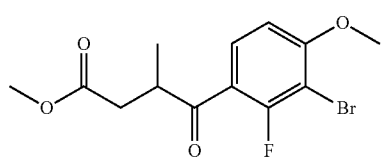

[Chem.60]

$^1$H-NMR (CDCl$_3$) δ: 1.22 (3H, dd, J=7.1, 0.9 Hz), 2.44 (1H, dd, J=16.7, 5.4 Hz), 2.95 (1H, ddd, J=16.7, 8.7, 1.8 Hz), 3.65 (3H, s), 3.73-3.83 (1H, m), 3.98 (3H, s), 6.79 (1H, dd, J=9.0, 1.2 Hz), 7.88 (1H, dd, J=9.0, 8.2 Hz).

Reference Example 48

Methyl 4-[4-(methoxymethyloxy)-3,5-dimethylphenyl]-3-methyl-4-oxobutanoate

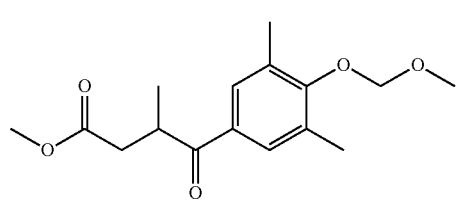

[Chem.61]

$^1$H-NMR (CDCl$_3$) δ: 1.21 (3H, d, J=7.2 Hz), 2.34 (6H, s), 2.44 (1H, dd, J=16.7, 5.9 Hz), 2.95 (1H, dd, J=16.7, 8.3 Hz), 3.62 (3H, s), 3.65 (3H, s), 3.85-3.96 (1H, m), 5.01 (2H, s), 7.68 (2H, s).

Reference Example 49

Methyl 4-(3-fluoro-4-methoxy-5-methylphenyl)-3-methyl-4-oxobutanoate

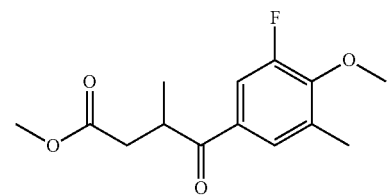

[Chem.62]

$^1$H-NMR (CDCl$_3$) δ: 1.21 (3H, d, J=7.2 Hz), 2.30 (3H, s), 2.45 (1H, dd, J=16.9, 5.6 Hz), 2.95 (1H, dd, J=16.9, 8.5 Hz), 3.65 (3H, s), 3.79-3.90 (1H, m), 4.01 (3H, d, J=2.9 Hz), 7.54-7.62 (2H, m).

Reference Example 50

Methyl 4-(2-fluoro-4-methoxy-3-methylphenyl)-3-methyl-4-oxobutanoate

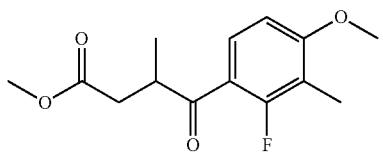

[Chem.63]

$^1$H-NMR (CDCl$_3$) δ: 1.21 (3H, dd, J=7.1, 0.9 Hz), 2.15 (3H, d, J=2.4 Hz), 2.41 (1H, dd, J=16.6, 5.8 Hz), 2.94 (1H, ddd, J=16.6, 8.3, 1.7 Hz), 3.65 (3H, s), 3.76-3.86 (1H, m), 3.90 (3H, s), 6.71 (1H, d, J=8.8 Hz), 7.74 (1H, t, J=8.8 Hz).

Reference Example 51

Methyl 4-(5-chloro-2-fluoro-4-methoxy-3-methylphenyl)-3-methyl-4-oxobutanoate

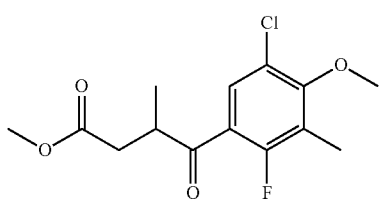

[Chem.64]

$^1$H-NMR (CDCl$_3$) δ: 1.21 (3H, dd, J=7.1, 0.9 Hz), 2.27 (3H, dd, J=2.7, 0.5 Hz), 2.43 (1H, dd, J=16.9, 5.4 Hz), 2.95 (1H, ddd, J=16.9, 8.7, 1.7 Hz), 3.66 (3H, s), 3.71-3.80 (1H, m), 3.88 (3H, s), 7.73 (1H, dd, J=7.6, 0.6 Hz).

Reference Example 52

Methyl 4-[4-benzyloxy-3-chloro-2-(methoxymethyloxy)phenyl]-3-methyl-4-oxobutanoate

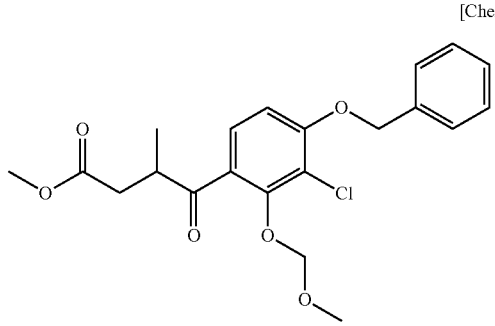

[Chem.65]

$^1$H-NMR (CDCl$_3$) δ: 1.14 (3H, d, J=7.1 Hz), 2.39 (1H, dd, J=16.6, 5.9 Hz), 2.86 (1H, dd, J=16.6, 8.1 Hz), 3.58 (3H, s), 3.66 (3H, s), 3.84-3.96 (1H, m), 5.12 (1H, d, J=5.6 Hz), 5.17 (1H, d, J=5.6 Hz), 5.21 (2H, s), 6.83 (1H, d, J=8.8 Hz), 7.31-7.49 (5H, m), 7.53 (1H, d, J=8.8 Hz).

Reference Example 53

Methyl 4-[4-benzyloxy-2-(methoxymethyloxy)-3-methylphenyl]-3-methyl-4-oxobutanoate

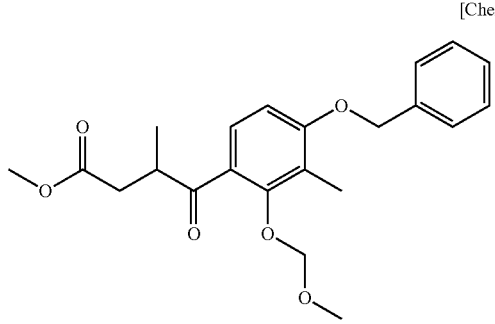

[Chem.66]

$^1$H-NMR (CDCl$_3$) δ: 1.14 (3H, d, J=7.1 Hz), 2.27 (3H, s), 2.37 (1H, dd, J=16.6, 6.1 Hz), 2.87 (1H, dd, J=16.6, 7.8 Hz), 3.54 (3H, s), 3.66 (3H, s), 3.83-3.95 (1H, m), 4.96 (1H, d, J=6.6 Hz), 5.02 (1H, d, J=6.1 Hz), 5.13 (2H, s), 6.75 (1H, d, J=8.8 Hz), 7.31-7.55 (6H, m).

Reference Example 54

Methyl 4-[3-chloro-2-fluoro-4-(methoxymethyloxy)-5-methylphenyl]-3-methyl-4-oxobutanoate

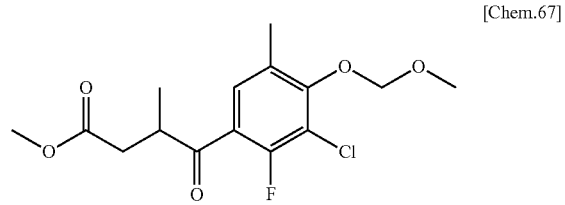

[Chem.67]

$^1$H-NMR (CDCl$_3$) δ: 1.22 (3H, dd, J=7.1, 0.9 Hz), 2.33 (3H, s), 2.44 (1H, dd, J=16.9, 5.4 Hz), 2.96 (1H, ddd, J=16.9, 8.8, 1.6 Hz), 3.64 (3H, s), 3.65 (3H, s), 3.71-3.81 (1H, m), 5.15-5.19 (2H, m), 7.60 (1H, dd, J=8.0, 0.7 Hz).

Reference Example 55

Production of methyl 4-{3-chloro-5-fluoro-4-[(1-hydroxycyclopropyl)methoxy]phenyl}-3-methyl-4-oxobutanoate

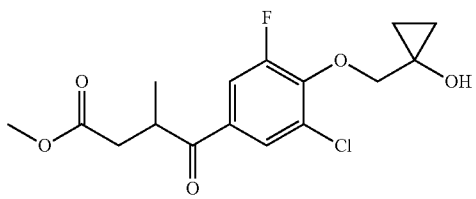

[Chem.68]

Under an argon atmosphere, to 3-chloro-5-fluoro-4-{[1-(triethylsilyloxy)cyclopropyl]methoxy}benzaldehyde (Reference example 20, 873 mg) were added trimethylsilyl cyanide (0.391 mL) and lithium chloride (6 mg), and the mixture was stirred at 50° C. for 2 hours. The mixture was allowed to cool to room temperature, and THF (10 mL) was added to the mixture. The mixture was stirred at −78° C. At the same temperature, lithium diisopropylamide (2.0 M, a mixed solution of THF/heptane/ethylbenzene, 1.34 mL) was added to the mixture, and the mixture was stirred for 30 minutes. To the mixture was added methyl crotonate (0.284 mL) at −78° C., and the mixture was stirred for 2 hours. Water was added to the mixture, and the mixture was extracted with ethyl acetate. The organic layer was washed with brine, dried over anhydrous sodium sulfate, and filtrated, and the solvent was removed. The residue was dissolved in THF (10 mL), and tetrabutylammonium fluoride (1.0 M THF solution, 2.92 mL) was added thereto. The reaction mixture was stirred at room temperature for one hour, and water was added thereto. The mixture was extracted with ethyl acetate. The organic layer was washed with brine, dried over anhydrous sodium sulfate, and filtrated, and the solvent was removed. The obtained crude product was purified by silica gel column chromatography (heptane:ethyl acetate=90:10 to 60:40) to afford the title compound as a pale yellow oil (352 mg).

¹H-NMR (CDCl₃) δ: 0.63-0.69 (2H, m), 0.92-0.98 (2H, m), 1.22 (3H, d, J=7.1 Hz), 2.47 (1H, dd, J=17.1, 5.1 Hz), 2.95 (1H, s), 2.98 (1H, dd, J=17.1, 9.0 Hz), 3.65 (3H, s), 3.76-3.86 (1H, m), 4.27 (2H, s), 7.67 (1H, dd, J=11.4, 2.1 Hz), 7.83-7.85 (1H, m).

The following compounds were prepared from each appropriate starting material in a similar manner to Reference example 55.

Reference Example 56

Methyl 4-{2,3-difluoro-4-[(1-hydroxycyclopropyl)methoxy]phenyl}-3-methyl-4-oxobutanoate

[Chem.69]

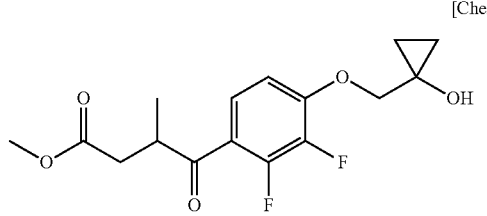

¹H-NMR (CDCl₃) δ: 0.72-0.78 (2H, m), 0.98-1.04 (2H, m), 1.22 (3H, d, J=7.1 Hz), 2.44 (1H, dd, J=16.8, 5.4 Hz), 2.77 (1H, s), 2.96 (1H, ddd, J=16.8, 8.8, 1.6 Hz), 3.65 (3H, s), 3.70-3.81 (1H, m), 4.15 (2H, s), 6.78-6.86 (1H, m), 7.61-7.68 (1H, m).

Reference Example 57

Methyl 4-{4-[(1-hydroxycyclopropyl)methoxy]-3,5-dimethylphenyl}-3-methyl-4-oxobutanoate

[Chem.70]

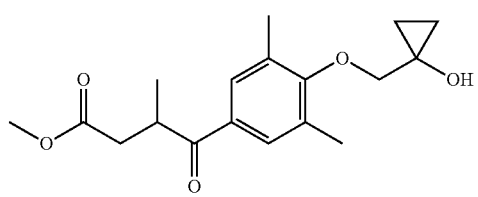

¹H-NMR (CDCl₃) δ: 0.68-0.73 (2H, m), 0.94-1.00 (2H, m), 1.21 (3H, d, J=7.1 Hz), 2.35 (6H, s), 2.44 (1H, dd, J=16.8, 5.7 Hz), 2.79 (1H, s), 2.95 (1H, dd, J=16.8, 8.5 Hz), 3.65 (3H, s), 3.85 (2H, s), 3.86-3.96 (1H, m), 7.68 (2H, s).

Reference Example 58

Methyl 4-{3-chloro-4-[(1-hydroxycyclopropyl)methoxy]-5-methylphenyl}-3-methyl-4-oxobutanoate

[Chem.71]

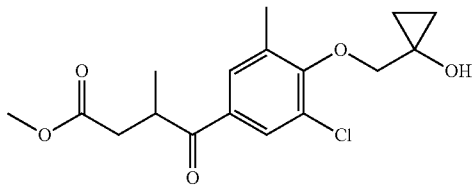

¹H-NMR (CDCl₃) δ: 0.69-0.74 (2H, m), 0.95-1.00 (2H, m), 1.21 (3H, d, J=7.2 Hz), 2.40 (3H, s), 2.46 (1H, dd, J=17.0, 5.4 Hz), 2.92 (1H, s), 2.96 (1H, dd, J=17.0, 8.9 Hz), 3.65 (3H, s), 3.79-3.90 (1H, m), 4.03 (2H, s), 7.74 (1H, d, J=2.1 Hz), 7.86 (1H, d, J=2.1 Hz).

Reference Example 59

Methyl 4-{3-fluoro-4-[(1-hydroxycyclopropyl)methoxy]-5-methylphenyl}-3-methyl-4-oxobutanoate

[Chem.72]

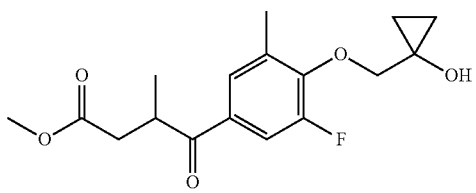

¹H-NMR (CDCl₃) δ: 0.65-0.73 (2H, m), 0.92-0.98 (2H, m), 1.21 (3H, d, J=7.2 Hz), 2.38 (3H, s), 2.45 (1H, dd, J=17.0, 5.5 Hz), 2.73 (1H, s), 2.96 (1H, dd, J=17.0, 8.7 Hz), 3.65 (3H, s), 3.79-3.91 (1H, m), 4.16-4.18 (2H, m), 7.58 (1H, dd, J=12.0, 1.8 Hz), 7.61-7.64 (1H, m).

Reference Example 60

Methyl 4-{2-fluoro-4-[(1-hydroxycyclopropyl)methoxy]-3-methylphenyl}-3-methyl-4-oxobutanoate

[Chem.73]

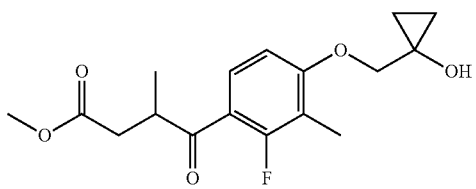

¹H-NMR (CDCl₃) δ: 0.71-0.77 (2H, m), 0.96-1.02 (2H, m), 1.21 (3H, d, J=7.1 Hz), 2.21 (3H, d, J=2.3 Hz), 2.41 (1H, dd, J=16.7, 5.7 Hz), 2.59 (1H, s), 2.94 (1H, ddd, J=16.7, 8.5, 1.7 Hz), 3.65 (3H, s), 3.76-3.87 (1H, m), 4.05-4.13 (2H, m), 6.68 (1H, d, J=8.8 Hz), 7.72 (1H, t, J=8.8 Hz).

Reference Example 61

Methyl 4-{3-chloro-2-fluoro-4-[(1-hydroxycyclopropyl)methoxy]phenyl}-3-methyl-4-oxobutanoate

[Chem.74]

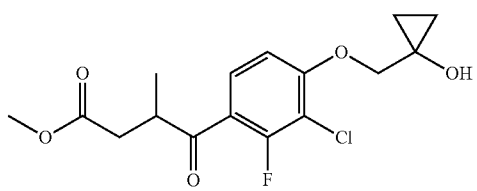

¹H-NMR (CDCl₃) δ: 0.74-0.79 (2H, m), 0.99-1.05 (2H, m), 1.22 (3H, dd, J=7.1, 0.9 Hz), 2.44 (1H, dd, J=16.8, 5.3 Hz), 2.82 (1H, s), 2.96 (1H, ddd, J=16.8, 8.8, 1.8 Hz), 3.65 (3H, s), 3.72-3.83 (1H, m), 4.15 (2H, s), 6.80 (1H, dd, J=9.0, 1.3 Hz), 7.80 (1H, dd, J=9.0, 8.1 Hz).

Reference Example 62

Production of 4-(3,5-dichloro-4-hydroxyphenyl)-3-methyl-4-oxobutanoic Acid

[Chem.75]

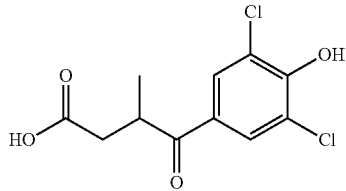

Under an argon atmosphere, to 3,5-dichloro-4-(methoxymethyloxy)benzaldehyde (Reference example 34, 3.28 g) were added trimethylsilyl cyanide (2.25 mL) and lithium chloride (30 mg), and the mixture was stirred at 50° C. for 2 hours. The mixture was allowed to cool to room temperature, and THF (40 mL) was added to the mixture. Lithium diisopropylamide (2.0 M, a mixed solution of THF/heptane/ethylbenzene, 7.67 mL) was added to the mixture at −78° C., and the mixture was stirred for 30 minutes at the same temperature. To the mixture was added methyl crotonate (1.63 mL) at −78° C., and the mixture was stirred for 2 hours. To the reaction mixture was added water, and the mixture was extracted with ethyl acetate. The organic layer was washed with brine, dried over anhydrous sodium sulfate. The solvent was removed and the obtained residue was dissolved in THF (40 mL), and tetrabutylammonium fluoride (1.0 M THF solution, 16.7 mL) was added to the solution. The reaction mixture was stirred at room temperature for one hour. And then, to the reaction mixture was added water, and the mixture was extracted with ethyl acetate. The organic layer was washed with brine, dried over anhydrous sodium sulfate, and filtrated, and the solvent was removed. The residue was purified by silica gel column chromatography (heptane:ethyl acetate=90:10 to 70:30), and the desired fractions were concentrated. The residue was added 1 M aqueous sodium hydroxide, and the aqueous solution was washed with methylene chloride. The aqueous layer was acidified with 6 M hydrochloric acid, and then the mixture was extracted with methylene chloride. The organic layer was washed with brine, dried over anhydrous sodium sulfate, and filtrated, and the solvent was removed to afford the title compound as a white solid (1.16 g).

¹H-NMR (CDCl₃) δ: 1.23 (3H, d, J=7.3 Hz), 2.51 (1H, dd, J=17.2, 5.0 Hz), 3.01 (1H, dd, J=17.2, 8.9 Hz), 3.72-3.85 (1H, m), 7.92 (2H, s).

Reference Example 63

Production of 4-(2-fluoro-4-methoxy-3-methylphenyl)-3-methyl-4-oxobutanoic Acid

[Chem.76]

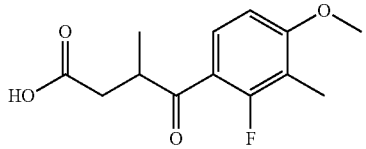

To a mixture of methyl 4-(2-fluoro-4-methoxy-3-methylphenyl)-3-methyl-4-oxobutanoate (Reference example 50, 7.8 g) in ethanol (60 mL) was added 5 M aqueous sodium hydroxide (17.5 mL), and the mixture was stirred at room temperature for one hour. The reaction mixture was diluted with water, and the mixture was acidified with 6 M hydrochloric acid at 0° C. The mixture was extracted with ethyl acetate. The organic layer was washed with brine, dried over anhydrous sodium sulfate, and filtrated, and the solvent was removed to afford the title compound as a white solid (7.9 g).

¹H-NMR (DMSO-d6) δ: 1.08 (3H, d, J=7.1 Hz), 2.10 (3H, d, J=1.8 Hz), 2.36 (1H, dd, J=16.8, 5.2 Hz), 2.69 (1H, dd, J=16.8, 8.9 Hz), 3.58-3.70 (1H, m), 3.90 (3H, s), 6.97 (1H, d, J=8.8 Hz), 7.71 (1H, t, J=8.8 Hz), 12.13 (1H, s).

The following compounds were prepared from each appropriate starting material in a similar manner to Reference example 63.

Reference Example 64

4-(3-Bromo-2-fluoro-4-methoxyphenyl)-3-methyl-4-oxobutanoic Acid

[Chem.77]

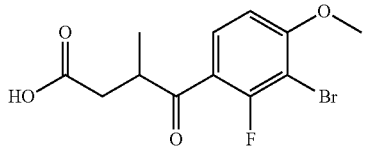

¹H-NMR (DMSO-d6) δ: 1.09 (3H, d, J=7.1 Hz), 2.39 (1H, dd, J=17.0, 5.1 Hz), 2.71 (1H, ddd, J=17.0, 8.9, 1.3 Hz), 3.58-3.69 (1H, m), 3.98 (3H, s), 7.12 (1H, dd, J=9.0, 1.0 Hz), 7.88 (1H, t, J=9.0 Hz), 12.17 (1H, brs).

Reference Example 65

4-(5-Chloro-2-fluoro-4-methoxy-3-methylphenyl)-3-methyl-4-oxobutanoic Acid

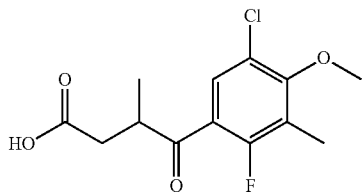

¹H-NMR (DMSO-d6) δ: 1.09 (3H, d, J=7.1 Hz), 2.24 (3H, d, J=2.6 Hz), 2.41 (1H, dd, J=17.0, 5.1 Hz), 2.70 (1H, ddd, J=17.0, 8.9, 1.3 Hz), 3.56-3.67 (1H, m), 3.84 (3H, s), 7.70 (1H, d, J=7.6 Hz), 12.21 (1H, brs).

Reference Example 66

4-[4-Benzyloxy-2-(methoxymethyloxy)-3-methylphenyl]-3-methyl-4-oxobutanoic Acid

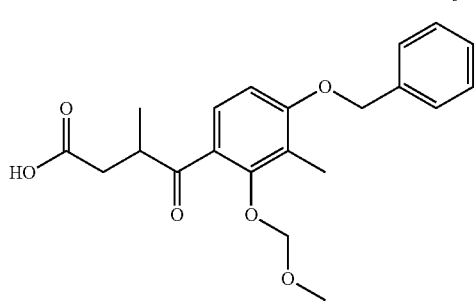

¹H-NMR (CDCl₃) δ:1.16 (3H, d, J=7.1 Hz), 2.26 (3H, s), 2.45 (1H, dd, J=16.6, 5.7 Hz), 2.90 (1H, dd, J=16.6, 7.8 Hz), 3.52 (3H, s), 3.85-3.97 (1H, m), 4.95-5.02 (2H, m), 5.13 (2H, s), 6.76 (1H, d, J=8.5 Hz), 7.31-7.53 (6H, m).

Reference Example 67

4-[4-Benzyloxy-3-chloro-2-(methoxymethyloxy)phenyl]-3-methyl-4-oxobutanoic Acid

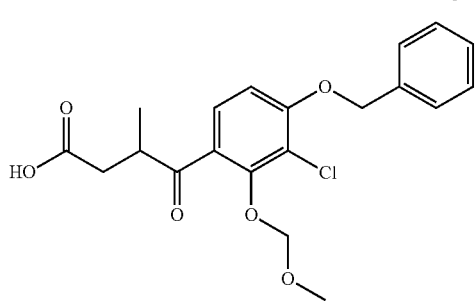

¹H-NMR (CDCl₃) δ: 1.16 (3H, d, J=7.1 Hz), 2.46 (1H, dd, J=16.7, 5.7 Hz), 2.91 (1H, dd, J=16.7, 7.9 Hz), 3.56 (3H, s), 3.86-3.95 (1H, m), 5.13 (2H, s), 5.21 (2H, s), 6.84 (1H, d, J=8.8 Hz), 7.32-7.49 (5H, m), 7.52 (1H, d, J=8.8 Hz).

Reference Example 68

4-{2,3-Difluoro-4-[(1-hydroxycyclopropyl)methoxy}phenyl]-3-methyl-4-oxobutanoic Acid

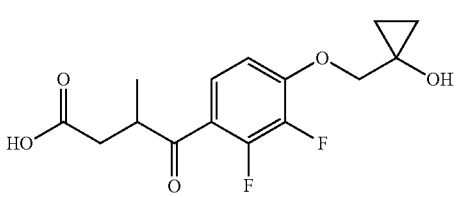

¹H-NMR (DMSO-d6) δ: 0.63-0.76 (4H, m), 1.10 (3H, d, J=7.1 Hz), 2.39 (1H, dd, J=17.0, 5.1 Hz), 2.71 (1H, dd, J=17.0, 8.5 Hz), 3.56-3.69 (1H, m), 4.18 (2H, s), 5.67 (1H, s), 7.14-7.21 (1H, m), 7.60-7.67 (1H, m), 12.17 (1H, brs).

Reference Example 69

4-{2-Fluoro-4-[(1-hydroxycyclopropyl)methoxy]-3-methylphenyl}-3-methyl-4-oxobutanoic Acid

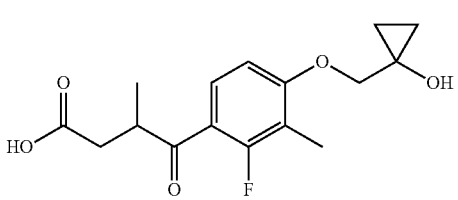

¹H-NMR (DMSO-d6) δ: 0.61-0.76 (4H, m), 1.08 (3H, d, J=7.1 Hz), 2.15 (3H, d, J=2.3 Hz), 2.35 (1H, dd, J=16.9, 5.3 Hz), 2.69 (1H, ddd, J=16.9, 8.9, 1.2 Hz), 3.59-3.70 (1H, m), 4.09 (2H, s), 5.63 (1H, s), 6.94 (1H, d, J=8.9 Hz), 7.66 (1H, t, J=8.9 Hz), 12.12 (1H, s).

Reference Example 70

4-{3-Chloro-2-fluoro-4-[(1-hydroxycyclopropyl)methoxy]phenyl}-3-methyl-4-oxobutanoic Acid

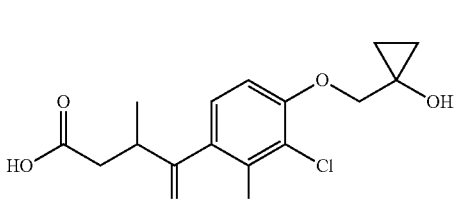

¹H-NMR (DMSO-d6) δ: 0.64-0.77 (4H, m), 1.09 (3H, d, J=7.1 Hz), 2.40 (1H, dd, J=17.0, 5.1 Hz), 2.70 (1H, ddd, J=17.0, 8.9, 1.1 Hz), 3.58-3.68 (1H, m), 4.21 (2H, s), 5.64 (1H, s), 7.18 (1H, dd, J=9.1, 1.0 Hz), 7.79 (1H, t, J=9.1 Hz), 12.18 (1H, brs).

Reference Example 71

Production of 4-(3-chloro-4-hydroxy-5-methylphenyl)-3-methyl-4-oxobutanoic Acid

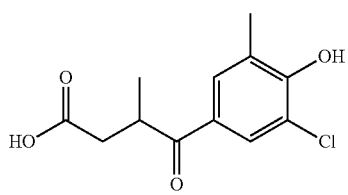

[Chem.84]

To a mixture of methyl 4-[4-(tert-butyldimethylsilyloxy)-3-chloro-5-methylphenyl]-3-methyl-4-oxobutanoate (Reference example 39, 500 mg) in methanol (10 mL) was added 5 M aqueous sodium hydroxide (0.520 mL). The reaction mixture was stirred at room temperature overnight, and then 5M aqueous sodium hydroxide (0.260 mL) was added to the reaction mixture. The reaction mixture was stirred at room temperature for 3 hours, and then at 50° C. for 2 hours. The reaction mixture was concentrated. To the obtained residue was added diethyl ether, and then the mixture was extracted with water. The separated aqueous layer was acidified with 6 M hydrochloric acid, and then the mixture was extracted with ethyl acetate. The organic layer was washed with water and brine, dried over anhydrous sodium sulfate, and filtrated, and the solvent was removed to afford the title compound as a pale yellow solid (317 mg).
$^1$H-NMR (DMSO-d6) δ: 1.06 (3H, d, J=7.1 Hz), 2.27 (3H, s), 2.36 (1H, dd, J=17.1, 4.9 Hz), 2.68 (1H, dd, J=17.1, 9.5 Hz), 3.75-3.88 (1H, m), 7.74-7.75 (1H, m), 7.80 (1H, d, J=2.0 Hz), 10.12 (1H, brs), 12.13 (1H, brs).

Reference Example 72

Production of 6-[3-chloro-2-fluoro-4-(methoxymethyloxy)-5-methylphenyl]-5-methyl-4,5-dihydro-2H-pyridazin-3-one

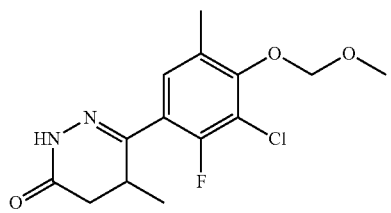

[Chem.85]

To a mixture of methyl 4-[3-chloro-2-fluoro-4-(methoxymethyloxy)-5-methylphenyl]-3-methyl-4-oxobutanoate (Reference example 54, 2.91 g) in ethanol (35 mL) was added 5 M aqueous sodium hydroxide (4.37 mL), and the reaction mixture was stirred at room temperature for 30 minutes. After cooling the reaction mixture at 0° C., the reaction mixture was acidified with 6 M hydrochloric acid, and the mixture was extracted with ethyl acetate. The organic layer was washed with brine, dried over anhydrous sodium sulfate, and filtrated, and the solvent was removed to afford a yellow oil (2.96 g). The oil was dissolved in ethanol (30 mL), and hydrazine monohydrate (1.3 mL) and acetic acid (1.5 mL) were added to the solution. The mixture was refluxed for 2 hours. The reaction mixture was allowed to cool to room temperature, saturated aqueous sodium bicarbonate was added thereto at 0° C., and then the mixture was extracted with ethyl acetate. The organic layer was washed with brine, dried over anhydrous sodium sulfate, and filtrated, and the solvent was removed. The obtained crude product was purified by silica gel column chromatography (heptane:ethyl acetate=77:23 to 47:53) to afford the title compound as a white solid (1.65 g).
$^1$H-NMR (DMSO-d6) δ: 1.05 (3H, d, J=7.2 Hz), 2.26 (1H, dd, J=16.7, 3.8 Hz), 2.29 (3H, s), 2.70 (1H, dd, J=16.7, 6.8 Hz), 3.10-3.20 (1H, m), 3.56 (3H, s), 5.13 (2H, s), 7.45 (1H, dd, J=8.5, 0.5 Hz), 11.08 (1H, s).

Reference Example 73

Production of 6-(2-fluoro-4-methoxy-3-methylphen-5-methyl-4,5-dihydro-2H-pyridazin-3-one

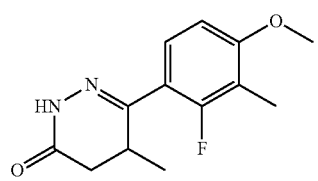

[Chem.86]

To a mixture of 4-(2-fluoro-4-methoxy-3-methylphenyl)-3-methyl-4-oxobutanoic acid (Reference example 63, 4.6 g) in ethanol (60 mL) were added hydrazine monohydrate (1.3 mL) and acetic acid (1.6 mL), and then the mixture was refluxed for 2 hours. The reaction mixture was allowed to cool to room temperature, and the obtained precipitates were collected on a filter to afford the title compound as a white solid (2.4 g).
$^1$H-NMR (DMSO-d6) δ: 1.03 (3H, d, J=7.2 Hz), 2.08 (3H, d, J=2.2 Hz), 2.23 (1H, dd, J=16.8, 3.7 Hz), 2.66 (1H, dd, J=16.8, 6.8 Hz), 3.07-3.17 (1H, m), 3.85 (3H, s), 6.88 (1H, d, J=8.8 Hz), 7.40 (1H, t, J=8.8 Hz), 10.92 (1H, s).

The following compounds were prepared from each appropriate starting material in a similar manner to Reference example 73.

Reference Example 74

6-(3,5-Difluoro-4-methoxyphenyl)-5-methyl-4,5-dihydro-2H-pyridazin-3-one

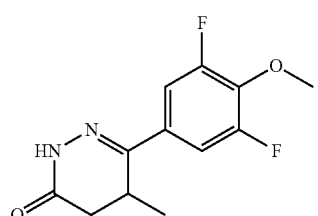

[Chem.87]

¹H-NMR (DMSO-d6) δ: 1.04 (3H, d, J=7.3 Hz), 2.24 (1H, d, J=16.8 Hz), 2.68 (1H, dd, J=16.8, 6.9 Hz), 3.33-3.44 (1H, m), 3.97 (3H, s), 7.47-7.57 (2H, m), 11.05 (1H, s).

Reference Example 75

6-(3-Chloro-5-fluoro-4-methoxyphenyl)-5-methyl-4,5-dihydro-2H-pyridazin-3-one

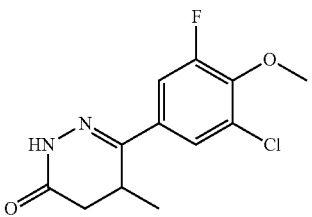

[Chem.88]

¹H-NMR (DMSO-d6) δ: 1.04 (3H, d, J=7.3 Hz), 2.24 (1H, d, J=16.8 Hz), 2.69 (1H, dd, J=16.8, 6.9 Hz), 3.36-3.45 (1H, m), 3.94 (3H, d, J=1.6 Hz), 7.62-7.71 (2H, m), 11.07 (1H, s).

Reference Example 76

6-(3-Chloro-2-fluoro-4-methoxyphenyl)-5-methyl-4,5-dihydro-2H-pyridazin-3-one

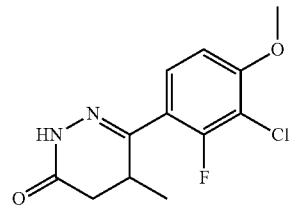

[Chem.89]

¹H-NMR (DMSO-d6) δ: 1.04 (3H, d, J=7.2 Hz), 2.25 (1H, dd, J=16.8, 3.6 Hz), 2.70 (1H, dd, J=16.8, 6.8 Hz), 3.09-3.20 (1H, m), 3.93 (3H, s), 7.09 (1H, d, J=9.0 Hz), 7.57 (1H, t, J=9.0 Hz), 11.03 (1H, s).

Reference Example 77

6-(2,4-Dimethoxy-3-methylphenyl)-5-methyl-4,5-dihydro-2H-pyridazin-3-one

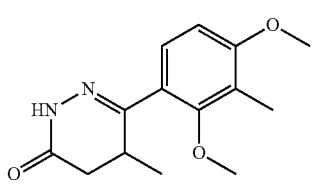

[Chem.90]

¹H-NMR (CDCl₃) δ: 1.08 (3H, d, J=7.3 Hz), 2.16 (3H, s), 2.43 (1H, dd, J=16.9, 4.5 Hz), 2.75 (1H, dd, J=16.9, 6.8 Hz), 3.28-3.38 (1H, m), 3.70 (3H, s), 3.85 (3H, s), 6.67 (1H, d, J=8.5 Hz), 7.15 (1H, d, J=8.5 Hz), 8.48 (1H, brs).

Reference Example 78

6-(3-Chloro-2,4-dimethoxyphenyl)-5-methyl-4,5-dihydro-2H-pyridazin-3-one

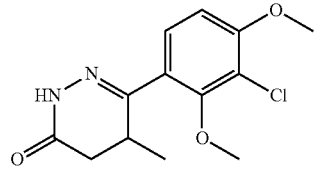

[Chem.91]

¹H-NMR (CDCl₃) δ: 1.10 (3H, d, J=7.3 Hz), 2.44 (1H, dd, J=17.0, 4.5 Hz), 2.75 (1H, dd, J=17.0, 6.8 Hz), 3.26-3.36 (1H, m), 3.85 (3H, s), 3.94 (3H, s), 6.77 (1H, d, J=8.5 Hz), 7.24 (1H, d, J=8.5 Hz), 8.45 (1H, brs).

Reference Example 79

6-[4-(Methoxymethyloxy)-3,5-dimethylphenyl]-5-methyl-4,5-dihydro-2H-pyridazin-3-one

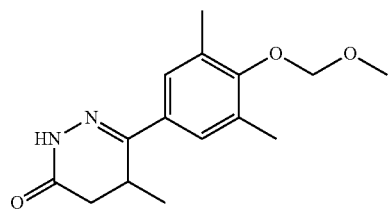

[Chem.92]

¹H-NMR (DMSO-d6) δ: 1.05 (3H, d, J=7.3 Hz), 2.22 (1H, d, J=16.9 Hz), 2.26 (6H, s), 2.65 (1H, dd, J=16.9, 6.8 Hz), 3.33-3.41 (1H, m), 3.51 (3H, s), 4.96 (2H, s), 7.46 (2H, s), 10.88 (1H, s).

Reference Example 80

6-(3,5-Dichloro-4-hydroxyphenyl)-5-methyl-4,5-dihydro-2H-pyridazin-3-one

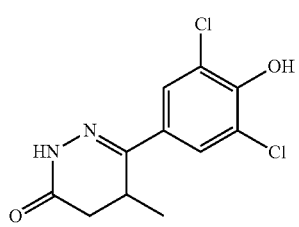

[Chem.93]

¹H-NMR (DMSO-d6) δ: 1.03 (3H, d, J=7.3 Hz), 2.21 (1H, d, J=16.7 Hz), 2.67 (1H, dd, J=16.7, 7.0 Hz), 3.26-3.46 (1H, m), 7.73 (2H, s), 10.57 (1H, s), 10.97 (1H, s).

Reference Example 81

6-(3-Fluoro-4-methoxy-5-methylphenyl)-5-methyl-4,5-dihydro-2H-pyridazin-3-one

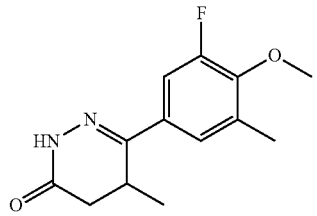
[Chem.94]

¹H-NMR (DMSO-d6) δ: 1.05 (3H, d, J=7.3 Hz), 2.23 (1H, d, J=16.9 Hz), 2.27 (3H, s), 2.67 (1H, dd, J=16.9, 6.9 Hz), 3.32-3.42 (1H, m), 3.86 (3H, d, J=1.7 Hz), 7.42-7.50 (2H, m), 10.96 (1H, s).

Reference Example 82

6-(5-Chloro-2-fluoro-4-methoxy-3-methylphenyl)-5-methyl-4,5-dihydro-2H-pyridazin-3-one

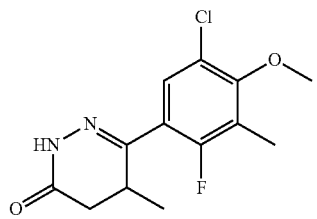
[Chem.95]

¹H-NMR (DMSO-d6) δ: 1.04 (3H, d, J=7.2 Hz), 2.21-2.29 (1H, m), 2.21 (3H, d, J=2.3 Hz), 2.69 (1H, dd, J=16.8, 6.8 Hz), 3.08-3.19 (1H, m), 3.80 (3H, s), 7.52 (1H, d, J=7.9 Hz), 11.07 (1H, s).

Reference Example 83

Production of 6-[4-benzyloxy-2-(methoxymethyloxy)-3-methylphenyl]-5-methyl-4,5-dihydro-2H-pyridazin-3-one

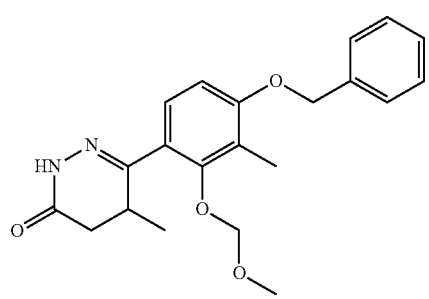
[Chem.96]

A mixture of 4-[4-benzyloxy-2-(methoxymethyloxy)-3-methylphenyl]-3-methyl-4-oxobutanoic acid (Reference example 66, 3.20 g) and hydrazine monohydrate (0.626 mL) in ethanol (30 mL) was stirred at room temperature for 3 days. The precipitates were collected on a filter to afford the title compound as a white solid (1.56 g).

¹H-NMR (CDCl₃) δ: 1.10 (3H, d, J=7.3 Hz), 2.28 (3H, s), 2.44 (1H, dd, J=16.9, 4.6 Hz), 2.82 (1H, dd, J=17.0, 7.0 Hz), 3.31-3.41 (1H, m), 3.53 (3H, s), 4.92 (1H, d, J=5.6 Hz), 5.03 (1H, d, J=5.6 Hz), 5.13 (2H, s), 6.78 (1H, d, J=8.5 Hz), 7.16 (1H, d, J=8.5 Hz), 7.33-7.49 (5H, m), 8.42 (1H, s).

The following compounds were prepared from each appropriate starting material in a similar manner to Reference example 83.

Reference Example 84

6-(3-Bromo-2-fluoro-4-methoxyphenyl)-5-methyl-4,5-dihydro-2H-pyridazin-3-one

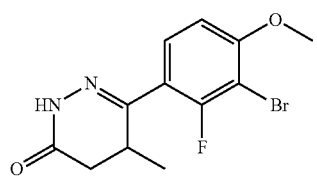
[Chem. 97]

¹H-NMR (DMSO-d6) δ: 1.04 (3H, d, J=7.2 Hz), 2.25 (1H, dd, J=16.9, 3.7 Hz), 2.69 (1H, dd, J=16.9, 6.8 Hz), 3.09-3.19 (1H, m), 3.92 (3H, s), 7.05 (1H, dd, J=8.9, 1.2 Hz), 7.60 (1H, t, J=8.9 Hz), 11.02 (1H, s).

Reference Example 85

6-[4-Benzyloxy-3-chloro-2-(methoxymethyloxy)phenyl]-5-methyl-4,5-dihydro-2H-pyridazin-3-one

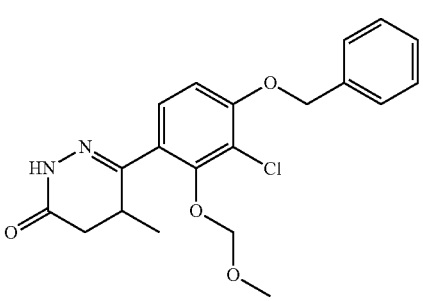
[Chem. 98]

¹H-NMR (CDCl₃) δ: 1.07 (3H, d, J=7.3 Hz), 2.42 (1H, dd, J=17.0, 4.8 Hz), 2.80 (1H, dd, J=17.0, 7.0 Hz), 3.30-3.41 (1H, m), 3.53 (3H, s), 5.03 (1H, d, J=5.6 Hz), 5.15-5.22 (3H, m), 6.82 (1H, d, J=8.8 Hz), 7.19 (1H, d, J=8.5 Hz), 7.31-7.49 (5H, m), 8.45 (1H, s).

Reference Example 86

Production of 6-(3-chloro-4-hydroxy-5-methyl-4,5-dihydro-2H-pyridazin-3-one

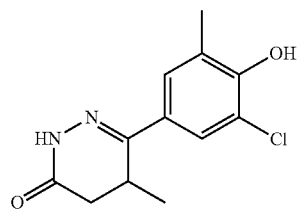

[Chem. 99]

To a mixture of methyl 4-[4-(tert-butyldimethylsilyloxy)-3-chloro-5-methylphenyl]-3-methyl-4-oxobutanoate (Reference example 39, 2.7 g) in ethanol (35 mL) were added hydrazine monohydrate (1.0 mL) and acetic acid (1.2 mL), and then the mixture was refluxed for 5 hours. The reaction mixture was allowed to cool to room temperature, saturated aqueous sodium bicarbonate was added thereto at 0° C., and then the mixture was extracted with ethyl acetate. The organic layer was washed with brine, dried over anhydrous sodium sulfate, and filtrated. The solvent was removed. The obtained crude solid was washed by trituration with diisopropyl ether, and then collected on a filter to afford the title compound as a white solid (1.5 g).

$^1$H-NMR (DMSO-d6) δ: 1.03 (3H, d, J=7.2 Hz), 2.20 (1H, d, J=16.8 Hz), 2.24 (3H, s), 2.65 (1H, dd, J=16.8, 6.9 Hz), 3.27-3.40 (1H, m), 7.50 (1H, d, J=2.2 Hz), 7.58 (1H, d, J=2.2 Hz), 9.47 (1H, brs), 10.86 (1H, s).

Reference Example 87

Production of 6-(3-bromo-5-chloro-4-hydroxyphenyl)-5-methyl-4,5-dihydro-2H-pyridazin-3-one

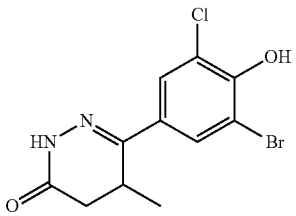

[Chem. 100]

To a mixture of methyl 4-[3-bromo-5-chloro-4-(methoxymethyloxy)phenyl]-3-methyl-4-oxobutanoate (Reference example 41, 1.15 g) in ethanol (15 mL) were added acetic acid (0.518 mL) and hydrazine monohydrate (0.440 mL), and then the mixture was refluxed for 13 hours. The reaction mixture was concentrated, water was added to the residue, and then the mixture was extracted with ethyl acetate. The organic layer was washed with water and brine, dried over anhydrous sodium sulfate, and filtrated, and the solvent was removed. The residue was recrystallized from heptane/ethyl acetate to afford the title compound as a pale yellow solid (713 mg).

$^1$H-NMR (DMSO-d6) δ: 1.03 (3H, d, J=7.3 Hz), 2.18-2.24 (1H, m), 2.66 (1H, dd, J=16.9, 6.8 Hz), 3.30-3.45 (1H, m), 7.76 (1H, d, J=2.2 Hz), 7.87 (1H, d, J=2.2 Hz), 10.50 (1H, brs), 10.98 (1H, s).

The following compound was prepared from the appropriate starting material in a similar manner to Reference example 87.

Reference Example 88

6-(3-Bromo-5-fluoro-4-hydroxyphenyl)-5-methyl-4,5-dihydro-2H-pyridazin-3-one

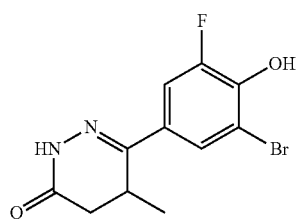

[Chem. 101]

$^1$H-NMR (DMSO-d6) δ: 1.03 (3H, d, J=7.3 Hz), 2.21 (1H, d, J=16.7 Hz), 2.67 (1H, dd, J=16.7, 6.8 Hz), 3.32-3.41 (1H, m), 7.59 (1H, dd, J=12.2, 2.1 Hz), 7.73 (1H, t, J=2.1 Hz), 10.85 (1H, brs), 10.95 (1H, s).

Reference Example 89

Production of 6-(3-chloro-2-fluoro-4-hydroxyphenyl)-5-methyl-4,5-dihydro-2H-pyridazin-3-one

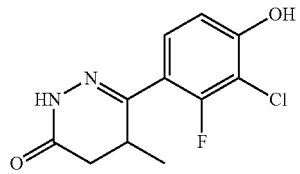

[Chem. 102]

To a mixture of 6-(3-chloro-2-fluoro-4-methoxyphenyl)-5-methyl-4,5-dihydro-2H-pyridazin-3-one (Reference example 76, 1.4 g) in methylene chloride (50 mL) was added aluminum chloride (14.2 g) at 0° C. Under an argon atmosphere, the reaction mixture was stirred at room temperature overnight. After cooling the reaction mixture at 0° C., ice in water and 5 M aqueous sodium hydroxide were added thereto. The separated aqueous layer was acidified with 6 M hydrochloric acid at 0° C., and then the mixture was extracted with ethyl acetate/THF. The organic layer was washed with brine, dried over anhydrous sodium sulfate, and filtrated, and the solvent was removed. The obtained solid was washed by trituration with ethanol, and then collected on a filter to afford the title compound as a pale yellow solid (0.9 g).

$^1$H-NMR (DMSO-d6) δ: 1.04 (3H, d, J=7.2 Hz), 2.23 (1H, dd, J=16.8, 3.4 Hz), 2.67 (1H, dd, J=16.8, 6.8 Hz), 3.06-3.18 (1H, m), 6.87 (1H, dd, J=8.8, 1.3 Hz), 7.41 (1H, t, J=8.8 Hz), 10.98 (1H, s), 11.04 (1H, s).

The following compounds were prepared from each appropriate starting material in a similar manner to Reference example 89.

Reference Example 90

6-(3,5-Difluoro-4-hydroxyphenyl)-5-methyl-4,5-dihydro-2H-pyridazin-3-one

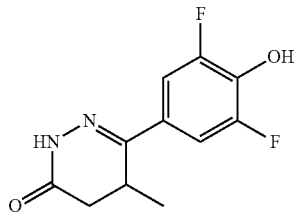

[Chem. 103]

$^1$H-NMR (DMSO-d6) δ: 1.03 (3H, d, J=7.2 Hz), 2.21 (1H, d, J=16.8 Hz), 2.66 (1H, dd, J=16.8, 6.9 Hz), 3.29-3.41 (1H, m), 7.39-7.50 (2H, m), 10.63 (1H, brs), 10.95 (1H, s).

Reference Example 91

6-(3-Chloro-5-fluoro-4-hydroxyphenyl)-5-methyl-4,5-dihydro-2H-pyridazin-3-one

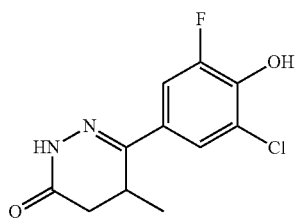

[Chem. 104]

$^1$H-NMR (DMSO-d6) δ: 1.03 (3H, d, J=7.3 Hz), 2.21 (1H, d, J=16.7 Hz), 2.67 (1H, dd, J=16.7, 7.0 Hz), 3.30-3.43 (1H, m), 7.51-7.65 (2H, m), 10.83 (1H, brs), 10.96 (1H, s).

Reference Example 92

Production of 6-(2-fluoro-4-hydroxy-3-methylphenyl)-5-methyl-4,5-dihydro-2H-pyridazin-3-one

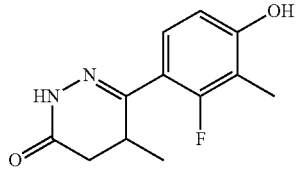

[Chem. 105]

Under an argon atmosphere, to a mixture of 6-(2-fluoro-4-methoxy-3-methylphenyl)-5-methyl-4,5-dihydro-2H-pyridazin-3-one (Reference example 73, 3.6 g) in methylene chloride (80 mL) was added dropwise boron tribromide (1 M methylene chloride solution, 100 mL) at 0° C., and then the mixture was stirred at room temperature for 3 days. To the reaction mixture was added ice in water, and the mixture was stirred at room temperature for 30 minutes. The mixture was extracted with a mixture of ethyl acetate/THF, and then the solvent was removed. The residue was dissolved in 1 M aqueous sodium hydroxide, and then washed with methylene chloride. To the separated aqueous layer was acidified with 6 M hydrochloric acid at 0° C., and then the mixture was extracted with ethyl acetate/THF. The organic layer was washed with brine, dried over anhydrous sodium sulfate, and filtrated, and the solvent was removed. The obtained solid was washed by trituration with diisopropyl ether, and then collected on a filter to afford the title compound as a gray solid (2.7 g).

$^1$H-NMR (DMSO-d6) δ: 1.03 (3H, d, J=7.1 Hz), 2.05 (3H, d, J=2.2 Hz), 2.21 (1H, dd, J=16.7, 3.4 Hz), 2.63 (1H, dd, J=16.7, 6.6 Hz), 3.05-3.16 (1H, m), 6.68 (1H, d, J=8.4 Hz), 7.24 (1H, t, J=8.4 Hz), 10.12 (1H, d, J=2.0 Hz), 10.86 (1H, s).

The following compounds were prepared from each appropriate starting material in a similar manner to Reference example 92.

Reference Example 93

6-(2,4-Dihydroxy-3-methylphenyl)-5-methyl-4,5-dihydro-2H-pyridazin-3-one

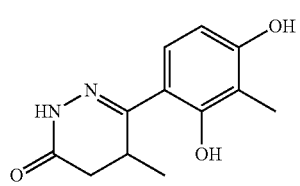

[Chem. 106]

$^1$H-NMR (DMSO-d6) δ: 1.09 (3H, d, J=7.3 Hz), 1.98 (3H, s), 2.21-2.28 (1H, m), 2.73 (1H, dd, J=16.9, 6.6 Hz), 3.41-3.51 (1H, m), 6.43 (1H, d, J=8.5 Hz), 7.27 (1H, d, J=8.5 Hz), 9.80 (1H, s), 10.97 (1H, s), 12.48 (1H, s).

Reference Example 94

6-(3-Bromo-2-fluoro-4-hydroxyphenyl)-5-methyl-4,5-dihydro-2H-pyridazin-3-one

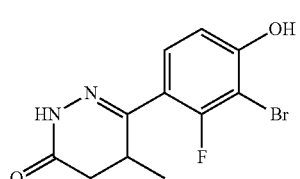

[Chem. 107]

$^1$H-NMR (DMSO-d6) δ: 1.04 (3H, d, J=7.2 Hz), 2.23 (1H, dd, J=16.8, 3.5 Hz), 2.67 (1H, dd, J=16.8, 6.7 Hz), 3.06-3.17 (1H, m), 6.84 (1H, dd, J=8.7, 1.3 Hz), 7.44 (1H, t, J=8.7 Hz), 10.96 (1H, s), 11.07 (1H, d, J=1.7 Hz).

Reference Example 95

6-(3-Fluoro-4-hydroxy-5-methylphen-5-methyl-4,5-dihydro-2H-pyridazin-3-one

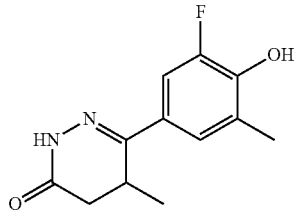

[Chem. 108]

$^1$H-NMR (DMSO-d6) δ: 1.04 (3H, d, J=7.3 Hz), 2.20 (1H, d, J=16.7 Hz), 2.21 (3H, s), 2.64 (1H, dd, J=16.7, 6.8 Hz), 3.29-3.39 (1H, m), 7.34-7.44 (2H, m), 9.79 (1H, s), 10.85 (1H, s).

Reference Example 96

6-(5-Chloro-2-fluoro-4-hydroxy-3-methylphenyl)-5-methylphen-5-methyl-4,5-dihydro-2H-pyridazin-3-one

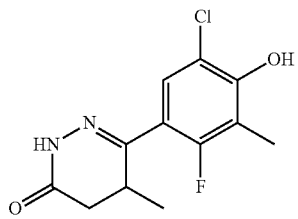

[Chem. 109]

$^1$H-NMR (DMSO-d6) δ: 1.03 (3H, d, J=7.2 Hz), 2.14 (3H, d, J=2.4 Hz), 2.22 (1H, dd, J=16.7, 3.7 Hz), 2.66 (1H, dd, J=16.7, 6.7 Hz), 3.07-3.17 (1H, m), 7.41 (1H, d, J=7.9 Hz), 10.00 (1H, s), 10.96 (1H, s).

Reference Example 97

Production of 6-(3-chloro-2,4-dihydroxyphenyl)-5-methyl-4,5-dihydro-2H-pyridazin-3-one

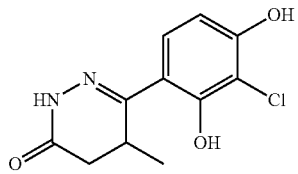

[Chem. 110]

Under an argon atmosphere, to a mixture of 6-(3-chloro-2,4-dimethoxyphenyl)-5-methyl-4,5-dihydro-2H-pyridazin-3-one (Reference example 78, 2.55 g) in methylene chloride (100 mL) was added dropwise boron tribromide (1 M methylene chloride solution, 45.1 mL) at 0° C. The mixture was stirred at room temperature for 3 days. The reaction was quenched by adding methanol slowly at 0° C., and then the solvent was removed. The residue was diluted with ethyl acetate, washed with water and brine, dried over anhydrous sodium sulfate, and filtrated. And, the solvent was removed. The mixture was dissolved in DMF (15 mL), lithium chloride (1.91 g) was added thereto. The mixture was stirred at 240° C. under microwave irradiation for 30 minutes. To the reaction mixture was added water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=67:33 to 33:67), and then recrystallized from ethanol to afford the title compound as a white solid (1.21 g).

$^1$H-NMR (DMSO-d6) δ: 1.10 (3H, d, J=7.3 Hz), 2.27 (1H, d, J=16.1 Hz), 2.78 (1H, dd, J=16.7, 6.7 Hz), 3.41-3.56 (1H, m), 6.57 (1H, d, J=8.9 Hz), 7.42 (1H, d, J=8.9 Hz), 10.67 (1H, brs), 11.07 (1H, s), 13.03 (1H, s).

Reference Example 98

Production of 6-[4-hydroxy-2-(methoxymethyloxy)-3-methylphenyl]-5-methyl-4,5-dihydro-2H-pyridazin-3-one

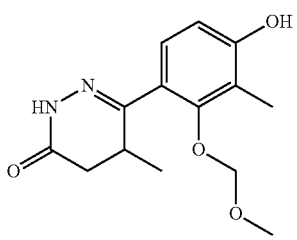

[Chem. 111]

A mixture of 6-[4-benzyloxy-2-(methoxymethyloxy)-3-methylphenyl]-5-methyl-4,5-dihydro-2H-pyridazin-3-one (Reference example 83, 1.55 g) and palladium-carbon (10% w/w, 100 mg) in ethanol/THF (1:1, 40 mL) was allowed to be under a hydrogen atmosphere. The mixture was stirred at room temperature for 2 hours, and then stirred at 40° C. for 2 hours. The mixture was filtered through a Celite pad, and the filtrate was concentrated. The residual solid was washed by trituration with diethyl ether, and then collected on a filter to afford the title compound as a white solid (1.13 g).

$^1$H-NMR (DMSO-d6) δ: 0.90 (3H, d, J=7.1 Hz), 2.07 (3H, s), 2.21 (1H, dd, J=16.7, 4.8 Hz), 2.63 (1H, dd, J=16.6, 6.8 Hz), 3.09-3.20 (1H, m), 3.41 (3H, s), 4.87-4.92 (2H, m), 6.64 (1H, d, J=8.3 Hz), 6.96 (1H, d, J=8.3 Hz), 9.73 (1H, s), 10.76 (1H, s).

The following compound was prepared from the appropriate starting material in a similar manner to Reference example 98.

Reference Example 99

6-[3-Chloro-4-hydroxy-2-(methoxymethyloxy)phenyl]-5-methyl-4,5-dihydro-2H-pyridazin-3-one

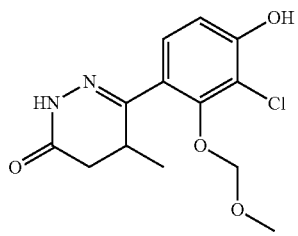

[Chem. 112]

$^1$H-NMR (CDCl$_3$) δ: 1.08 (3H, d, J=7.3 Hz), 2.42 (1H, dd, J=17.0, 4.6 Hz), 2.79 (1H, dd, J=17.0, 7.0 Hz), 3.27-3.39 (1H, m), 3.54 (3H, s), 5.02 (1H, d, J=5.6 Hz), 5.14 (1H, d, J=5.6 Hz), 5.84 (1H, brs), 6.88 (1H, d, J=8.5 Hz), 7.19 (1H, d, J=8.5 Hz), 8.47 (1H, s).

Reference Example 100

6-[3-Bromo-2-fluoro-4-(methoxymethyloxy)phenyl]-5-methyl-4,5-dihydro-2H-pyridazin-3-one

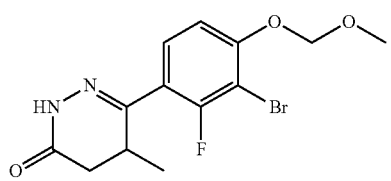

[Chem. 113]

To a mixture of 6-(3-bromo-2-fluoro-4-hydroxyphenyl)-5-methyl-4,5-dihydro-2H-pyridazin-3-one (Reference example 94, 2.37 g) in methylene chloride (30 mL) were added N,N-diisopropylethylamine (2.06 mL) and chloromethyl methyl ether (1.16 mL), and then the mixture was stirred at room temperature for 3 hours. To the reaction mixture was added water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=80:20 to 67:33) to afford the title compound as a white solid (1.97 g).

$^1$H-NMR (DMSO-d6) δ: 1.04 (3H, d, J=7.3 Hz), 2.25 (1H, dd, J=16.9, 3.7 Hz), 2.69 (1H, dd, J=16.9, 6.8 Hz), 3.08-3.20 (1H, m), 3.42 (3H, s), 5.38 (2H, s), 7.12 (1H, dd, J=8.8, 1.2 Hz), 7.59 (1H, t, J=8.8 Hz), 11.05 (1H, brs).

Reference Example 101

Production of 6-[2-fluoro-4-(methoxymethyloxy)-3-vinylphenyl]-5-methyl-4,5-dihydro-2H-pyridazin-3-one

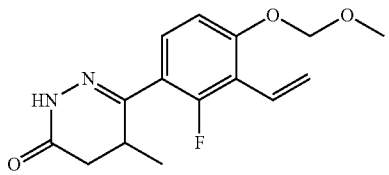

[Chem. 114]

To a mixture of 6-[3-bromo-2-fluoro-4-(methoxymethyloxy)phenyl]-5-methyl-4,5-dihydro-2H-pyridazin-3-one (Reference example 100, 4.87 g) in 1,2-dimethoxyethane/water (3:1, 32 mL) were added potassium vinyltrifluoroborate (3.78 g), potassium carbonate (4.87 g), and [1,1'-bis(diphenylphosphino)ferrocene]palladium(II) dichloride complex with methylene chloride (1.15 g). Then, the mixture was stirred at 150° C. under microwave irradiation for one hour. The reaction mixture was poured into water/ethyl acetate, and then the mixture was filtered through a Celite pad. And, the filtrate was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=80:20 to 67:33) to afford the title compound as a pale yellow solid (3.01 g).

$^1$H-NMR (CDCl$_3$) δ: 1.20 (3H, d, J=7.1 Hz), 2.43 (1H, dd, J=16.9, 3.4 Hz), 2.74 (1H, dd, J=16.9, 6.6 Hz), 3.21-3.33 (1H, m), 3.50 (3H, s), 5.26 (2H, s), 5.54-5.60 (1H, m), 5.98-6.08 (1H, m), 6.81 (1H, dd, J=18.1, 12.0 Hz), 6.95 (1H, dd, J=8.8, 1.0 Hz), 7.37 (1H, t, J=8.8 Hz), 8.60 (1H, brs).

Reference Example 102

Production of 6-[3-ethyl-2-fluoro-4-(methoxymethyloxy)phenyl]-5-methyl-4,5-dihydro-2H-pyridazin-3-one

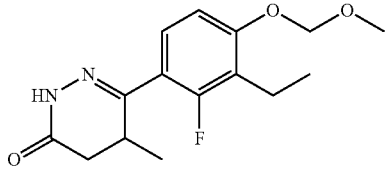

[Chem. 115]

To a mixture of 6-[2-fluoro-4-(methoxymethyloxy)-3-vinylphenyl]-5-methyl-4,5-dihydro-2H-pyridazin-3-one (Reference example 101, 292 mg) in ethanol (10 mL) was added platinum-carbon (1 w/w %, 195 mg). The reaction mixture was stirred at room temperature for 4 hours under a hydrogen atmosphere. The reaction mixture was filtered through a Celite pad, and then the filtrate was concentrated to afford the title compound as a white solid (280 mg).

$^1$H-NMR (CDCl$_3$) δ: 1.16 (3H, t, J=7.6 Hz), 1.20 (3H, d, J=7.3 Hz), 2.42 (1H, dd, J=16.9, 3.4 Hz), 2.66-2.79 (3H, m), 3.21-3.34 (1H, m), 3.49 (3H, s), 5.24 (2H, s), 6.90 (1H, dd, J=8.8, 1.0 Hz), 7.33 (1H, t, J=8.8 Hz), 8.53 (1H, brs).

Reference Example 103

Production of 6-(3-ethyl-2-fluoro-4-hydroxyphenyl)-5-methyl-4,5-dihydro-2H-pyridazin-3-one

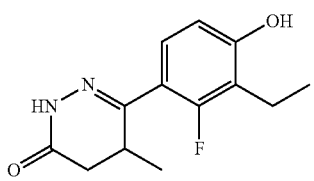

[Chem. 116]

To a mixture of 6-[3-ethyl-2-fluoro-4-(methoxymethyloxy)phenyl]-5-methyl-4,5-dihydro-2H-pyridazin-3-one (Reference example 102, 280 mg) in ethanol (10 mL) was added 6 M hydrochloric acid (0.476 mL), and then the mixture was stirred at 60° C. for 7 hours. To the reaction mixture was added water, and then the mixture was extracted with ethyl acetate. The organic layer was washed with water and brine, dried over anhydrous sodium sulfate, and then filtrated, and the solvent was removed. The obtained crude product was purified by silica gel column chromatography (heptane:ethyl acetate=33:67 to 17:83) to afford the title compound as a white solid (151 mg).

$^1$H-NMR (DMSO-d6) δ: 1.03 (3H, d, J=7.3 Hz), 1.08 (3H, t, J=7.3 Hz), 2.20 (1H, dd, J=16.9, 3.7 Hz), 2.52-2.68 (3H, m), 3.04-3.18 (1H, m), 6.68 (1H, d, J=8.5 Hz), 7.24 (1H, t, J=8.8 Hz), 10.09 (1H, brs), 10.87 (1H, brs).

The following compounds were prepared from each appropriate starting material in a similar manner to Reference example 103.

Reference Example 104

6-(4-Hydroxy-3,5-dimethylphenyl)-5-methyl-4,5-dihydro-2H-pyridazin-3-one

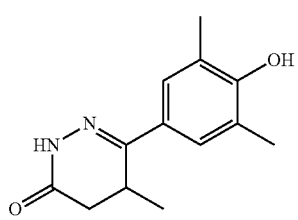

[Chem. 117]

$^1$H-NMR (DMSO-d6) δ: 1.04 (3H, d, J=7.3 Hz), 2.19 (6H, s), 2.19 (1H, d, J=16.7 Hz), 2.61 (1H, dd, J=16.7, 6.8 Hz), 3.27-3.38 (1H, m), 7.36 (2H, s), 8.59 (1H, s), 10.75 (1H, s).

Reference Example 105

6-(2-Fluoro-4-hydroxy-3-vinylphenyl)-5-methyl-4,5-dihydro-2H-pyridazin-3-one

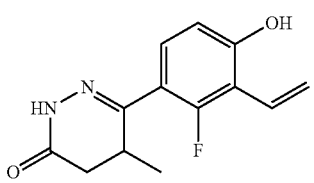

[Chem. 118]

$^1$H-NMR (DMSO-d6) δ: 1.03 (3H, d, J=7.3 Hz), 2.21 (1H, dd, J=16.9, 3.7 Hz), 2.64 (1H, dd, J=16.9, 6.8 Hz), 3.04-3.16 (1H, m), 5.45-5.53 (1H, m), 5.96-6.05 (1H, m), 6.71-6.81 (2H, m), 7.30 (1H, t, J=8.8 Hz), 10.56 (1H, d, J=1.2 Hz), 10.91 (1H, s).

Reference Example 106

6-(3-Chloro-2-fluoro-4-hydroxy-5-methylphenyl)-5-methyl-4,5-dihydro-2H-pyridazin-3-one

[Chem. 119]

$^1$H-NMR (DMSO-d6) δ: 1.04 (3H, d, J=7.2 Hz), 2.19-2.27 (1H, m), 2.20 (3H, s), 2.67 (1H, dd, J=16.7, 6.7 Hz), 3.08-3.18 (1H, m), 7.32 (1H, d, J=8.8 Hz), 10.02 (1H, s), 10.97 (1H, s).

Reference Example 107

Production of 6-[2-(methoxymethyloxy)-3-methyl-4-(2-oxopropoxy)phenyl]-5-methyl-4,5-dihydro-2H-pyridazin-3-one

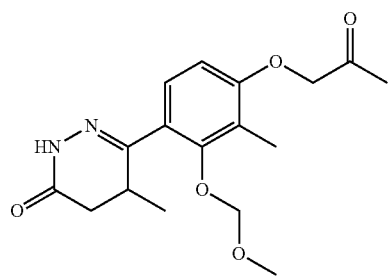

[Chem. 120]

To a mixture of 6-[4-hydroxy-2-(methoxymethyloxy)-3-methylphenyl]-5-methyl-4,5-dihydro-2H-pyridazin-3-one (Reference example 98, 140 mg) and potassium carbonate (83 mg) in DMF (3 mL) was added bromoacetone (0.052 mL) at 0° C., and the mixture was stirred at the same temperature for 2 hours. The reaction mixture was poured into water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=60:40 to 40:60). The obtained solid was washed by trituration with diethyl ether, and then collected on a filter to afford the title compound as a white solid (120 mg).

$^1$H-NMR (CDCl$_3$) δ: 1.07 (3H, d, J=7.3 Hz), 2.28 (3H, s), 2.32 (3H, s), 2.41 (1H, dd, J=17.0, 4.6 Hz), 2.79 (1H, dd, J=17.0, 7.0 Hz), 3.26-3.37 (1H, m), 3.51 (3H, s), 4.56 (2H, s), 4.90 (1H, d, J=5.6 Hz), 5.00 (1H, d, J=5.6 Hz), 6.52 (1H, d, J=8.5 Hz), 7.13 (1H, d, J=8.5 Hz), 8.42 (1H, s).

The following compounds were prepared from each appropriate starting material in a similar manner to Reference example 107.

Reference Example 108

6-[2,3-Difluoro-4-(2-oxopropoxy)phenyl]-5-methyl-4,5-dihydro-2H-pyridazin-3-one

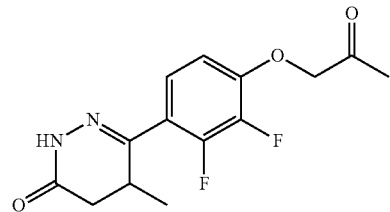

[Chem. 121]

$^1$H-NMR (DMSO-d6) δ: 1.05 (3H, d, J=7.3 Hz), 2.16 (3H, s), 2.25 (1H, dd, J=16.7, 3.3 Hz), 2.70 (1H, dd, J=16.7, 6.8 Hz), 3.10-3.23 (1H, m), 5.04 (2H, s), 6.91-7.01 (1H, m), 7.28-7.38 (1H, m), 11.03 (1H, s).

Reference Example 109

6-[3,5-Dichloro-4-(2-oxopropoxy)phenyl]-5-methyl-4,5-dihydro-2H-pyridazin-3-one

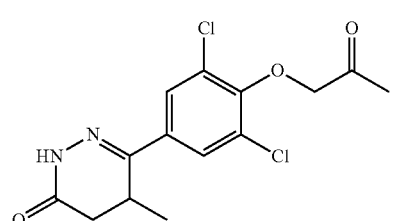

[Chem. 122]

$^1$H-NMR (DMSO-d6) δ: 1.04 (3H, d, J=7.3 Hz), 2.20-2.28 (1H, m), 2.23 (3H, s), 2.70 (1H, dd, J=16.7, 7.0 Hz), 3.37-3.49 (1H, m), 4.73 (2H, s), 7.84 (2H, s), 11.10 (1H, s).

Reference Example 110

6-[3-Chloro-2-fluoro-4-(2-oxopropoxy)phenyl]-5-methyl-4,5-dihydro-2H-pyridazin-3-one

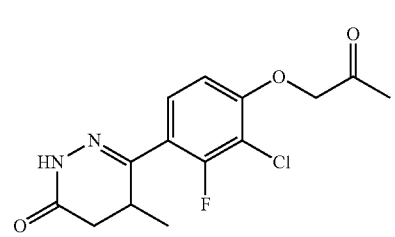

[Chem. 123]

$^1$H-NMR (DMSO-d6) δ: 1.04 (3H, d, J=7.1 Hz), 2.18 (3H, s), 2.25 (1H, dd, J=16.6, 3.7 Hz), 2.69 (1H, dd, J=16.6, 6.8 Hz), 3.10-3.19 (1H, m), 5.06 (2H, s), 6.95 (1H, dd, J=8.9, 1.5 Hz), 7.49 (1H, t, J=8.9 Hz), 11.03 (1H, s).

Reference Example 111

6-[3-Chloro-2-(methoxymethyloxy)-4-(2-oxopropoxy)phenyl]-5-methyl-4,5-dihydro-2H-pyridazin-3-one

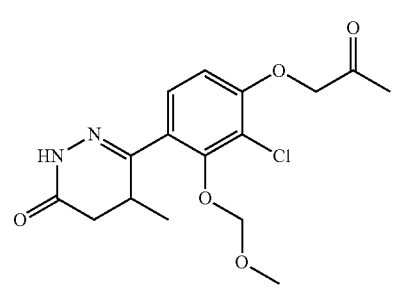

[Chem. 124]

$^1$H-NMR (CDCl$_3$) δ: 1.08 (3H, d, J=7.3 Hz), 2.37 (3H, s), 2.42 (1H, dd, J=17.0, 4.9 Hz), 2.80 (1H, dd, J=17.0, 7.0 Hz), 3.29-3.40 (1H, m), 3.54 (3H, s), 4.60 (2H, s), 5.04 (1H, d, J=5.6 Hz), 5.18 (1H, d, J=5.6 Hz), 6.63 (1H, d, J=8.8 Hz), 7.22 (1H, d, J=8.8 Hz), 8.44 (1H, s).

Reference Example 112

6-[3-Chloro-5-fluoro-4-(2-oxopropox)phenyl]-5-methyl-4,5-dihydro-2H-pyridazin-3-one

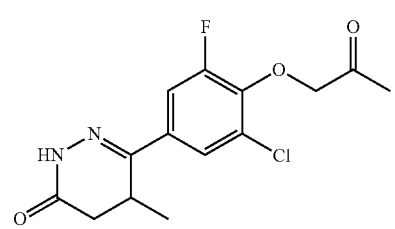

[Chem. 125]

¹H-NMR (DMSO-d6) δ: 1.04 (3H, d, J=7.3 Hz), 2.17 (3H, s), 2.24 (1H, d, J=16.8 Hz), 2.69 (1H, dd, J=16.8, 6.9 Hz), 3.35-3.45 (1H, m), 4.95 (2H, d, J=2.0 Hz), 7.62 (1H, dd, J=13.2, 2.1 Hz), 7.67-7.71 (1H, m), 11.06 (1H, s).

Reference Example 113

6-[3-Bromo-5-fluoro-4-(2-oxopropoxy)phenyl]-5-methyl-4,5-dihydro-2H-pyridazin-3-one

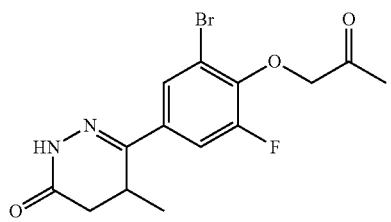
[Chem. 126]

¹H-NMR (DMSO-d6) δ: 1.04 (3H, d, J=7.3 Hz), 2.19 (3H, s), 2.23 (1H, d, J=16.8 Hz), 2.69 (1H, dd, J=16.8, 6.9 Hz), 3.34-3.45 (1H, m), 4.92 (2H, d, J=2.1 Hz), 7.65 (1H, dd, J=13.4, 2.1 Hz), 7.82 (1H, t, J=2.1 Hz), 11.06 (1H, s).

Reference Example 114

6-[3-Bromo-2-fluoro-4-(2-oxopropoxy)phenyl]-5-methyl-4,5-dihydro-2H-pyridazin-3-one

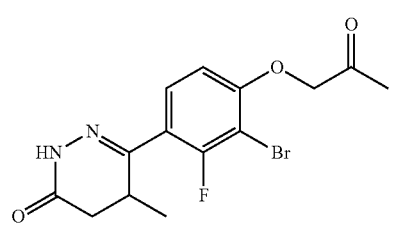
[Chem.127]

¹H-NMR (DMSO-d6) δ: 1.04 (3H, d, J=7.2 Hz), 2.19 (3H, s), 2.25 (1H, dd, J=16.8, 3.7 Hz), 2.69 (1H, dd, J=16.8, 6.7 Hz), 3.08-3.19 (1H, m), 5.04 (2H, s), 6.90 (1H, dd, J=8.9, 1.2 Hz), 7.52 (1H, t, J=8.9 Hz), 11.02 (1H, s).

Reference Example 115

6-[3,5-Dimethyl-4-(2-oxopropoxy)phenyl]-5-methyl-4,5-dihydro-2H-pyridazin-3-one

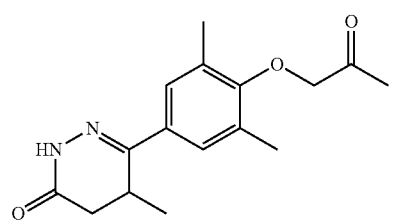
[Chem.128]

¹H-NMR (DMSO-d6) δ: 1.05 (3H, d, J=7.3 Hz), 2.17 (3H, s), 2.22 (1H, d, J=16.8 Hz), 2.24 (6H, s), 2.64 (1H, dd, J=16.8, 6.8 Hz), 3.31-3.42 (1H, m), 4.52 (2H, s), 7.45 (2H, s), 10.88 (1H, s).

Reference Example 116

6-[3-Fluoro-5-methyl-4-(2-oxopropoxy)phenyl]-5-methyl-4,5-dihydro-2H-pyridazin-3-one

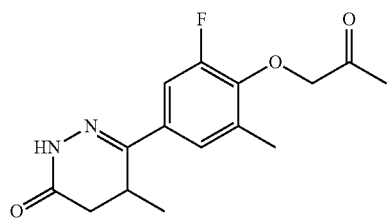
[Chem.129]

¹H-NMR (DMSO-d6) δ: 1.05 (3H, d, J=7.3 Hz), 2.14 (3H, s), 2.22 (1H, d, J=16.7 Hz), 2.31 (3H, s), 2.66 (1H, dd, J=16.7, 6.8 Hz), 3.32-3.42 (1H, m), 4.84 (2H, d, J=1.7 Hz), 7.40-7.48 (2H, m), 10.95 (1H, s).

Reference Example 117

6-[3-Chloro-5-methyl-4-(2-oxopropoxy)phenyl]-5-methyl-4,5-dihydro-2H-pyridazin-3-one

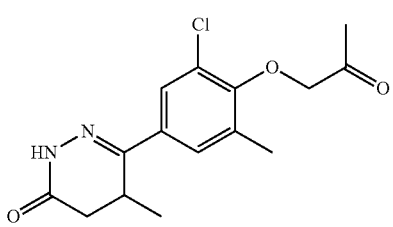
[Chem.130]

¹H-NMR (CDCl₃) δ: 1.24 (3H, d, J=7.3 Hz), 2.36 (3H, s), 2.38 (3H, s), 2.47 (1H, dd, J=17.1, 1.2 Hz), 2.69 (1H, dd, J=17.1, 6.8 Hz), 3.23-3.33 (1H, m), 4.51 (2H, s), 7.50 (1H, d, J=2.2 Hz), 7.62 (1H, d, J=2.2 Hz), 8.73 (1H, brs).

Reference Example 118

6-[3-Bromo-5-chloro-4-(2-oxopropoxy)phenyl]-5-methyl-4,5-dihydro-2H-pyridazin-3-one

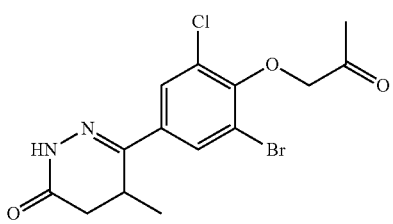
[Chem.131]

¹H-NMR (CDCl₃) δ: 1.25 (3H, d, J=7.3 Hz), 2.45 (3H, s), 2.45-2.55 (1H, m), 2.70 (1H, dd, J=17.1, 6.8 Hz), 3.20-3.31 (1H, m), 4.54 (2H, s), 7.75 (1H, d, J=2.2 Hz), 7.87 (1H, d, J=2.2 Hz), 8.58 (1H, brs).

Reference Example 119

6-[2-Fluoro-3-methyl-4-(2-oxopropoxy)phenyl]-5-methyl-4,5-dihydro-2H-pyridazin-3-one

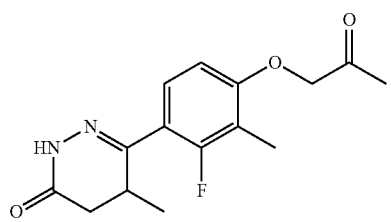

[Chem.132]

¹H-NMR (DMSO-d6) δ: 1.03 (3H, d, J=7.2 Hz), 2.14 (3H, d, J=2.0 Hz), 2.18 (3H, s), 2.23 (1H, dd, J=16.9, 3.6 Hz), 2.66 (1H, dd, J=16.9, 6.7 Hz), 3.07-3.17 (1H, m), 4.92 (2H, s), 6.74 (1H, d, J=8.7 Hz), 7.33 (1H, t, J=8.7 Hz), 10.93 (1H, s).

Reference Example 120

6-[2-Fluoro-4-(2-oxopropoxy)-3-vinylphenyl]-5-methyl-4,5-dihydro-2H-pyridazin-3-one

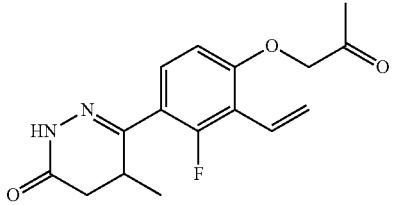

[Chem.133]

¹H-NMR (CDCl₃) δ: 1.20 (3H, d, J=6.8 Hz), 2.31 (3H, s), 2.43 (1H, dd, J=17.1, 3.7 Hz), 2.74 (1H, dd, J=17.1, 6.8 Hz), 3.21-3.33 (1H, m), 4.63 (2H, s), 5.59-5.66 (1H, m), 6.06-6.13 (1H, m), 6.56 (1H, dd, J=8.8, 1.0 Hz), 6.85 (1H, dd, J=18.1, 12.0 Hz), 7.39 (1H, t, J=8.8 Hz), 8.58 (1H, brs).

Reference Example 121

6-[3-Ethyl-2-fluoro-4-(2-oxopropoxy)phenyl]-5-methyl-4,5-dihydro-2H-pyridazin-3-one

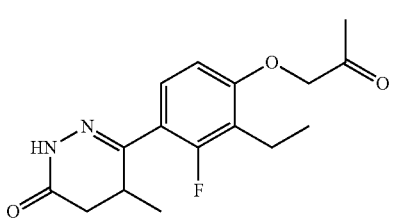

[Chem.134]

¹H-NMR (CDCl₃) δ: 1.16-1.24 (6H, m), 2.31 (3H, s), 2.42 (1H, dd, J=16.9, 3.4 Hz), 2.69-2.83 (3H, m), 3.20-3.33 (1H, m), 4.58 (2H, s), 6.51 (1H, d, J=8.8 Hz), 7.35 (1H, t, J=8.8 Hz), 8.48 (1H, brs).

Reference Example 122

6-[2,3-Difluoro-4-(2-oxobutoxy)phenyl]-5-methyl-4,5-dihydro-2H-pyridazin-3-one

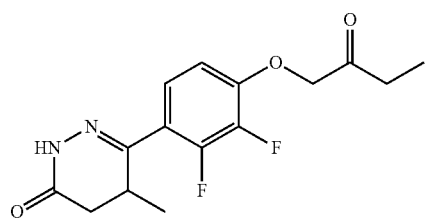

[Chem.135]

¹H-NMR (DMSO-d6) δ: 0.98 (3H, t, J=7.3 Hz), 1.05 (3H, d, J=7.1 Hz), 2.25 (1H, dd, J=16.7, 3.3 Hz), 2.48-2.58 (2H, m), 2.70 (1H, dd, J=16.7, 6.8 Hz), 3.09-3.22 (1H, m), 5.05 (2H, s), 6.89-7.01 (1H, m), 7.29-7.38 (1H, m), 11.03 (1H, s).

Reference Example 123

6-[3-Chloro-5-fluoro-4-(2-oxobutoxy)phenyl]-5-methyl-4,5-dihydro-2H-pyridazin-3-one

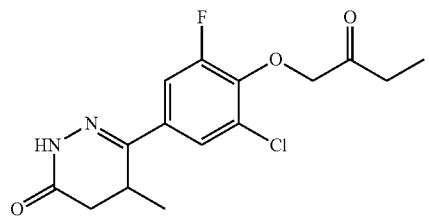

[Chem.136]

¹H-NMR (DMSO-d6) δ: 0.98 (3H, t, J=7.3 Hz), 1.04 (3H, d, J=7.3 Hz), 2.24 (1H, d, J=16.9 Hz), 2.54 (2H, q, J=7.3 Hz), 2.69 (1H, dd, J=16.9, 7.1 Hz), 3.34-3.45 (1H, m), 4.96 (2H, d, J=2.0 Hz), 7.58-7.64 (1H, m), 7.67-7.72 (1H, m), 11.06 (1H, s).

Reference Example 124

6-[3,5-Dichloro-4-(2-oxobutoxy)phenyl]-5-methyl-4,5-dihydro-2H-pyridazin-3-one

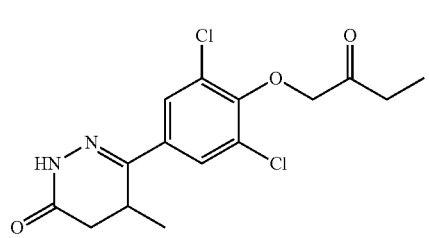

[Chem.137]

¹H-NMR (DMSO-d6) δ: 1.00 (3H, t, J=7.3 Hz), 1.04 (3H, d, J=7.3 Hz), 2.24 (1H, d, J=16.9 Hz), 2.62 (2H, q, J=7.3 Hz), 2.70 (1H, dd, J=16.9, 7.1 Hz), 3.38-3.49 (1H, m), 4.75 (2H, s), 7.84 (2H, s), 11.10 (1H, s).

Reference Example 125

6-[3-Chloro-2-fluoro-4-(2-oxobutoxy)phenyl]-5-methyl-4,5-dihydro-2H-pyridazin-3-one

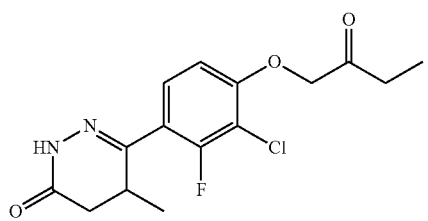

[Chem.138]

¹H-NMR (DMSO-d6) δ: 0.98 (3H, t, J=7.2 Hz), 1.04 (3H, d, J=7.3 Hz), 2.25 (1H, dd, J=16.7, 3.7 Hz), 2.56 (2H, q, J=7.2 Hz), 2.69 (1H, dd, J=16.7, 6.7 Hz), 3.10-3.19 (1H, m), 5.07 (2H, s), 6.94 (1H, dd, J=8.8, 1.5 Hz), 7.49 (1H, t, J=8.8 Hz), 11.03 (1H, s).

Reference Example 126

6-[3-Chloro-5-methyl-4-(2-oxobutoxy)phenyl]-5-methyl-4,5-dihydro-2H-pyridazin-3-one

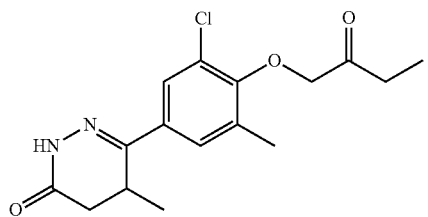

[Chem.139]

¹H-NMR (CDCl₃) δ:1.17 (3H, t, J=7.3 Hz), 1.24 (3H, d, J=7.3 Hz), 2.36 (3H, s), 2.47 (1H, dd, J=17.1, 1.0 Hz), 2.65-2.80 (3H, m), 3.23-3.33 (1H, m), 4.53 (2H, s), 7.49 (1H, dd, J=2.2, 0.7 Hz), 7.62 (1H, d, J=2.2 Hz), 8.76 (1H, brs).

Reference Example 127

6-[3-Bromo-5-chloro-4-(2-oxobutoxy)phenyl]-5-methyl-4,5-dihydro-2H-pyridazin-3-one

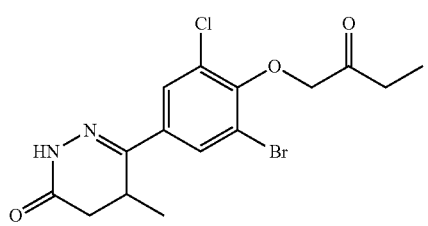

[Chem.140]

¹H-NMR (CDCl₃) δ: 1.17 (3H, t, J=7.3 Hz), 1.25 (3H, d, J=7.3 Hz), 2.49 (1H, dd, J=16.9, 1.0 Hz), 2.70 (1H, dd, J=16.9, 6.8 Hz), 2.83 (2H, q, J=7.3 Hz), 3.20-3.31 (1H, m), 4.57 (2H, s), 7.75 (1H, d, J=2.2 Hz), 7.87 (1H, d, J=2.2 Hz), 8.77 (1H, brs).

Reference Example 128

6-[2-Fluoro-4-(2-oxobutoxy)-3-vinylphenyl]-5-methyl-4,5-dihydro-2H-pyridazin-3-one

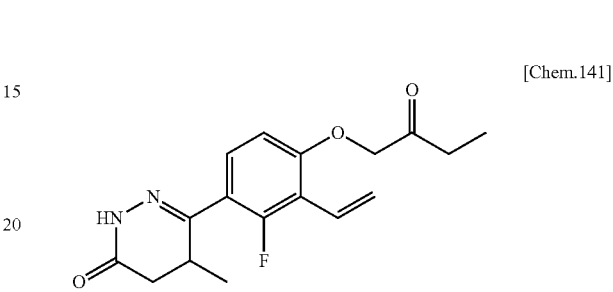

[Chem.141]

¹H-NMR (CDCl₃) δ: 1.13 (3H, t, J=7.3 Hz), 1.20 (3H, d, J=7.1 Hz), 2.43 (1H, dd, J=16.9, 3.4 Hz), 2.63 (2H, q, J=7.3 Hz), 2.73 (1H, dd, J=16.9, 6.6 Hz), 3.21-3.33 (1H, m), 4.65 (2H, s), 5.59-5.66 (1H, m), 6.06-6.15 (1H, m), 6.54-6.59 (1H, m), 6.85 (1H, dd, J=18.1, 12.0 Hz), 7.39 (1H, t, J=8.5 Hz), 8.64 (1H, brs).

Reference Example 129

Production of methyl 3-[2-bromo-6-chloro-4-(4-methyl-6-oxo-4,5-dihydro-1H-pyridazin-3-yl)phenoxy]-2,2-dimethylpropionate

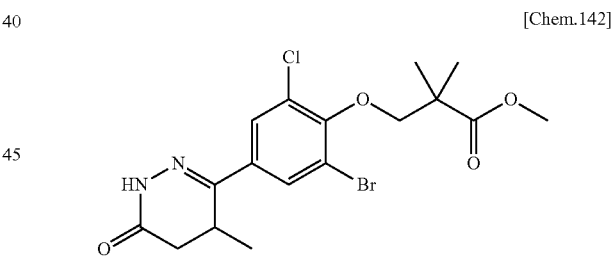

[Chem.142]

A suspension of 6-(3-bromo-5-chloro-4-hydroxyphenyl)-5-methyl-4,5-dihydro-2H-pyridazin-3-one (Reference example 87, 500 mg), methyl 2,2-dimethyl-3-(methylsulfonyloxy)propanoate (430 mg), and cesium carbonate (769 mg) in NMP (4 mL) was stirred at 150° C. under microwave irradiation for 1.5 hours. To the reaction mixture was added water, and the mixture was extracted with ethyl acetate. The organic layer was washed with saturated aqueous sodium bicarbonate and brine, dried over anhydrous sodium sulfate, and filtrated, and the solvent was removed. The obtained crude product was purified by silica gel column chromatography (heptane:ethyl acetate=50:50 to 33:67) to afford the title compound as a pale yellow solid (342 mg).

¹H-NMR (CDCl₃) δ 1.24 (3H, d, J=7.6 Hz), 1.41 (6H, s), 2.48 (1H, dd, J=17.1, 1.0 Hz), 2.69 (1H, dd, J=17.1, 6.8 Hz), 3.20-3.30 (1H, m), 3.74 (3H, s), 4.08 (2H, s), 7.72 (1H, d, J=2.2 Hz), 7.84 (1H, d, J=2.2 Hz), 8.67 (1H, brs).

The following compounds were prepared from each appropriate starting material in a similar manner to Reference example 129.

Reference Example 130

Methyl 3-[2-bromo-6-fluoro-4-(4-methyl-6-oxo-4,5-dihydro-1H-pyridazin-3-yl)phenoxy]-2,2-dimethyl-propionate

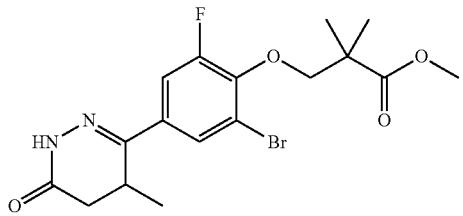
[Chem.143]

$^1$H-NMR (DMSO-d6) δ: 1.04 (3H, d, J=7.3 Hz), 1.28 (6H, s), 2.23 (1H, d, J=16.8 Hz), 2.69 (1H, dd, J=16.8, 6.9 Hz), 3.35-3.45 (1H, m), 3.63 (3H, s), 4.16 (2H, d, J=1.5 Hz), 7.67 (1H, dd, J=12.8, 2.1 Hz), 7.80 (1H, t, J=2.1 Hz), 11.07 (1H, s).

Reference Example 131

Methyl 3-[2-bromo-3-fluoro-4-(4-methyl-6-oxo-4,5-dihydro-1H-pyridazin-3-yl)phenoxy]-2,2-dimethyl-propionate

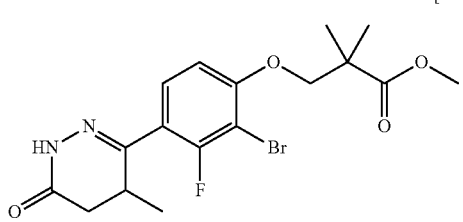
[Chem.144]

$^1$H-NMR (DMSO-d6) δ: 1.04 (3H, d, J=7.2 Hz), 1.29 (6H, s), 2.25 (1H, dd, J=16.8, 3.7 Hz), 2.69 (1H, dd, J=16.8, 6.8 Hz), 3.09-3.20 (1H, m), 3.63 (3H, s), 4.14 (2H, s), 7.05 (1H, dd, J=8.9, 1.1 Hz), 7.58 (1H, t, J=8.9 Hz), 11.02 (1H, s).

Reference Example 132

Methyl 3-[2,6-dimethyl-4-(4-methyl-6-oxo-4,5-dihydro-1H-pyridazin-3-yl)phenoxy]-2,2-dimethylpropionate

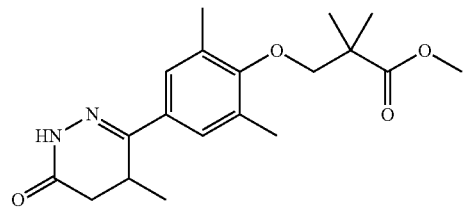
[Chem.145]

$^1$H-NMR (DMSO-d6) δ: 1.05 (3H, d, J=7.3 Hz), 1.28 (6H, s), 2.17-2.27 (1H, m), 2.22 (6H, s), 2.64 (1H, dd, J=16.7, 6.8 Hz), 3.30-3.40 (1H, m), 3.67 (3H, s), 3.74 (2H, s), 7.44 (2H, s), 10.87 (1H, s).

Reference Example 133

Methyl 3-[2-chloro-6-methyl-4-(4-methyl-6-oxo-4,5-dihydro-1H-pyridazin-3-yl)phenoxy]-2,2-dimethylpropionate

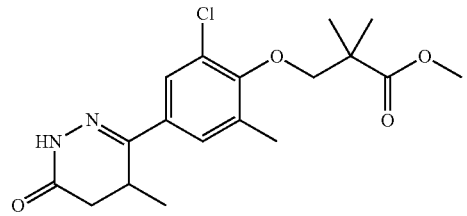
[Chem.146]

$^1$H-NMR (CDCl$_3$) δ: 1.23 (3H, d, J=7.3 Hz), 1.38 (6H, s), 2.31 (3H, s), 2.46 (1H, dd, J=16.8, 1.0 Hz), 2.68 (1H, dd, J=16.8, 6.8 Hz), 3.23-3.33 (1H, m), 3.75 (3H, s), 3.95 (2H, s), 7.46 (1H, d, J=2.2 Hz), 7.59 (1H, d, J=2.2 Hz), 8.73 (1H, brs).

Reference Example 134

Methyl 3-[2-fluoro-6-methyl-4-(4-methyl-6-oxo-4,5-dihydro-1H-pyridazin-3-yl)phenoxy]-2,2-dimethyl-propionate

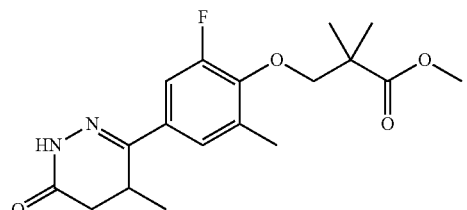
[Chem.147]

¹H-NMR (CDCl₃) δ: 1.24 (3H, t, J=6.8 Hz), 1.34 (6H, s), 2.25 (3H, s), 2.46 (1H, d, J=17.0 Hz), 2.69 (1H, dd, J=17.0, 6.8 Hz), 3.23-3.32 (1H, m), 3.72 (3H, s), 4.09-4.14 (2H, m), 7.28-7.36 (2H, m), 8.53 (1H, s).

Reference Example 135

Production of 2,2-difluoro-3-[3-fluoro-2-methyl-4-(4-methyl-6-oxo-4,5-dihydro-1H-pyridazin-3-yl)phenoxy]propyl Methanesulfonate

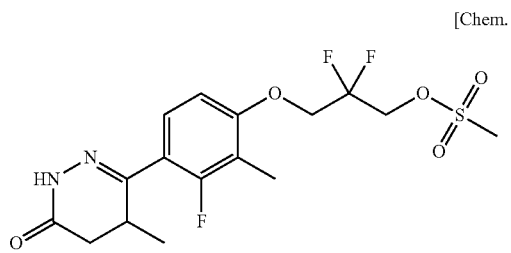

[Chem.148]

A suspension of 6-(2-fluoro-4-hydroxy-3-methylphenyl)-5-methyl-4,5-dihydro-2H-pyridazin-3-one (Reference example 92, 500 mg), 2,2-difluoro-3-(methylsulfonyloxy)propyl methanesulfonate (1.70 g), and cesium carbonate (2.07 g) in NMP (4 mL) was stirred at 150° C. under microwave irradiation for 1.5 hours. To the reaction mixture was added water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=65:35 to 45:55) to afford the title compound as a pale yellow amorphous (324 mg).

¹H-NMR (DMSO-d6) δ: 1.03 (3H, d, J=7.3 Hz), 2.13 (3H, d, J=2.2 Hz), 2.24 (1H, dd, J=16.7, 3.8 Hz), 2.67 (1H, dd, J=16.7, 6.7 Hz), 3.04-3.19 (1H, m), 3.32 (3H, s), 4.54 (2H, t, J=12.6 Hz), 4.73 (2H, t, J=13.4 Hz), 6.98 (1H, d, J=8.8 Hz), 7.41 (1H, t, J=8.8 Hz), 10.96 (1H, s).

The following compounds were prepared from each appropriate starting material in a similar manner to Reference example 135.

Reference Example 136

3-[2,3-Difluoro-4-(4-methyl-6-oxo-4,5-dihydro-1H-pyridazin-3-yl)phenoxy]-2,2-difluoropropyl Methanesulfonate

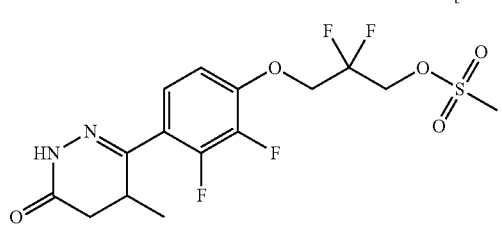

[Chem.149]

¹H-NMR (DMSO-d6) δ: 1.05 (3H, d, J=7.3 Hz), 2.26 (1H, dd, J=16.9, 3.4 Hz), 2.71 (1H, dd, J=16.9, 6.7 Hz), 3.13-3.22 (1H, m), 3.32 (3H, s), 4.60-4.76 (4H, m), 7.16-7.26 (1H, m), 7.38-7.47 (1H, m), 11.06 (1H, s).

Reference Example 137

3-[2,6-Dichloro-4-(4-methyl-6-oxo-4,5-dihydro-1H-pyridazin-3-yl)phenoxy]-2,2-difluoropropyl Methanesulfonate

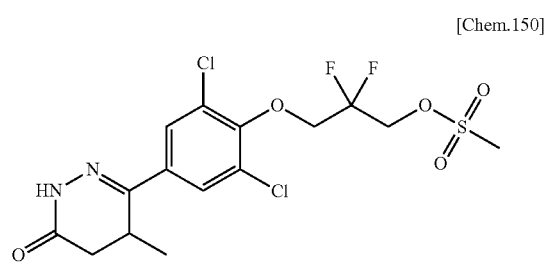 [SMILES: CC1CC(=O)NN=C1c1cc(Cl)c(OCC(F)(F)COS(C)(=O)=O)c(Cl)c1]

[Chem.150]

¹H-NMR (DMSO-d6) δ: 1.04 (3H, d, J=7.3 Hz), 2.25 (1H, d, J=16.9 Hz), 2.70 (1H, dd, J=16.9, 6.8 Hz), 3.34 (3H, s), 3.39-3.51 (1H, m), 4.49 (2H, t, J=13.1 Hz), 4.76 (2H, t, J=13.6 Hz), 7.81-7.90 (2H, m), 11.12 (1H, s).

Reference Example 138

3-[2-Chloro-3-fluoro-4-(4-methyl-6-oxo-4,5-dihydro-1H-pyridazin-3-yl)phenoxy]-2,2-difluoropropyl Methanesulfonate

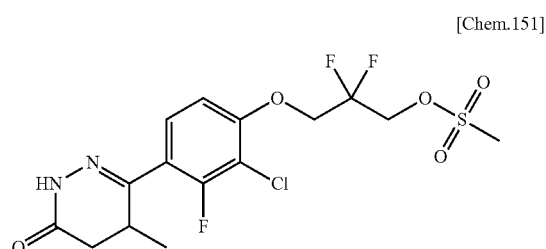

[Chem.151]

¹H-NMR (DMSO-d6) δ: 1.04 (3H, d, J=7.1 Hz), 2.26 (1H, dd, J=16.9, 3.7 Hz), 2.70 (1H, dd, J=16.9, 6.8 Hz), 3.07-3.21 (1H, m), 3.33 (3H, s), 4.58-4.78 (4H, m), 7.17-7.25 (1H, m), 7.55-7.63 (1H, m), 11.06 (1H, s).

Reference Example 139

3-[2-Chloro-6-fluoro-4-(4-methyl-6-oxo-4,5-dihydro-1H-pyridazin-3-yl)phenoxy]-2,2-difluoropropyl Methanesulfonate

[Chem.152]

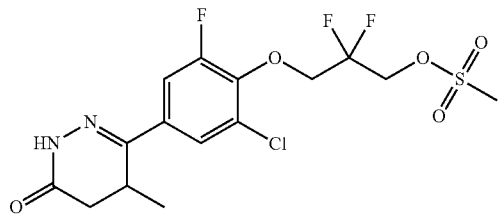

$^1$H-NMR (DMSO-d6) δ: 1.04 (3H, d, J=7.1 Hz), 2.25 (1H, d, J=17.0 Hz), 2.70 (1H, dd, J=17.0, 7.0 Hz), 3.32 (3H, s), 3.37-3.49 (1H, m), 4.58 (2H, t, J=13.1 Hz), 4.73 (2H, t, J=13.6 Hz), 7.65-7.75 (2H, m), 11.10 (1H, s).

Reference Example 140

3-[2-Bromo-3-fluoro-4-(4-methyl-6-oxo-4,5-dihydro-1H-pyridazin-3-yl)phenoxy]-2,2-difluoropropyl Methanesulfonate

[Chem.153]

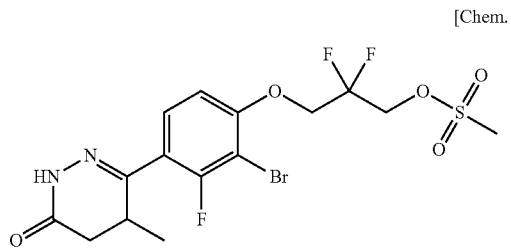

$^1$H-NMR (DMSO-d6) δ: 1.04 (3H, d, J=7.1 Hz), 2.26 (1H, dd, J=16.6, 3.8 Hz), 2.70 (1H, dd, J=16.6, 6.8 Hz), 3.07-3.20 (1H, m), 3.36 (3H, s), 4.55-4.81 (4H, m), 7.16 (1H, d, J=8.8 Hz), 7.62 (1H, t, J=8.8 Hz), 11.06 (1H, s).

Reference Example 141

2,2-Difluoro-3-[3-(methoxymethyloxy)-2-methyl-4-(4-methyl-6-oxo-4,5-dihydro-1H-pyridazin-3-yl)phenoxy]propyl Methanesulfonate

[Chem.154]

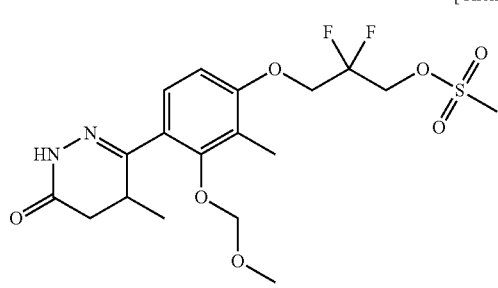

$^1$H-NMR (CDCl$_3$) δ: 1.07 (3H, d, J=7.3 Hz), 2.22 (3H, s), 2.42 (1H, dd, J=17.1, 4.9 Hz), 2.79 (1H, dd, J=17.1, 7.0 Hz), 3.10 (3H, s), 3.25-3.37 (1H, m), 3.51 (3H, s), 4.29 (2H, t, J=11.4 Hz), 4.61 (2H, t, J=11.8 Hz), 4.89 (1H, d, J=5.9 Hz), 5.00 (1H, d, J=5.6 Hz), 6.67 (1H, d, J=8.5 Hz), 7.16 (1H, d, J=8.5 Hz), 8.43 (1H, brs).

Reference Example 142

2,2-Difluoro-3-[3-fluoro-4-(4-methyl-6-oxo-4,5-dihydro-1H-pyridazin-3-yl)-2-vinylphenoxy]propyl Methanesulfonate

[Chem.155]

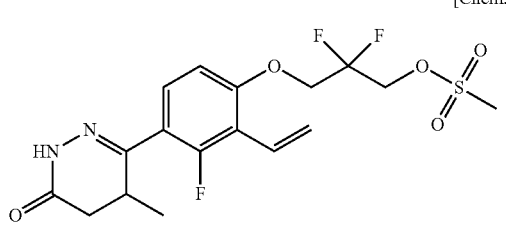

$^1$H-NMR (CDCl$_3$) δ: 1.20 (3H, d, J=7.1 Hz), 2.43 (1H, dd, J=17.1, 3.7 Hz), 2.70-2.80 (1H, m), 3.09 (3H, s), 3.21-3.32 (1H, m), 4.34 (2H, t, J=11.2 Hz), 4.58 (2H, t, J=11.7 Hz), 5.59-5.65 (1H, m), 5.95-6.03 (1H, m), 6.69-6.80 (2H, m), 7.43 (1H, t, J=8.5 Hz), 8.47 (1H, brs).

Reference Example 143

3-[2-Chloro-6-methyl-4-(4-methyl-6-oxo-4,5-dihydro-1H-pyridazin-3-yl)phenoxy]-2,2-difluoropropyl Methanesulfonate

[Chem.156]

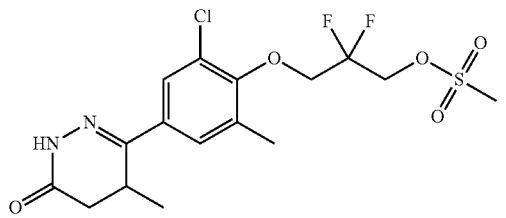

$^1$H-NMR (DMSO-d6) δ: 1.05 (3H, d, J=7.1 Hz), 2.24 (1H, d, J=16.9 Hz), 2.34 (3H, s), 2.68 (1H, dd, J=16.9, 6.8 Hz), 3.30-3.45 (1H, m), 3.31 (3H, s), 4.37 (2H, t, J=13.2 Hz), 4.75 (2H, t, J=13.6 Hz), 7.64 (1H, d, J=2.0 Hz), 7.70 (1H, d, J=2.0 Hz), 11.01 (1H, s).

Reference Example 144

Production of 6-{4-[(Z)-4-(tert-butyldimethylsilyloxy)-2-butenyloxy]-3-chloro-2-fluorophenyl}-5-methyl-4,5-dihydro-2H-pyridazin-3-one

[Chem. 157]

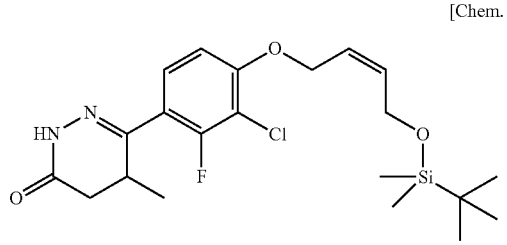

A mixture of 6-(3-chloro-2-fluoro-4-hydroxyphenyl)-5-methyl-4,5-dihydro-2H-pyridazin-3-one (Reference example 89, 250 mg), (Z)-4-(tert-butyldimethylsilyloxy)-2-buten-1-ol (217 mg), bis(2-methoxyethyl) azodicarboxylate (251 mg), and triphenylphosphine (281 mg) in THF (10 mL) was stirred at room temperature overnight. Bis(2-methoxyethyl) azodicarboxylate (251 mg) and triphenylphosphine (281 mg) were added to the reaction mixture, and then the reaction mixture was stirred at room temperature for 4 hours. The solvent was removed, and the obtained crude product was purified by silica gel column chromatography (heptane:ethyl acetate=65:35 to 45:55) to afford the title compound as a white solid (296 mg).

$^1$H-NMR (CDCl$_3$) δ: 0.09 (6H, s), 0.92 (9H, s), 1.21 (3H, d, J=7.1 Hz), 2.44 (1H, dd, J=17.1, 3.2 Hz), 2.74 (1H, dd, J=17.1, 6.7 Hz), 3.22-3.32 (1H, m), 4.33 (2H, dd, J=5.3, 1.3 Hz), 4.81 (2H, dd, J=5.5, 1.1 Hz), 5.65-5.86 (2H, m), 6.78 (1H, dd, J=8.8, 1.5 Hz), 7.45 (1H, t, J=8.8 Hz), 8.47 (1H, s).

The following compounds were prepared from each appropriate starting material in a similar manner to Reference example 144.

Reference Example 145

6-{4-[(Z)-4-(tert-Butyldimethylsilyloxy)-2-butenyloxy]-3-chloro-5-methylphenyl}-5-methyl-4,5-dihydro-2H-pyridazin-3-one

[Chem. 158]

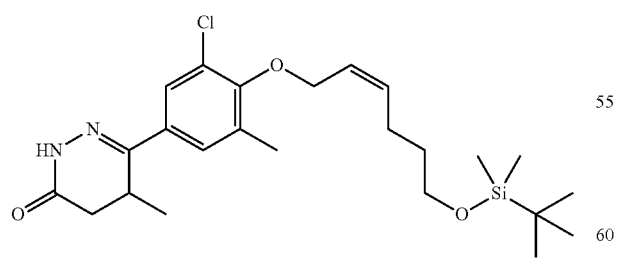

$^1$H-NMR (CDCl$_3$) δ: 0.06 (6H, s), 0.89 (9H, s), 1.24 (3H, d, J=7.6 Hz), 2.34 (3H, s), 2.47 (1H, dd, J=17.1, 1.0 Hz), 2.70 (1H, dd, J=17.1, 6.8 Hz), 3.24-3.33 (1H, m), 4.25-4.28 (2H, m), 4.57-4.61 (2H, m), 5.74-5.87 (2H, m), 7.47-7.49 (1H, m), 7.61 (1H, d, J=2.2 Hz), 8.60 (1H, brs).

Reference Example 146

6-{4-[(Z)-4-(tert-Butyldimethysilyloxy)-2-butenyloxy]-2-fluoro-3-vinylphenyl}-5-methyl-4,5-dihydro-2H-pyridazin-3-one

[Chem. 159]

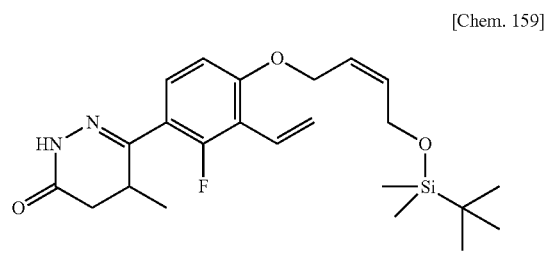 [SMILES: C=Cc1c(OC/C=C\CO[Si](C)(C)C(C)(C)C)ccc(C2=NNC(=O)CC2C)c1F]

$^1$H-NMR (CDCl$_3$) δ: 0.09 (6H, s), 0.91 (9H, s), 1.19 (3H, d, J=7.3 Hz), 2.42 (1H, dd, J=16.9 3.4 Hz), 2.73 (1H, dd, J=16.9, 6.6 Hz), 3.21-3.32 (1H, m), 4.28-4.34 (2H, m), 4.71-4.77 (2H, m), 5.50-5.58 (1H, m), 5.68-5.83 (2H, m), 6.04-6.09 (1H, m), 6.71 (1H, d, J=8.5 Hz), 6.80 (1H, dd, J=18.1, 12.2 Hz), 7.38 (1H, t, J=8.5 Hz), 8.52 (1H, brs).

Reference Example 147

6-{4-[(Z)-4-(tert-Butyldimethylsilyloxy)-2-butenyloxy]-2-fluoro-3-methylphenyl}-5-methyl-4,5-dihydro-2H-pyridazin-3-one

[Chem. 160]

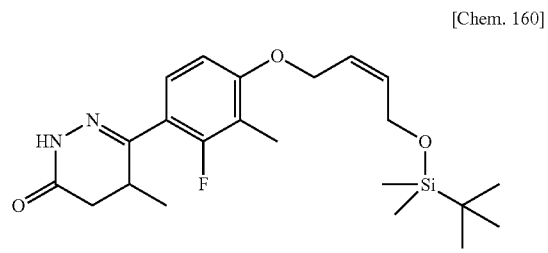

$^1$H-NMR (CDCl$_3$) δ: 0.09 (6H, s), 0.91 (9H, s), 1.20 (3H, d, J=7.1 Hz), 2.15 (3H, d, J=2.2 Hz), 2.42 (1H, dd, J=17.0, 3.5 Hz), 2.73 (1H, dd, J=17.0, 6.7 Hz), 3.20-3.33 (1H, m), 4.28-4.34 (2H, m), 4.67-4.75 (2H, m), 5.66-5.83 (2H, m), 6.66 (1H, d, J=8.8 Hz), 7.34 (1H, t, J=8.8 Hz), 8.43 (1H, s).

Reference Example 148

6-{4-[(Z)-4-(tert-Butyldimethylsilyloxy)-2-butenyloxy]-2,3-difluorophenyl}-5-methyl-4,5-dihydro-2H-pyridazin-3-one

[Chem. 161]

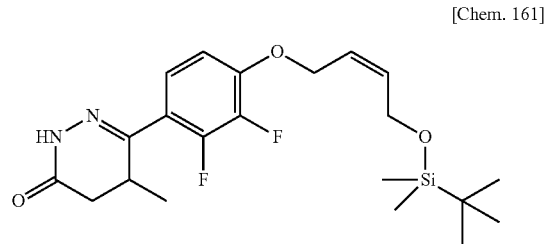 [SMILES: CC1CC(=O)NN=C1c1ccc(OC/C=C\CO[Si](C)(C)C(C)(C)C)c(F)c1F]

¹H-NMR (CDCl₃) δ: 0.09 (6H, s), 0.91 (9H, s), 1.22 (3H, d, J=7.1 Hz), 2.45 (1H, dd, J=17.0, 3.3 Hz), 2.74 (1H, dd, J=17.0, 6.7 Hz), 3.21-3.33 (1H, m), 4.32 (2H, dd, J=5.4, 1.5 Hz), 4.80 (2H, dd, J=5.9, 1.2 Hz), 5.66-5.75 (1H, m), 5.75-5.84 (1H, m), 6.75-6.84 (1H, m), 7.25-7.34 (1H, m), 8.51 (1H, brs).

Reference Example 149

6-{4-[(Z)-4-(tert-Butyldimethylsilyloxy)-2-butenyloxy]-3-chloro-5-fluorophenyl}-5-methyl-4,5-dihydro-2H-pyridazin-3-one

[Chem. 162]

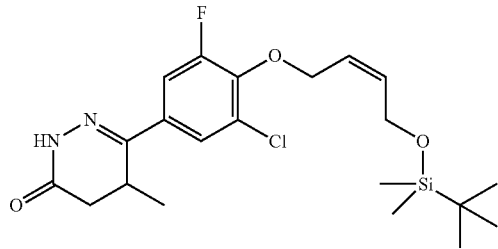

¹H-NMR (CDCl₃) δ: 0.06 (6H, s), 0.89 (9H, s), 1.24 (3H, d, J=7.6 Hz), 2.49 (1H, dd, J=17.0, 0.7 Hz), 2.70 (1H, dd, J=17.0, 7.0 Hz), 3.18-3.31 (1H, m), 4.26 (2H, d, J=3.9 Hz), 4.78 (2H, d, J=4.2 Hz), 5.73-5.83 (2H, m), 7.44 (1H, dd, J=12.0, 2.2 Hz), 7.54 (1H, t, J=2.2 Hz), 8.54 (1H, s).

Reference Example 150

6-{3-Bromo-4-[(Z)-4-(tert-butyldimethylsilyloxy)-2-butenyloxy]-5-fluorophenyl}-5-methyl-4,5-dihydro-2H-pyridazin-3-one

[Chem. 163]

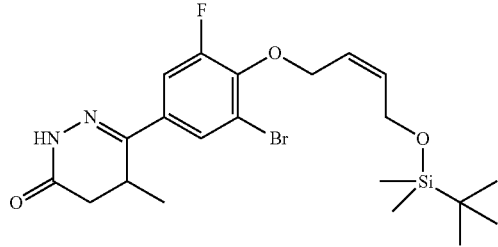

¹H-NMR (CDCl₃) δ: 0.06 (6H, s), 0.89 (9H, s), 1.24 (3H, d, J=7.3 Hz), 2.48 (1H, dd, J=17.1, 1.5 Hz), 2.70 (1H, dd, J=17.1, 6.8 Hz), 3.18-3.31 (1H, m), 4.27 (2H, d, J=4.6 Hz), 4.78 (2H, d, J=5.1 Hz), 5.73-5.83 (2H, m), 7.48 (1H, dd, J=12.1, 2.1 Hz), 7.70 (1H, t, J=2.1 Hz), 8.61 (1H, brs).

Reference Example 151

6-{4-[3-(tert-Butyldimethylsilyloxy)propoxy]-3-chloro-2-hydroxyphenyl}-5-methyl-4,5-dihydro-2H-pyridazin-3-one

[Chem. 164]

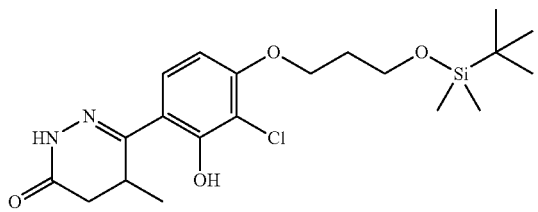

¹H-NMR (CDCl₃) δ: 0.04 (6H, s), 0.88 (9H, s), 1.30 (3H, d, J=7.3 Hz), 2.04 (2H, quintet, J=6.1 Hz), 2.52 (1H, d, J=17.1 Hz), 2.74 (1H, dd, J=17.1, 6.6 Hz), 3.38-3.50 (1H, m), 3.85 (2H, t, J=6.1 Hz), 4.19 (2H, t, J=6.1 Hz), 6.56 (1H, d, J=8.8 Hz), 7.30 (1H, d, J=8.8 Hz), 8.47 (1H, brs), 12.38 (1H, s).

Reference Example 152

6-{4-[3-(tert-Butyldimethylsilyloxy)propoxy]-2-hydroxy-3-methylphenyl}-5-methyl-4,5-dihydro-2H-pyridazin-3-one

[Chem. 165]

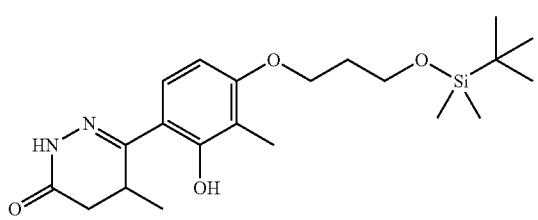

¹H-NMR (CDCl₃) δ: 0.04 (6H, s), 0.89 (9H, s), 1.29 (3H, d, J=7.3 Hz), 2.01 (2H, quintet, J=6.1 Hz), 2.13 (3H, s), 2.46-2.54 (1H, m), 2.72 (1H, dd, J=16.8, 6.6 Hz), 3.40-3.52 (1H, m), 3.83 (2H, t, J=6.1 Hz), 4.11 (2H, t, J=6.1 Hz), 6.48 (1H, d, J=8.8 Hz), 7.23-7.28 (1H, m), 8.37 (1H, brs), 11.89 (1H, s).

Reference Example 153

6-{4-[3-(tert-Butyldimethylsilyloxy)propoxy]-2-fluoro-3-vinylphenyl}-5-methyl-4,5-dihydro-2H-pyridazin-3-one

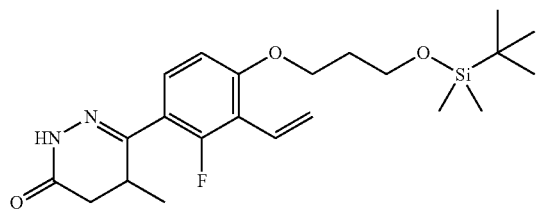

[Chem. 166]

$^1$H-NMR (CDCl$_3$) δ: 0.04 (6H, s), 0.88 (9H, s), 1.19 (3H, d, J=7.1 Hz), 2.03 (2H, quintet, J=6.1 Hz), 2.42 (1H, dd, J=16.9, 3.4 Hz), 2.73 (1H, dd, J=16.9, 6.6 Hz), 3.21-3.33 (1H, m), 3.82 (2H, t, J=6.1 Hz), 4.15 (2H, t, J=6.1 Hz), 5.49-5.57 (1H, m), 5.99-6.08 (1H, m), 6.73 (1H, d, J=8.8 Hz), 6.80 (1H, dd, J=18.1, 12.2 Hz), 7.38 (1H, t, J=8.8 Hz), 8.53 (1H, brs).

Reference Example 154

6-{4-[4-(tert-Butyldimethylsilyloxy)butoxy]-3-chloro-5-methylphenyl}-5-methyl-4,5-dihydro-2H-pyridazin-3-one

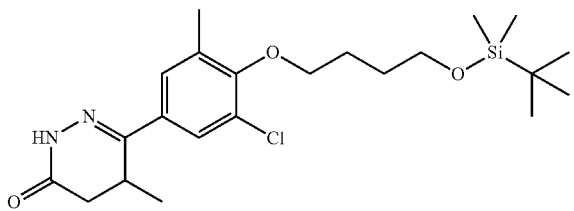

[Chem. 167]

$^1$H-NMR (CDCl$_3$) δ: 0.06 (6H, s), 0.90 (9H, s), 1.24 (3H, d, J=7.3 Hz), 1.70-1.80 (2H, m), 1.85-1.95 (2H, m), 2.33 (3H, s), 2.43-2.51 (1H, m), 2.68 (1H, dd, J=16.9, 6.8 Hz), 3.23-3.34 (1H, m), 3.70 (2H, t, J=6.4 Hz), 3.96 (2H, t, J=6.4 Hz), 7.47 (1H, dd, J=2.2, 0.7 Hz), 7.57-7.61 (1H, m), 8.54 (1H, s).

Reference Example 155

6-{3-Bromo-4-[4-(tert-butyldimethylsilyloxy)butoxy]-5-fluorophenyl}-5-methyl-4,5-dihydro-2H-pyridazin-3-one

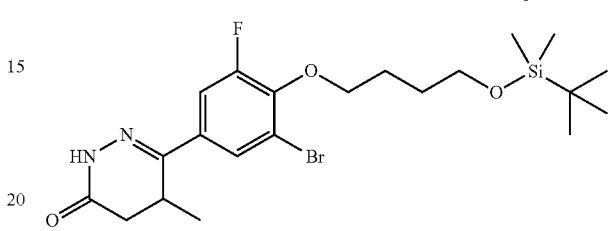

[Chem. 168]

$^1$H-NMR (CDCl$_3$) δ: 0.06 (6H, s), 0.89 (9H, s), 1.24 (3H, d, J=7.3 Hz), 1.69-1.79 (2H, m), 1.83-1.93 (2H, m), 2.48 (1H, dd, J=16.9, 1.0 Hz), 2.70 (1H, dd, J=16.9, 6.8 Hz), 3.18-3.32 (1H, m), 3.69 (2H, t, J=6.2 Hz), 4.19 (2H, td, J=6.5, 1.3 Hz), 7.48 (1H, dd, J=12.2, 2.2 Hz), 7.67-7.72 (1H, m), 8.55 (1H, brs).

Reference Example 156

6-{4-[4-(tert-Butyldimethylsilyloxy)butoxy]-3,5-dichlorophenyl}-5-methyl-4,5-dihydro-2H-pyridazin-3-one

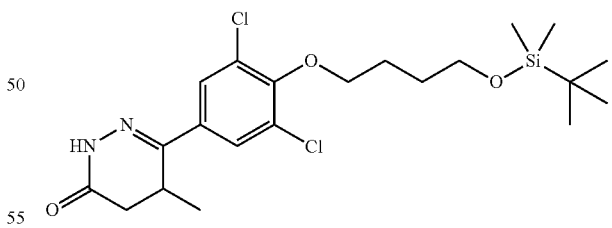

[Chem. 169]

$^1$H-NMR (CDCl$_3$) δ: 0.06 (6H, s), 0.90 (9H, s), 1.25 (3H, d, J=7.3 Hz), 1.71-1.82 (2H, m), 1.88-1.98 (2H, m), 2.49 (1H, d, J=16.9 Hz), 2.70 (1H, dd, J=16.9, 6.8 Hz), 3.19-3.33 (1H, m), 3.71 (2H, t, J=6.2 Hz), 4.08 (2H, t, J=6.5 Hz), 7.68 (2H, s), 8.53 (1H, brs).

Reference Example 157

6-{4-[4-(tert-Butyldimethylsilyloxy)butoxy]-2,3-difluorophenyl}-5-methyl-4,5-dihydro-2H-pyridazin-3-one

[Chem. 170]

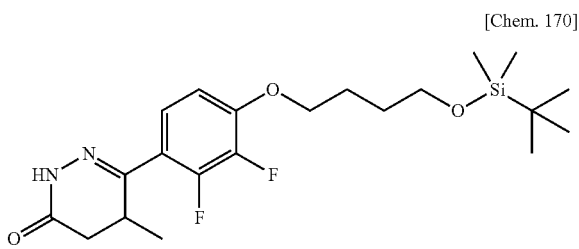 [SMILES: CC1CC(=O)NN=C1c1ccc(OCCCCO[Si](C)(C)C(C)(C)C)c(F)c1F]

¹H-NMR (CDCl₃) δ: 0.06 (6H, s), 0.90 (9H, s), 1.21 (3H, d, J=7.1 Hz), 1.64-1.76 (2H, m), 1.86-1.96 (2H, m), 2.45 (1H, dd, J=17.0, 2.9 Hz), 2.74 (1H, dd, J=17.0, 6.7 Hz), 3.20-3.34 (1H, m), 3.69 (2H, t, J=6.1 Hz), 4.12 (2H, t, J=6.5 Hz), 6.74-6.81 (1H, m), 7.24-7.34 (1H, m), 8.55 (1H, brs).

Reference Example 158

6-{4-[4-(tert-Butyldimethylsilyloxy)butoxy]-2-fluoro-3-methylphenyl}-5-methyl-4,5-dihydro-2H-pyridazin-3-one

[Chem. 171]

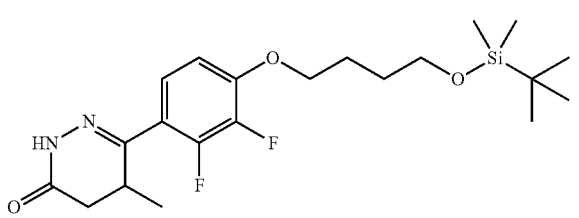

¹H-NMR (CDCl₃) δ: 0.06 (6H, s), 0.90 (9H, s), 1.19 (3H, d, J=7.1 Hz), 1.67-1.76 (2H, m), 1.82-1.94 (2H, m), 2.15 (3H, d, J=2.2 Hz), 2.42 (1H, dd, J=16.9, 3.5 Hz), 2.73 (1H, dd, J=16.9, 6.8 Hz), 3.22-3.33 (1H, m), 3.69 (2H, t, J=6.2 Hz), 4.03 (2H, t, J=6.3 Hz), 6.65 (1H, d, J=8.8 Hz), 7.34 (1H, t, J=8.8 Hz), 8.48 (1H, s).

Reference Example 159

6-{4-[4-(tert-Butyldimethylsilyloxy)butoxy]-3-chloro-2-fluorophenyl}-5-methyl-4,5-dihydro-2H-pyridazin-3-one

[Chem.172]

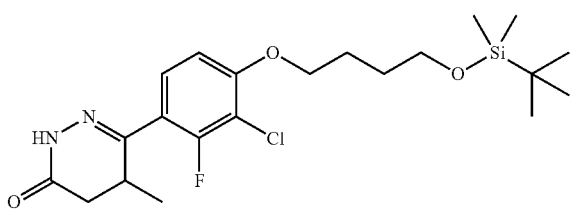

¹H-NMR (CDCl₃) δ: 0.06 (6H, s), 0.90 (9H, s), 1.21 (3H, d, J=7.3 Hz), 1.68-1.78 (2H, m), 1.87-1.99 (2H, m), 2.44 (1H, dd, J=17.0, 3.3 Hz), 2.74 (1H, dd, J=17.0, 6.7 Hz), 3.22-3.34 (1H, m), 3.70 (2H, t, J=6.2 Hz), 4.12 (2H, t, J=6.5 Hz), 6.76 (1H, dd, J=8.8, 1.2 Hz), 7.45 (1H, t, J=8.8 Hz), 8.49 (1H, s).

Reference Example 160

6-{4-[4-(tert-Butyldimethylsilyloxy)butoxy]-2-hydroxy-3-methylphenyl}-5-methyl-4,5-dihydro-2H-pyridazin-3-one

[Chem.173]

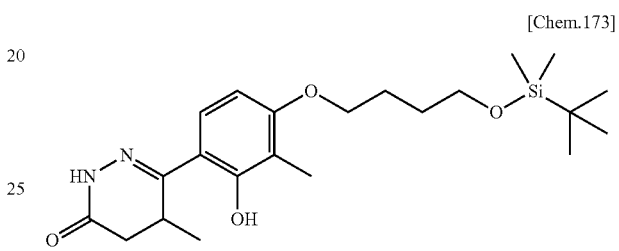

¹H-NMR (CDCl₃) δ: 0.06 (6H, s), 0.90 (9H, s), 1.28 (3H, d, J=7.6 Hz), 1.67-1.77 (2H, m), 1.83-1.94 (2H, m), 2.14 (3H, s), 2.49 (1H, d, J=17.1 Hz), 2.72 (1H, dd, J=17.1, 6.6 Hz), 3.40-3.50 (1H, m), 3.69 (2H, t, J=6.4 Hz), 4.03 (2H, t, J=6.4 Hz), 6.46 (1H, d, J=9.0 Hz), 7.24 (1H, d, J=9.0 Hz), 8.48 (1H, brs), 11.90 (1H, s).

Reference Example 161

6-{4-[4-(tert-Butyldimethylsilyloxy)butoxy]-3-chloro-2-hydroxyphenyl}-5-methyl-4,5-dihydro-2H-pyridazin-3-one

[Chem.174]

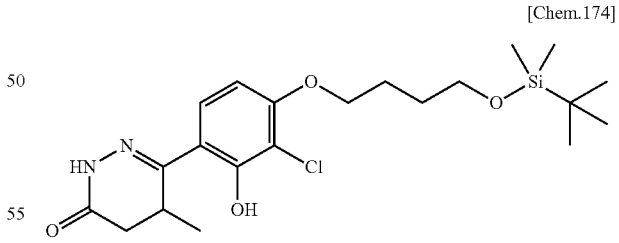

¹H-NMR (CDCl₃) δ: 0.06 (6H, s), 0.90 (9H, s), 1.29 (3H, d, J=7.6 Hz), 1.68-1.78 (2H, m), 1.88-1.98 (2H, m), 2.49-2.55 (1H, m), 2.74 (1H, dd, J=17.1, 6.6 Hz), 3.38-3.48 (1H, m), 3.70 (2H, t, J=6.4 Hz), 4.11 (2H, t, J=6.4 Hz), 6.53 (1H, d, J=9.0 Hz), 7.29 (1H, d, J=9.0 Hz), 8.57 (1H, brs), 12.40 (1H, s).

Reference Example 162

6-{4-[4-(tert-Butyldimethylsilyloxy)butoxy]-2-fluoro-3-vinylphenyl}-5-methyl-4,5-dihydro-2H-pyridazin-3-one

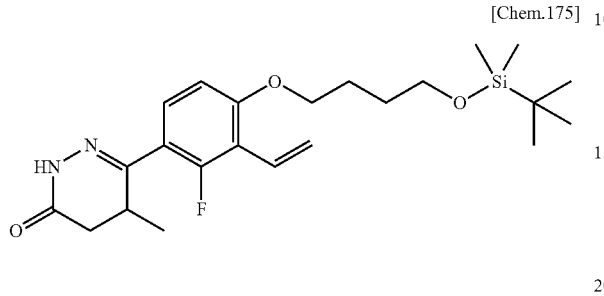

[Chem.175]

$^1$H-NMR (CDCl$_3$) δ: 0.06 (6H, s), 0.90 (9H, s), 1.19 (3H, d, J=7.1 Hz), 1.66-1.76 (2H, m), 1.86-1.97 (2H, m), 2.42 (1H, dd, J=16.9, 3.4 Hz), 2.73 (1H, dd, J=16.9, 6.6 Hz), 3.21-3.32 (1H, m), 3.69 (2H, t, J=6.4 Hz), 4.07 (2H, t, J=6.4 Hz), 5.49-5.57 (1H, m), 6.01-6.09 (1H, m), 6.70 (1H, d, J=8.1 Hz), 6.81 (1H, dd, J=18.1, 12.0 Hz), 7.35-7.40 (1H, m), 8.51 (1H, brs).

Reference Example 163

6-{4-[4-(tert-Butyldimethylsilyloxy)butoxy]-3-ethyl-2-fluorophenyl}-5-methyl-4,5-dihydro-2H-pyridazin-3-one

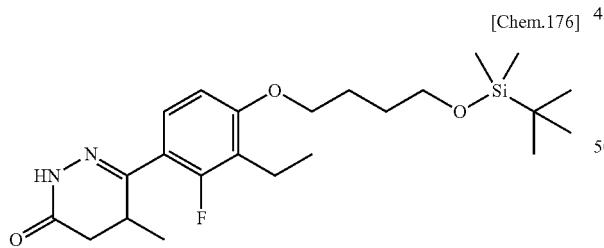

[Chem.176]

$^1$H-NMR (CDCl$_3$) δ: 0.06 (6H, s), 0.90 (9H, s), 1.14 (3H, t, J=7.3 Hz), 1.19 (3H, d, J=7.3 Hz), 1.66-1.76 (2H, m), 1.82-1.94 (2H, m), 2.41 (1H, dd, J=17.1, 3.4 Hz), 2.64-2.78 (3H, m), 3.21-3.32 (1H, m), 3.69 (2H, t, J=6.4 Hz), 4.03 (2H, t, J=6.4 Hz), 6.66 (1H, d, J=8.5 Hz), 7.34 (1H, t, J=8.5 Hz), 8.48 (1H, brs).

Reference Example 164

6-{4-[(E)-4-(tert-Butyldimethylsilyloxy)-2-butenyloxy]-3-chloro-2-fluorophenyl}-5-methyl-4,5-dihydro-2H-pyridazin-3-one

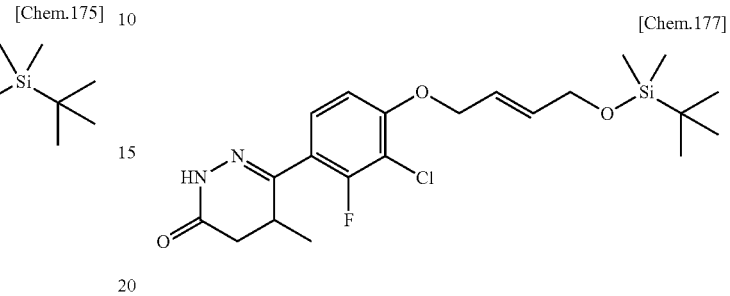

[Chem.177]

$^1$H-NMR (CDCl$_3$) δ: 0.08 (6H, s), 0.92 (9H, s), 1.21 (3H, d, J=7.1 Hz), 2.44 (1H, dd, J=17.0, 3.3 Hz), 2.74 (1H, dd, J=17.0, 6.7 Hz), 3.23-3.32 (1H, m), 4.22-4.25 (2H, m), 4.66-4.69 (2H, m), 5.90-6.03 (2H, m), 6.77 (1H, dd, J=8.8, 1.5 Hz), 7.45 (1H, t, J=8.8 Hz), 8.49 (1H, brs).

Reference Example 165

6-{4-[5-(tert-Butyldimethylsilyloxy)pentoxy]-3-chloro-2-fluorophenyl}-5-methyl-4,5-dihydro-2H-pyridazin-3-one

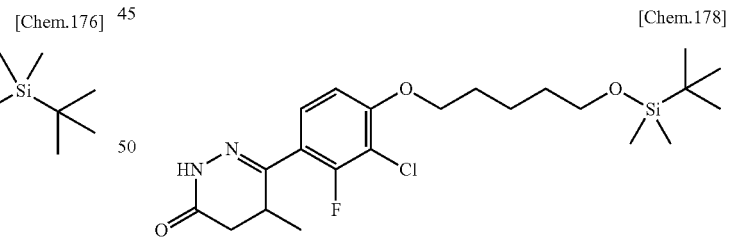

[Chem.178]

$^1$H-NMR (CDCl$_3$) δ: 0.05 (6H, s), 0.89 (9H, s), 1.20 (3H, d, J=7.3 Hz), 1.50-1.65 (4H, m), 1.88 (2H, quintet, J=6.6 Hz), 2.43 (1H, dd, J=17.1, 3.2 Hz), 2.73 (1H, dd, J=17.1, 6.8 Hz), 3.22-3.33 (1H, m), 3.65 (2H, t, J=6.1 Hz), 4.08 (2H, t, J=6.6 Hz), 6.75 (1H, dd, J=9.0, 1.5 Hz), 7.42-7.49 (1H, m), 8.49 (1H, brs).

Reference Example 166

Production of 2,2-difluoro-3-[3-fluoro-2-methyl-4-(4-methyl-6-oxo-4,5-dihydro-1H-pyridazin-3-yl)phenoxy]propyl Benzoate

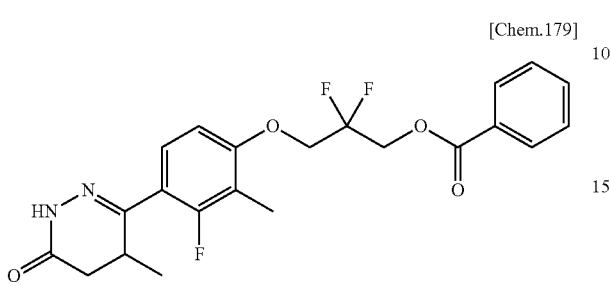

[Chem.179]

A mixture of 2,2-difluoro-3-[3-fluoro-2-methyl-4-(4-methyl-6-oxo-4,5-dihydro-1H-pyridazin-3-yl)phenoxy]propyl methanesulfonate (Reference example 135, 324 mg) and sodium benzoate (229 mg) in DMF (4 mL) was stirred at 180° C. under microwave irradiation for 30 minutes. To the reaction mixture was added water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=70:30 to 50:50) to afford the title compound as a white solid (253 mg).

$^1$H-NMR (DMSO-d6) δ: 1.02 (3H, d, J=7.1 Hz), 2.12 (3H, d, J=2.2 Hz), 2.23 (1H, dd, J=16.7, 3.8 Hz), 2.67 (1H, dd, J=16.7, 6.8 Hz), 3.03-3.19 (1H, m), 4.63 (2H, t, J=12.7 Hz), 4.84 (2H, t, J=13.8 Hz), 7.01 (1H, d, J=8.8 Hz), 7.40 (1H, t, J=8.8 Hz), 7.52-7.60 (2H, m), 7.67-7.75 (1H, m), 7.98-8.05 (2H, m), 10.96 (1H, s).

The following compounds were prepared from each appropriate starting material in a similar manner to Reference example 166.

Reference Example 167

3-[2,3-Difluoro-4-(4-methyl-6-oxo-4,5-dihydro-1H-pyridazin-3-yl)phenoxy]-2,2-difluoropropyl Benzoate

[Chem.180]

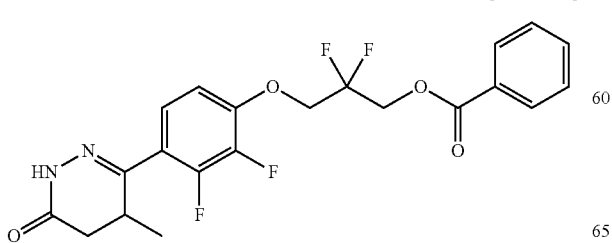

$^1$H-NMR (DMSO-d6) δ: 1.04 (3H, d, J=7.1 Hz), 2.25 (1H, dd, J=16.9, 3.4 Hz), 2.71 (1H, dd, J=16.9, 6.8 Hz), 3.08-3.22 (1H, m), 4.67-4.87 (4H, m), 7.20-7.27 (1H, m), 7.37-7.46 (1H, m), 7.53-7.60 (2H, m), 7.68-7.74 (1H, m), 7.98-8.05 (2H, m), 11.06 (1H, s).

Reference Example 168

3-[2,6-Dichloro-4-(4-methyl-6-oxo-4,5-dihydro-1H-pyridazin-3-yl)phenoxy]-2,2-difluoropropyl Benzoate

[Chem.181]

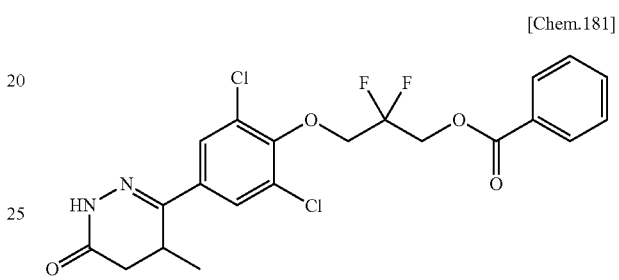

$^1$H-NMR (DMSO-d6) δ: 1.03 (3H, d, J=7.3 Hz), 2.24 (1H, d, J=16.9 Hz), 2.69 (1H, dd, J=16.9, 6.8 Hz), 3.39-3.49 (1H, m), 4.56 (2H, t, J=12.8 Hz), 4.86 (2H, t, J=13.6 Hz), 7.54-7.61 (2H, m), 7.68-7.76 (1H, m), 7.83-7.88 (2H, m), 7.99-8.06 (2H, m), 11.12 (1H, s).

Reference Example 169

3-[2-Chloro-3-fluoro-4-(4-methyl-6-oxo-4,5-dihydro-1H-pyridazin-3-yl)phenoxy]-2,2-difluoropropyl Benzoate

[Chem.182]

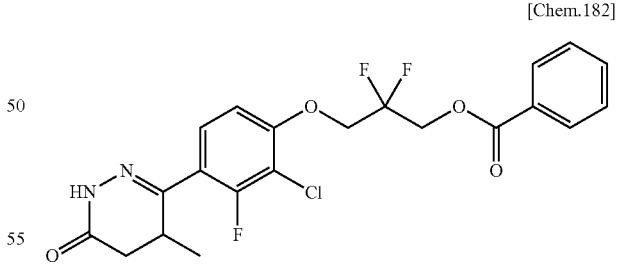

$^1$H-NMR (DMSO-d6) δ: 1.03 (3H, d, J=7.3 Hz), 2.25 (1H, dd, J=16.9, 3.7 Hz), 2.70 (1H, dd, J=16.9, 6.8 Hz), 3.06-3.21 (1H, m), 4.67-4.91 (4H, m), 7.20-7.28 (1H, m), 7.52-7.63 (3H, m), 7.67-7.74 (1H, m), 7.98-8.05 (2H, m), 11.05 (1H, s).

Reference Example 170

3-[2-Chloro-6-fluoro-4-(4-methyl-6-oxo-4,5-di-hydro-1H-pyridazin-3-yl)phenoxy]-2,2-difluoropropyl Benzoate

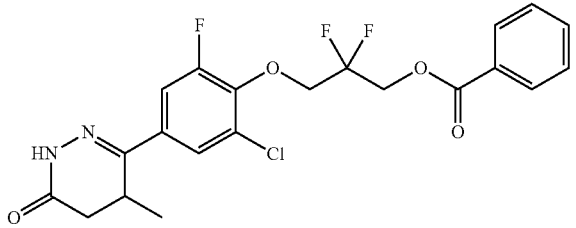

[Chem.183]

¹H-NMR (DMSO-d6) δ: 1.03 (3H, d, J=7.3 Hz), 2.24 (1H, d, J=16.7 Hz), 2.69 (1H, dd, J=16.7, 7.0 Hz), 3.34-3.45 (1H, m), 4.67 (2H, t, J=12.9 Hz), 4.83 (2H, t, J=13.7 Hz), 7.52-7.61 (2H, m), 7.64-7.75 (3H, m), 7.98-8.04 (2H, m), 11.09 (1H, s).

Reference Example 171

3-[2-Bromo-3-fluoro-4-(4-methyl-6-oxo-4,5-di-hydro-1H-pyridazin-3-yl)phenoxy]-2,2-difluoropropyl Benzoate

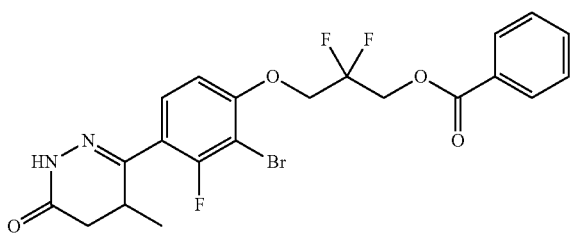

[Chem.184]

¹H-NMR (DMSO-d6) δ: 1.03 (3H, d, J=7.3 Hz), 2.25 (1H, dd, J=16.9, 3.9 Hz), 2.70 (1H, dd, J=16.9, 6.8 Hz), 3.07-3.19 (1H, m), 4.75 (2H, t, J=12.6 Hz), 4.84 (2H, t, J=13.9 Hz), 7.19 (1H, dd, J=8.8, 1.2 Hz), 7.53-7.64 (3H, m), 7.67-7.74 (1H, m), 7.98-8.04 (2H, m), 11.05 (1H, s).

Reference Example 172

3-[2-Chloro-6-methyl-4-(4-methyl-6-oxo-4,5-di-hydro-1H-pyridazin-3-yl)phenoxy]-2,2-difluoropropyl Benzoate

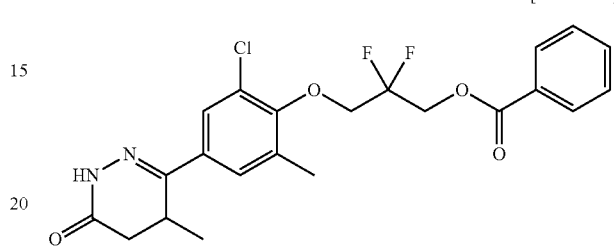

[Chem.185]

¹H-NMR (DMSO-d6) δ: 1.04 (3H, d, J=7.3 Hz), 2.23 (1H, d, J=16.9 Hz), 2.33 (3H, s), 2.68 (1H, dd, J=16.9, 6.8 Hz), 3.27-3.43 (1H, m), 4.45 (2H, t, J=12.9 Hz), 4.85 (2H, t, J=13.6 Hz), 7.55-7.61 (2H, m), 7.62-7.64 (1H, m), 7.67-7.69 (1H, m), 7.70-7.75 (1H, m), 8.00-8.07 (2H, m), 11.01 (1H, s).

Reference Example 173

2,2-Difluoro-3-[3-fluoro-4-(4-methyl-6-oxo-4,5-dihydro-1H-pyridazin-3-yl)-2-vinylphenoxy]propyl Benzoate

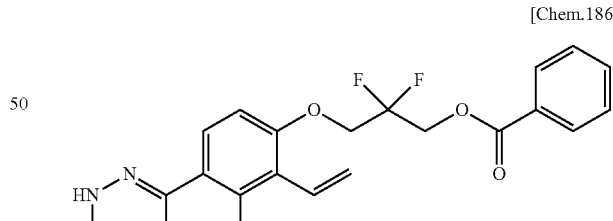

[Chem.186]

¹H-NMR (CDCl₃) δ: 1.19 (3H, d, J=7.1 Hz), 2.43 (1H, dd, J=17.1, 3.7 Hz), 2.70-2.80 (1H, m), 3.19-3.31 (1H, m), 4.39 (2H, t, J=11.2 Hz), 4.75 (2H, t, J=12.5 Hz), 5.55-5.62 (1H, m), 5.97-6.05 (1H, m), 6.70-6.81 (2H, m), 7.37-7.49 (3H, m), 7.56-7.64 (1H, m), 8.00-8.06 (2H, m), 8.51 (1H, brs).

Reference Example 174

Production of (3R)-4-(3-chloro-4-hydroxy-5-methylphenyl)-3-methyl-N-[(1S)-1-(4-nitrophenyl)ethyl]-4-oxobutanamide

[Chem. 187]

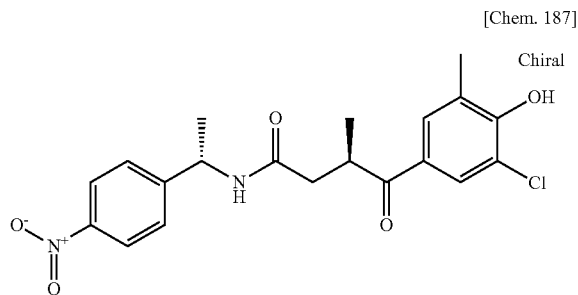 [SMILES: Cc1cc(C(=O)[C@H](C)CC(=O)N[C@@H](C)c2ccc([N+](=O)[O-])cc2)cc(Cl)c1O]

To a mixture of 4-(3-chloro-4-hydroxy-5-methylphenyl)-3-methyl-4-oxobutanoic acid (Reference example 71, 317 mg) in DMF (10 mL) were added (S)-1-(4-nitrophenyl)ethylamine hydrochloride (275 mg), triethylamine (0.189 mL), 1-hydroxybenzotriazole monohydrate (208 mg), and 1-(3-dimethylaminopropyl)-3-ethylcarbodiimide hydrochloride (260 mg). The reaction mixture was stirred at room temperature for 3 days. To the reaction mixture was added saturated aqueous sodium bicarbonate, and the mixture was extracted with ethyl acetate. The organic layer was washed with water and brine, dried over anhydrous sodium sulfate, and filtrated, and the solvent was removed. The obtained crude diastereomer was purified by silica gel column chromatography (heptane:ethyl acetate=67:33 to 25:75) to afford the title compound as a pale yellow amorphous (206 mg).

$^1$H-NMR (CDCl$_3$) δ: 1.18 (3H, d, J=7.1 Hz), 1.44 (3H, d, J=7.1 Hz), 2.30-2.38 (4H, m), 2.80 (1H, dd, J=14.9, 9.0 Hz), 3.85-3.97 (1H, m), 5.07 (1H, quintet, J=7.1 Hz), 5.99 (1H, d, J=6.8 Hz), 6.08 (1H, s), 7.41-7.48 (2H, m), 7.70 (1H, d, J=1.5 Hz), 7.85 (1H, d, J=2.2 Hz), 8.15-8.22 (2H, m).

Reference Example 175

Production of 2-{2-chloro-6-methyl-4-[(2R)-2-methyl-3-{[(1S)-1-(4-nitrophenyl)ethyl]carbamoyl}propanoyl]phenoxy}ethyl 4-bromobenzoate

[Chem. 188]

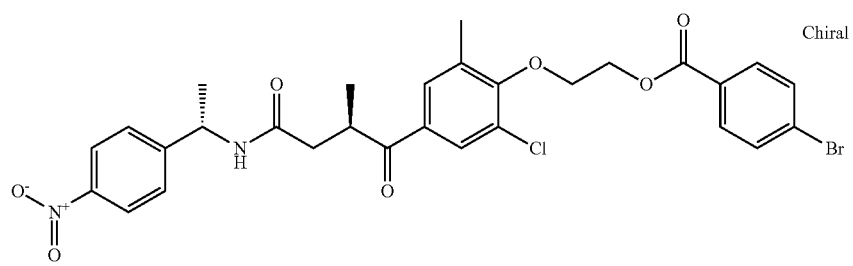

To a mixture of (3R)-4-(3-chloro-4-hydroxy-5-methylphenyl)-3-methyl-N-[(1S)-1-(4-nitrophenyl)ethyl]-4-oxobutanamide (Reference example 174, 206 mg) in THF (5.0 mL) were added 2-hydroxyethyl 4-bromobenzoate (162 mg) and triphenylphosphine (174 mg), and the mixture was cooled on ice bath. Bis(2-methoxyethyl) azodicarboxylate (155 mg) was slowly added to the reaction mixture, and then the reaction mixture was stirred at room temperature overnight. The solvent was removed, and the obtained crude product was purified by silica gel column chromatography (heptane:ethyl acetate=67:33 to 33:67) to afford the title compound as a colorless solid (205 mg).

$^1$H-NMR (CDCl$_3$) δ: 1.17 (3H, d, J=7.3 Hz), 1.45 (3H, d, J=7.1 Hz), 2.31-2.39 (4H, m), 2.82 (1H, dd, J=14.9, 9.3 Hz), 3.85-3.96 (1H, m), 4.32-4.38 (2H, m), 4.64-4.70 (2H, m), 5.08 (1H, quintet, J=7.1 Hz), 5.96 (1H, d, J=7.1 Hz), 7.41-7.47 (2H, m), 7.57-7.63 (2H, m), 7.71 (1H, d, J=1.5 Hz), 7.85 (1H, d, J=2.2 Hz), 7.87-7.93 (2H, m), 8.15-8.21 (2H, m).

The obtained compound was recrystallized from ethyl acetate/heptane to give a single crystal thereof. According to the X-ray crystal structure analysis of the single crystal, the stereochemistry at the 3rd position of the butanamide moiety thereof was determined as R.

<Crystallographic Data>

Composition formula: $C_{29}H_{28}BrClN_2O_7$, Molecular weight: 631.90, monoclinic Space group P2$_1$(#4), a=4.7154(5)Å, b=20.026(2)Å, c=15.3231(18)Å, V=1433.7(3)Å$^3$, Z=2, Dc=1.464 g/cm$^3$, R-factor=0.1308

Reference Example 176

Production of 3-bromo-2-fluoro-4-hydroxy-5-methylbenzaldehyde

[Chem. 189]

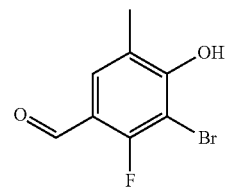

To a solution of 2-fluoro-4-hydroxy-5-methylbenzaldehyde (3.39 g) in acetic acid (20 mL) was added pyridinium bromide perbromide (8.44 g), and the mixture was stirred at 75° C. for one hour. The reaction mixture was allowed to cool to room temperature. To the reaction mixture was added water, and the precipitates were collected on a filter, washed with water, and dried to afford the title compound as a pale brown solid (4.77 g).

¹H-NMR (DMSO-d6) δ: 2.25 (3H, s), 7.59 (1H, dd, J=8.1, 0.7 Hz), 10.02 (1H, s), 10.82 (1H, brs).

The following compound was prepared from the appropriate starting material in a similar manner to Reference example 28.

Reference Example 177

2-Fluoro-4-(methoxymethyloxy)-3,5-dimethylbenzaldehyde

[Chem. 190]

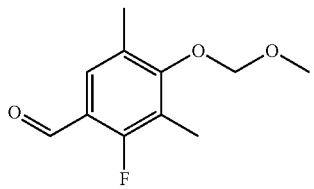

¹H-NMR (CDCl₃) δ: 2.25 (3H, d, J=2.3 Hz), 2.29 (3H, s), 3.62 (3H, s), 5.03 (2H, s), 7.55 (1H, d, J=7.9 Hz), 10.27 (1H, s).

The following compound was prepared from the appropriate starting material in a similar manner to Reference example 30.

Reference Example 178

3-Chloro-2,5-difluoro-4-methoxybenzaldehyde

[Chem. 191]

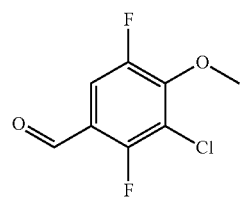

¹H-NMR (CDCl₃) δ: 4.16 (3H, d, J=3.4 Hz), 7.53 (1H, dd, J=11.4, 6.3 Hz), 10.23 (1H, d, J=3.2 Hz).

Reference Example 179

Production of 5-chloro-2,4-dihydroxy-3-methylbenzaldehyde

[Chem. 192]

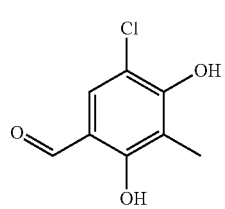

To a mixture of 2,4-dihydroxy-3-methylbenzaldehyde (6.09 g) in dichloroethane (80 mL) was added N-chlorosuccinimide (6.41 g), and the mixture was stirred at 60° C. for 3 hours. The solvent was removed, and the residue was dissolved in ethyl acetate. The solution was washed with water and brine, dried over anhydrous sodium sulfate, filtrated, and then concentrated. The obtained crude product was purified by silica gel column chromatography (heptane: ethyl acetate=95:5 to 74:26) to afford the title compound as a white solid (6.76 g).

¹H-NMR (DMSO-d6) δ: 2.07 (3H, d, J=0.6 Hz), 7.68-7.70 (1H, m), 9.77 (1H, s), 10.52 (1H, brs), 11.36 (1H, s).

Reference Example 180

Production of 2,4-bis(benzyloxy)-5-chloro-3-methylbenzaldehyde

[Chem. 193]

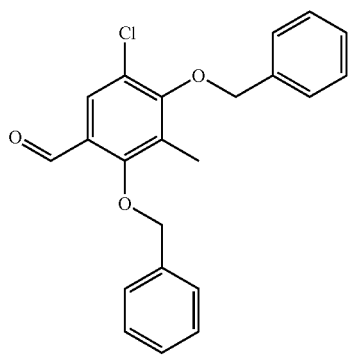

To a mixture of 5-chloro-2,4-dihydroxy-3-methylbenzaldehyde (Reference example 179, 6.76 g) in DMF (75 mL) were added potassium carbonate (15.0 g) and benzyl bromide (10.8 mL), and the mixture was stirred at room temperature for one hour. To the reaction mixture was added water, and the mixture was extracted with ethyl acetate. The organic layer was washed with water and brine, dried over anhydrous sodium sulfate, filtrated, and concentrated. The obtained solid was washed by trituration with diisopropyl ether, and then collected on a filter to afford the title compound as a pale brown solid (11.3 g).

¹H-NMR (DMSO-d6) δ: 2.20 (3H, d, J=0.5 Hz), 5.03 (2H, s), 5.05 (2H, s), 7.35-7.55 (10H, m), 7.66-7.67 (1H, m), 9.99 (1H, s).

The following compound was prepared from the appropriate starting material in a similar manner to Reference example 180.

Reference Example 181

2,4-Bis(benzyloxy)-3-chloro-5-methylbenzaldehyde

[Chem. 194]

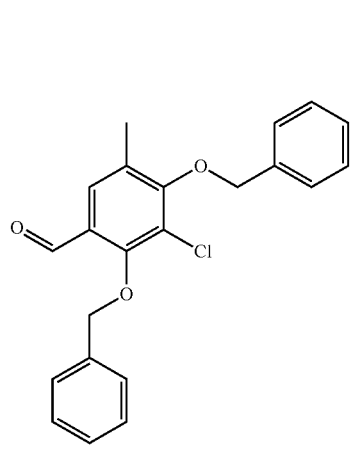

$^1$H-NMR (CDCl$_3$) δ: 2.25 (3H, d, J=0.7 Hz), 5.06 (2H, s), 5.14 (2H, s), 7.35-7.53 (10H, m), 7.58 (1H, d, J=0.7 Hz), 10.05 (1H, s).

Reference Example 182

Production of 4-benzyloxy-5-chloro-2-hydroxy-3-methylbenzaldehyde

[Chem. 195]

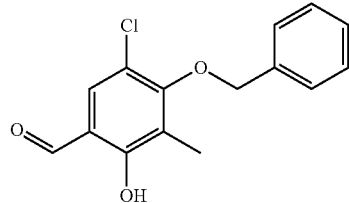

To a mixture of 2,4-bis(benzyloxy)-5-chloro-3-methylbenzaldehyde (Reference example 180, 11.33 g) in toluene (140 mL)/diethyl ether (20 mL) was added magnesium bromide (8.53 g). Under an argon atmosphere, the mixture was stirred at 100° C. for one hour. The reaction mixture was allowed to cool to room temperature, 1 M hydrochloric acid was added thereto, and then the mixture was extracted with ethyl acetate. The organic layer was washed with brine, dried over anhydrous sodium sulfate, filtrated, and then concentrated. The obtained crude product was purified by silica gel column chromatography (heptane:ethyl acetate=95:5 to 90:10 to 75:25) to afford the title compound as a white solid (4.26 g).

$^1$H-NMR (CDCl$_3$) δ: 2.15 (3H, d, J=0.5 Hz), 5.02 (2H, s), 7.34-7.53 (6H, m), 9.77 (1H, s), 11.37 (1H, s).

The following compounds were prepared from each appropriate starting material in a similar manner to Reference example 182.

Reference Example 183

4-Benzyloxy-3-chloro-2-hydroxy-5-methylbenzaldehyde

[Chem. 196]

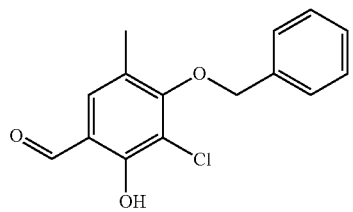

$^1$H-NMR (CDCl$_3$) δ: 2.21 (3H, d, J=0.9 Hz), 5.08 (2H, s), 7.29-7.31 (1H, m), 7.36-7.53 (5H, m), 9.79 (1H, s), 11.57 (1H, s).

The following compounds were prepared from each appropriate starting material in a similar manner to Reference example 32.

Reference Example 184

2-Fluoro-4-(methoxymethyloxy)-5-methylbenzaldehyde

[Chem. 197]

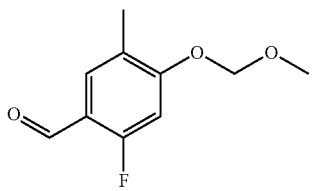

$^1$H-NMR (CDCl$_3$) δ: 2.22 (3H, s), 3.49 (3H, s), 5.26 (2H, s), 6.85 (1H, d, J=12.5 Hz), 7.65 (1H, dd, J=8.1, 0.7 Hz), 10.21 (1H, s).

Reference Example 185

3-Bromo-2-fluoro-4-(methoxymethyloxy)-5-methylbenzaldehyde

[Chem. 198]

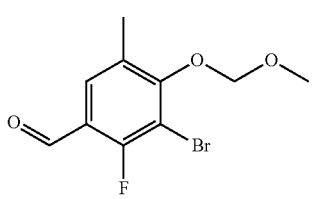

$^1$H-NMR (CDCl$_3$) δ: 2.36-2.39 (3H, m), 3.66 (3H, s), 5.18 (2H, s), 7.67 (1H, dd, J=7.7, 0.7 Hz), 10.26 (1H, s).

Reference Example 186

4-Benzyloxy-3-chloro-2-(methoxymethyloxy)-5-methylbenzaldehyde

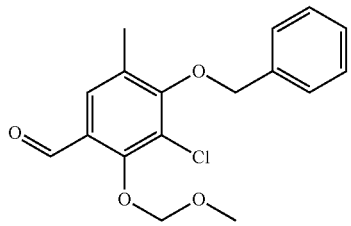
[Chem. 199]

¹H-NMR (CDCl₃) δ: 2.26 (3H, d, J=0.7 Hz), 3.63 (3H, s), 5.03 (2H, s), 5.20 (2H, s), 7.34-7.51 (5H, m), 7.62-7.63 (1H, m), 10.27 (1H, s).

Reference Example 187

4-Benzyloxy-5-chloro-2-(methoxymethyloxy)-3-methylbenzaldehyde

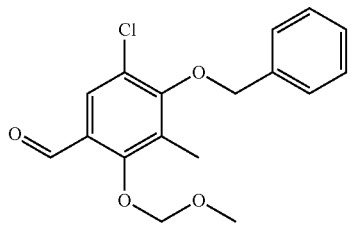
[Chem. 200]

¹H-NMR (CDCl₃) δ: 2.19 (3H, d, J=0.5 Hz), 3.58 (3H, s), 5.03 (2H, s), 5.04 (2H, s), 7.34-7.50 (5H, m), 7.78-7.80 (1H, m), 10.20 (1H, s).

The following compounds were prepared from each appropriate starting material in a similar manner to Reference example 41.

Reference Example 188

Methyl 4-[2-fluoro-4-(methoxymethyloxy)-5-methylphenyl]-3-methyl-4-oxobutanoate

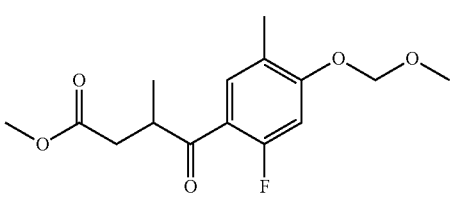
[Chem. 201]

¹H-NMR (CDCl₃) δ: 1.21 (3H, d, J=7.1 Hz), 2.20 (3H, s), 2.41 (1H, dd, J=16.7, 5.9 Hz), 2.94 (1H, ddd, J=16.7, 8.4, 1.8 Hz), 3.49 (3H, s), 3.65 (3H, s), 3.73-3.84 (1H, m), 5.24 (2H, s), 6.83 (1H, d, J=13.2 Hz), 7.69 (1H, d, J=8.5 Hz).

Reference Example 189

Methyl 4-(3-chloro-2,5-difluoro-4-methoxyphenyl)-3-methyl-4-oxobutanoate

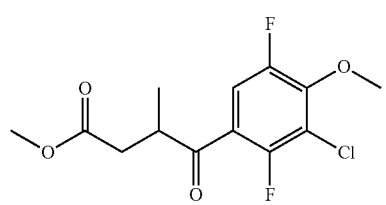
[Chem. 202]

¹H-NMR (CDCl₃) δ:1.22 (3H, dd, J=7.2, 1.0 Hz), 2.45 (1H, dd, J=17.0, 5.1 Hz), 2.97 (1H, ddd, J=17.0, 9.1, 1.9 Hz), 3.65 (3H, s), 3.69-3.80 (1H, m), 4.12 (3H, d, J=3.1 Hz), 7.57 (1H, dd, J=12.1, 6.5 Hz).

Reference Example 190

Methyl 4-[2-fluoro-4-(methoxymethyloxy)-3,5-dimethylphenyl]-3-methyl-4-oxobutanoate

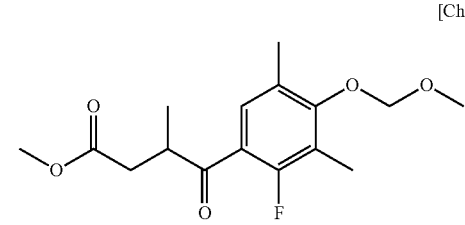
[Chem. 203]

¹H-NMR (CDCl₃) δ: 1.21 (3H, d, J=7.1 Hz), 2.24 (3H, d, J=2.7 Hz), 2.27 (3H, s), 2.42 (1H, dd, J=16.7, 5.7 Hz), 2.94 (1H, ddd, J=16.7, 8.4, 1.6 Hz), 3.61 (3H, s), 3.65 (3H, s), 3.73-3.86 (1H, m), 5.00 (2H, s), 7.52 (1H, d, J=8.5 Hz).

Reference Example 191

Methyl 4-[4-benzyloxy-3-chloro-2-(methoxymethyloxy)-5-methylphenyl]-3-methyl-4-oxobutanoate

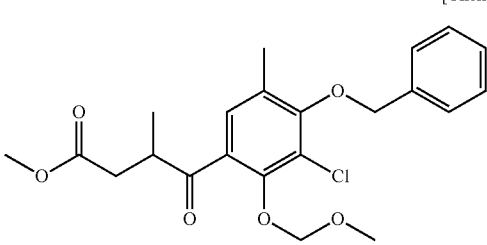
[Chem. 204]

¹H-NMR (CDCl₃) δ:1.15 (3H, d, J=7.3 Hz), 2.25 (3H, d, J=0.6 Hz), 2.40 (1H, dd, J=16.6, 6.1 Hz), 2.87 (1H, dd, J=16.6, 7.8 Hz), 3.57 (3H, s), 3.68 (3H, s), 3.82-3.92 (1H, m), 5.00 (2H, s), 5.08 (1H, d, J=5.6 Hz), 5.13 (1H, d, J=5.6 Hz), 7.32-7.33 (1H, m), 7.35-7.53 (5H, m).

Reference Example 192

Methyl 4-[4-benzyloxy-5-chloro-2-(methoxymethyl-oxy)-3-methylphenyl]-3-methyl-4-oxobutanoate

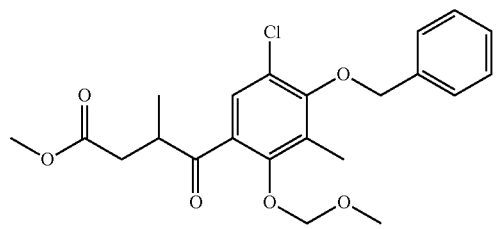
[Chem. 205]

$^1$H-NMR (CDCl$_3$) δ: 1.14 (3H, d, J=7.2 Hz), 2.23 (3H, d, J=0.5 Hz), 2.39 (1H, dd, J=16.7, 5.9 Hz), 2.87 (1H, dd, J=16.7, 8.1 Hz), 3.50 (3H, s), 3.68 (3H, s), 3.76-3.87 (1H, m), 4.92 (1H, d, J=6.0 Hz), 4.99 (1H, d, J=6.0 Hz), 5.00 (2H, s), 7.34-7.52 (6H, m).

The following compounds were prepared from each appropriate starting material in a similar manner to Reference example 63.

Reference Example 193

4-(3-Chloro-2,5-difluoro-4-methoxyphenyl)-3-methyl-4-oxobutanoic Acid

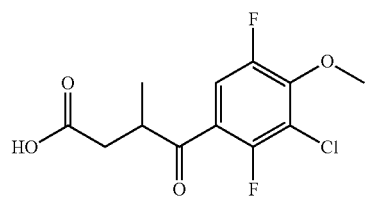
[Chem. 206]

$^1$H-NMR (DMSO-d6) δ: 1.10 (3H, d, J=7.1 Hz), 2.43 (1H, dd, J=17.0, 5.1 Hz), 2.71 (1H, ddd, J=17.0, 8.8, 1.2 Hz), 3.57-3.69 (1H, m), 4.08 (3H, d, J=2.9 Hz), 7.73 (1H, dd, J=12.2, 6.7 Hz), 12.25 (1H, s).

Reference Example 194

4-[2-Fluoro-4-(methoxymethyloxy)-3,5-dimethyl-phenyl]-3-methyl-4-oxobutanoic Acid

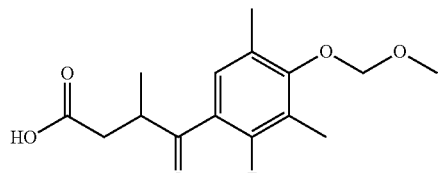
[Chem. 207]

$^1$H-NMR (DMSO-d6) δ: 1.08 (3H, d, J=7.1 Hz), 2.19 (3H, d, J=2.4 Hz), 2.25 (3H, s), 2.37 (1H, dd, J=16.9, 5.3 Hz), 2.69 (1H, ddd, J=16.9, 8.9, 1.3 Hz), 3.52 (3H, s), 3.58-3.68 (1H, m), 5.04 (2H, s), 7.50 (1H, d, J=8.5 Hz), 12.16 (1H, brs).

Reference Example 195

4-[4-Benzyloxy-3-chloro-2-(methoxymethyloxy)-5-methylphenyl]-3-methyl-4-oxobutanoic Acid

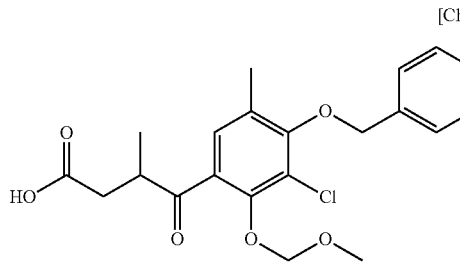
[Chem. 208]

$^1$H-NMR (DMSO-d6) δ: 1.05 (3H, d, J=7.2 Hz), 2.25 (3H, s), 2.34 (1H, dd, J=16.7, 6.0 Hz), 2.64 (1H, dd, J=16.7, 7.7 Hz), 3.45 (3H, s), 3.67-3.77 (1H, m), 4.98-5.02 (3H, m), 5.04 (1H, d, J=5.9 Hz), 7.34-7.56 (6H, m), 12.16 (1H, brs).

Reference Example 196

4-[4-Benzyloxy-5-chloro-2-(methoxymethyloxy)-3-methylphenyl]-3-methyl-4-oxobutanoic Acid

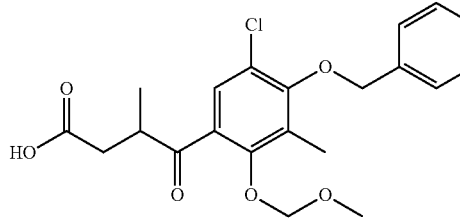
[Chem. 209]

$^1$H-NMR (DMSO-d6) δ: 1.05 (3H, d, J=7.1 Hz), 2.20 (3H, d, J=0.5 Hz), 2.34 (1H, dd, J=16.8, 5.9 Hz), 2.64 (1H, dd, J=16.8, 7.8 Hz), 3.40 (3H, s), 3.64-3.74 (1H, m), 4.90 (1H, d, J=6.1 Hz), 4.95 (1H, d, J=6.1 Hz), 4.99 (2H, s), 7.36-7.53 (5H, m), 7.55-7.56 (1H, m), 12.22 (1H, brs).

The following compounds were prepared from each appropriate starting material in a similar manner to Reference example 73.

Reference Example 197

6-(3-Chloro-2,5-difluoro-4-methoxyphenyl)-5-methyl-4,5-dihydro-2H-pyridazin-3-one

[Chem. 210]

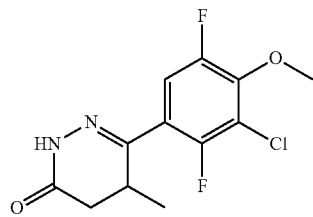

¹H-NMR (DMSO-d6) δ: 1.05 (3H, d, J=7.2 Hz), 2.26 (1H, dd, J=16.9, 3.7 Hz), 2.71 (1H, dd, J=16.9, 6.8 Hz), 3.12-3.22 (1H, m), 4.00 (3H, d, J=2.1 Hz), 7.57 (1H, dd, J=12.3, 7.1 Hz), 11.14 (1H, s).

Reference Example 198

6-[2-Fluoro-4-(methoxymethyloxy)-3,5-dimethylphenyl]-5-methyl-4,5-dihydro-2H-pyridazin-3-one

[Chem. 211]

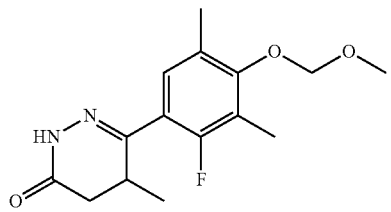

¹H-NMR (DMSO-d6) δ: 1.04 (3H, d, J=7.2 Hz), 2.17 (3H, d, J=2.4 Hz), 2.20-2.27 (1H, m), 2.23 (3H, s), 2.66 (1H, dd, J=16.7, 6.7 Hz), 3.07-3.18 (1H, m), 3.52 (3H, s), 5.00 (2H, s), 7.26 (1H, d, J=8.8 Hz), 10.98 (1H, s).

Reference Example 199

6-[4-Benzyloxy-3-chloro-2-(methoxymethyloxy)-5-methylphenyl]-5-methyl-4,5-dihydro-2H-pyridazin-3-one

[Chem. 212]

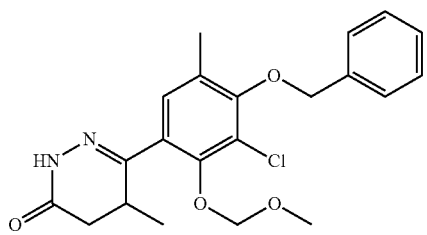

¹H-NMR (DMSO-d6) δ: 0.94 (3H, d, J=7.2 Hz), 2.24 (3H, d, J=0.7 Hz), 2.26 (1H, dd, J=16.7, 5.4 Hz), 2.67 (1H, dd, J=16.7, 7.0 Hz), 3.11-3.23 (1H, m), 3.46 (3H, s), 4.96 (2H, s), 5.01-5.06 (2H, m), 7.18-7.19 (1H, m), 7.34-7.55 (5H, m), 10.96 (1H, s).

Reference Example 200

6-[4-Benzyloxy-5-chloro-2-(methoxymethyloxy)-3-methylphenyl]-5-methyl-4,5-dihydro-2H-pyridazin-3-one

[Chem. 213]

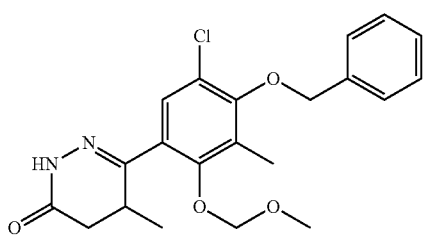

¹H-NMR (DMSO-d6) δ: 0.94 (3H, d, J=7.2 Hz), 2.21 (3H, s), 2.26 (1H, dd, J=16.8, 5.8 Hz), 2.67 (1H, dd, J=16.8, 6.9 Hz), 3.10-3.20 (1H, m), 3.42 (3H, s), 4.93 (1H, d, J=6.0 Hz), 4.95 (1H, d, J=6.0 Hz), 4.96 (2H, s), 7.29-7.31 (1H, m), 7.35-7.54 (5H, m), 10.95 (1H, s).

Reference Example 201

6-[2-Fluoro-4-(methoxymethyloxy)-5-methylphenyl]-5-methyl-4,5-dihydro-2H-pyridazin-3-one

[Chem. 214]

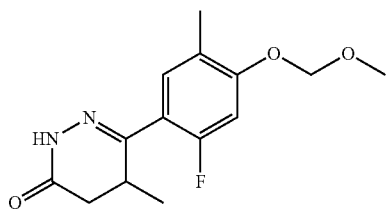

¹H-NMR (DMSO-d6) δ: 1.04 (3H, d, J=7.3 Hz), 2.17 (3H, s), 2.22 (1H, dd, J=16.7, 3.3 Hz), 2.66 (1H, dd, J=16.7, 6.8 Hz), 3.10-3.18 (1H, m), 3.39 (3H, s), 5.28 (2H, s), 6.95 (1H, d, J=13.4 Hz), 7.42 (1H, dd, J=9.0, 0.7 Hz), 10.95 (1H, s).

The following compound was prepared from the appropriate starting material in a similar manner to Reference example 92.

Reference Example 202

6-(3-Chloro-2,5-difluoro-4-hydroxyphenyl)-5-methyl-4,5-dihydro-2H-pyridazin-3-one

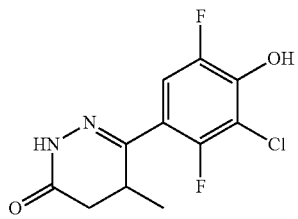

[Chem. 215]

$^1$H-NMR (DMSO-d6) δ: 1.05 (3H, d, J=7.2 Hz), 2.24 (1H, dd, J=16.8, 3.4 Hz), 2.68 (1H, dd, J=16.8, 6.8 Hz), 3.10-3.21 (1H, m), 7.45 (1H, dd, J=11.7, 7.2 Hz), 11.05 (1H, s), 11.37 (1H, brs).

The following compounds were prepared from each appropriate starting material in a similar manner to Reference example 98.

Reference Example 203

6-[3-Chloro-4-hydroxy-2-(methoxymethyloxy)-5-methylphenyl]-5-methyl-4,5-dihydro-2H-pyridazin-3-one

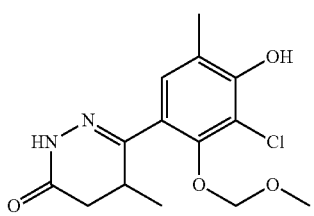

[Chem. 216]

$^1$H-NMR (DMSO-d6) δ: 0.92 (3H, d, J=7.3 Hz), 2.18 (3H, d, J=0.7 Hz), 2.23 (1H, dd, J=16.7, 5.1 Hz), 2.64 (1H, dd, J=16.7, 6.8 Hz), 3.12-3.22 (1H, m), 3.44 (3H, s), 4.96 (1H, d, J=5.7 Hz), 4.99 (1H, d, J=5.7 Hz), 7.03-7.05 (1H, m), 9.50 (1H, brs), 10.86 (1H, s).

Reference Example 204

6-[5-Chloro-4-hydroxy-2-(methoxymethyloxy)-3-methylphenyl]-5-methyl-4,5-dihydro-2H-pyridazin-3-one

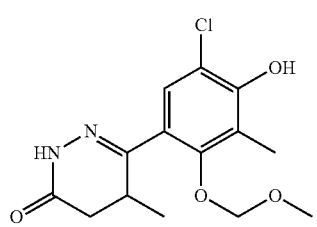

[Chem.217]

$^1$H-NMR (DMSO-d6) δ: 0.91 (3H, d, J=7.3 Hz), 2.16 (3H, s), 2.23 (1H, dd, J=16.8, 5.4 Hz), 2.64 (1H, dd, J=16.8, 7.0 Hz), 3.10-3.19 (1H, m), 3.41 (3H, s), 4.89 (1H, d, J=6.0 Hz), 4.91 (1H, d, J=6.0 Hz), 7.13-7.15 (1H, m), 9.54 (1H, s), 10.85 (1H, s).

The following compounds were prepared from each appropriate starting material in a similar manner to Reference example 103.

Reference Example 205

6-(2-Fluoro-4-hydroxy-5-methylphenyl)-5-methyl-4,5-dihydro-2H-pyridazin-3-one

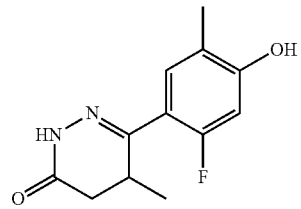

[Chem.218]

$^1$H-NMR (DMSO-d6) δ: 1.03 (3H, d, J=7.1 Hz), 2.09 (3H, s), 2.20 (1H, dd, J=16.7, 3.1 Hz), 2.64 (1H, dd, J=16.7, 6.7 Hz), 3.08-3.16 (1H, m), 6.59 (1H, d, J=13.2 Hz), 7.32 (1H, dd, J=9.3, 0.7 Hz), 10.19 (1H, brs), 10.87 (1H, s).

Reference Example 206

6-(2-Fluoro-4-hydroxy-3,5-dimethylphenyl)-5-methyl-4,5-dihydro-2H-pyridazin-3-one

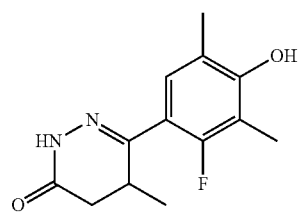

[Chem.219]

$^1$H-NMR (DMSO-d6) δ: 1.03 (3H, d, J=7.2 Hz), 2.10 (3H, d, J=2.2 Hz), 2.15 (3H, s), 2.20 (1H, dd, J=16.7, 3.4 Hz), 2.63 (1H, dd, J=16.7, 6.7 Hz), 3.05-3.16 (1H, m), 7.14 (1H, d, J=9.0 Hz), 9.03 (1H, s), 10.87 (1H, s).

The following compounds were prepared from each appropriate starting material in a similar manner to Reference example 107.

Reference Example 207

6-[5-Chloro-2-fluoro-3-methyl-4-(2-oxopropoxy)phenyl]-5-methyl-4,5-dihydro-2H-pyridazin-3-one

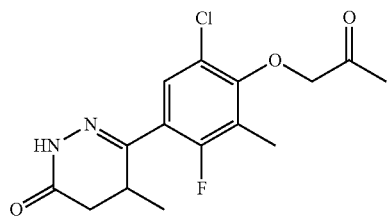

[Chem.220]

$^1$H-NMR (DMSO-d6) δ: 1.04 (3H, d, J=7.2 Hz), 2.18 (3H, s), 2.21-2.29 (4H, m), 2.69 (1H, dd, J=16.8, 6.8 Hz), 3.07-3.17 (1H, m), 4.72 (2H, s), 7.53 (1H, d, J=7.8 Hz), 11.07 (1H, s).

Reference Example 208

6-[3-Chloro-2-fluoro-5-methyl-4-(2-oxopropoxy)phenyl]-5-methyl-4,5-dihydro-2H-pyridazin-3-one

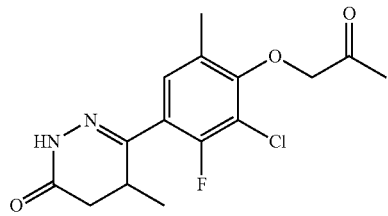

[Chem.221]

$^1$H-NMR (DMSO-d6) δ: 1.04 (3H, d, J=7.2 Hz), 2.19 (3H, s), 2.22-2.30 (1H, m), 2.28 (3H, s), 2.70 (1H, dd, J=16.8, 6.8 Hz), 3.09-3.19 (1H, m), 4.73 (2H, s), 7.44 (1H, d, J=8.4 Hz), 11.08 (1H, s).

Reference Example 209

6-[3-Chloro-2,5-difluoro-4-(2-oxopropoxy)phenyl]-5-methyl-4,5-dihydro-2H-pyridazin-3-one

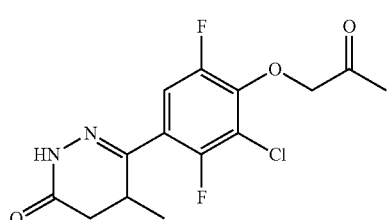

[Chem.222]

$^1$H-NMR (DMSO-d6) δ: 1.05 (3H, d, J=7.2 Hz), 2.16 (3H, s), 2.26 (1H, dd, J=16.8, 3.5 Hz), 2.70 (1H, dd, J=16.8, 6.8 Hz), 3.12-3.21 (1H, m), 5.02-5.07 (2H, m), 7.53 (1H, dd, J=13.0, 7.1 Hz), 11.13 (1H, s).

Reference Example 210

6-[3-Chloro-2-(methoxymethyloxy)-5-methyl-4-(2-oxopropoxy)phenyl]-5-methyl-4,5-dihydro-2H-pyridazin-3-one

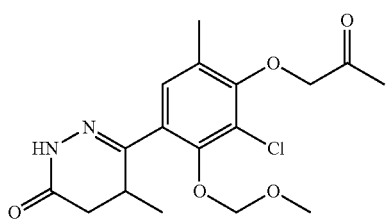

[Chem.223]

$^1$H-NMR (DMSO-d6) δ: 0.93 (3H, d, J=7.3 Hz), 2.19 (3H, s), 2.25 (1H, dd, J=16.8, 5.6 Hz), 2.26 (3H, d, J=0.7 Hz), 2.66 (1H, dd, J=16.8, 6.9 Hz), 3.10-3.20 (1H, m), 3.45 (3H, s), 4.66 (2H, s), 5.01 (1H, d, J=5.9 Hz), 5.02 (1H, d, J=5.9 Hz), 7.17-7.18 (1H, m), 10.95 (1H, s).

Reference Example 211

6-[3-Chloro-2-(methyloxy)-4-(2-oxobutoxy)phenyl]-5-methyl-4,5-dihydro-2H-pyridazin-3-one

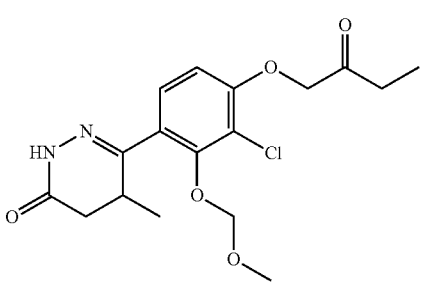

[Chem.224]

$^1$H-NMR (CDCl$_3$) δ: 1.07 (3H, d, J=7.3 Hz), 1.14 (3H, t, J=7.3 Hz), 2.41 (1H, dd, J=16.9, 4.6 Hz), 2.69-2.85 (3H, m), 3.30-3.40 (1H, m), 3.54 (3H, s), 4.63 (2H, s), 5.04 (1H, d, J=5.6 Hz), 5.18 (1H, d, J=5.6 Hz), 6.63 (1H, d, J=8.8 Hz), 7.21 (1H, d, J=8.8 Hz), 8.52 (1H, brs).

Reference Example 212

Production of 6-[3-chloro-4-(2-hydroxy-2-methyl-propoxy)-2-(methoxymethyloxy)phenyl]-5-methyl-4,5-dihydro-2H-pyridazin-3-one

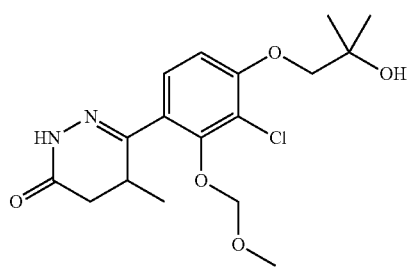

[Chem.225]

A mixture of 6-[3-chloro-4-hydroxy-2-(methoxymethyloxy)phenyl]-5-methyl-4,5-dihydro-2H-pyridazin-3-one (Reference example 99, 130 mg), 1-chloro-2-methyl-2-propanol (0.268 mL), and potassium carbonate (241 mg) in ethanol (2.0 mL)/water (0.2 mL) was stirred at 80° C. for 7 hours. The reaction mixture was poured into aqueous sodium hydroxide, and the mixture was extracted with ethyl acetate. The organic layer was washed with water and brine, dried over anhydrous sodium sulfate, and filtrated. The solvent was removed to afford the title compound as a colorless oil (130 mg).

$^1$H-NMR (CDCl$_3$) δ: 1.07 (3H, d, J=7.3 Hz), 1.39 (6H, s), 2.42 (1H, dd, J=17.0, 4.8 Hz), 2.80 (1H, dd, J=17.0, 7.0 Hz), 3.30-3.41 (1H, m), 3.53 (3H, s), 3.87 (2H, s), 5.01-5.06 (1H, m), 5.14-5.20 (1H, m), 6.76 (1H, d, J=8.5 Hz), 7.22 (1H, d, J=8.5 Hz), 8.44 (1H, brs).

The following compounds were prepared from each appropriate starting material in a similar manner to Reference example 212.

Reference Example 213

6-[3-Chloro-4-(2-hydroxy-2-methylpropoxy)-2-(methoxymethyloxy)-5-methylphenyl]-5-methyl-4,5-dihydro-2H-pyridazin-3-one

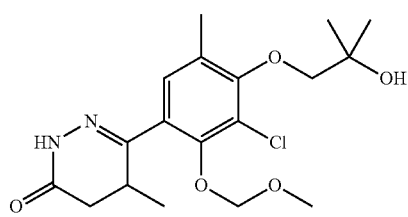

[Chem.226]

$^1$H-NMR (DMSO-d6) δ: 0.93 (3H, d, J=7.3 Hz), 1.28 (6H, s), 2.21-2.29 (1H, m), 2.27 (3H, d, J=0.7 Hz), 2.66 (1H, dd, J=16.8, 6.9 Hz), 3.10-3.20 (1H, m), 3.45 (3H, s), 3.64 (2H, s), 4.64 (1H, s), 5.00 (1H, d, J=5.8 Hz), 5.02 (1H, d, J=5.8 Hz), 7.15-7.16 (1H, m), 10.94 (1H, s).

Reference Example 214

6-[4-(2-Hydroxy-2-methylpropoxy)-2-(methoxymethyloxy)-3-methylphenyl]-5-methyl-5-dihydro-2H-pyridazin-3-one

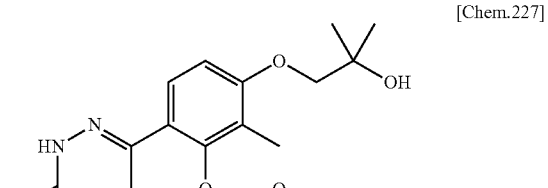

[Chem.227]

$^1$H-NMR (CDCl$_3$) δ: 1.07 (3H, d, J=7.3 Hz), 1.38 (6H, s), 2.16 (1H, s), 2.24 (3H, s), 2.41 (1H, dd, J=17.1, 4.6 Hz), 2.79 (1H, dd, J=17.1, 6.8 Hz), 3.28-3.38 (1H, m), 3.51 (3H, s), 3.82 (2H, s), 4.89 (1H, d, J=5.6 Hz), 5.00 (1H, d, J=5.6 Hz), 6.67 (1H, d, J=8.5 Hz), 7.14 (1H, d, J=8.5 Hz), 8.46 (1H, brs).

Reference Example 215

6-[5-Chloro-4-(2-hydroxy-2-methylpropoxy)-2-(methoxymethyloxy)-3-methylphenyl]-5-methyl-4,5-dihydro-2H-pyridazin-3-one

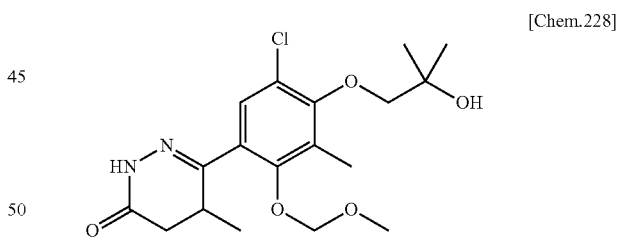

[Chem.228]

$^1$H-NMR (DMSO-d6) δ: 0.93 (3H, d, J=7.3 Hz), 1.28 (6H, s), 2.251 (1H, dd, J=16.8, 5.8 Hz), 2.255 (3H, d, J=0.6 Hz), 2.66 (1H, dd, J=16.8, 6.9 Hz), 3.09-3.20 (1H, m), 3.42 (3H, s), 3.64 (2H, s), 4.66 (1H, s), 4.92 (1H, d, J=6.0 Hz), 4.96 (1H, d, J=6.0 Hz), 7.24-7.25 (1H, m), 10.94 (1H, s).

The following compounds were prepared from each appropriate starting material in a similar manner to Reference example 135.

Reference Example 216

3-[6-Chloro-3-fluoro-2-methyl-4-(4-methyl-6-oxo-4,5-dihydro-1H-pyridazin-3-yl)phenoxy]-2,2-difluoropropyl Methanesulfonate

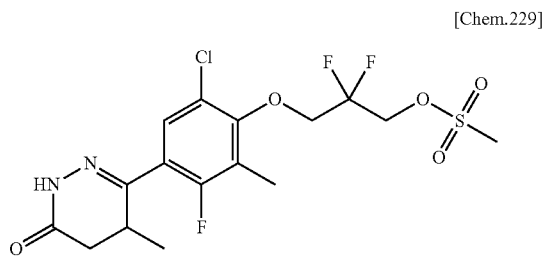 [SMILES: Cc1c(F)c(C2=NNC(=O)CC2C)cc(Cl)c1OCC(F)(F)COS(C)(=O)=O]

[Chem.229]

$^1$H-NMR (DMSO-d6) δ: 1.04 (3H, d, J=7.2 Hz), 2.22-2.30 (4H, m), 2.69 (1H, dd, J=16.8, 6.8 Hz), 3.09-3.18 (1H, m), 3.34 (3H, s), 4.43 (2H, t, J=13.3 Hz), 4.75 (2H, t, J=13.5 Hz), 7.57 (1H, d, J=7.8 Hz), 11.09 (1H, s).

Reference Example 217

3-[2-Chloro-3-fluoro-6-methyl-4-(4-methyl-6-oxo-4,5-dihydro-1H-pyridazin-3-yl)phenoxy]-2,2-difluoropropyl methanesulfonate

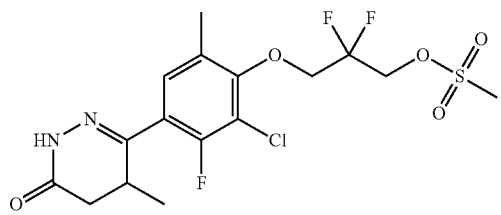

[Chem.230]

$^1$H-NMR (DMSO-d6) δ: 1.05 (3H, d, J=7.2 Hz), 2.26 (1H, dd, J=16.8, 3.8 Hz), 2.30 (3H, s), 2.70 (1H, dd, J=16.8, 6.8 Hz), 3.10-3.20 (1H, m), 3.34 (3H, s), 4.44 (2H, t, J=13.2 Hz), 4.75 (2H, t, J=13.5 Hz), 7.48 (1H, d, J=8.2 Hz), 11.10 (1H, s).

Reference Example 218

2,2-Difluoro-3-[3-fluoro-2,6-dimethyl-4-(4-methyl-6-oxo-4,5-dihydro-1H-pyridazin-3-yl)phenoxy]propyl Methanesulfonate

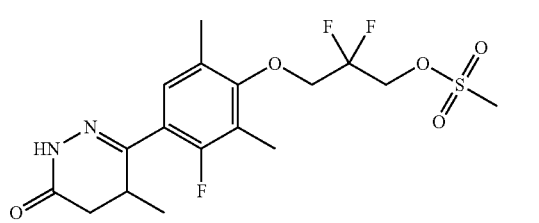

[Chem.231]

$^1$H-NMR (DMSO-d6) δ: 1.04 (3H, d, J=7.2 Hz), 2.19 (3H, d, J=2.3 Hz), 2.24 (1H, dd, J=16.8, 3.8 Hz), 2.25 (3H, s), 2.67 (1H, dd, J=16.8, 6.8 Hz), 3.06-3.17 (1H, m), 3.31 (3H, s), 4.27 (2H, t, J=13.2 Hz), 4.74 (2H, t, J=13.6 Hz), 7.28 (1H, d, J=8.8 Hz), 11.00 (1H, s).

Reference Example 219

3-[2-Chloro-3,6-difluoro-4-(4-methyl-6-oxo-4,5-dihydro-1H-pyridazin-3-yl)phenoxy]-2,2-difluoropropyl methanesulfonate

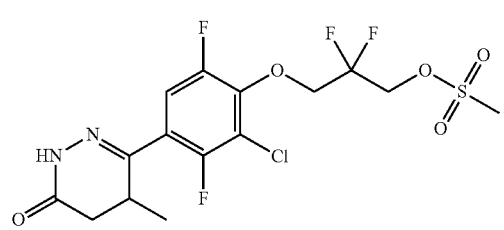

[Chem.232]

$^1$H-NMR (DMSO-d6) δ: 1.05 (3H, d, J=7.2 Hz), 2.27 (1H, dd, J=16.9, 3.8 Hz), 2.71 (1H, dd, J=16.9, 6.8 Hz), 3.13-3.22 (1H, m), 3.31 (3H, s), 4.60-4.78 (4H, m), 7.63 (1H, dd, J=12.0, 7.0 Hz), 11.17 (1H, s).

The following compounds were prepared from each appropriate starting material in a similar manner to Reference example 144.

Reference Example 220

6-(4-{[(1S*,2R*)-2-(tert-Butyldimethylsilyloxymethyl)cyclopropyl]methoxy}-3-chloro-2-fluorophenyl)-5-methyl-4,5-dihydro-2H-pyridazin-3-one

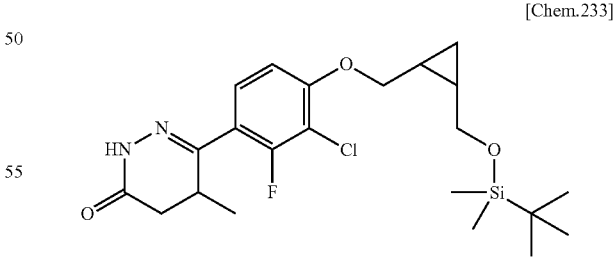

[Chem.233]

$^1$H-NMR (CDCl$_3$) δ: 0.04 (3H, s), 0.05 (3H, s), 0.49 (1H, d, J=5.6 Hz), 0.85-0.95 (10H, m), 1.21 (3H, d, J=7.1 Hz), 1.25-1.37 (1H, m), 1.38-1.49 (1H, m), 2.44 (1H, dd, J=17.1, 3.2 Hz), 2.74 (1H, dd, J=17.1, 6.7 Hz), 3.22-3.33 (1H, m), 3.65-3.73 (1H, m), 3.81-3.88 (1H, m), 4.13-4.23 (2H, m), 6.73-6.79 (1H, m), 7.42-7.49 (1H, m), 8.53 (1H, s).

Reference Example 221

6-(4-[{(1S*,2R*)-2-(tert-Butyldimethylsilyloxymethyl)cyclopropyl]methoxy}-3-chloro-5-methylphenyl)-5-methyl-4,5-dihydro-2H-pyridazin-3-one

[Chem.234]

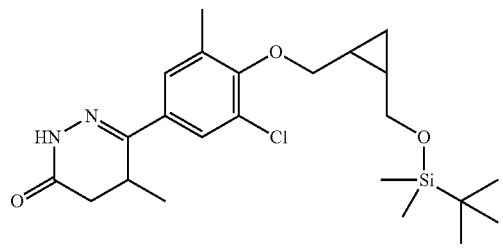

$^1$H-NMR (CDCl$_3$) δ: 0.046 (3H, s), 0.054 (3H, s), 0.38-0.45 (1H, m), 0.87-0.94 (10H, m), 1.22-1.34 (4H, m), 1.39-1.51 (1H, m), 2.36 (3H, s), 2.43-2.51 (1H, m), 2.69 (1H, dd, J=17.1, 6.8 Hz), 3.23-3.34 (1H, m), 3.71 (2H, d, J=7.1 Hz), 3.94 (1H, dd, J=10.4, 7.9 Hz), 4.12 (1H, dd, J=10.4, 7.4 Hz), 7.48 (1H, d, J=2.2 Hz), 7.60 (1H, d, J=2.2 Hz), 8.54 (1H, brs).

Reference Example 222

6-(4-{[(1S*,2S*)-2-(tert-Butyldimethylsilyloxymethyl)cyclopropyl]methoxy}-3-chloro-2-fluorophenyl)-5-methyl-4,5-dihydro-2H-pyridazin-3-one

[Chem.235]

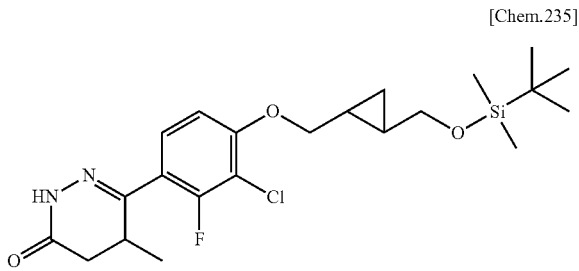 [SMILES: CC1CC(=O)NN=C1c1ccc(OCC2CC2CO[Si](C)(C)C(C)(C)C)c(Cl)c1F]

$^1$H-NMR (CDCl$_3$) δ: 0.06 (6H, s), 0.58-0.70 (2H, m), 0.89 (9H, s), 1.08-1.17 (1H, m), 1.18-1.29 (4H, m), 2.44 (1H, dd, J=17.0, 3.3 Hz), 2.74 (1H, dd, J=17.0, 6.7 Hz), 3.22-3.33 (1H, m), 3.52-3.66 (2H, m), 3.91-4.07 (2H, m), 6.71-6.79 (1H, m), 7.44 (1H, t, J=8.5 Hz), 8.51 (1H, brs).

Reference Example 223

6-{4-[(Z)-4-(tert-Butyldimethylsilyloxy)-2-butenyloxy]-2-fluoro-3,5-dimethylphenyl}-5-methyl-4,5-dihydro-2H-pyridazin-3-one

[Chem.236]

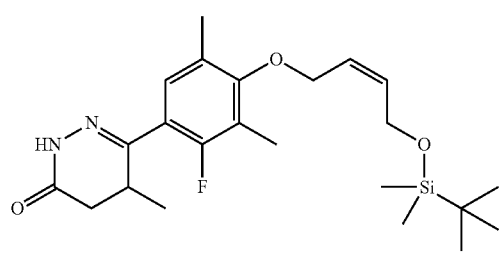

$^1$H-NMR (CDCl$_3$) δ: 0.06 (6H, s), 0.89 (9H, s), 1.20 (3H, d, J=7.2 Hz), 2.22 (3H, d, J=2.4 Hz), 2.26 (3H, s), 2.43 (1H, dd, J=17.0, 3.4 Hz), 2.74 (1H, dd, J=17.0, 6.7 Hz), 3.22-3.32 (1H, m), 4.21-4.28 (2H, m), 4.42 (2H, d, J=5.3 Hz), 5.72-5.86 (2H, m), 7.21 (1H, d, J=8.8 Hz), 8.47 (1H, brs).

Reference Example 224

6-{4-[(Z)-4-(tert-Butyldimethylsilyloxy)-2-butenyloxy]-3-chloro-2-fluoro-5-methylphenyl}-5-methyl-4,5-dihydro-2H-pyridazin-3-one

[Chem.237]

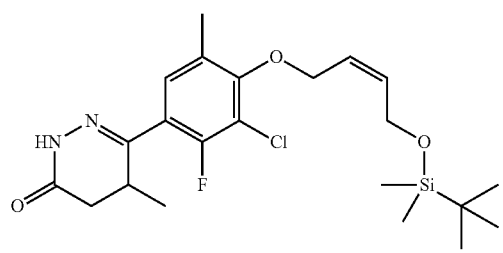

$^1$H-NMR (CDCl$_3$) δ: 0.06 (6H, s), 0.89 (9H, s), 1.21 (3H, dd, J=7.2, 0.6 Hz), 2.27-2.30 (3H, m), 2.45 (1H, dd, J=17.0, 3.4 Hz), 2.74 (1H, dd, J=17.0, 6.7 Hz), 3.22-3.31 (1H, m), 4.25-4.28 (2H, m), 4.59-4.63 (2H, m), 5.74-5.87 (2H, m), 7.31 (1H, dd, J=8.3, 0.7 Hz), 8.52 (1H, s).

Reference Example 225

6-{4-[(Z)-4-(tert-Butyldimethylsilyloxy)-2-butenyloxy]-3-chloro-2,5-difluorophenyl}-5-methyl-4,5-dihydro-2H-pyridazin-3-one

[Chem.238]

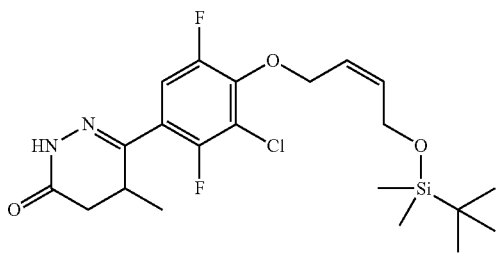

$^1$H-NMR (CDCl$_3$) δ: 0.06 (6H, s), 0.89 (9H, s), 1.22 (3H, d, J=7.2 Hz), 2.46 (1H, dd, J=17.0, 3.1 Hz), 2.73 (1H, dd, J=17.0, 6.8 Hz), 3.25-3.34 (1H, m), 4.25-4.29 (2H, m), 4.82-4.86 (2H, m), 5.71-5.84 (2H, m), 7.34 (1H, dd, J=11.7, 7.0 Hz), 8.55 (1H, s).

Reference Example 226

6-{4-[(Z)-4-(tert-Butyldimethylsilyloxy)-2-butenyloxy]-2-hydroxy-3-methylphenyl}-5-methyl-4,5-dihydro-2H-pyridazin-3-one

[Chem.239]

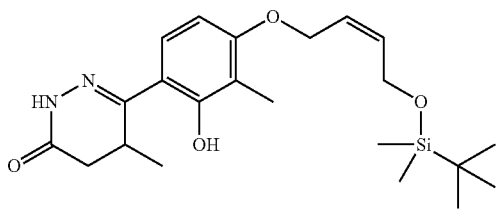

$^1$H-NMR (CDCl$_3$) δ: 0.09 (6H, s), 0.92 (9H, s), 1.29 (3H, d, J=7.3 Hz), 2.14 (3H, s), 2.47-2.53 (1H, m), 2.73 (1H, dd, J=16.9, 6.6 Hz), 3.40-3.51 (1H, m), 4.30-4.35 (2H, m), 4.67-4.71 (2H, m), 5.69-5.80 (2H, m), 6.46 (1H, d, J=8.8 Hz), 7.21-7.28 (1H, m), 8.38 (1H, s), 11.90 (1H, s).

Reference Example 227

6-{4-[(Z)-4-(tert-Butyldimethylsilyloxy)-2-butenyloxy]-3-chloro-2-hydroxyphenyl}-5-methyl-4,5-dihydro-2H-pyridazin-3-one

[Chem.240]

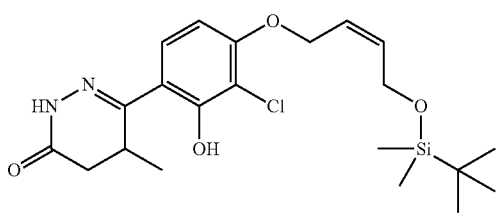

$^1$H-NMR (CDCl$_3$) δ: 0.12 (6H, s), 0.95 (9H, s), 1.33 (3H, d, J=7.6 Hz), 2.52-2.59 (1H, m), 2.78 (1H, dd, J=17.1, 6.6 Hz), 3.41-3.53 (1H, m), 4.34-4.40 (2H, m), 4.80-4.86 (2H, m), 5.72-5.86 (2H, m), 6.58 (1H, d, J=9.3 Hz), 7.32 (1H, d, J=9.3 Hz), 8.40-8.53 (1H, m), 12.41 (1H, d, J=2.4 Hz).

Reference Example 228

Production of 6-[4-(3-hydroxypropoxy)-2-(methoxymethyloxy)-3-methylphenyl]-5-methyl-4,5-dihydro-2H-pyridazin-3-one

[Chem.241]

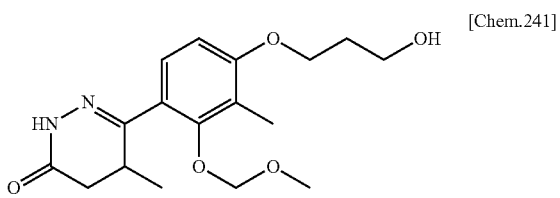 [SMILES: COCOc1c(C2=NNC(=O)CC2C)ccc(OCCCO)c1C]

To a mixture of 6-[4-hydroxy-2-(methoxymethyloxy)-3-methylphenyl]-5-methyl-4,5-dihydro-2H-pyridazin-3-one (Reference example 98, 611 mg), 3-(tert-butyldimethylsilyloxy)propan-1-ol (627 mg), and triphenylphosphine (864 mg) in THF (12 mL) was added bis(2-methoxyethyl) azodicarboxylate (771 mg) at 0° C., and then the mixture was stirred at room temperature overnight. The solvent was removed, and then the residue was purified by silica gel column chromatography (heptane:ethyl acetate=85:15 to 35:65) to afford a pale yellow oil (1.04 g). The oil was dissolved in THF (10 mL), tetrabutylammonium fluoride (1.0 M THF solution, 2.76 mL) was added to the mixture at 0° C., and then the mixture was stirred at room temperature for 2.5 hours. The reaction mixture was concentrated, water was added to the residue, and then the mixture was extracted with ethyl acetate. The organic layer was washed with brine, dried over anhydrous sodium sulfate, and filtrated, and the solvent was removed. The obtained crude product was purified by silica gel column chromatography (heptane:ethyl acetate=50:50 to 0:100) to afford the title compound as a colorless amorphous (635 mg).

$^1$H-NMR (CDCl$_3$) δ: 1.06 (3H, d, J=7.3 Hz), 1.77-1.85 (1H, m), 2.09 (2H, quintet, J=6.0 Hz), 2.19 (3H, s), 2.41 (1H, dd, J=17.1, 4.6 Hz), 2.78 (1H, dd, J=17.1, 7.0 Hz), 3.28-3.37 (1H, m), 3.50 (3H, s), 3.87-3.91 (2H, m), 4.15 (2H, t, J=6.0 Hz), 4.88 (1H, d, J=5.6 Hz), 4.98 (1H, d, J=5.6 Hz), 6.70 (1H, d, J=8.5 Hz), 7.14 (1H, d, J=8.5 Hz), 8.56 (1H, brs).

The following compounds were prepared from each appropriate starting material in a similar manner to Reference example 228.

Reference Example 229

6-[3-Chloro-4-[(Z)-4-hydroxy-2-butenyloxy]-2-(methoxymethyloxy)phenyl]-5-methyl-4,5-dihydro-2H-pyridazin-3-one

[Chem.242]

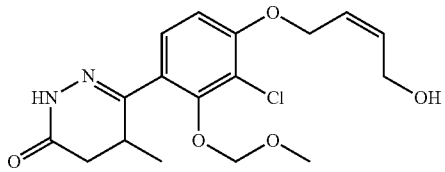

$^1$H-NMR (CDCl$_3$) δ: 1.07 (3H, d, J=7.3 Hz), 1.63-1.68 (1H, m), 2.42 (1H, dd, J=17.0, 4.8 Hz), 2.80 (1H, dd, J=17.0, 7.0 Hz), 3.31-3.40 (1H, m), 3.53 (3H, s), 4.29-4.35 (2H, m), 4.72-4.77 (2H, m), 5.02 (1H, d, J=5.6 Hz), 5.16 (1H, d, J=5.6 Hz), 5.83-5.96 (2H, m), 6.78 (1H, d, J=8.5 Hz), 7.22 (1H, d, J=8.5 Hz), 8.52 (1H, s).

Reference Example 230

6-[3-Chloro-4-(4-hydroxybutoxy)-2-(methoxymethyloxy)phenyl]-5-methyl-4,5-dihydro-2H-pyridazin-3-one

[Chem.243]

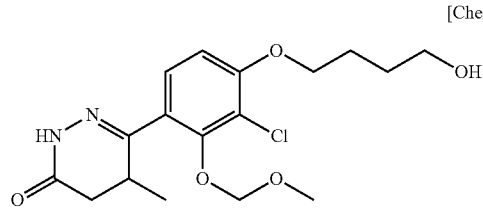

$^1$H-NMR (CDCl$_3$) δ: 1.07 (3H, d, J=7.3 Hz), 1.50-1.54 (1H, m), 1.77-1.85 (2H, m), 1.94-2.01 (2H, m), 2.42 (1H, dd, J=17.0, 4.8 Hz), 2.80 (1H, dd, J=17.0, 7.0 Hz), 3.32-3.40 (1H, m), 3.53 (3H, s), 3.74-3.79 (2H, m), 4.11 (2H, t, J=6.1 Hz), 5.01 (1H, d, J=5.6 Hz), 5.16 (1H, d, J=5.6 Hz), 6.77 (1H, d, J=8.8 Hz), 7.21 (1H, d, J=8.8 Hz), 8.45 (1H, brs).

Reference Example 231

6-[3-Chloro-4-(3-hydroxypropoxy)-2-(methoxymethyloxy)-5-methylphenyl]-5-methyl-4,5-dihydro-2H-pyridazin-3-one

[Chem.244]

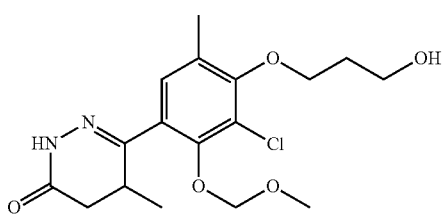

$^1$H-NMR (CDCl$_3$) δ: 1.08 (3H, d, J=7.6 Hz), 1.90 (1H, t, J=5.5 Hz), 2.07-2.13 (2H, m), 2.30 (3H, d, J=0.7 Hz), 2.42 (1H, dd, J=17.0, 4.9 Hz), 2.80 (1H, dd, J=17.0, 7.0 Hz), 3.30-3.39 (1H, m), 3.52 (3H, s), 3.97 (2H, td, J=5.9, 5.5 Hz), 4.09 (2H, t, J=5.9 Hz), 4.98 (1H, d, J=5.4 Hz), 5.12 (1H, d, J=5.4 Hz), 7.08 (1H, d, J=0.7 Hz), 8.49 (1H, s).

The following compounds were prepared from each appropriate starting material in a similar manner to Reference example 166.

Reference Example 232

3-[6-Chloro-3-fluoro-2-methyl-4-(4-methyl-6-oxo-4,5-dihydro-1H-pyridazin-3-yl)phenoxy]-2,2-difluoropropyl Benzoate

[Chem.245]

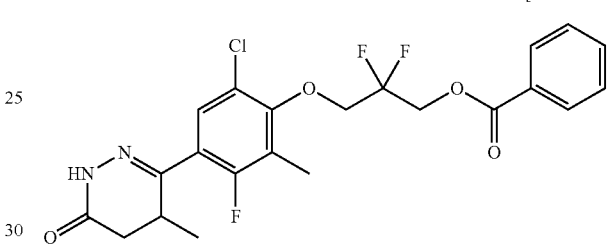

$^1$H-NMR (DMSO-d6) δ: 1.03 (3H, d, J=7.2 Hz), 2.20-2.30 (1H, m), 2.24 (3H, d, J=2.4 Hz), 2.69 (1H, dd, J=16.7, 6.7 Hz), 3.07-3.18 (1H, m), 4.51 (2H, t, J=13.2 Hz), 4.85 (2H, t, J=13.6 Hz), 7.52-7.62 (3H, m), 7.70-7.75 (1H, m), 8.00-8.07 (2H, m), 11.09 (1H, s).

Reference Example 233

3-[2-Chloro-3-fluoro-6-methyl-4-(4-methyl-6-oxo-4,5-dihydro-1H-pyridazin-3-yl)phenoxy]-2,2-difluoropropyl benzoate

[Chem.246]

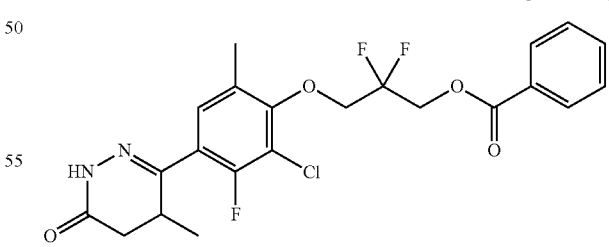

$^1$H-NMR (DMSO-d6) δ: 1.04 (3H, d, J=7.1 Hz), 2.26 (1H, dd, J=16.8, 3.7 Hz), 2.30 (3H, s), 2.70 (1H, dd, J=16.8, 6.8 Hz), 3.09-3.19 (1H, m), 4.52 (2H, t, J=13.1 Hz), 4.85 (2H, t, J=13.6 Hz), 7.47 (1H, d, J=7.9 Hz), 7.55-7.62 (2H, m), 7.69-7.76 (1H, m), 8.01-8.07 (2H, m), 11.10 (1H, s).

Reference Example 234

2,2-Difluoro-3-[3-fluoro-2,6-dimethyl-4-(4-methyl-6-oxo-4,5-dihydro-1H-pyridazin-3-yl)phenoxy]propyl benzoate

[Chem.247]

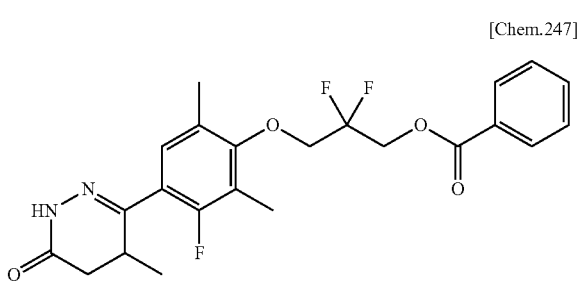 [SMILES: Cc1cc(C2=NNC(=O)CC2C)c(F)c(C)c1OCC(F)(F)COC(=O)c1ccccc1]

$^1$H-NMR (DMSO-d6) δ: 1.03 (3H, d, J=7.2 Hz), 2.18 (3H, d, J=2.2 Hz), 2.23 (3H, s), 2.24 (1H, dd, J=16.7, 3.9 Hz), 2.66 (1H, dd, J=16.7, 6.8 Hz), 3.06-3.16 (1H, m), 4.36 (2H, t, J=13.2 Hz), 4.84 (2H, t, J=13.7 Hz), 7.27 (1H, d, J=8.9 Hz), 7.54-7.62 (2H, m), 7.69-7.75 (1H, m), 8.02-8.08 (2H, m), 11.00 (1H, s).

Reference Example 235

3-[2-Chloro-3,6-difluoro-4-(4-methyl-6-oxo-4,5-dihydro-1H-pyridazin-3-yl)phenoxy]-2,2-difluoropropyl benzoate

[Chem.248]

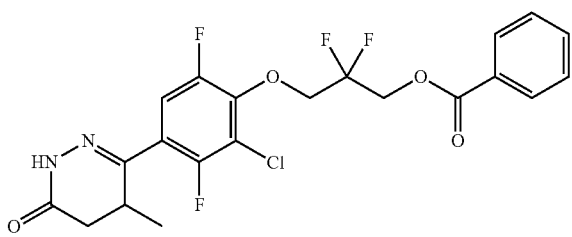

$^1$H-NMR (DMSO-d6) δ: 1.04 (3H, d, J=7.2 Hz), 2.27 (1H, dd, J=16.8, 3.6 Hz), 2.71 (1H, dd, J=16.8, 6.9 Hz), 3.11-3.21 (1H, m), 4.75 (2H, t, J=13.0 Hz), 4.83 (2H, t, J=13.7 Hz), 7.52-7.65 (3H, m), 7.68-7.75 (1H, m), 7.97-8.05 (2H, m), 11.17 (1H, s).

Reference Example 236

Production of 3-[2-chloro-3-hydroxy-4-(4-methyl-6-oxo-4,5-dihydro-1H-pyridazin-3-yl)phenoxy]-2,2-difluoropropyl benzoate

[Chem.249]

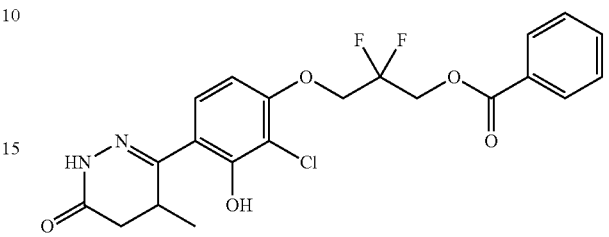

A suspension of 6-[3-chloro-4-hydroxy-2-(methoxymethyloxy)phenyl]-5-methyl-4,5-dihydro-2H-pyridazin-3-one (Reference example 99, 350 mg), 2,2-difluoro-3-(methylsulfonyloxy)propyl methanesulfonate (943 mg), and cesium carbonate (1.53 g) in NMP (2.0 mL) was stirred at 150° C. under microwave irradiation for 30 minutes. To the reaction mixture was added water, and the mixture was extracted with ethyl acetate. The organic layer was washed with water and brine, dried over anhydrous sodium sulfate, and filtrated, and the solvent was removed. The residue was purified by silica gel column chromatography (heptane:ethyl acetate=50:50 to 0:100) to afford a mixture containing the desired intermediate. A solution of the obtained mixture and sodium benzoate (121 mg) in NMP (2.0 mL) was stirred at 180° C. under microwave irradiation for 30 minutes. To the reaction mixture was added water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=67:33 to 33:67) and then by diol silica gel column chromatography (heptane:ethyl acetate=75:25 to 33:67) to afford the title compound as a colorless solid (38 mg).

$^1$H-NMR (CDCl$_3$) δ: 1.28 (3H, d, J=7.3 Hz), 2.53 (1H, d, J=16.6 Hz), 2.75 (1H, dd, J=16.6, 6.6 Hz), 3.38-3.43 (1H, m), 4.42 (2H, t, J=11.2 Hz), 4.48 (2H, t, J=12.7 Hz), 6.55 (1H, d, J=9.3 Hz), 7.31 (1H, d, J=9.3 Hz), 7.41-7.48 (2H, m), 7.55-7.63 (1H, m), 8.00-8.06 (2H, m), 9.10 (1H, s), 12.54 (1H, s).

Reference Example 237

Production of 4-benzyloxy-1-bromo-2-fluoro-3-(trifluoromethyl)benzene

[Chem.250]

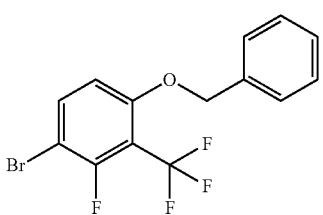

Under an argon atmosphere, to a mixture of 4-benzyloxy-1-bromo-2-fluorobenzene (6.10 g) in THF (20 mL) was added dropwise lithium diisopropylamide (2.0 M, a mixed solution of THF/heptane/ethylbenzene, 13.6 mL) at −78° C. The reaction mixture was stirred at the same temperature for 30 minutes, and then iodine (6.61 g) was added thereto. The reaction mixture was stirred at −78° C. for 1.5 hours. To the reaction mixture was added water, and the mixture was extracted with ethyl acetate. The organic layer was washed with aqueous sodium thiosulfate, saturated aqueous sodium bicarbonate, and then brine, dried over anhydrous sodium sulfate, filtrated, and then concentrated. The residue was purified by silica gel column chromatography (heptane:ethyl acetate=100:0 to 95:5 to 91:9), and then the obtained solid was washed by trituration with heptane to afford a white solid (5.12 g). The white solid (5.12 g) was dissolved in NMP (40 mL), and then methyl difluoro(fluorosulfonyl)acetate (12.8 mL) and copper iodide (4.79 g) were added thereto. Under an argon atmosphere, the mixture was stirred at 100° C. for 18 hours. The reaction mixture was allowed to cool to room temperature, water and ethyl acetate were added thereto, and then the mixture was filtered through a Celite pad. The separated organic layer was washed with water and brine, dried over anhydrous sodium sulfate, filtrated, and then concentrated. The obtained crude product was purified by silica gel column chromatography (heptane:ethyl acetate=100:0 to 83:17) to afford the title compound as a white solid (3.93 g).

$^1$H-NMR (CDCl$_3$) δ: 5.17 (2H, s), 6.74 (1H, d, J=8.8 Hz), 7.31-7.43 (5H, m), 7.57-7.63 (1H, m).

The following compound was prepared from the appropriate starting material in a similar manner to Reference example 20.

Reference Example 238

4-Benzyloxy-2-fluoro-3-(trifluoromethyl)benzaldehyde

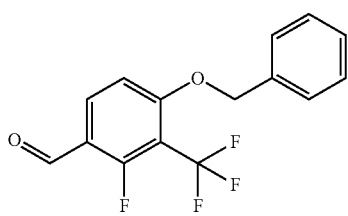

[Chem.251]

$^1$H-NMR (CDCl$_3$) δ: 5.28 (2H, s), 6.95 (1H, d, J=8.8 Hz), 7.32-7.45 (5H, m), 8.01 (1H, dd, J=8.8, 7.9 Hz), 10.25 (1H, s).

The following compound was prepared from the appropriate starting material in a similar manner to Reference example 41.

Reference Example 239

Methyl 4-[4-benzyloxy-2-fluoro-3-(trifluoromethyl)phenyl]-3-methyl-4-oxobutanoate

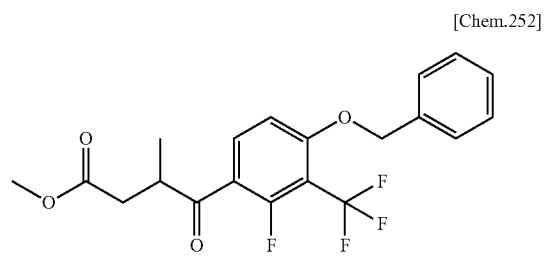 [SMILES: COC(=O)CC(C)C(=O)c1ccc(OCc2ccccc2)c(C(F)(F)F)c1F]

[Chem.252]

$^1$H-NMR (CDCl$_3$) δ: 1.22 (3H, dd, J=7.0, 0.9 Hz), 2.44 (1H, dd, J=16.8, 5.2 Hz), 2.95 (1H, ddd, J=16.8, 8.9, 1.8 Hz), 3.64 (3H, s), 3.69-3.79 (1H, m), 5.25 (2H, s), 6.91 (1H, d, J=9.0 Hz), 7.31-7.44 (5H, m), 7.96-8.03 (1H, m).

The following compound was prepared from the appropriate starting material in a similar manner to Reference example 63.

Reference Example 240

4-[4-Benzyloxy-2-fluoro-3-(trifluoromethyl)phenyl]-3-methyl-4-oxobutanoic Acid

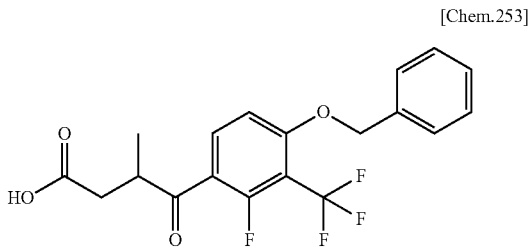 [SMILES: CC(CC(=O)O)C(=O)c1ccc(OCc2ccccc2)c(C(F)(F)F)c1F]

[Chem.253]

$^1$H-NMR (DMSO-d6) δ: 1.10 (3H, d, J=7.1 Hz), 2.41 (1H, dd, J=17.0, 5.3 Hz), 2.71 (1H, ddd, J=17.0, 9.0, 0.9 Hz), 3.55-3.67 (1H, m), 5.39 (2H, s), 7.32-7.49 (6H, m), 8.05-8.13 (1H, m), 12.20 (1H, s).

The following compound was prepared from the appropriate starting material in a similar manner to Reference example 83.

Reference Example 241

6-[4-Benzyloxy-2-fluoro-3-(trifluoromethyl)phenyl]-5-methyl-4,5-dihydro-2H-pyridazin-3-one

[Chem.254]

¹H-NMR (DMSO-d6) δ: 1.04 (3H, d, J=7.2 Hz), 2.25 (1H, dd, J=16.7, 4.2 Hz), 2.69 (1H, dd, J=16.7, 6.7 Hz), 3.05-3.19 (1H, m), 5.34 (2H, s), 7.28 (1H, d, J=9.2 Hz), 7.32-7.50 (5H, m), 7.77-7.87 (1H, m), 11.05 (1H, s).

The following compound was prepared from the appropriate starting material in a similar manner to Reference example 98.

Reference Example 242

6-[2-Fluoro-4-hydroxy-3-(trifluoromethyl)phenyl]-5-methyl-4,5-dihydro-2H-pyridazin-3-one

[Chem.255]

¹H-NMR (DMSO-d6) δ: 1.04 (3H, d, J=7.2 Hz), 2.23 (1H, dd, J=16.7, 3.8 Hz), 2.67 (1H, dd, J=16.8, 6.8 Hz), 3.04-3.15 (1H, m), 6.90 (1H, d, J=8.8 Hz), 7.61-7.68 (1H, m), 10.99 (1H, s), 11.40 (1H, brs).

Example 1

Production of 6-[3-bromo-5-chloro-4-(2-hydroxy-2-methylpropoxy)phenyl]-5-methyl-4,5-dihydro-2H-pyridazin-3-one

[Chem.256]

To the mixture of 6-(3-Bromo-5-chloro-4-hydroxyphenyl)-5-methyl-4,5-dihydro-2H-pyridazin-3-one (Reference example 87, 300 mg) was dissolved in ethanol-water (4:1, 10 mL) were added 1-chloro-2-methyl-2-propanol (0.388 mL) and potassium carbonate (522 mg). The reaction mixture was refluxed for 8 hours. To the reaction mixture was added water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=67:33 to 33:67). The obtained solid was recrystallized from 2-propanol to afford the title compound as a white powder (107 mg).

Melting point: 176.6-178.2° C.

The following compounds were prepared from each appropriate starting material in a similar manner to Example 1.

Example 2

6-[3,5-Dichloro-4-(2-hydroxy-2-methylpropoxy)phenyl]-5-methyl-4,5-dihydro-2H-pyridazin-3-one

[Chem.257]

¹H-NMR (DMSO-d6) δ: 1.05 (3H, d, J=7.3 Hz), 1.29 (6H, s), 2.24 (1H, d, J=16.7 Hz), 2.69 (1H, dd, J=16.7, 7.0 Hz), 3.37-3.49 (1H, m), 3.75 (2H, s), 4.68 (1H, brs), 7.82 (2H, s), 11.09 (1H, s).

Example 3

6-[3-Chloro-2-fluoro-4-(2-hydroxyethoxy)phenyl]-5-methyl-4,5-dihydro-2H-pyridazin-3-one

[Chem.258]

¹H-NMR (DMSO-d6) δ: 1.04 (3H, d, J=7.3 Hz), 2.25 (1H, dd, J=16.7, 3.5 Hz), 2.69 (1H, dd, J=16.7, 6.7 Hz), 3.10-3.20 (1H, m), 3.76 (2H, dt, J=5.4, 5.0 Hz), 4.17 (2H, t, J=5.0 Hz), 4.91 (1H, t, J=5.4 Hz), 7.10 (1H, dd, J=8.9, 1.5 Hz), 7.53 (1H, t, J=8.9 Hz), 11.01 (1H, s).

Example 4

6-[3-Chloro-4-(2-hydroxyethoxy)-5-methylphenyl]-5-methyl-4,5-dihydro-2H-pyridazin-3-one

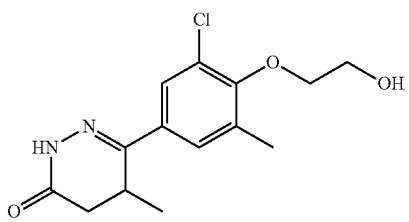

[Chem.259]

Melting point: 157.4-157.6° C.

Example 5

Production of 6-[3-chloro-2-fluoro-4-(3-hydroxy-2,2-dimethylpropoxy)phenyl]-5-methyl-4,5-dihydro-2H-pyridazin-3-one

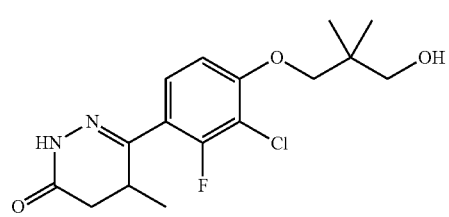

[Chem.260]

A suspension of 6-(3-chloro-2-fluoro-4-hydroxyphenyl)-5-methyl-4,5-dihydro-2H-pyridazin-3-one (Reference example 89, 302 mg), 3-bromo-2,2-dimethyl-1-propanol (0.434 mL), and cesium carbonate (767 mg) in NMP (3 mL) was stirred at 130° C. under microwave irradiation for one hour. The reaction mixture was poured into water, and the mixture was extracted with ethyl acetate. The organic layer was washed with water and brine, dried over anhydrous sodium sulfate, and filtrated, and the solvent was removed. The obtained crude product was purified by amino silica gel column chromatography (heptane:ethyl acetate=50:50 to 0:100 to ethyl acetate:methanol=90:10), and the desired fractions were concentrated. The residue was crystallized from ethyl acetate, and the precipitates were collected on a filter to afford the title compound as a white powder (37 mg).

$^1$H-NMR (DMSO-d6) δ: 0.96 (6H, s), 1.04 (3H, d, J=7.1 Hz), 2.25 (1H, dd, J=16.9, 3.7 Hz), 2.69 (1H, dd, J=16.9, 6.8 Hz), 3.11-3.18 (1H, m), 3.31 (2H, d, J=5.4 Hz), 3.86 (2H, s), 4.65 (1H, t, J=5.4 Hz), 7.06 (1H, dd, J=8.8, 1.5 Hz), 7.53 (1H, t, J=8.8 Hz), 11.01 (1H, s).

The following compounds were prepared from each appropriate starting material in a similar manner to Example 5.

Example 6

6-[3,5-Difluoro-4-(3-hydroxy-2,2-dimethylpropoxy)phenyl]-5-methyl-4,5-dihydro-2H-pyridazin-3-one

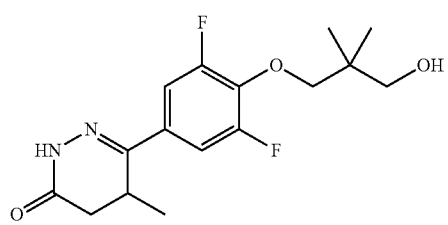

[Chem.261]

$^1$H-NMR (DMSO-d6) δ: 0.93 (6H, s), 1.04 (3H, d, J=7.3 Hz), 2.23 (1H, d, J=16.7 Hz), 2.68 (1H, dd, J=16.7, 7.0 Hz), 3.27 (2H, d, J=5.3 Hz), 3.34-3.42 (1H, m), 3.92 (2H, s), 4.62 (1H, t, J=5.3 Hz), 7.44-7.57 (2H, m), 11.05 (1H, s).

Example 7

6-[3-Chloro-5-fluoro-4-(3-hydroxy-2,2-dimethylpropoxy)phenyl]-5-methyl-4,5-dihydro-2H-pyridazin-3-one

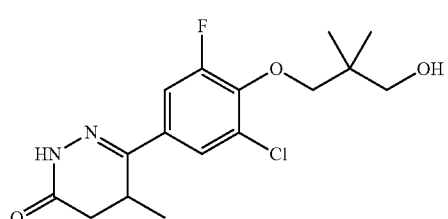

[Chem.262]

$^1$H-NMR (DMSO-d6) δ: 0.96 (6H, s), 1.04 (3H, d, J=7.3 Hz), 2.23 (1H, d, J=16.9 Hz), 2.69 (1H, dd, J=16.9, 6.8 Hz), 3.29-3.34 (2H, m), 3.36-3.46 (1H, m), 3.92 (2H, d, J=1.7 Hz), 4.61 (1H, brs), 7.63 (1H, dd, J=12.8, 2.1 Hz), 7.66-7.68 (1H, m), 11.06 (1H, s).

Example 8

6-[2-Fluoro-4-(3-hydroxy-2,2-dimethylpropoxy)-3-methylphenyl]-5-methyl-4,5-dihydro-2H-pyridazin-3-one

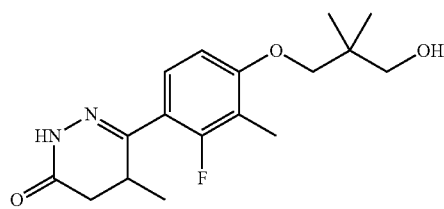

[Chem.263]

¹H-NMR (DMSO-d6) δ: 0.95 (6H, s), 1.03 (3H, d, J=7.2 Hz), 2.11 (3H, d, J=2.2 Hz), 2.22 (1H, dd, J=16.7, 3.7 Hz), 2.66 (1H, dd, J=16.7, 6.7 Hz), 3.07-3.16 (1H, m), 3.29-3.32 (2H, m), 3.75 (2H, s), 4.63 (1H, t, J=5.4 Hz), 6.84 (1H, d, J=8.5 Hz), 7.37 (1H, t, J=8.5 Hz), 10.91 (1H, s).

Example 9

6-[2,3-Difluoro-4-(3-hydroxy-2,2-dimethylpropoxy)phenyl]-5-methyl-4,5-dihydro-2H-pyridazin-3-one

[Chem.264]

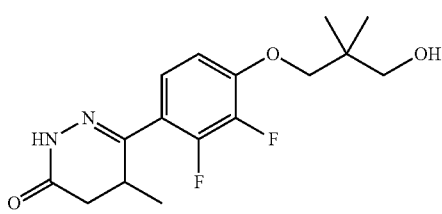

¹H-NMR (DMSO-d6) δ: 0.94 (6H, s), 1.05 (3H, d, J=7.3 Hz), 2.25 (1H, dd, J=16.7, 3.3 Hz), 2.70 (1H, dd, J=16.7, 7.0 Hz), 3.10-3.22 (1H, m), 3.28 (2H, d, J=5.4 Hz), 3.85 (2H, s), 4.67 (1H, t, J=5.4 Hz), 7.03-7.14 (1H, m), 7.30-7.45 (1H, m), 11.02 (1H, s).

Example 10

6-[2,3-Difluoro-4-(3-hydroxypropoxy)phenyl]-5-methyl-4,5-dihydro-2H-pyridazin-3-one

[Chem.265]

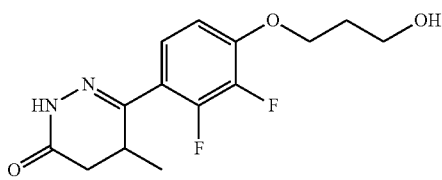

¹H-NMR (DMSO-d6) δ: 1.05 (3H, d, J=7.1 Hz), 1.84-1.95 (2H, m), 2.25 (1H, dd, J=16.9, 3.3 Hz), 2.70 (1H, dd, J=16.9, 6.8 Hz), 3.09-3.23 (1H, m), 3.49-3.64 (2H, m), 4.20 (2H, t, J=6.3 Hz), 4.59 (1H, t, J=5.1 Hz), 7.03-7.15 (1H, m), 7.34-7.44 (1H, m), 11.03 (1H, s).

Example 11

6-[3-Bromo-5-fluoro-4-(3-hydroxypropoxy)phenyl]-5-methyl-4,5-dihydro-2H-pyridazin-3-one

[Chem.266]

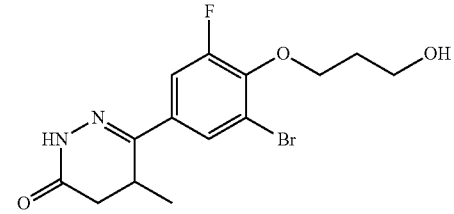

¹H-NMR (DMSO-d6) δ: 1.04 (3H, d, J=7.3 Hz), 1.82-1.92 (2H, m), 2.23 (1H, d, J=16.8 Hz), 2.69 (1H, dd, J=16.8, 6.9 Hz), 3.35-3.45 (1H, m), 3.55-3.64 (2H, m), 4.16-4.24 (2H, m), 4.54 (1H, t, J=4.8 Hz), 7.67 (1H, dd, J=12.7, 2.1 Hz), 7.82 (1H, t, J=2.1 Hz), 11.07 (1H, s).

Example 12

6-[3-Bromo-2-fluoro-4-(3-hydroxypropoxy)phenyl]-5-methyl-4,5-dihydro-2H-pyridazin-3-one

[Chem.267]

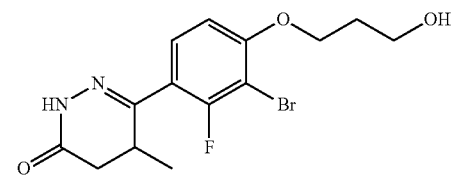

¹H-NMR (DMSO-d6) δ: 1.04 (3H, d, J=7.2 Hz), 1.85-1.95 (2H, m), 2.24 (1H, dd, J=16.9, 3.7 Hz), 2.69 (1H, dd, J=16.9, 6.8 Hz), 3.09-3.19 (1H, m), 3.56-3.64 (2H, m), 4.20 (2H, t, J=6.2 Hz), 4.58 (1H, t, J=5.2 Hz), 7.04 (1H, dd, J=8.9, 1.0 Hz), 7.58 (1H, t, J=8.9 Hz), 11.02 (1H, s).

Example 13

6-[3,5-Difluoro-4-(3-hydroxypropoxy)phenyl]-5-methyl-4,5-dihydro-2H-pyridazin-3-one

[Chem.268]

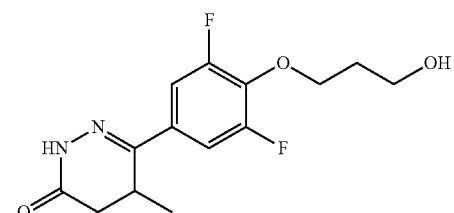

¹H-NMR (DMSO-d6) δ: 1.05 (3H, d, J=7.3 Hz), 1.77-1.89 (2H, m), 2.24 (1H, d, J=16.7 Hz), 2.68 (1H, dd, J=16.7, 7.0 Hz), 3.33-3.47 (1H, m), 3.51-3.62 (2H, m), 4.23 (2H, t, J=6.3 Hz), 4.53 (1H, t, J=5.0 Hz), 7.45-7.61 (2H, m), 11.06 (1H, s).

Example 14

6-[4-(3-Hydroxypropoxy)-3,5-dimethylphenyl]-5-methyl-4,5-dihydro-2H-pyridazin-3-one

[Chem.269]

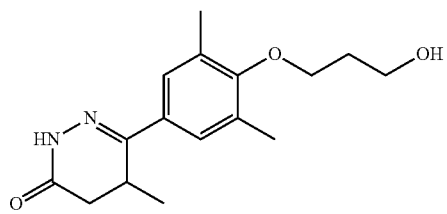

$^1$H-NMR (DMSO-d6) δ: 1.05 (3H, d, J=7.2 Hz), 1.84-1.93 (2H, m), 2.21 (1H, d, J=16.8 Hz), 2.24 (6H, s), 2.64 (1H, dd, J=16.8, 6.9 Hz), 3.30-3.40 (1H, m), 3.58-3.66 (2H, m), 3.82 (2H, t, J=6.4 Hz), 4.50 (1H, t, J=5.1 Hz), 7.44 (2H, s), 10.86 (1H, s).

Example 15

6-[3-Chloro-5-fluoro-4-(3-hydroxypropoxy)phenyl]-5-methyl-4,5-dihydro-2H-pyridazin-3-one

[Chem.270]

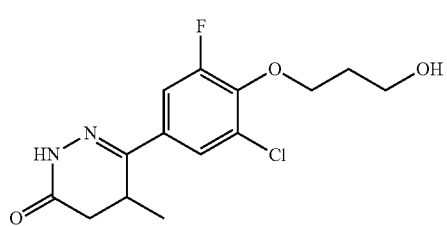

$^1$H-NMR (DMSO-d6) δ: 1.04 (3H, d, J=7.3 Hz), 1.80-1.92 (2H, m), 2.24 (1H, d, J=16.9 Hz), 2.69 (1H, dd, J=16.9, 7.0 Hz), 3.35-3.47 (1H, m), 3.52-3.64 (2H, m), 4.14-4.26 (2H, m), 4.53 (1H, t, J=5.1 Hz), 7.60-7.72 (2H, m), 11.06 (1H, s).

Example 16

6-[3,5-Dichloro-4-(3-hydroxypropoxy)phenyl]-5-methyl-4,5-dihydro-2H-pyridazin-3-one

[Chem.271]

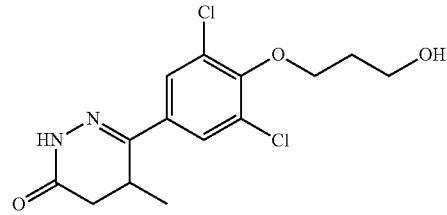

$^1$H-NMR (DMSO-d6) δ: 1.04 (3H, d, J=7.3 Hz), 1.87-1.98 (2H, m), 2.23 (1H, d, J=17.0 Hz), 2.69 (1H, dd, J=17.0, 7.0 Hz), 3.36-3.49 (1H, m), 3.57-3.66 (2H, m), 4.10 (2H, t, J=6.5 Hz), 4.53 (1H, t, J=5.1 Hz), 7.82 (2H, s), 11.08 (1H, s).

Example 17

6-[3-Chloro-4-(3-hydroxypropoxy)-5-methylphenyl]-5-methyl-4,5-dihydro-2H-pyridazin-3-one

[Chem.272]

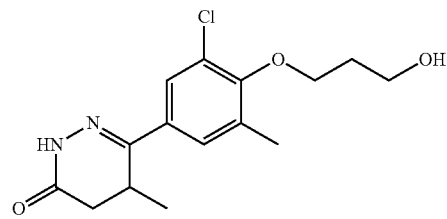

Melting point: 129.7-132.6° C.

Example 18

6-[3-Bromo-5-chloro-4-(3-hydroxypropoxy)phenyl]-5-methyl-4,5-dihydro-2H-pyridazin-3-one

[Chem.273]

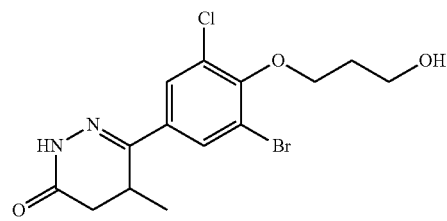

Melting point: 153.0-156.6° C.

Example 19

6-[3-Chloro-2-fluoro-4-(3-hydroxypropoxy)phenyl]-5-methyl-4,5-dihydro-2H-pyridazin-3-one

[Chem.274]

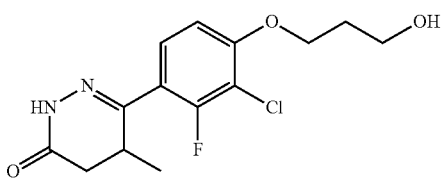

$^1$H-NMR (DMSO-d6) δ: 1.04 (3H, d, J=7.3 Hz), 1.87-1.93 (2H, m), 2.25 (1H, dd, J=16.7, 3.5 Hz), 2.70 (1H, dd, J=16.7, 6.7 Hz), 3.10-3.19 (1H, m), 3.56-3.62 (2H, m), 4.21 (2H, t, J=6.3 Hz), 4.59 (1H, t, J=5.1 Hz), 7.09 (1H, dd, J=8.8, 1.5 Hz), 7.55 (1H, t, J=8.8 Hz), 11.02 (1H, s).

Example 20

6-[3-Fluoro-4-(3-hydroxypropoxy)-5-methylphenyl]-5-methyl-4,5-dihydro-2H-pyridazin-3-one

[Chem.275]

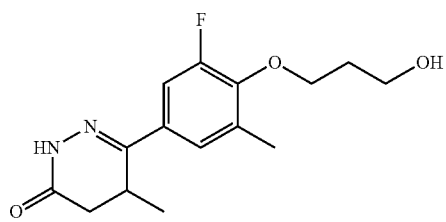

$^1$H-NMR (DMSO-d6) δ: 1.05 (3H, d, J=7.2 Hz), 1.80-1.90 (2H, m), 2.22 (1H, d, J=16.8 Hz), 2.27 (3H, s), 2.66 (1H, dd, J=16.8, 6.9 Hz), 3.31-3.41 (1H, m), 3.55-3.62 (2H, m), 4.06-4.13 (2H, m), 4.52 (1H, t, J=5.1 Hz), 7.40-7.48 (2H, m), 10.95 (1H, s).

Example 21

6-[2-Fluoro-4-(3-hydroxypropoxy)-3-methylphenyl]-5-methyl-4,5-dihydro-2H-pyridazin-3-one

[Chem.276]

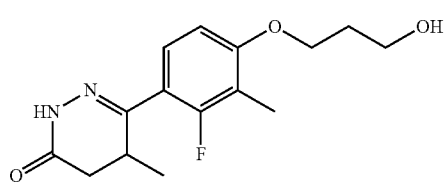

$^1$H-NMR (DMSO-d6) δ: 1.03 (3H, d, J=7.2 Hz), 1.84-1.93 (2H, m), 2.08 (3H, d, J=2.2 Hz), 2.22 (1H, dd, J=16.8, 3.7 Hz), 2.66 (1H, dd, J=16.8, 6.7 Hz), 3.07-3.17 (1H, m), 3.55-3.63 (2H, m), 4.10 (2H, t, J=6.2 Hz), 4.56 (1H, t, J=5.2 Hz), 6.87 (1H, d, J=8.8 Hz), 7.38 (1H, t, J=8.8 Hz), 10.92 (1H, s).

Example 22

6-[3-Chloro-2-fluoro-4-(3-hydroxypropoxy)-5-methylphenyl]-5-methyl-4,5-dihydro-2H-pyridazin-3-one

[Chem. 277]

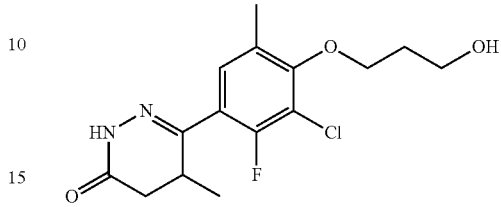

$^1$H-NMR (DMSO-d6) δ: 1.05 (3H, d, J=7.2 Hz), 1.87-1.96 (2H, m), 2.22-2.29 (1H, m), 2.27 (3H, s), 2.69 (1H, dd, J=16.8, 6.8 Hz), 3.09-3.19 (1H, m), 3.59-3.66 (2H, m), 4.02 (2H, t, J=6.5 Hz), 4.54 (1H, t, J=5.1 Hz), 7.43 (1H, d, J=8.7 Hz), 11.07 (1H, s).

Example 23

6-[3-Ethyl-2-fluoro-4-(3-hydroxypropoxy)phenyl]-5-methyl-4,5-dihydro-2H-pyridazin-3-one

[Chem. 278]

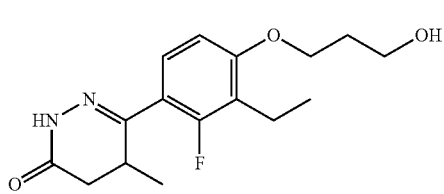

$^1$H-NMR (CDCl$_3$) δ: 1.15 (3H, t, J=7.6 Hz), 1.19 (3H, d, J=7.3 Hz), 1.56-1.62 (1H, m), 2.09 (2H, quintet, J=6.1 Hz), 2.41 (1H, dd, J=16.9, 3.4 Hz), 2.63-2.78 (3H, m), 3.21-3.33 (1H, m), 3.85-3.93 (2H, m), 4.16 (2H, t, J=6.1 Hz), 6.70 (1H, d, J=8.3 Hz), 7.33-7.38 (1H, m), 8.49 (1H, brs).

Example 24

Production of 6-[3-bromo-2-fluoro-4-(2-hydroxy-2-methylpropoxy)phenyl]-5-methyl-4,5-dihydro-2H-pyridazin-3-one

[Chem. 279]

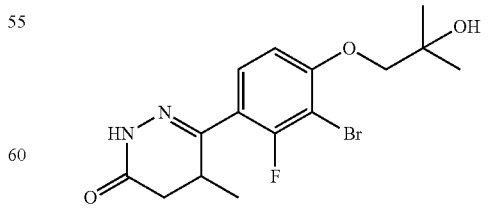

Under an argon atmosphere, to a solution of 6-[3-bromo-2-fluoro-4-(2-oxopropoxy)phenyl]-5-methyl-4,5-dihydro-2H-pyridazin-3-one (Reference example 114, 357 mg) in THF (10 mL) was added dropwise methyl-magnesium bromide (3 M diethyl ether solution, 1.0 mL) at 0° C. The reaction mixture was stirred at room temperature for 23 hours. The reaction mixture was cooled at 0° C., aqueous ammonium chloride was added thereto, and the mixture was extracted with ethyl acetate. The organic layer was washed with brine, dried over anhydrous sodium sulfate, and filtrated, and the solvent was removed. The obtained crude product was purified by silica gel column chromatography (heptane:ethyl acetate=33:67 to 6:94). The obtained solid was washed by trituration with diisopropyl ether, and then collected on a filter to afford the title compound as a white solid (18 mg).

$^1$H-NMR (DMSO-d6) δ: 1.04 (3H, d, J=7.3 Hz), 1.25 (6H, s), 2.24 (1H, dd, J=16.8, 3.7 Hz), 2.69 (1H, dd, J=16.8, 6.8 Hz), 3.09-3.19 (1H, m), 3.86 (2H, s), 4.70 (1H, s), 7.03 (1H, dd, J=8.9, 1.2 Hz), 7.57 (1H, t, J=8.9 Hz), 11.01 (1H, s).

The following compounds were prepared from each appropriate starting material in a similar manner to Example 24.

Example 25

6-[3-Chloro-5-fluoro-4-(2-hydroxy-2-methylpropoxy)phenyl]-5-methyl-4,5-dihydro-2H-pyridazin-3-one

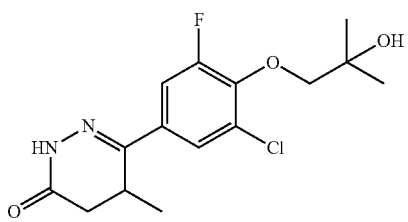

[Chem. 280]

$^1$H-NMR (DMSO-d6) δ: 1.05 (3H, d, J=7.3 Hz), 1.25 (6H, s), 2.24 (1H, d, J=16.7 Hz), 2.69 (1H, dd, J=16.7, 7.0 Hz), 3.35-3.45 (1H, m), 3.87 (2H, d, J=1.2 Hz), 4.64 (1H, s), 7.64 (1H, dd, J=12.7, 2.2 Hz), 7.68 (1H, t, J=2.2 Hz), 11.06 (1H, s).

Example 26

6-[3-Bromo-5-fluoro-4-(2-hydroxy-2-methylpropoxy)phenyl]-5-methyl-4,5-dihydro-2H-pyridazin-3-one

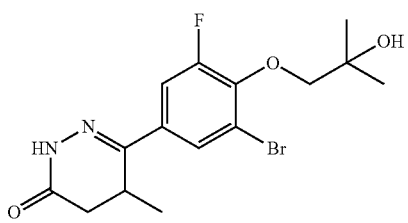

[Chem. 281]

$^1$H-NMR (DMSO-d6) δ: 1.04 (3H, d, J=7.3 Hz), 1.26 (6H, s), 2.23 (1H, d, J=16.8 Hz), 2.69 (1H, dd, J=16.8, 6.9 Hz), 3.34-3.45 (1H, m), 3.86 (2H, d, J=1.3 Hz), 4.64 (1H, s), 7.67 (1H, dd, J=12.9, 2.1 Hz), 7.81 (1H, t, J=2.1 Hz), 11.06 (1H, s).

Example 27

Production of 6-[2,3-difluoro-4-(2-hydroxy-2-methylpropoxy)phenyl]-5-methyl-4,5-dihydro-2H-pyridazin-3-one

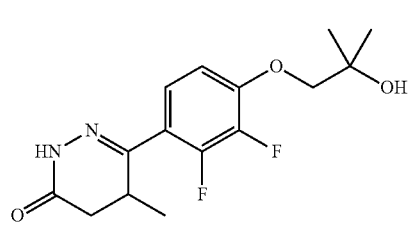

[Chem. 282]

A suspension of 6-(2,3-difluoro-4-hydroxyphenyl)-5-methyl-4,5-dihydro-2H-pyridazin-3-one (480 mg), 2,2-dimethyloxirane (0.231 mL), and potassium carbonate (415 mg) in DMF (3 mL) was stirred at 160° C. under microwave irradiation for 30 minutes. The reaction mixture was poured into water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=60:40 to 33:67). The obtained solid was washed by trituration with diisopropyl ether, and then collected on a filter to afford the title compound as a white solid (326 mg).

$^1$H-NMR (DMSO-d6) δ: 1.05 (3H, d, J=7.3 Hz), 1.21 (6H, s), 2.25 (1H, dd, J=16.9, 3.4 Hz), 2.70 (1H, dd, J=16.9, 6.7 Hz), 3.11-3.21 (1H, m), 3.87 (2H, s), 4.71 (1H, s), 7.06-7.13 (1H, m), 7.34-7.41 (1H, m), 11.02 (1H, s).

The following compounds were prepared from each appropriate starting material in a similar manner to Example 27.

Example 28

6-[2-Hydroxy-4-(2-hydroxy-2-methylpropoxy)-3-methylphenyl]-5-methyl-4,5-dihydro-2H-pyridazin-3-one

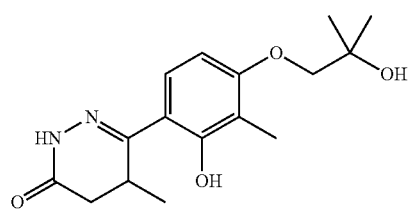

[Chem. 283]

$^1$H-NMR (DMSO-d6) δ: 1.10 (3H, d, J=7.3 Hz), 1.23 (6H, s), 2.05 (3H, s), 2.23-2.31 (1H, m), 2.76 (1H, dd, J=16.7, 6.7 Hz), 3.47-3.57 (1H, m), 3.74 (2H, s), 4.65 (1H, s), 6.55 (1H, d, J=9.0 Hz), 7.42 (1H, d, J=9.0 Hz), 11.03 (1H, s), 12.46 (1H, s).

Example 29

6-[3-Chloro-2-fluoro-4-(2-hydroxy-2-methyl-propoxy)phenyl]-5-methyl-4,5-dihydro-2H-pyridazin-3-one

[Chem. 284]

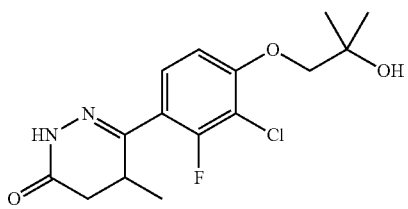

¹H-NMR (DMSO-d6) δ: 1.04 (3H, d, J=7.3 Hz), 1.24 (6H, s), 2.25 (1H, dd, J=16.9, 3.7 Hz), 2.70 (1H, dd, J=16.9, 6.7 Hz), 3.09-3.20 (1H, m), 3.87 (2H, s), 4.71 (1H, s), 7.06-7.11 (1H, m), 7.53 (1H, t, J=8.8 Hz), 11.02 (1H, s).

Example 30

6-[3,5-Difluoro-4-(2-hydroxy-2-methylpropoxy)phenyl]-5-methyl-4,5-dihydro-2H-pyridazin-3-one

[Chem. 285]

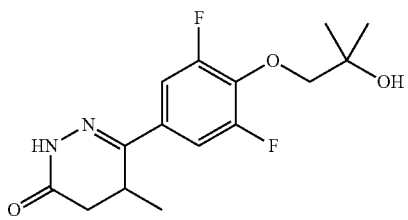

¹H-NMR (DMSO-d6) δ: 1.05 (3H, d, J=7.3 Hz), 1.20 (6H, s), 2.20-2.27 (1H, m), 2.68 (1H, dd, J=16.7, 7.0 Hz), 3.33-3.43 (1H, m), 3.89 (2H, s), 4.61 (1H, s), 7.46-7.55 (2H, m), 11.05 (1H, s).

Example 31

6-[3-Chloro-4-(2-hydroxy-2-methylpropoxy)-5-methylphenyl]-5-methyl-4,5-dihydro-2H-pyridazin-3-one

[Chem. 286]

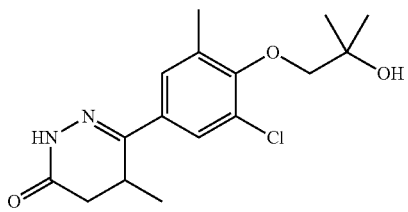

¹H-NMR (DMSO-d6) δ: 1.05 (3H, d, J=7.3 Hz), 1.28 (6H, s), 2.19-2.26 (1H, m), 2.33 (3H, s), 2.67 (1H, dd, J=16.9, 6.8 Hz), 3.33-3.43 (1H, m), 3.64 (2H, s), 4.64 (1H, s), 7.58-7.67 (2H, m), 10.98 (1H, s).

Example 32

6-[4-(2-Hydroxy-2-methylpropoxy)-3,5-dimethylphenyl]-5-methyl-4,5-dihydro-2H-pyridazin-3-one

[Chem. 287]

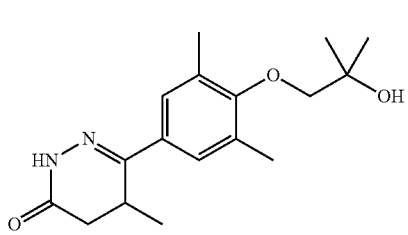

¹H-NMR (DMSO-d6) δ: 1.05 (3H, d, J=7.4 Hz), 1.27 (6H, s), 2.21 (1H, d, J=16.7 Hz), 2.26 (6H, s), 2.64 (1H, dd, J=16.7, 6.8 Hz), 3.32-3.40 (1H, m), 3.46-3.52 (2H, m), 4.60 (1H, s), 7.45 (2H, s), 10.87 (1H, s).

Example 33

6-[3-Fluoro-4-(2-hydroxy-2-methylpropoxy)-5-methylphenyl]-5-methyl-4,5-dihydro-2H-pyridazin-3-one

[Chem. 288]

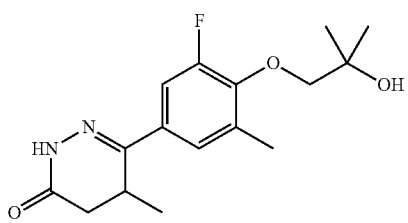

¹H-NMR (DMSO-d6) δ: 1.05 (3H, d, J=7.2 Hz), 1.23 (6H, s), 2.22 (1H, d, J=16.7 Hz), 2.30 (3H, s), 2.66 (1H, dd, J=16.7, 6.8 Hz), 3.31-3.42 (1H, m), 3.77 (2H, d, J=1.5 Hz), 4.61 (1H, s), 7.41-7.49 (2H, m), 10.95 (1H, s).

Example 34

6-[2-Fluoro-4-(2-hydroxy-2-methylpropoxy)-3-methylphenyl]-5-methyl-4,5-dihydro-2H-pyridazin-3-one

[Chem. 289]

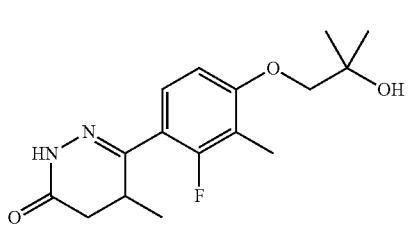

¹H-NMR (DMSO-d6) δ: 1.03 (3H, d, J=7.2 Hz), 1.23 (6H, s), 2.13 (3H, d, J=2.2 Hz), 2.23 (1H, dd, J=16.7, 3.7 Hz), 2.66 (1H, dd, J=16.7, 6.7 Hz), 3.06-3.18 (1H, m), 3.76 (2H, s), 4.68 (1H, s), 6.84 (1H, d, J=8.7 Hz), 7.37 (1H, t, J=8.7 Hz), 10.92 (1H, s).

Example 35

6-[5-Chloro-2-fluoro-4-(2-hydroxy-2-methyl-propoxy)-3-methylphenyl]-5-methyl-4,5-dihydro-2H-pyridazin-3-one

[Chem. 290]

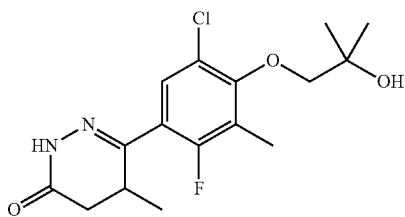

$^1$H-NMR (DMSO-d6) δ: 1.04 (3H, d, J=7.1 Hz), 1.28 (6H, s), 2.21-2.29 (1H, m), 2.24 (3H, d, J=2.4 Hz), 2.68 (1H, dd, J=16.8, 6.8 Hz), 3.08-3.19 (1H, m), 3.67 (2H, s), 4.69 (1H, s), 7.52 (1H, d, J=7.9 Hz), 11.06 (1H, s).

Example 36

6-[3-Chloro-2-fluoro-4-(2-hydroxy-2-methyl-propoxy)-5-methylphenyl]-5-methyl-4,5-dihydro-2H-pyridazin-3-one

[Chem. 291]

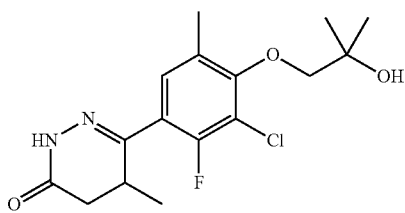

$^1$H-NMR (DMSO-d6) δ: 1.05 (3H, d, J=7.2 Hz), 1.28 (6H, s), 2.25 (1H, dd, J=16.9, 3.8 Hz), 2.29 (3H, s), 2.69 (1H, dd, J=16.8, 6.8 Hz), 3.09-3.20 (1H, m), 3.68 (2H, s), 4.67 (1H, s), 7.43 (1H, d, J=8.4 Hz), 11.07 (1H, s).

Example 37

6-{3-Chloro-5-fluoro-4-[3,3,3-trifluoro-2-hydroxy-2-(trifluoromethyl)propoxy]phenyl}-5-methyl-4,5-dihydro-2H-pyridazin-3-one

[Chem. 292]

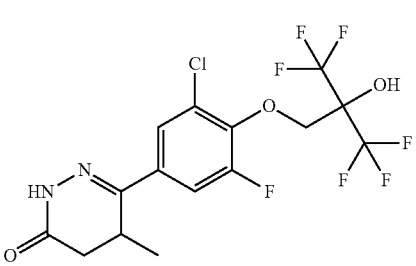

$^1$H-NMR (DMSO-d6) δ: 1.04 (3H, d, J=7.3 Hz), 2.24 (1H, d, J=16.7 Hz), 2.70 (1H, dd, J=16.7, 7.0 Hz), 3.36-3.47 (1H, m), 4.48 (2H, s), 7.66-7.74 (2H, m), 8.46 (1H, brs), 11.11 (1H, s).

Example 38

6-{3-Bromo-5-fluoro-4-[3,3,3-trifluoro-2-hydroxy-2-(trifluoromethyl)propoxy]phenyl}-5-methyl-4,5-dihydro-2H-pyridazin-3-one

[Chem.293]

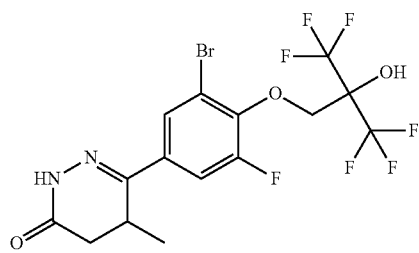

$^1$H-NMR (DMSO-d6) δ: 1.04 (3H, d, J=7.3 Hz), 2.19-2.30 (1H, m), 2.70 (1H, dd, J=16.7, 7.0 Hz), 3.35-3.48 (1H, m), 4.47 (2H, s), 7.72 (1H, dd, J=12.7, 2.2 Hz), 7.82-7.86 (1H, m), 8.44 (1H, s), 11.10 (1H, s).

Example 39

6-{3-Chloro-4-[(2S)-2-hydroxypropoxy]-5-methylphenyl}-5-methyl-4,5-dihydro-2H-pyridazin-3-one

[Chem.294]

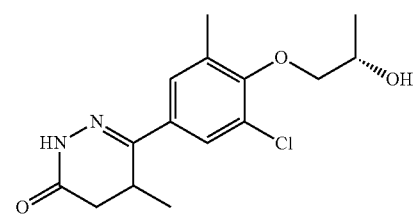

$^1$H-NMR (CDCl$_3$) δ: 1.24 (3H, d, J=7.3 Hz), 1.28 (3H, d, J=6.6 Hz), 2.36 (3H, s), 2.47 (1H, dd, J=16.9, 1.2 Hz), 2.61 (1H, d, J=3.4 Hz), 2.69 (1H, dd, J=16.9, 6.8 Hz), 3.23-3.34 (1H, m), 3.77-3.83 (1H, m), 3.91-3.96 (1H, m), 4.20-4.31 (1H, m), 7.49 (1H, d, J=2.2 Hz), 7.61 (1H, d, J=2.2 Hz), 8.62 (1H, s).

Example 40

6-{3-Chloro-4-[(2R)-2-hydroxypropoxy]-5-methl-phenyl}-5-methyl-4,5-dihydro-2H-pyridazin-3-one

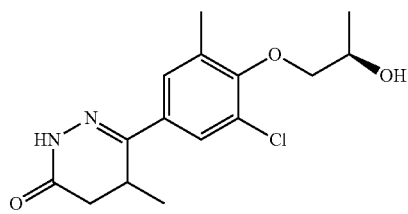

[Chem.295]

$^1$H-NMR (DMSO-d6) δ: 1.05 (3H, d, J=7.1 Hz), 1.19 (3H, d, J=6.4 Hz), 2.20-2.26 (1H, m), 2.33 (3H, s), 2.66 (1H, dd, J=16.9, 6.8 Hz), 3.32-3.42 (1H, m), 3.67-3.83 (2H, m), 3.92-4.03 (1H, m), 4.86 (1H, brs), 7.60 (1H, d, J=2.0 Hz), 7.65 (1H, d, J=2.0 Hz), 10.98 (1H, s).

Example 41

Production of 6-{3-chloro-5-fluoro-4-[(1-hydroxycyclopropyl)methoxy]phenyl}-5-methyl-4,5-dihydro-2H-pyridazin-3-one

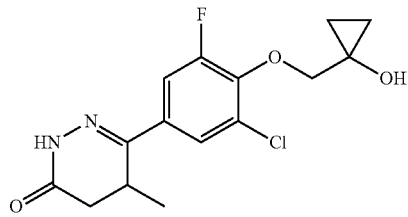

[Chem.296]

To a mixture of methyl 4-{3-chloro-5-fluoro-4-[(1-hydroxycyclopropyl)methoxy]phenyl}-3-methyl-4-oxobutanoate (Reference example 55, 352 mg) in ethanol (10 mL) were added hydrazine monohydrate (0.149 mL) and acetic acid (0.175 mL), and then the mixture was refluxed for 8 hours. Water was added to the reaction mixture, and the mixture was extracted with ethyl acetate. The organic layer was washed with brine, dried over anhydrous sodium sulfate, and filtrated, and the solvent was removed. The obtained crude product was purified by silica gel column chromatography (heptane:ethyl acetate=25:75 to 0:100), and the desired fractions were concentrated. The residue was recrystallized from 2-propanol to afford the title compound as a white solid (91 mg).

$^1$H-NMR (DMSO-d6) δ: 0.61-0.73 (4H, m), 1.04 (3H, d, J=7.3 Hz), 2.23 (1H, d, J=16.7 Hz), 2.69 (1H, dd, J=16.7, 7.0 Hz), 3.35-3.46 (1H, m), 4.10 (2H, s), 5.54 (1H, s), 7.63 (1H, dd, J=12.5, 2.2 Hz), 7.66-7.69 (1H, m), 11.06 (1H, s).

The following compounds were prepared from each appropriate starting material in a similar manner to Example 41.

Example 42

6-{2,3-Difluoro-4-[(1-hydroxycyclopropyl)methoxy]phenyl}-5-methyl-4,5-dihydro-2H-pyridazin-3-one

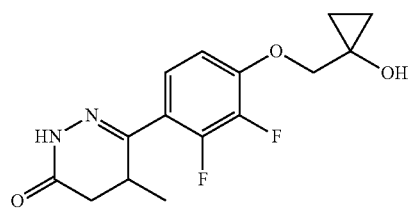

[Chem.297]

$^1$H-NMR (DMSO-d6) δ: 0.61-0.75 (4H, m), 1.05 (3H, d, J=7.2 Hz), 2.25 (1H, dd, J=16.8, 3.4 Hz), 2.70 (1H, dd, J=16.8, 6.8 Hz), 3.12-3.22 (1H, m), 4.12 (2H, s), 5.65 (1H, s), 7.05-7.13 (1H, m), 7.33-7.41 (1H, m), 11.02 (1H, s).

Example 43

6-{4-[(1-Hydroxycyclopropyl)methoxy]-3,5-dimethylphenyl}-5-methyl-4,5-dihydro-2H-pyridazin-3-one

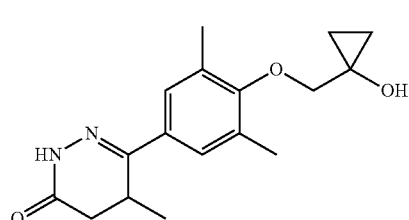

[Chem.298]

$^1$H-NMR (DMSO-d6) δ: 0.58-0.72 (4H, m), 1.05 (3H, d, J=7.3 Hz), 2.21 (1H, d, J=16.8 Hz), 2.27 (6H, s), 2.64 (1H, dd, J=16.8, 6.9 Hz), 3.30-3.39 (1H, m), 3.74 (2H, s), 5.62 (1H, s), 7.44 (2H, s), 10.86 (1H, s).

Example 44

6-{3-Chloro-4-[(1-hydroxycyclopropyl)methoxy]-5-methylphenyl}-5-methyl-4,5-dihydro-2H-pyridazin-3-one

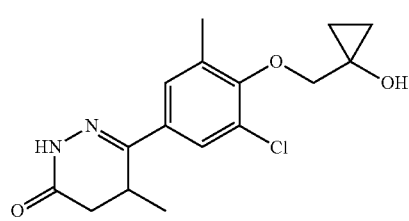

[Chem.299]

$^1$H-NMR (DMSO-d6) δ: 0.60-0.74 (4H, m), 1.05 (3H, d, J=7.3 Hz), 2.23 (1H, d, J=16.7 Hz), 2.36 (3H, s), 2.67 (1H, dd, J=16.7, 7.0 Hz), 3.32-3.43 (1H, m), 3.90 (2H, s), 5.62 (1H, s), 7.59 (1H, d, J=2.1 Hz), 7.65 (1H, d, J=2.1 Hz), 10.97 (1H, s).

Example 45

6-{3-Fluoro-4-[(1-hydroxycyclopropyl)methoxy]-5-methylphenyl}-5-methyl-4,5-dihydro-2H-pyridazin-3-one

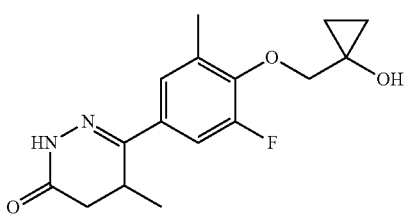
[Chem.300]

$^1$H-NMR (DMSO-d6) δ: 0.55-0.70 (4H, m), 1.05 (3H, d, J=7.2 Hz), 2.22 (1H, d, J=16.8 Hz), 2.33 (3H, s), 2.66 (1H, dd, J=16.8, 6.8 Hz), 3.32-3.42 (1H, m), 4.00 (2H, s), 5.53 (1H, s), 7.40-7.48 (2H, m), 10.95 (1H, s).

Example 46

6-{2-Fluoro-4-[(1-hydroxycyclopropyl)methoxy]-3-methylphenyl}-5-methyl-4,5-dihydro-2H-pyridazin-3-one

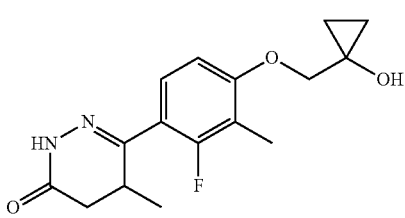
[Chem.301]

$^1$H-NMR (DMSO-d6) δ: 0.60-0.75 (4H, m), 1.03 (3H, d, J=7.2 Hz), 2.13 (3H, d, J=2.2 Hz), 2.22 (1H, dd, J=16.8, 3.7 Hz), 2.66 (1H, dd, J=16.8, 6.7 Hz), 3.07-3.18 (1H, m), 4.03 (2H, s), 5.60 (1H, s), 6.86 (1H, d, J=8.7 Hz), 7.35 (1H, t, J=8.7 Hz), 10.92 (1H, s).

Example 47

6-{3-Chloro-2-fluoro-4-[(1-hydroxycyclopropyl)methoxy]phenyl}-5-methyl-4,5-dihydro-2H-pyridazin-3-one

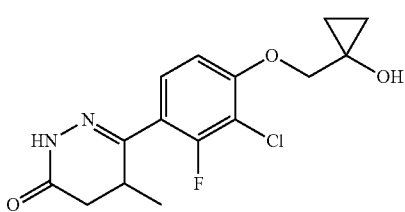
[Chem.302]

$^1$H-NMR (DMSO-d6) δ: 0.61-0.76 (4H, m), 1.04 (3H, d, J=7.2 Hz), 2.25 (1H, dd, J=16.7, 3.7 Hz), 2.70 (1H, dd, J=16.7, 6.8 Hz), 3.10-3.19 (1H, m), 4.15 (2H, s), 5.61 (1H, s), 7.10 (1H, dd, J=9.0, 1.3 Hz), 7.52 (1H, t, J=9.0 Hz), 11.03 (1H, s).

Example 48

Production of 6-[3-bromo-2-fluoro-4-(2-hydroxypropoxy)phenyl]-5-methyl-4,5-dihydro-2H-pyridazin-3-one

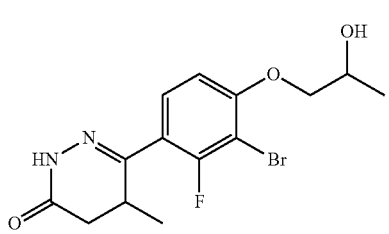
[Chem.303]

To a mixture of 6-[3-bromo-2-fluoro-4-(2-oxopropoxy)phenyl]-5-methyl-4,5-dihydro-2H-pyridazin-3-one (Reference example 114, 321 mg) in methanol (4.5 mL) was added sodium borohydride (68 mg) at 0° C., and then the mixture was stirred at the same temperature for one hour. To the reaction mixture were added water and brine, and then the mixture was extracted with ethyl acetate. The organic layer was dried over anhydrous sodium sulfate, and filtrated, and the solvent was removed. The obtained solid was washed by trituration with diisopropyl ether, and then collected on a filter to afford the title compound as a white solid (270 mg).

$^1$H-NMR (DMSO-d6) δ: 1.04 (3H, d, J=7.2 Hz), 1.20 (3H, d, J=6.0 Hz), 2.24 (1H, dd, J=16.8, 3.7 Hz), 2.69 (1H, dd, J=16.8, 6.8 Hz), 3.09-3.19 (1H, m), 3.88-4.08 (3H, m), 4.92 (1H, d, J=4.6 Hz), 7.04 (1H, dd, J=8.9, 1.1 Hz), 7.57 (1H, t, J=8.9 Hz), 11.01 (1H, s).

The following compounds were prepared from each appropriate starting material in a similar manner to Example 48.

Example 49

6-[2,3-Difluoro-4-(2-hydroxypropoxy)phenyl]-5-methyl-4,5-dihydro-2H-pyridazin-3-one

[Chem.304]

$^1$H-NMR (DMSO-d6) δ: 1.05 (3H, d, J=7.1 Hz), 1.16 (3H, d, J=6.1 Hz), 2.25 (1H, dd, J=16.9, 3.2 Hz), 2.70 (1H, dd, J=16.9, 6.8 Hz), 3.10-3.22 (1H, m), 3.91-4.05 (3H, m), 4.96 (1H, d, J=4.6 Hz), 7.05-7.14 (1H, m), 7.33-7.42 (1H, m), 11.03 (1H, s).

Example 50

6-[3-Bromo-5-fluoro-4-(2-hydroxypropoxy)phenyl]-5-methyl-4,5-dihydro-2H-pyridazin-3-one

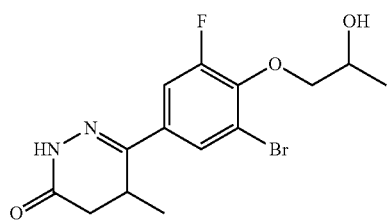
[Chem.305]

$^1$H-NMR (DMSO-d6) δ: 1.04 (3H, d, J=7.2 Hz), 1.20 (3H, d, J=6.1 Hz), 2.23 (1H, d, J=16.8 Hz), 2.69 (1H, dd, J=16.8, 6.9 Hz), 3.35-3.45 (1H, m), 3.83-4.07 (3H, m), 4.86 (1H, d, J=4.8 Hz), 7.67 (1H, dd, J=12.7, 2.1 Hz), 7.81 (1H, t, J=2.1 Hz), 11.06 (1H, s).

Example 51

6-[4-(2-Hydroxypropoxy)-3,5-dimethylphenyl]-5-methyl-4,5-dihydro-2H-pyridazin-3-one

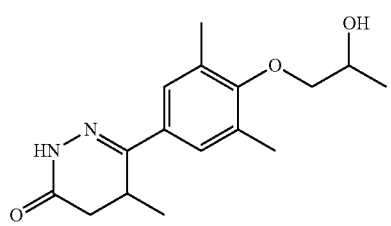
[Chem.306]

$^1$H-NMR (DMSO-d6) δ: 1.05 (3H, d, J=7.4 Hz), 1.19 (3H, d, J=6.3 Hz), 2.21 (1H, d, J=16.7 Hz), 2.26 (6H, s), 2.64 (1H, dd, J=16.7, 6.8 Hz), 3.29-3.40 (1H, m), 3.54-3.66 (2H, m), 3.91-4.01 (1H, m), 4.85 (1H, d, J=4.9 Hz), 7.44 (2H, s), 10.86 (1H, s).

Example 52

6-[3-Chloro-5-fluoro-4-(2-hydroxypropoxy)phenyl]-5-methyl-4,5-dihydro-2H-pyridazin-3-one

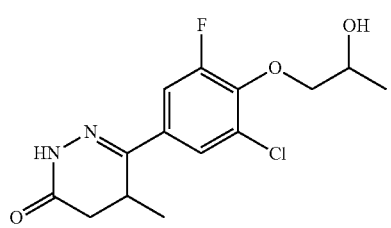
[Chem.307]

$^1$H-NMR (DMSO-d6) δ: 1.04 (3H, d, J=7.3 Hz), 1.18 (3H, d, J=5.9 Hz), 2.24 (1H, d, J=16.9 Hz), 2.69 (1H, dd, J=16.9, 6.8 Hz), 3.35-3.46 (1H, m), 3.81-4.06 (3H, m), 4.86 (1H, d, J=4.6 Hz), 7.58-7.72 (2H, m), 11.06 (1H, s).

Example 53

6-[3,5-Dichloro-4-(2-hydroxypropoxy)phenyl]-5-methyl-4,5-dihydro-2H-pyridazin-3-one

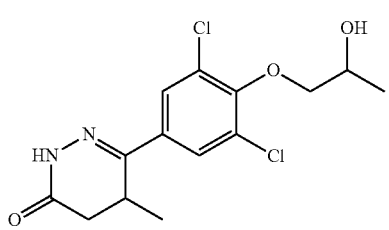
[Chem.308]

$^1$H-NMR (DMSO-d6) δ: 1.04 (3H, d, J=7.3 Hz), 1.21 (3H, d, J=6.1 Hz), 2.24 (1H, d, J=16.7 Hz), 2.69 (1H, dd, J=16.7, 7.0 Hz), 3.37-3.47 (1H, m), 3.74-3.81 (1H, m), 3.89-3.96 (1H, m), 3.97-4.07 (1H, m), 4.89 (1H, d, J=4.9 Hz), 7.82 (2H, s), 11.09 (1H, s).

Example 54

6-[3-Chloro-2-fluoro-4-(2-hydroxypropoxy)phenyl]-5-methyl-4,5-dihydro-2H-pyridazin-3-one

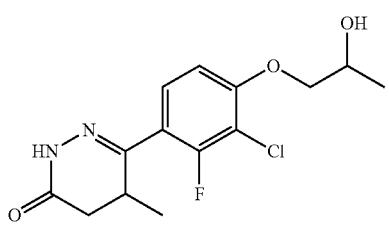
[Chem.309]

$^1$H-NMR (DMSO-d6) δ: 1.04 (3H, d, J=7.3 Hz), 1.18 (3H, d, J=6.1 Hz), 2.25 (1H, dd, J=16.9, 3.7 Hz), 2.70 (1H, dd, J=16.9, 6.8 Hz), 3.10-3.19 (1H, m), 3.91-4.05 (3H, m), 4.93 (1H, d, J=4.6 Hz), 7.09 (1H, dd, J=8.8, 1.2 Hz), 7.53 (1H, t, J=8.8 Hz), 11.02 (1H, s).

Example 55

6-[3-Chloro-4-(2-hydroxypropoxy)-5-methylphenyl]-5-methyl-4,5-dihydro-2H-pyridazin-3-one

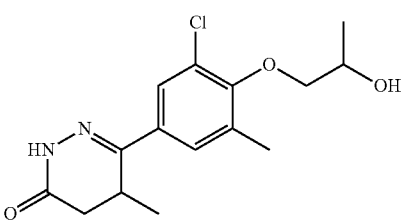
[Chem.310]

$^1$H-NMR (CDCl$_3$) δ: 1.24 (3H, d, J=7.3 Hz), 1.28 (3H, d, J=6.4 Hz), 2.36 (3H, s), 2.47 (1H, dd, J=16.8, 1.0 Hz), 2.61 (1H, d, J=3.7 Hz), 2.69 (1H, dd, J=16.8, 6.8 Hz), 3.23-3.33 (1H, m), 3.77-3.83 (1H, m), 3.92-3.96 (1H, m), 4.19-4.31 (1H, m), 7.49 (1H, dd, J=2.2, 0.5 Hz), 7.61 (1H, d, J=2.2 Hz), 8.67 (1H, brs).

Example 56

6-[3-Fluoro-4-(2-hydroxypropoxy)-5-methylphenyl]-5-methyl-4,5-dihydro-2H-pyridazin-3-one

[Chem.311]

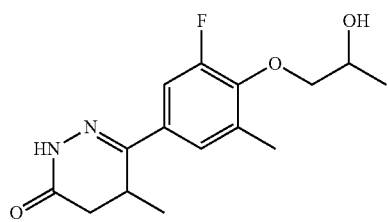

$^1$H-NMR (DMSO-d6) δ: 1.05 (3H, d, J=7.3 Hz), 1.16 (3H, d, J=6.1 Hz), 2.22 (1H, d, J=16.7 Hz), 2.29 (3H, s), 2.66 (1H, dd, J=16.7, 6.8 Hz), 3.30-3.42 (1H, m), 3.80-3.97 (3H, m), 4.83 (1H, d, J=4.6 Hz), 7.40-7.50 (2H, m), 10.95 (1H, s).

Example 57

6-[3-Bromo-5-chloro-4-(2-hydroxypropoxy)phenyl]-5-methyl-4,5-dihydro-2H-pyridazin-3-one

[Chem.312]

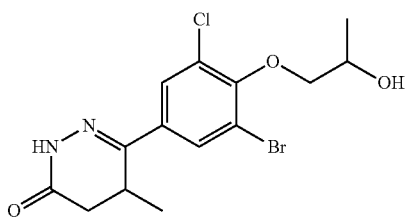

$^1$H-NMR (CDCl$_3$) δ: 1.24 (3H, d, J=7.3 Hz), 1.28 (3H, d, J=6.4 Hz), 2.49 (1H, dd, J=17.1, 1.0 Hz), 2.66-2.75 (2H, m), 3.20-3.31 (1H, m), 3.88-3.94 (1H, m), 4.10-4.14 (1H, m), 4.21-4.34 (1H, m), 7.74 (1H, d, J=2.2 Hz), 7.87 (1H, d, J=2.2 Hz), 8.72 (1H, brs).

Example 58

6-[2-Fluoro-4-(2-hydroxypropoxy)-3-methylphenyl]-5-methyl-4,5-dihydro-2H-pyridazin-3-one

[Chem.313]

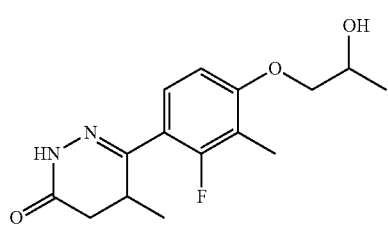

$^1$H-NMR (DMSO-d6) δ: 1.03 (3H, d, J=7.2 Hz), 1.18 (3H, d, J=6.2 Hz), 2.11 (3H, d, J=2.2 Hz), 2.22 (1H, dd, J=16.8, 3.7 Hz), 2.66 (1H, dd, J=16.8, 6.7 Hz), 3.06-3.18 (1H, m), 3.80-4.03 (3H, m), 4.89 (1H, d, J=4.8 Hz), 6.86 (1H, d, J=8.7 Hz), 7.36 (1H, t, J=8.7 Hz), 10.92 (1H, s).

Example 59

6-[2-Fluoro-4-(2-hydroxypropoxy)-3-vinylphenyl]-5-methyl-4,5-dihydro-2H-pyridazin-3-one

[Chem.314]

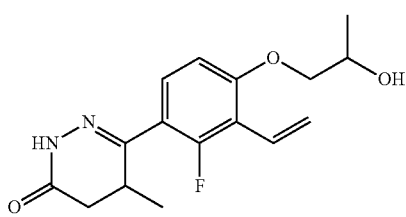

$^1$H-NMR (DMSO-d6) δ: 1.04 (3H, d, J=7.3 Hz), 1.18 (3H, d, J=6.1 Hz), 2.23 (1H, dd, J=16.9, 3.9 Hz), 2.66 (1H, dd, J=16.9, 6.8 Hz), 3.06-3.18 (1H, m), 3.86-4.06 (3H, m), 4.93 (1H, d, J=4.6 Hz), 5.51-5.59 (1H, m), 6.02-6.10 (1H, m), 6.81 (1H, dd, J=18.1, 12.0 Hz), 6.94 (1H, d, J=8.8 Hz), 7.43 (1H, t, J=8.8 Hz), 10.96 (1H, brs).

Example 60

6-[3-Ethyl-2-fluoro-4-(2-hydroxypropoxy)phenyl]-5-methyl-4,5-dihydro-2H-pyridazin-3-one

[Chem.315]

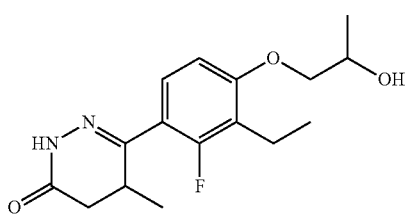

$^1$H-NMR (CDCl$_3$) δ: 1.16 (3H, t, J=7.6 Hz), 1.20 (3H, d, J=7.3 Hz), 1.32 (3H, d, J=6.4 Hz), 2.13-2.18 (1H, m), 2.42 (1H, dd, J=16.9, 3.4 Hz), 2.66-2.78 (3H, m), 3.21-3.33 (1H, m), 3.84-3.91 (1H, m), 3.98 (1H, dd, J=9.0, 3.4 Hz), 4.18-4.30 (1H, m), 6.68 (1H, d, J=8.5 Hz), 7.36 (1H, t, J=8.5 Hz), 8.49 (1H, brs).

Example 61

6-[2,3-Difluoro-4-(2-hydroxybutoxy)phenyl]-5-methyl-4,5-dihydro-2H-pyridazin-3-one

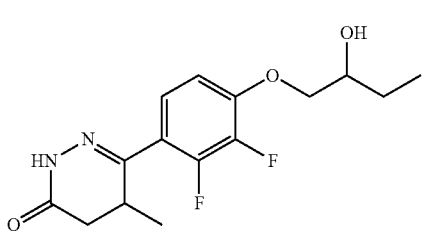
[Chem.316]

¹H-NMR (DMSO-d6) δ: 0.93 (3H, t, J=7.4 Hz), 1.05 (3H, d, J=7.1 Hz), 1.34-1.48 (1H, m), 1.50-1.63 (1H, m), 2.25 (1H, dd, J=16.9, 3.3 Hz), 2.70 (1H, dd, J=16.9, 6.8 Hz), 3.09-3.23 (1H, m), 3.67-3.78 (1H, m), 3.94-4.07 (2H, m), 4.93 (1H, d, J=5.4 Hz), 7.06-7.14 (1H, m), 7.31-7.43 (1H, m), 11.02 (1H, s).

Example 62

6-[3-Chloro-5-fluoro-4-(2-hydroxybutoxy)phenyl]-5-methyl-4,5-dihydro-2H-pyridazin-3-one

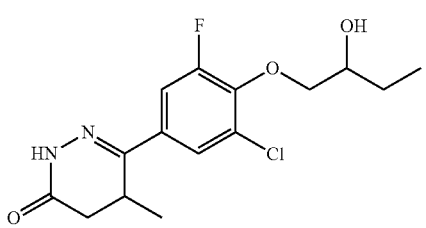
[Chem.317]

¹H-NMR (DMSO-d6) δ: 0.92 (3H, t, J=7.4 Hz), 1.04 (3H, d, J=7.3 Hz), 1.34-1.50 (1H, m), 1.56-1.71 (1H, m), 2.24 (1H, d, J=17.0 Hz), 2.69 (1H, dd, J=17.0, 7.0 Hz), 3.35-3.46 (1H, m), 3.63-3.75 (1H, m), 3.92-4.09 (2H, m), 4.82 (1H, d, J=5.4 Hz), 7.57-7.72 (2H, m), 11.06 (1H, s).

Example 63

6-[3,5-Dichloro-4-(2-hydroxybutoxy)phenyl]-5-methyl-4,5-dihydro-2H-pyridazin-3-one

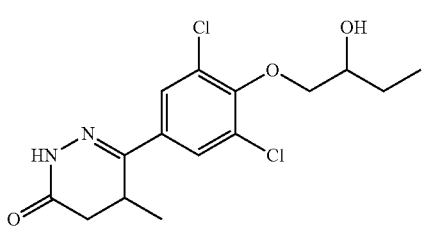
[Chem.318]

¹H-NMR (DMSO-d6) δ: 0.95 (3H, t, J=7.4 Hz), 1.04 (3H, d, J=7.3 Hz), 1.35-1.52 (1H, m), 1.60-1.76 (1H, m), 2.24 (1H, d, J=16.9 Hz), 2.69 (1H, dd, J=16.9, 6.8 Hz), 3.37-3.47 (1H, m), 3.71-3.81 (1H, m), 3.82-3.88 (1H, m), 3.89-3.96 (1H, m), 4.85 (1H, d, J=5.4 Hz), 7.82 (2H, s), 11.08 (1H, s).

Example 64

6-[3-Chloro-2-fluoro-4-(2-hydroxybutoxy)phenyl]-5-methyl-4,5-dihydro-2H-pyridazin-3-one

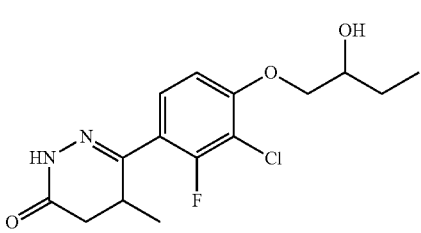
[Chem.319]

¹H-NMR (DMSO-d6) δ: 0.93 (3H, t, J=7.4 Hz), 1.04 (3H, d, J=7.1 Hz), 1.39-1.50 (1H, m), 1.56-1.67 (1H, m), 2.25 (1H, dd, J=16.7, 3.7 Hz), 2.69 (1H, dd, J=16.7, 6.7 Hz), 3.10-3.18 (1H, m), 3.71-3.78 (1H, m), 3.98-4.06 (2H, m), 4.90 (1H, d, J=5.4 Hz), 7.10 (1H, dd, J=8.9, 1.5 Hz), 7.53 (1H, t, J=8.9 Hz), 11.02 (1H, s).

Example 65

6-[3-Chloro-4-(2-hydroxybutoxy)-5-methylphenyl]-5-methyl-4,5-dihydro-2H-pyridazin-3-one

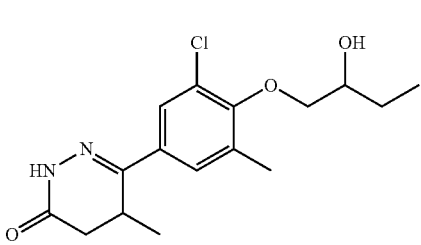
[Chem.320]

¹H-NMR (CDCl₃) δ: 1.04 (3H, t, J=7.6 Hz), 1.24 (3H, d, J=7.3 Hz), 1.61 (2H, quintet, J=7.6 Hz), 2.36 (3H, s), 2.47 (1H, dd, J=16.8, 1.0 Hz), 2.56 (1H, d, J=3.9 Hz), 2.69 (1H, dd, J=16.8, 6.8 Hz), 3.23-3.34 (1H, m), 3.83-3.88 (1H, m), 3.93-4.04 (2H, m), 7.47-7.51 (1H, m), 7.61 (1H, d, J=2.2 Hz), 8.65 (1H, brs).

Example 66

6-[3-Bromo-5-chloro-4-(2-hydroxybutoxy)phenyl]-5-methyl-4,5-dihydro-2H-pyridazin-3-one

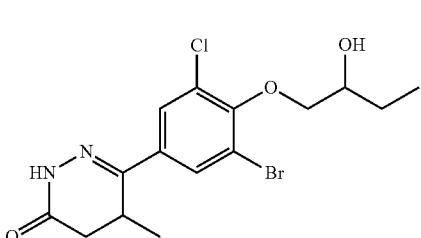
[Chem.321]

¹H-NMR (CDCl₃) δ: 1.05 (3H, t, J=7.3 Hz), 1.24 (3H, d, J=7.3 Hz), 1.62 (2H, quintet, J=6.8 Hz), 2.49 (1H, d, J=16.9 Hz), 2.63-2.75 (2H, m), 3.20-3.31 (1H, m), 3.93-4.06 (2H, m), 4.10-4.18 (1H, m), 7.74 (1H, d, J=2.2 Hz), 7.86 (1H, d, J=2.2 Hz), 8.66 (1H, brs).

Example 67

6-[2-Fluoro-4-(2-hydroxybutoxy)-3-vinylphenyl]-5-methyl-4,5-dihydro-2H-pyridazin-3-one

[Chem.322]

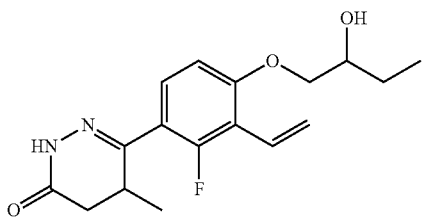

¹H-NMR (CDCl₃) δ: 1.05 (3H, t, J=7.3 Hz), 1.19 (3H, d, J=7.3 Hz), 1.59-1.70 (2H, m), 2.15 (1H, d, J=3.7 Hz), 2.42 (1H, dd, J=17.1, 3.7 Hz), 2.73 (1H, dd, J=17.1, 6.8 Hz), 3.21-3.33 (1H, m), 3.90-4.10 (3H, m), 5.53-5.61 (1H, m), 5.97-6.06 (1H, m), 6.69-6.75 (1H, m), 6.78 (1H, dd, J=18.1, 12.0 Hz), 7.40 (1H, t, J=8.8 Hz), 8.55 (1H, brs).

Example 68

Production of 6-[3-bromo-5-chloro-4-(3-hydroxy-2,2-dimethylpropoxy)phenyl]-5-methyl-4,5-dihydro-2H-pyridazin-3-one

[Chem.323]

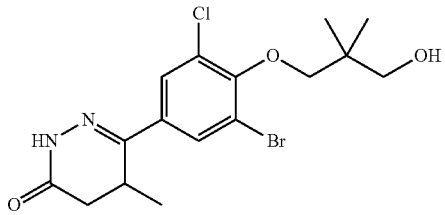

Under an argon atmosphere, to a mixture of methyl 3-[2-bromo-6-chloro-4-(4-methyl-6-oxo-4,5-dihydro-1H-pyridazin-3-yl)phenoxy]-2,2-dimethylpropionate (Reference example 129, 342 mg) in THF (10 mL) was slowly added diisobutylaluminum hydride (1 M n-hexane solution, 3.17 mL) at 0° C. The mixture was stirred at room temperature for 2 hours, hydrochloric acid was added to the reaction mixture, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=50:50 to 25:75). The obtained solid was recrystallized from 2-propanol to afford the title compound as a white powder (111 mg).
Melting point: 198.0-199.7° C.
The following compounds were prepared from each appropriate starting material in a similar manner to Example 68.

Example 69

6-[3-Bromo-5-fluoro-4-(3-hydroxy-2,2-dimethylpropoxy)phenyl]-5-methyl-4,5-dihydro-2H-pyridazin-3-one

[Chem.324]

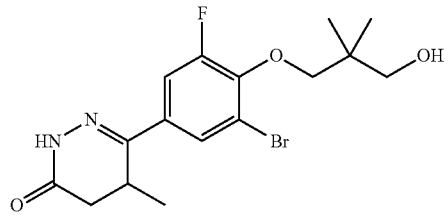

¹H-NMR (DMSO-d6) δ: 0.98 (6H, s), 1.04 (3H, d, J=7.3 Hz), 2.23 (1H, d, J=16.9 Hz), 2.69 (1H, dd, J=16.9, 6.8 Hz), 3.30-3.34 (2H, m), 3.34-3.45 (1H, m), 3.92 (2H, d, J=1.8 Hz), 4.61 (1H, t, J=5.3 Hz), 7.66 (1H, dd, J=13.1, 2.2 Hz), 7.79-7.83 (1H, m), 11.05 (1H, s).

Example 70

6-[3-Bromo-2-fluoro-4-(3-hydroxy-2,2-dimethylpropoxy)phenyl]-5-methyl-4,5-dihydro-2H-pyridazin-3-one

[Chem.325]

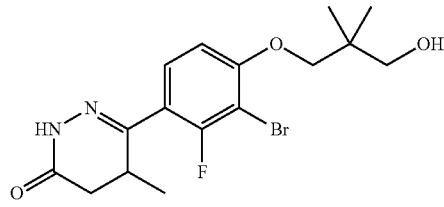

¹H-NMR (DMSO-d6) δ: 0.97 (6H, s), 1.04 (3H, d, J=7.2 Hz), 2.24 (1H, dd, J=16.8, 3.7 Hz), 2.69 (1H, dd, J=16.8, 6.8 Hz), 3.09-3.19 (1H, m), 3.33 (2H, d, J=5.4 Hz), 3.85 (2H, s), 4.65 (1H, t, J=5.4 Hz), 7.01 (1H, dd, J=8.9, 1.2 Hz), 7.57 (1H, t, J=8.9 Hz), 11.01 (1H, s).

Example 71

6-[4-(3-Hydroxy-2,2-dimethylpropoxy)-3,5-dimethylphenyl]-5-methyl-4,5-dihydro-2H-pyridazin-3-one

[Chem.326]

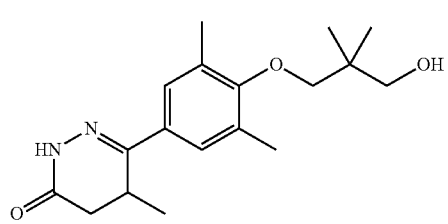

¹H-NMR (DMSO-d6) δ: 0.99 (6H, s), 1.05 (3H, d, J=7.2 Hz), 2.21 (1H, d, J=16.8 Hz), 2.25 (6H, s), 2.64 (1H, dd, J=16.8, 6.8 Hz), 3.30-3.38 (3H, m), 3.47 (2H, s), 4.58 (1H, t, J=5.1 Hz), 7.44 (2H, s), 10.86 (1H, s).

Example 72

6-[3-Chloro-4-(3-hydroxy-2,2-dimethylpropoxy)-5-methylphenyl]-5-methyl-4,5-dihydro-2H-pyridazin-3-one

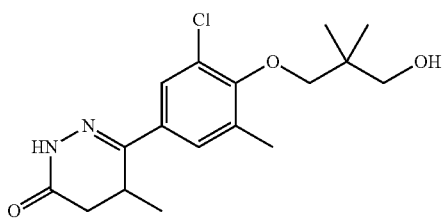

[Chem.327]

¹H-NMR (CDCl₃) δ: 1.09 (6H, s), 1.24 (3H, d, J=7.6 Hz), 2.14 (1H, t, J=6.4 Hz), 2.35 (3H, s), 2.47 (1H, dd, J=16.8, 1.0 Hz), 2.69 (1H, dd, J=16.8, 6.8 Hz), 3.23-3.34 (1H, m), 3.65 (2H, d, J=6.4 Hz), 3.74 (2H, s), 7.48 (1H, dd, J=2.2, 0.7 Hz), 7.61 (1H, d, J=2.2 Hz), 8.63 (1H, brs).

Example 73

6-[3-Fluoro-4-(3-hydroxy-2,2-dimethylpropoxy)-5-methylphenyl]-5-methyl-4,5-dihydro-2H-pyridazin-3-one

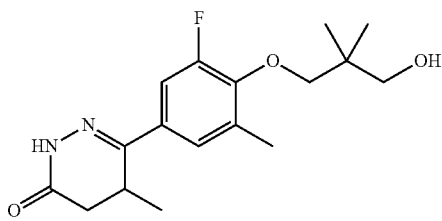

[Chem.328]

¹H-NMR (DMSO-d6) δ: 0.95 (6H, s), 1.05 (3H, d, J=7.2 Hz), 2.22 (1H, d, J=16.7 Hz), 2.28 (3H, s), 2.66 (1H, dd, J=16.7, 7.0 Hz), 3.27-3.42 (3H, m), 3.79 (2H, d, J=1.7 Hz), 4.60 (1H, t, J=5.3 Hz), 7.39-7.48 (2H, m), 10.94 (1H, s).

Example 74

Production of 6-[2-hydroxy-4-(2-hydroxypropoxy)-3-methylphenyl]-5-methyl-4,5-dihydro-2H-pyridazin-3-one

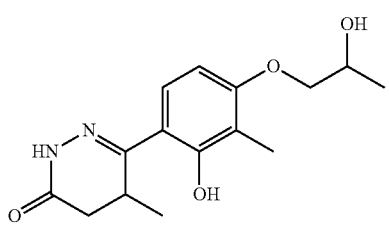

[Chem.329]

To a mixture of 6-[2-(methoxymethyloxy)-3-methyl-4-(2-oxopropoxy)phenyl]-5-methyl-4,5-dihydro-2H-pyridazin-3-one (Reference example 107, 120 mg) in methanol (2 mL) was added sodium borohydride (27 mg) at 0° C., and the mixture was stirred at room temperature for one hour. The reaction mixture was poured into water, and the mixture was extracted with ethyl acetate. The organic layer was washed with water and brine, and dried over anhydrous sodium sulfate. The solvent was removed and the residue was dissolved in ethanol (2 mL), and hydrogen chloride (2 M ethanol solution, 0.359 mL) was added to the mixture. The reaction mixture was stirred at room temperature for 2 days. The precipitates were collected on a filter to afford the title compound as a pale yellow solid (83 mg).

¹H-NMR (DMSO-d6) δ: 1.10 (3H, d, J=7.3 Hz), 1.18 (3H, d, J=6.1 Hz), 2.03 (3H, s), 2.27 (1H, d, J=16.9 Hz), 2.76 (1H, dd, J=16.9, 6.6 Hz), 3.47-3.57 (1H, m), 3.76-3.83 (1H, m), 3.86-3.92 (1H, m), 3.92-4.02 (1H, m), 4.86 (1H, brs), 6.57 (1H, d, J=9.0 Hz), 7.42 (1H, d, J=9.0 Hz), 11.03 (1H, s), 12.46 (1H, s).

The following compound was prepared from the appropriate starting material in a similar manner to Example 74.

Example 75

6-[3-Chloro-2-hydroxy-4-(2-hydroxypropoxy)phenyl]-5-methyl-4,5-dihydro-2H-pyridazin-3-one

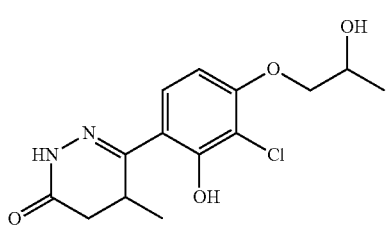

[Chem.330]

¹H-NMR (DMSO-d6) δ: 1.11 (3H, d, J=7.3 Hz), 1.19 (3H, d, J=5.9 Hz), 2.26-2.34 (1H, m), 2.80 (1H, dd, J=16.7, 6.7 Hz), 3.50-3.60 (1H, m), 3.83-3.93 (1H, m), 3.94-4.05 (2H, m), 4.87-4.94 (1H, m), 6.74 (1H, d, J=9.0 Hz), 7.55 (1H, d, J=9.0 Hz), 11.13 (1H, s), 13.01 (1H, s).

Example 76

Production of 6-{3-chloro-2-fluoro-4-[(Z)-4-hydroxy-2-butenyloxy]phenyl}-5-methyl-4,5-dihydro-2H-pyridazin-3-one

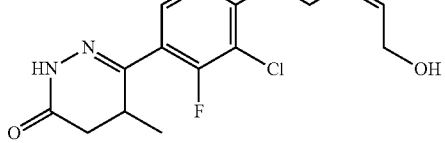
[Chem.331]

To a mixture of 6-{4-[(Z)-4-(tert-butyldimethylsilyloxy)-2-butenyloxy]-3-chloro-2-fluorophenyl}-5-methyl-4,5-dihydro-2H-pyridazin-3-one (Reference example 144, 296 mg) in THF (5 mL) was added tetrabutylammonium fluoride (1.0 M THF solution, 0.805 mL), and then the mixture was stirred at room temperature overnight. The reaction mixture was concentrated, and the obtained crude product was purified by silica gel column chromatography (heptane:ethyl acetate=10:90 to 0:100). The obtained solid was washed by trituration with diisopropyl ether, and then collected on a filter to afford the title compound as a white solid (135 mg).

$^1$H-NMR (DMSO-d6) δ: 1.04 (3H, d, J=7.1 Hz), 2.25 (1H, dd, J=16.9, 3.4 Hz), 2.69 (1H, dd, J=16.9, 6.8 Hz), 3.09-3.21 (1H, m), 4.11 (2H, t, J=5.0 Hz), 4.78-4.89 (3H, m), 5.59-5.70 (1H, m), 5.73-5.83 (1H, m), 7.09 (1H, dd, J=9.0, 1.2 Hz), 7.54 (1H, t, J=9.0 Hz), 11.03 (1H, s).

The following compounds were prepared from each appropriate starting material in a similar manner to Example 76.

Example 77

6-[3-Chloro-2-hydroxy-4-(3-hydroxypropoxy)phenyl]-5-methyl-4,5-dihydro-2H-pyridazin-3-one

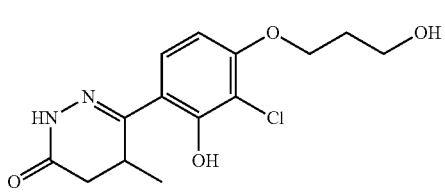
[Chem.332]

Melting point: 225.0-225.3° C.

Example 78

6-[2-Hydroxy-4-(3-hydroxypropoxy)-3-methylphenyl]-5-methyl-4,5-dihydro-2H-pyridazin-3-one

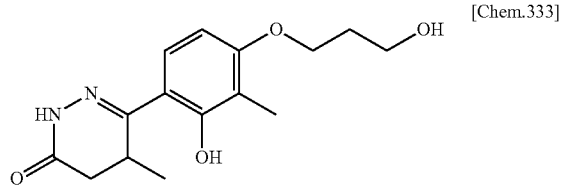 [SMILES: Cc1c(OCCCO)ccc(C2=NNC(=O)CC2C)c1O]
[Chem.333]

Melting point: 199.1-200.1° C.

Example 79

6-[3-Chloro-4-(4-hydroxybutoxy)-5-methylphenyl]-5-methyl-4,5-dihydro-2H-pyridazin-3-one

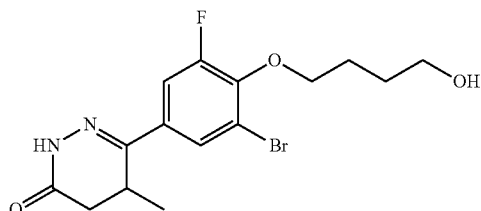
[Chem.334]

$^1$H-NMR (CDCl$_3$) δ: 1.24 (3H, d, J=7.6 Hz), 1.57 (1H, t, J=5.4 Hz), 1.78-1.98 (4H, m), 2.34 (3H, s), 2.43-2.51 (1H, m), 2.68 (1H, dd, J=16.9, 6.8 Hz), 3.23-3.34 (1H, m), 3.76 (2H, q, J=6.1 Hz), 3.98 (2H, t, J=6.1 Hz), 7.47 (1H, dd, J=2.2, 0.7 Hz), 7.58-7.62 (1H, m), 8.63 (1H s).

Example 80

6-[3-Bromo-5-fluoro-4-(4-hydroxybutoxy)phenyl]-5-methyl-4,5-dihydro-2H-pyridazin-3-one

[Chem.335]

$^1$H-NMR (CDCl$_3$) δ: 1.24 (3H, d, J=7.3 Hz), 1.42 (1H, t, J=5.5 Hz), 1.77-1.87 (2H, m), 1.88-1.97 (2H, m), 2.48 (1H, dd, J=17.0, 0.9 Hz), 2.70 (1H, dd, J=17.0, 6.8 Hz), 3.19-3.32 (1H, m), 3.76 (2H, q, J=5.5 Hz), 4.21 (2H, td, J=6.1, 1.2 Hz), 7.48 (1H, dd, J=12.3, 2.1 Hz), 7.70 (1H, t, J=2.1 Hz), 8.53 (1H, brs).

Example 81

6-[3,5-Dichloro-4-(4-hydroxybutoxy)phenyl]-5-methyl-4,5-dihydro-2H-pyridazin-3-one

[Chem.336]

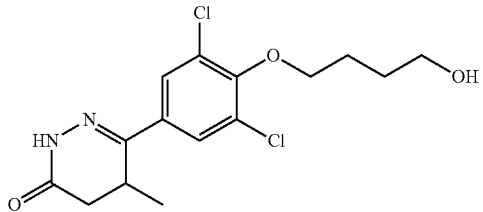

¹H-NMR (CDCl₃) δ: 1.25 (3H, d, J=7.3 Hz), 1.47 (1H, t, J=5.5 Hz), 1.79-1.90 (2H, m), 1.92-2.02 (2H, m), 2.49 (1H, dd, J=17.1, 1.0 Hz), 2.70 (1H, dd, J=17.1, 6.8 Hz), 3.17-3.33 (1H, m), 3.77 (2H, q, J=5.5 Hz), 4.10 (2H, t, J=6.2 Hz), 7.69 (2H, s), 8.58 (1H, brs).

Example 82

6-[2,3-Difluoro-4-(4-hydroxybutoxy)phenyl]-5-methyl-4,5-dihydro-2H-pyridazin-3-one

[Chem. 337]

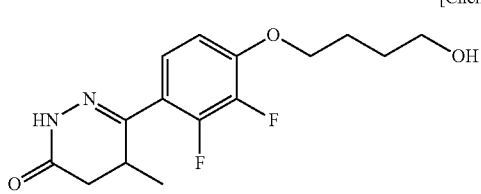

¹H-NMR (CDCl₃) δ: 1.22 (3H, d, J=7.1 Hz), 1.44 (1H, t, J=5.4 Hz), 1.72-1.84 (2H, m), 1.90-2.00 (2H, m), 2.45 (1H, dd, J=17.0, 3.1 Hz), 2.74 (1H, dd, J=17.0, 6.7 Hz), 3.21-3.33 (1H, m), 3.75 (2H, q, J=5.4 Hz), 4.13 (2H, t, J=6.2 Hz), 6.74-6.84 (1H, m), 7.27-7.35 (1H, m), 8.51 (1H, brs).

Example 83

6-[2-Fluoro-4-(4-hydroxybutoxy)-3-methylphenyl]-5-methyl-4,5-dihydro-2H-pyridazin-3-one

[Chem. 338]

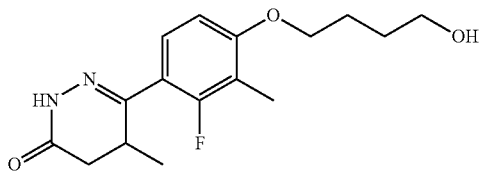

¹H-NMR (CDCl₃) δ: 1.20 (3H, d, J=7.1 Hz), 1.41 (1H, t, J=5.4 Hz), 1.73-1.84 (2H, m), 1.85-2.00 (2H, m), 2.15 (3H, d, J=2.4 Hz), 2.42 (1H, dd, J=17.0, 3.3 Hz), 2.74 (1H, dd, J=17.0, 6.7 Hz), 3.22-3.33 (1H, m), 3.75 (2H, q, J=5.4 Hz), 4.05 (2H, t, J=6.1 Hz), 6.66 (1H, d, J=8.8 Hz), 7.35 (1H, t, J=8.8 Hz), 8.46 (1H, brs).

Example 84

6-[3-Chloro-2-fluoro-4-(4-hydroxybutoxy)phenyl]-5-methyl-4,5-dihydro-2H-pyridazin-3-one

[Chem. 339]

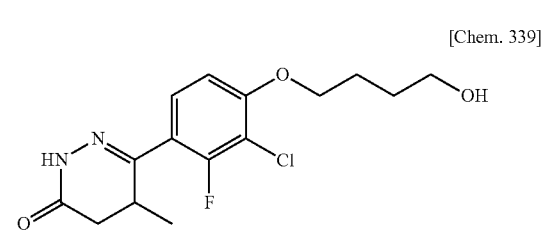 [SMILES: CC1CC(=O)NN=C1c1ccc(OCCCCO)c(Cl)c1F]

¹H-NMR (CDCl₃) δ: 1.21 (3H, d, J=7.3 Hz), 1.48 (1H, t, J=5.5 Hz), 1.76-1.85 (2H, m), 1.93-2.02 (2H, m), 2.44 (1H, dd, J=17.0, 3.3 Hz), 2.74 (1H, dd, J=17.0, 6.7 Hz), 3.17-3.34 (1H, m), 3.76 (2H, q, J=5.5 Hz), 4.14 (2H, t, J=6.1 Hz), 6.77 (1H, dd, J=8.9, 1.3 Hz), 7.46 (1H, t, J=8.9 Hz), 8.53 (1H, brs).

Example 85

6-[2-Fluoro-4-(3-hydroxypropoxy)-3-vinylphenyl]-5-methyl-4,5-dihydro-2H-pyridazin-3-one

[Chem. 340]

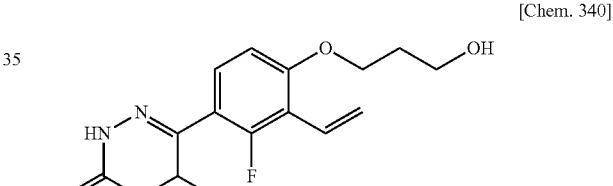

¹H-NMR (CDCl₃) δ: 1.19 (3H, d, J=6.8 Hz), 1.70 (1H, t, J=5.1 Hz), 2.10 (2H, quintet, J=6.1 Hz), 2.42 (1H, dd, J=17.1, 3.7 Hz), 2.73 (1H, dd, J=17.1, 6.8 Hz), 3.21-3.33 (1H, m), 3.86-3.91 (2H, m), 4.20 (2H, t, J=6.1 Hz), 5.52-5.59 (1H, m), 5.98-6.06 (1H, m), 6.74 (1H, dd, J=8.8, 0.5 Hz), 6.78 (1H, dd, J=18.1, 12.0 Hz), 7.39 (1H, t, J=8.8 Hz), 8.62 (1H, brs).

Example 86

6-{3-Chloro-4-[(Z)-4-hydroxy-2-butenyloxy]-5-methylphenyl}-5-methyl-4,5-dihydro-2H-pyridazin-3-one

[Chem. 341]

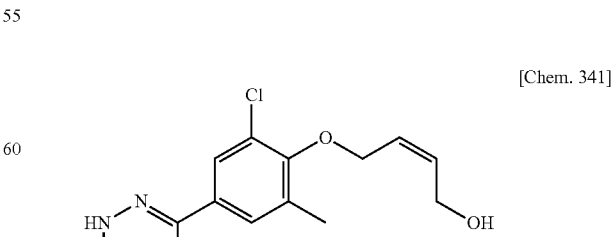

¹H-NMR (DMSO-d6) δ: 1.05 (3H, d, J=7.3 Hz), 2.23 (1H, d, J=16.7 Hz), 2.31 (3H, s), 2.67 (1H, dd, J=16.7, 7.0 Hz), 3.33-3.43 (1H, m), 4.00-4.04 (2H, m), 4.53-4.56 (2H, m), 4.77 (1H, t, J=5.4 Hz), 5.69-5.78 (2H, m), 7.61 (1H, dd, J=2.2, 0.7 Hz), 7.67 (1H, d, J=2.2 Hz), 10.99 (1H, s).

Example 87

6-[2-Hydroxy-4-(4-hydroxybutoxy)-3-methylphenyl]-5-methyl-4,5-dihydro-2H-pyridazin-3-one

[Chem. 342]

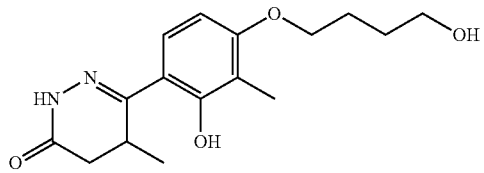

Melting point: 178.7-179.9° C.

Example 88

6-[3-Chloro-2-hydroxy-4-(4-hydroxybutoxy)phenyl]-5-methyl-4,5-dihydro-2H-pyridazin-3-one

[Chem. 343]

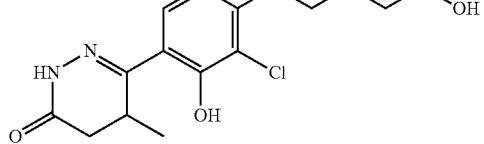

Melting point: 204.5-204.9° C.

Example 89

6-[2-Fluoro-4-(4-hydroxybutoxy)-3-vinylphenyl]-5-methyl-4,5-dihydro-2H-pyridazin-3-one

[Chem. 344]

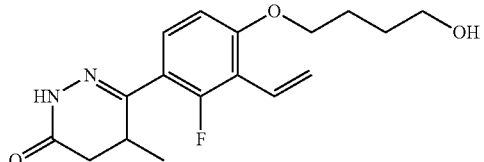

Melting point: 106.4-107.4° C.

Example 90

6-[3-Chloro-2-fluoro-4-[(E)-4-hydroxy-2-butenyloxy]phenyl}-5-methyl-4,5-dihydro-2H-pyridazin-3-one

[Chem. 345]

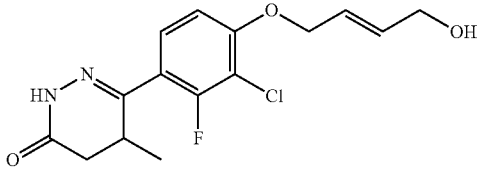

¹H-NMR (DMSO-d6) δ: 1.04 (3H, d, J=7.1 Hz), 2.25 (1H, dd, J=16.9, 3.7 Hz), 2.69 (1H, dd, J=16.9, 6.7 Hz), 3.11-3.19 (1H, m), 3.98-4.02 (2H, m), 4.73 (2H, dd, J=5.6, 1.2 Hz), 4.83 (1H, t, J=5.5 Hz), 5.81-5.89 (1H, m), 5.96-6.04 (1H, m), 7.10 (1H, dd, J=9.0, 1.2 Hz), 7.54 (1H, dd, J=9.0, 8.8 Hz), 11.02 (1H, brs).

Example 91

6-[3-Chloro-2-fluoro-4-(5-hydroxypentoxy)phenyl]-5-methyl-4,5-dihydro-2H-pyridazin-3-one

[Chem. 346]

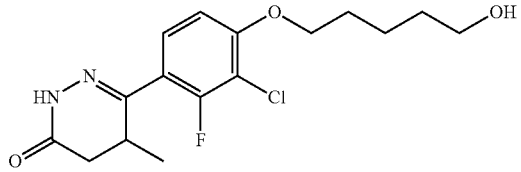

¹H-NMR (CDCl₃) δ: 1.20 (3H, dd, J=7.3, 0.5 Hz), 1.38 (1H, t, J=5.1 Hz), 1.54-1.72 (4H, m), 1.85-1.96 (2H, m), 2.43 (1H, dd, J=16.9, 3.2 Hz), 2.73 (1H, dd, J=16.9, 6.6 Hz), 3.21-3.33 (1H, m), 3.66-3.74 (2H, m), 4.10 (2H, t, J=6.4 Hz), 6.75 (1H, dd, J=9.0, 1.5 Hz), 7.42-7.50 (1H, m), 8.66 (1H, brs).

Example 92

6-[2-Fluoro-4-[(Z)-4-hydroxy-2-butenyloxy]-3-methylphenyl]-5-methyl-4,5-dihydro-2H-pyridazin-3-one

[Chem. 347]

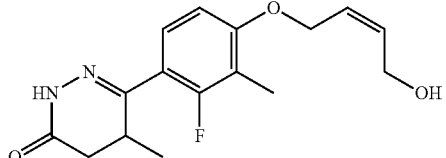

¹H-NMR (DMSO-d6) δ: 1.03 (3H, d, J=7.3 Hz), 2.09 (3H, d, J=2.2 Hz), 2.23 (1H, dd, J=16.7, 3.7 Hz), 2.66 (1H, dd,

J=16.7, 6.7 Hz), 3.06-3.18 (1H, m), 4.10 (2H, t, J=5.3 Hz), 4.71 (2H, d, J=5.6 Hz), 4.82 (1H, t, J=5.3 Hz), 5.59-5.69 (1H, m), 5.70-5.80 (1H, m), 6.88 (1H, d, J=8.9 Hz), 7.37 (1H, t, J=8.9 Hz), 10.92 (1H, s).

Example 93

6-{2,3-Difluoro-4-[(Z)-4-hydroxy-2-butenyloxy]phenyl}-5-methyl-4,5-dihydro-2H-pyridazin-3-one

[Chem. 348]

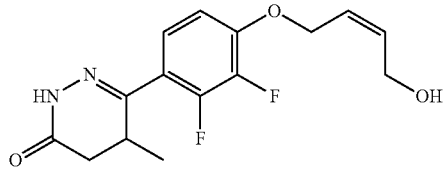

¹H-NMR (DMSO-d6) δ: 1.05 (3H, d, J=7.1 Hz), 2.25 (1H, dd, J=16.9, 3.4 Hz), 2.70 (1H, dd, J=16.9, 6.8 Hz), 3.09-3.23 (1H, m), 4.08-4.13 (2H, m), 4.80 (2H, d, J=6.1 Hz), 4.84 (1H, t, J=5.4 Hz), 5.59-5.70 (1H, m), 5.72-5.82 (1H, m), 7.05-7.15 (1H, m), 7.34-7.43 (1H, m), 11.03 (1H, s).

Example 94

6-{3-Chloro-5-fluoro-4-[(Z)-4-hydroxy-2-butenyloxy]phenyl}-5-methyl-4,5-dihydro-2H-pyridazin-3-one

[Chem. 349]

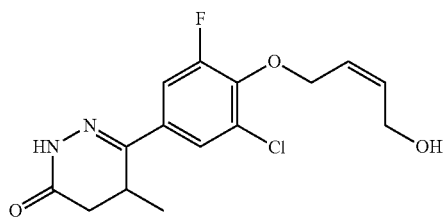

¹H-NMR (DMSO-d6) δ: 1.04 (3H, d, J=7.1 Hz), 2.24 (1H, d, J=16.7 Hz), 2.69 (1H, dd, J=16.7, 7.0 Hz), 3.35-3.46 (1H, m), 3.96-4.03 (2H, m), 4.71-4.83 (3H, m), 5.61-5.81 (2H, m), 7.64 (1H, dd, J=12.3, 2.1 Hz), 7.69 (1H, t, J=2.1 Hz), 11.07 (1H, s).

Example 95

6-{3-Bromo-5-fluoro-4-[(Z)-4-hydroxy-2-butenyloxy]phenyl}-5-methyl-4,5-dihydro-2H-pyridazin-3-one

[Chem. 350]

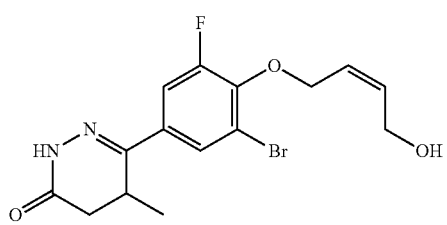

¹H-NMR (DMSO-d6) δ: 1.04 (3H, d, J=7.3 Hz), 2.23 (1H, d, J=16.9 Hz), 2.69 (1H, dd, J=16.9, 6.8 Hz), 3.34-3.46 (1H, m), 3.96-4.07 (2H, m), 4.68-4.84 (3H, m), 5.60-5.81 (2H, m), 7.67 (1H, dd, J=12.5, 2.2 Hz), 7.82 (1H, t, J=2.2 Hz), 11.07 (1H, s).

Example 96

6-{2-Fluoro-4-[(Z)-4-hydroxy-2-butenyloxy]-3-vinylphenyl}-5-methyl-4,5-dihydro-2H-pyridazin-3-one

[Chem. 351]

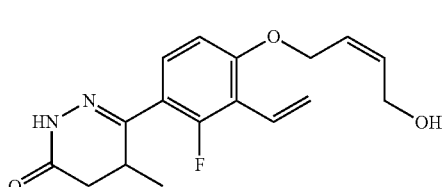

¹H-NMR (CDCl₃) δ: 1.19 (3H, d, J=7.3 Hz), 1.68 (1H, t, J=5.6 Hz), 2.42 (1H, dd, J=17.1, 3.7 Hz), 2.73 (1H, dd, J=17.1, 6.8 Hz), 3.20-3.34 (1H, m), 4.30 (2H, t, J=5.1 Hz), 4.72 (2H, d, J=5.1 Hz), 5.51-5.59 (1H, m), 5.79-5.95 (2H, m), 5.99-6.09 (1H, m), 6.72 (1H, d, J=8.8 Hz), 6.80 (1H, dd, J=18.1, 12.2 Hz), 7.39 (1H, t, J=8.8 Hz), 8.62 (1H, brs).

Example 97

6-[3-Ethyl-2-fluoro-4-(4-hydroxybutoxy)phenyl]-5-methyl-4,5-dihydro-2H-pyridazin-3-one

[Chem. 352]

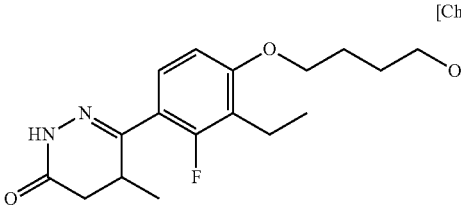

¹H-NMR (CDCl₃) δ: 1.14 (3H, t, J=7.6 Hz), 1.20 (3H, d, J=7.3 Hz), 1.38 (1H, t, J=5.4 Hz), 1.73-1.84 (2H, m), 1.87-1.98 (2H, m), 2.41 (1H, dd, J=17.1, 3.4 Hz), 2.64-2.78 (3H, m), 3.21-3.34 (1H, m), 3.71-3.79 (2H, m), 4.05 (2H, t, J=6.4 Hz), 6.67 (1H, d, J=8.8 Hz), 7.35 (1H, t, J=8.8 Hz), 8.47 (1H, brs).

Example 98

Production of 6-[3-chloro-4-(4-hydroxy-2,2-dimethylbutoxy)-5-methylphenyl]-5-methyl-4,5-dihydro-2H-pyridazin-3-one

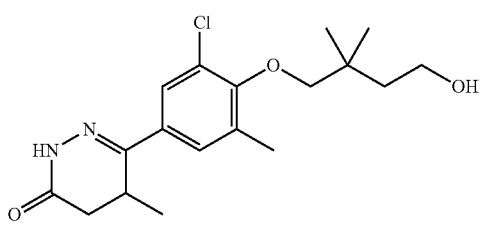

[Chem. 353]

To a mixture of 6-(3-chloro-4-hydroxy-5-methylphenyl)-5-methyl-4,5-dihydro-2H-pyridazin-3-one (Reference example 86, 255 mg), 4-(tert-butyldimethylsilyloxy)-2,2-dimethylbutan-1-ol (258 mg), and triphenylphosphine (291 mg) in THF (10 mL) was added bis(2-methoxyethyl) azodicarboxylate (260 mg) at 0° C., and then the mixture was stirred at room temperature overnight. The solvent was removed, and then the residue was purified by silica gel column chromatography (heptane:ethyl acetate=50:50) to afford a pale yellow solid (165 mg). The obtained solid was dissolved in THF (5 mL). To the solution was added tetrabutylammonium fluoride (1.0 M THF solution, 0.424 mL) at 0° C., and then the solution was stirred at 50° C. for 2 hours. To the reaction mixture was added water, and the mixture was extracted with ethyl acetate. The organic layer was washed with brine, dried over anhydrous sodium sulfate, and filtrated, and the solvent was removed. The obtained crude product was purified by silica gel column chromatography (heptane:ethyl acetate=50:50 to 0:100), and the desired fractions were concentrated. The residue was crystallized from diisopropyl ether/ethyl acetate, and the precipitates were collected on a filter to afford the title compound as a white powder (59 mg).

$^1$H-NMR (DMSO-d6) δ: 1.05 (3H, d, J=7.3 Hz), 1.06 (6H, s), 1.60 (2H, t, J=7.3 Hz), 2.22 (1H, d, J=16.5 Hz), 2.31 (3H, s), 2.67 (1H, dd, J=16.5, 7.0 Hz), 3.34-3.42 (1H, m), 3.52-3.59 (2H, m), 3.58 (2H, s), 4.32 (1H, t, J=5.0 Hz), 7.59-7.61 (1H, m), 7.65-7.67 (1H, m), 10.98 (1H, s).

The following compounds were prepared from each appropriate starting material in a similar manner to Example 98.

Example 99

6-[3-Chloro-5-fluoro-4-(4-hydroxy-2,2-dimethylbutoxy)phenyl]-5-methyl-4,5-dihydro-2H-pyridazin-3-one

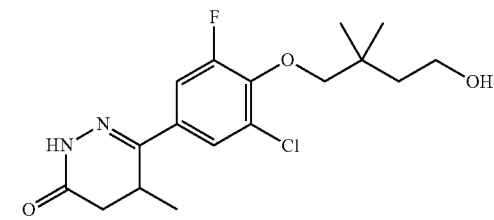

[Chem. 354]

$^1$H-NMR (DMSO-d6) δ: 1.03 (6H, s), 1.04 (3H, d, J=7.6 Hz), 1.57 (2H, t, J=7.3 Hz), 2.23 (1H, d, J=16.7 Hz), 2.69 (1H, dd, J=16.7, 7.0 Hz), 3.35-3.46 (1H, m), 3.52 (2H, t, J=7.3 Hz), 3.83 (2H, d, J=1.5 Hz), 4.32 (1H, brs), 7.64 (1H, dd, J=12.6, 2.1 Hz), 7.68 (1H, t, J=2.1 Hz), 11.06 (1H, s).

Example 100

6-[3,5-Dichloro-4-(4-hydroxy-2,2-dimethylbutoxy)phenyl]-5-methyl-4,5-dihydro-2H-pyridazin-3-one

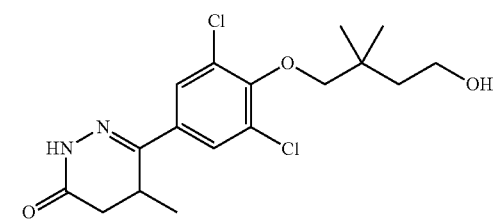

[Chem. 355]

$^1$H-NMR (DMSO-d6) δ: 1.04 (3H, d, J=7.1 Hz), 1.07 (6H, s), 1.60 (2H, t, J=7.3 Hz), 2.23 (1H, d, J=16.7 Hz), 2.69 (1H, dd, J=16.7, 7.0 Hz), 3.36-3.47 (1H, m), 3.55 (2H, t, J=7.3 Hz), 3.71 (2H, s), 4.19-4.45 (1H, m), 7.82 (2H, s), 11.08 (1H, s).

Example 101

6-[3-Fluoro-4-(4-hydroxy-2,2-dimethylbutoxy)-5-methylphenyl]-5-methyl-4,5-dihydro-2H-pyridazin-3-one

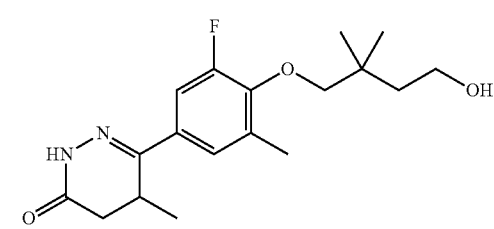

[Chem. 356]

¹H-NMR (DMSO-d6) δ: 1.02 (6H, s), 1.05 (3H, d, J=7.3 Hz), 1.57 (2H, t, J=7.3 Hz), 2.22 (1H, d, J=16.6 Hz), 2.28 (3H, s), 2.66 (1H, dd, J=16.6, 6.8 Hz), 3.27-3.42 (1H, m), 3.48-3.57 (2H, m), 3.72 (2H, d, J=1.5 Hz), 4.32 (1H, t, J=5.0 Hz), 7.40-7.48 (2H, m), 10.95 (1H, s).

Example 102

6-[2,3-Difluoro-4-(4-hydroxy-2,2-dimethylbutoxy)phenyl]-5-methyl-4,5-dihydro-2H-pyridazin-3-one

[Chem. 357]

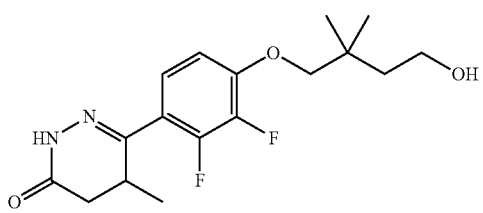

¹H-NMR (DMSO-d6) δ: 1.00 (6H, s), 1.05 (3H, d, J=7.3 Hz), 1.55 (2H, t, J=7.3 Hz), 2.25 (1H, dd, J=16.9, 3.4 Hz), 2.70 (1H, dd, J=16.9, 6.8 Hz), 3.09-3.22 (1H, m), 3.51 (2H, t, J=7.3 Hz), 3.82 (2H, s), 4.34 (1H, brs), 7.02-7.12 (1H, m), 7.38 (1H, td, J=8.7, 2.2 Hz), 11.02 (1H, s).

Example 103

6-[3-Chloro-2-fluoro-4-(4-hydroxy-2,2-dimethylbutoxy)phenyl]-5-methyl-4,5-dihydro-2H-pyridazin-3-one

[Chem. 358]

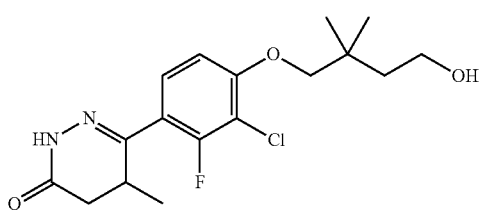

¹H-NMR (DMSO-d6) δ: 1.03 (6H, s), 1.04 (3H, d, J=7.3 Hz), 1.57 (2H, t, J=7.4 Hz), 2.25 (1H, dd, J=16.9, 3.7 Hz), 2.69 (1H, dd, J=16.9, 6.7 Hz), 3.07-3.22 (1H, m), 3.51 (2H, t, J=7.4 Hz), 3.83 (2H, s), 4.34 (1H, brs), 7.05 (1H, dd, J=9.0, 1.2 Hz), 7.53 (1H, t, J=9.0 Hz), 11.01 (1H, s).

Example 104

Production of 2-fluoro-6-(2-hydroxypropoxy)-3-(4-methyl-6-oxo-4,5-dihydro-1H-pyridazin-3-yl)benzonitrile

[Chem. 359]

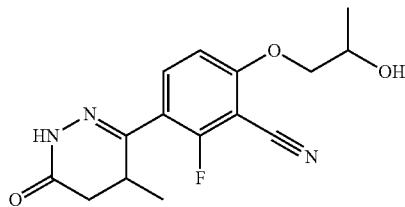

A mixture of 6-[3-bromo-2-fluoro-4-(2-hydroxypropoxy)phenyl]-5-methyl-4,5-dihydro-2H-pyridazin-3-one (Example 48, 180 mg), zinc cyanide (105 mg), and tetrakis(triphenylphosphine)palladium (29 mg) in DMF (2.5 mL) was stirred at 150° C. under microwave irradiation for 30 minutes. To the reaction mixture were added ethyl acetate and water, and then the mixture was filtered through a Celite pad. The organic layer was separated, washed with brine, dried with anhydrous sodium sulfate, filtrated, and then concentrated. The obtained crude product was purified by silica gel column chromatography (heptane:ethyl acetate=40:60 to 0:100), and the desired fractions were concentrated. The residue was crystallized from diisopropyl ether. The precipitates were collected on a filter to afford the title compound as a white solid (93 mg).

¹H-NMR (DMSO-d6) δ: 1.05 (3H, d, J=7.3 Hz), 1.18 (3H, d, J=6.2 Hz), 2.26 (1H, dd, J=16.9, 3.4 Hz), 2.71 (1H, dd, J=16.9, 6.8 Hz), 3.11-3.22 (1H, m), 3.95-4.14 (3H, m), 4.99 (1H, d, J=4.8 Hz), 7.21 (1H, d, J=9.0 Hz), 7.90 (1H, t, J=9.0 Hz), 11.09 (1H, s).

The following compound was prepared from the appropriate starting material in a similar manner to Example 104.

Example 105

2-Fluoro-6-(2-hydroxy-2-methylpropoxy)-3-(4-methyl-6-oxo-4,5-dihydro-1H-pyridazin-3-yl)benzonitrile

[Chem. 360]

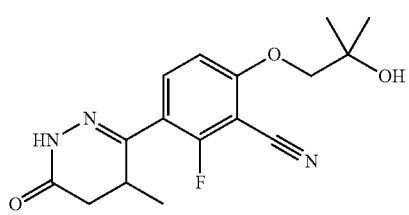

¹H-NMR (DMSO-d6) δ: 1.05 (3H, d, J=7.1 Hz), 1.23 (6H, s), 2.26 (1H, dd, J=16.9, 3.4 Hz), 2.71 (1H, dd, J=16.9, 6.8 Hz), 3.12-3.22 (1H, m), 3.97 (2H, s), 4.77 (1H, s), 7.21 (1H, d, J=9.0 Hz), 7.90 (1H, t, J=9.0 Hz), 11.09 (1H, s).

Example 106

Production of 2-fluoro-6-(3-hydroxypropoxy)-3-(4-methyl-6-oxo-4,5-dihydro-1H-pyridazin-3-yl)benzonitrile

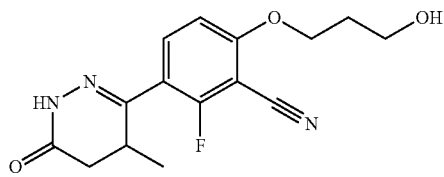

[Chem. 361]

A mixture of 6-[3-bromo-2-fluoro-4-(3-hydroxypropoxy)phenyl]-5-methyl-4,5-dihydro-2H-pyridazin-3-one (Example 12, 150 mg), zinc cyanide (108 mg), and tetrakis(triphenylphosphine)palladium (24 mg) in DMF (1.5 mL) was stirred at 100° C. overnight. The reaction mixture was allowed to cool to room temperature, and then tetrakis(triphenylphosphine)palladium (97 mg) was added thereto. The reaction mixture was stirred at 100° C. further for one day. The reaction mixture was allowed to cool to room temperature, water and ethyl acetate were added to the reaction mixture, and then the mixture was filtered through a Celite pad. The organic layer of the filtrate was separated, washed with water and brine, dried with anhydrous sodium sulfate, filtrated, and then concentrated to afford a solid (191 mg). The solid was dissolved in DMF (2.0 mL), imidazole (34 mg) and tert-butyldimethylchlorosilane (69 mg) were added to the mixture, and the mixture was stirred at room temperature overnight. Imidazole (34 mg) and tert-butyldimethylchlorosilane (69 mg) were further added thereto, and the mixture was stirred at room temperature for 30 minutes. To the reaction mixture was added water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=85:15 to 15:85) to afford a white solid (45 mg). To a solution of the obtained white solid (45 mg) in THF (1.0 mL) under ice-cold was added tetrabutylammonium fluoride (1.0 M THF solution, 0.16 mL). The mixture was stirred at room temperature for one hour. To the reaction mixture were added water and brine, and the mixture was extracted with ethyl acetate. The organic layer was dried over anhydrous sodium sulfate, and filtrated, and the solvent was removed. The obtained crude product was purified by silica gel column chromatography (heptane:ethyl acetate=10:90 to 0:100 to ethyl acetate:methanol=90:10). The obtained solid was washed by trituration with diisopropyl ether, and then collected on a filter to afford the title compound as a white solid (26 mg).

$^1$H-NMR (DMSO-d6) δ: 1.05 (3H, d, J=7.0 Hz), 1.86-1.96 (2H, m), 2.26 (1H, d, J=16.9 Hz), 2.70 (1H, dd, J=16.9, 6.5 Hz), 3.12-3.22 (1H, m), 3.53-3.64 (2H, m), 4.25-4.33 (2H, m), 4.58-4.66 (1H, m), 7.20 (1H, d, J=8.9 Hz), 7.92 (1H, t, J=8.9 Hz), 11.09 (1H, s).

Example 107

Production of 6-[4-(2,2-difluoro-3-hydroxypropoxy)-2-fluoro-3-methylphenyl]-5-methyl-4,5-dihydro-2H-pyridazin-3-one

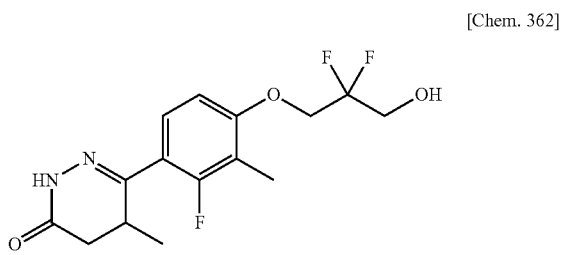 [SMILES: Cc1c(OCC(F)(F)CO)ccc(C2=NNC(=O)CC2C)c1F]

[Chem. 362]

To a mixture of 2,2-difluoro-3-[3-fluoro-2-methyl-4-(4-methyl-6-oxo-4,5-dihydro-1H-pyridazin-3-yl)phenoxy]propyl benzoate (Reference example 166, 253 mg) in methanol (2 mL) was added 5 M aqueous sodium hydroxide (0.349 mL), and the mixture was stirred at room temperature for 2 hours. To the reaction mixture was added water, and the mixture was extracted with ethyl acetate. The organic layer was washed with water and brine, dried over anhydrous sodium sulfate, and filtrated, and the solvent was removed. The obtained crude solid was recrystallized from heptane/ethyl acetate to afford the title compound as a white solid (117 mg).

$^1$H-NMR (DMSO-d6) δ: 1.03 (3H, d, J=7.1 Hz), 2.11 (3H, d, J=2.2 Hz), 2.23 (1H, dd, J=16.7, 3.8 Hz), 2.67 (1H, dd, J=16.7, 6.7 Hz), 3.06-3.20 (1H, m), 3.71-3.87 (2H, m), 4.39 (2H, t, J=12.6 Hz), 5.65-5.73 (1H, m), 6.97 (1H, d, J=8.8 Hz), 7.40 (1H, t, J=8.8 Hz), 10.95 (1H, s).

The following compounds were prepared from each appropriate starting material in a similar manner to Example 107.

Example 108

6-[4-(2,2-Difluoro-3-hydroxypropoxy)-2,3-difluorophenyl]-5-methyl-4,5-dihydro-2H-pyridazin-3-one

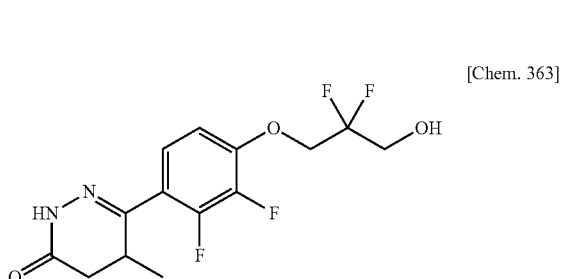

[Chem. 363]

$^1$H-NMR (DMSO-d6) δ: 1.05 (3H, d, J=7.2 Hz), 2.25 (1H, dd, J=16.8, 3.4 Hz), 2.71 (1H, dd, J=16.8, 6.8 Hz), 3.12-3.23 (1H, m), 3.76 (2H, td, J=13.7, 6.3 Hz), 4.51 (2H, t, J=12.8 Hz), 5.71 (1H, t, J=6.3 Hz), 7.15-7.24 (1H, m), 7.38-7.46 (1H, m), 11.06 (1H, s).

Example 109

6-[3,5-Dichloro-4-(2,2-difluoro-3-hydroxypropoxy)phenyl]-5-methyl-4,5-dihydro-2H-pyridazin-3-one

[Chem. 364]

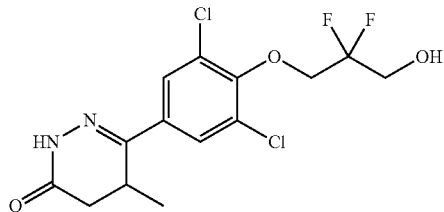

$^1$H-NMR (DMSO-d6) δ: 1.04 (3H, d, J=7.3 Hz), 2.24 (1H, d, J=16.9 Hz), 2.70 (1H, dd, J=16.9, 6.8 Hz), 3.37-3.49 (1H, m), 3.82 (2H, td, J=13.9, 6.1 Hz), 4.38 (2H, t, J=13.2 Hz), 5.65 (1H, t, J=6.1 Hz), 7.85 (2H, s), 11.11 (1H, s).

Example 110

6-[3-Chloro-4-(2,2-difluoro-3-hydroxypropoxy)-2-fluorophenyl]-5-methyl-4,5-dihydro-2H-pyridazin-3-one

[Chem. 365]

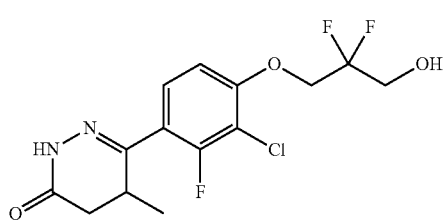

$^1$H-NMR (DMSO-d6) δ: 1.04 (3H, d, J=7.1 Hz), 2.25 (1H, dd, J=16.9, 3.8 Hz), 2.70 (1H, dd, J=16.9, 6.8 Hz), 3.09-3.22 (1H, m), 3.80 (2H, td, J=13.7, 6.2 Hz), 4.51 (2H, t, J=12.6 Hz), 5.70 (1H, t, J=6.2 Hz), 7.19 (1H, dd, J=9.0, 1.5 Hz), 7.53-7.61 (1H, m), 11.04 (1H, s).

Example 111

6-[3-Chloro-4-(2,2-difluoro-3-hydroxypropoxy)-5-fluorophenyl]-5-methyl-4,5-dihydro-2H-pyridazin-3-one

[Chem. 366]

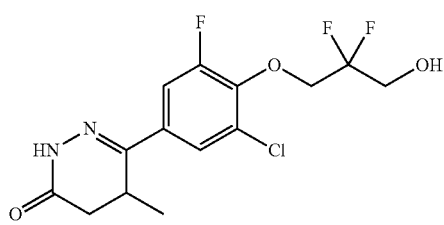

$^1$H-NMR (DMSO-d6) δ: 1.05 (3H, d, J=7.3 Hz), 2.24 (1H, d, J=16.9 Hz), 2.69 (1H, dd, J=16.9, 7.1 Hz), 3.36-3.47 (1H, m), 3.80 (2H, td, J=13.8, 6.1 Hz), 4.47 (2H, t, J=13.1 Hz), 5.65 (1H, t, J=6.1 Hz), 7.63-7.74 (2H, m), 11.09 (1H, s).

Example 112

6-[3-Bromo-4-(2,2-difluoro-3-hydroxypropoxy)-2-fluorophenyl]-5-methyl-4,5-dihydro-2H-pyridazin-3-one

[Chem. 367]

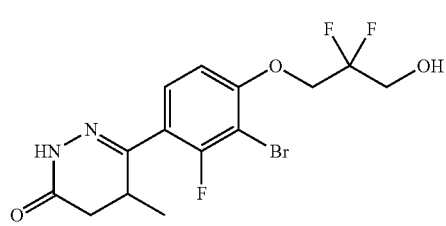

$^1$H-NMR (DMSO-d6) δ: 1.04 (3H, d, J=7.1 Hz), 2.25 (1H, dd, J=16.9, 3.7 Hz), 2.70 (1H, dd, J=16.9, 6.8 Hz), 3.08-3.21 (1H, m), 3.82 (2H, td, J=13.8, 6.2 Hz), 4.50 (2H, t, J=12.3 Hz), 5.70 (1H, t, J=6.2 Hz), 7.15 (1H, dd, J=8.8, 1.2 Hz), 7.60 (1H, t, J=8.8 Hz), 11.04 (1H, s).

Example 113

6-[3-Chloro-4-(2,2-difluoro-3-hydroxypropoxy)-5-methylphenyl]-5-methyl-4,5-dihydro-2H-pyridazin-3-one

[Chem. 368]

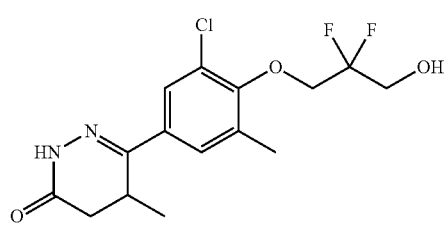

$^1$H-NMR (DMSO-d6) δ: 1.05 (3H, d, J=7.3 Hz), 2.23 (1H, d, J=16.7 Hz), 2.33 (3H, s), 2.68 (1H, dd, J=16.7, 7.0 Hz), 3.33-3.45 (1H, m), 3.81 (2H, td, J=13.9, 6.0 Hz), 4.27 (2H, t, J=13.4 Hz), 5.65 (1H, t, J=6.0 Hz), 7.62 (1H, d, J=2.2 Hz), 7.68 (1H, d, J=2.2 Hz), 11.00 (1H, s).

Example 114

6-[4-(2,2-Difluoro-3-hydroxypropoxy)-2-fluoro-3-vinylphenyl]-5-methyl-4,5-dihydro-2H-pyridazin-3-one

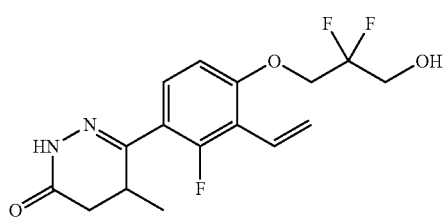

[Chem. 369]

$^1$H-NMR (CDCl$_3$) δ: 1.19 (3H, d, J=7.1 Hz), 2.13 (1H, t, J=7.1 Hz), 2.42 (1H, dd, J=17.1, 3.7 Hz), 2.73 (1H, dd, J=17.1, 6.8 Hz), 3.20-3.31 (1H, m), 4.00 (2H, td, J=12.5, 7.1 Hz), 4.34 (2H, t, J=11.5 Hz), 5.56-5.63 (1H, m), 5.98-6.06 (1H, m), 6.70-6.83 (2H, m), 7.41 (1H, t, J=8.5 Hz), 8.57 (1H, brs).

Example 115

Production of 6-[4-(2,2-difluoro-3-hydroxy-propoxy)-2-hydroxy-3-methylphenyl]-5-methyl-4,5-dihydro-2H-pyridazin-3-one

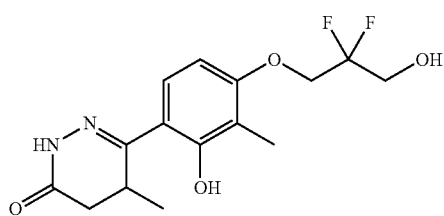

[Chem. 370]

A mixture of 2,2-difluoro-3-[3-(methoxymethyloxy)-2-methyl-4-(4-methyl-6-oxo-4,5-dihydro-1H-pyridazin-3-yl)phenoxy]propyl methanesulfonate (Reference example 141, 80 mg) and sodium benzoate (51 mg) in DMF (2 mL) was stirred at 180° C. under microwave irradiation for 30 minutes. The reaction mixture was poured into water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=50:50) to afford a colorless oil. The oil was dissolved in ethanol (2 mL), 5 M aqueous sodium hydroxide (0.046 mL) was added thereto, and the mixture was stirred at room temperature for one hour. The mixture was poured into water, and the mixture was extracted with ethyl acetate. The organic layer was washed with water and brine, and dried over anhydrous sodium sulfate, filtrated, and concentrated. The residue was dissolved in ethanol (2 mL), hydrogen chloride (2 M ethanol solution, 0.058 mL) was added thereto, and the mixture was stirred at room temperature overnight. The precipitates were collected on a filter to afford the title compound as a white solid (20 mg).

$^1$H-NMR (DMSO-d6) δ: 1.10 (3H, d, J=7.3 Hz), 2.04 (3H, s), 2.27 (1H, d, J=16.6 Hz), 2.77 (1H, dd, J=16.7, 6.7 Hz), 3.47-3.61 (1H, m), 3.73-3.86 (2H, m), 4.35 (2H, t, J=12.7 Hz), 5.66 (1H, t, J=6.2 Hz), 6.66 (1H, d, J=9.0 Hz), 7.46 (1H, d, J=9.0 Hz), 11.06 (1H, s), 12.54 (1H, s).

Example 116

Production of (5R)-(−)-6-[3-chloro-4-(2-hydroxy-ethoxy)-5-methylphenyl]-5-methyl-4,5-dihydro-2H-pyridazin-3-one

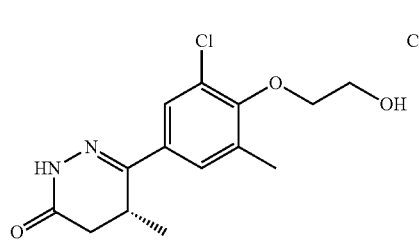

[Chem. 371]

To a mixture of 2-{2-chloro-6-methyl-4-[(2R)-2-methyl-3-{[(1S)-1-(4-nitrophenyl)ethyl]carbamoyl}propanoyl]phenoxy}ethyl 4-bromobenzoate (Reference example 175, 300 mg) in 2-propanol (5.0 mL) were added acetic acid (0.272 mL) and hydrazine monohydrate (0.115 mL), and then the mixture was stirred at 60° C. overnight. The reaction mixture was concentrated, water was added to the residue, and the mixture was extracted with ethyl acetate. The organic layer was washed with water and brine, dried over anhydrous sodium sulfate, and filtrated, and the solvent was removed. The residue was purified by silica gel column chromatography (heptane:ethyl acetate=80:20 to 50:50). The obtained solid was washed by trituration with ethyl acetate/heptane, and then collected on a filter to afford a colorless solid (168 mg). The solid was dissolved in ethanol (5.0 mL), and 5 M aqueous sodium hydroxide (0.140 mL) was added to the mixture. The mixture was stirred at room temperature for 15 minutes, water was added to the solution, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=25:75 to 0:100). The obtained solid was recrystallized from ethyl acetate/heptane to afford the title compound as a colorless solid (50 mg, >99% ee). The optical purity was determined by high performance liquid chromatography (HPLC) analysis.

Optical rotation: [α]$_D^{24}$ −322.4° (c=0.21, MeOH)

$^1$H-NMR (CDCl$_3$) δ: 1.24 (3H, d, J=7.3 Hz), 2.28 (1H, t, J=6.4 Hz), 2.37 (3H, s), 2.44-2.52 (1H, m), 2.69 (1H, dd, J=16.9, 6.8 Hz), 3.23-3.34 (1H, m), 3.94-4.01 (2H, m), 4.03-4.13 (2H, m), 7.49-7.50 (1H, m), 7.62 (1H, d, J=2.0 Hz), 8.59 (1H, brs).

<HPLC Conditions of Optical Purity Analysis>
Column: Daicel CHIRALPAK IA column (0.46 cmφ×25 cm)
Eluent: hexane/ethanol=60/40
Flow rate: 1.0 ml/min
Detection: UV (254 nm).
Retention time: 7.22 min (>99% ee).

Each absolute configuration of Examples 117-127 shown below was extrapolated by comparison with Example 116.

Example 117

(5R)-(−)-6-[3,5-Difluoro-4-(2-hydroxy-2-methyl-propoxy)phenyl]-5-methyl-4,5-dihydro-2H-pyridazin-3-one

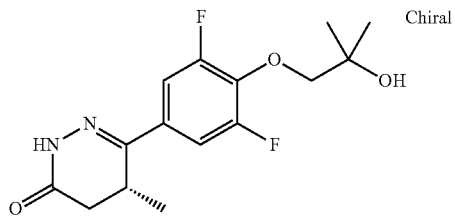

[Chem. 372]

6-[3,5-Difluoro-4-(2-hydroxy-2-methylpropoxy)phenyl]-5-methyl-4,5-dihydro-2H-pyridazin-3-one (Example 30, 267 mg) was optically-resolved by chiral column chromatography according to the following preparative condition, and then recrystallized from heptane/ethanol to afford the title compound as a white solid (33 mg, 99% ee).

<Preparative Condition>
Column: Daicel CHIRALFLASH IA (3.0 cmφ×10 cm)
Eluent: hexane/ethanol=60/40
Flow rate: 12 ml/min
Detection: UV (254 nm).
<HPLC Conditions of Optical Purity Analysis>
Column: Daicel CHIRALPAK AS-RH (0.46 cmφ×15 cm)
Eluent: acetonitrile/water=50/50
Flow rate: 1.0 ml/min
Detection: UV (254 nm).
Retention time: 4.6 min
$[\alpha]_D^{24}$ −306.4° (c=0.25, MeOH)
$^1$H-NMR (DMSO-d6) δ: 1.05 (3H, d, J=7.3 Hz), 1.20 (6H, s), 2.23 (1H, d, J=16.7 Hz), 2.68 (1H, dd, J=16.7, 7.0 Hz), 3.34-3.44 (1H, m), 3.89 (2H, s), 4.62 (1H, s), 7.43-7.60 (2H, m), 11.05 (1H, s).

Example 118

Production of (5R)-(−)-6-[3-chloro-2-fluoro-4-(2-hydroxy-2-methylpropoxy)phenyl]-5-methyl-4,5-dihydro-2H-pyridazin-3-one

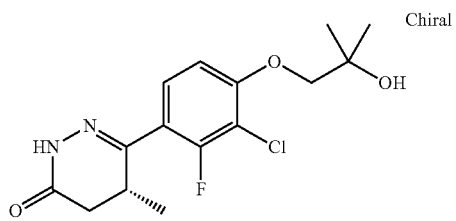

[Chem. 373]

6-[3-Chloro-2-fluoro-4-(2-hydroxy-2-methylpropoxy)phenyl]-5-methyl-4,5-dihydro-2H-pyridazin-3-one (Example 29, 200 mg) was optically-resolved by chiral column chromatography according to the following preparative condition, and then recrystallized from 2-propanol to afford the title compound as a white solid (46 mg, 95% ee).

<Preparative Condition>
Column: Daicel CHIRALFLASH IA (3.0 cmφ×10 cm)
Eluent: hexane/ethanol=70/30
Flow rate: 12 ml/min
Detection: UV (254 nm).
<HPLC Conditions of Optical Purity Analysis>
Column: Daicel CHIRALPAK IA (0.46 cmφ×25 cm)
Eluent: hexane/ethanol=30/70
Flow rate: 1.0 ml/min
Detection: UV (254 nm).
Retention time: 5.2 min
Optical rotation: $[\alpha]_D^{24}$ −123.0° (c=0.28, MeOH)
$^1$H-NMR (DMSO-d6) δ: 1.04 (3H, d, J=7.2 Hz), 1.24 (6H, s), 2.25 (1H, dd, J=16.8, 3.5 Hz), 2.70 (1H, dd, J=16.8, 6.8 Hz), 3.09-3.20 (1H, m), 3.87 (2H, s), 4.69 (1H, s), 7.08 (1H, dd, J=9.0, 1.3 Hz), 7.49-7.58 (1H, m), 11.01 (1H, s).

The following compound was prepared from the appropriate starting material in a similar manner to Example 118.

Example 119

Production of (5R)-(−)-6-{3-chloro-5-fluoro-4-[(1-hydroxycyclopropyl)methoxy]phenyl}-5-methyl-4,5-dihydro-2H-pyridazin-3-one

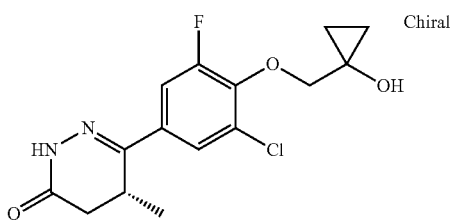

[Chem. 374]

Optical purity: >99% ee
<HPLC Conditions of Optical Purity Analysis>
Column: Daicel CHIRALPAK IA (0.46 cmφ×25 cm)
Eluent: hexane/ethanol=40/60
Flow rate: 1.0 ml/min
Detection: UV (254 nm).
Retention time: 6.0 min
Optical rotation: $[\alpha]_D^{24}$ −274.6° (c=0.31, MeOH)
$^1$H-NMR (DMSO-d6) δ: 0.61-0.73 (4H, m), 1.04 (3H, d, J=7.3 Hz), 2.23 (1H, d, J=16.7 Hz), 2.69 (1H, dd, J=16.7, 6.7 Hz), 3.34-3.47 (1H, m), 4.10 (2H, s), 5.54 (1H, s), 7.58-7.72 (2H, m), 11.06 (1H, s).

Example 120

Production of (5R)-(-)-6-[4-(2,2-difluoro-3-hydroxypropoxy)-2-fluoro-3-methylphenyl]-5-methyl-4,5-dihydro-2H-pyridazin-3-one

[Chem. 375]

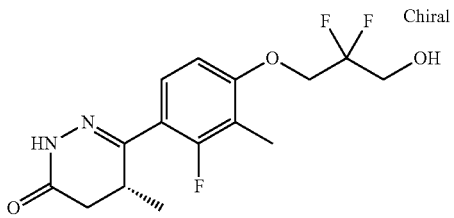

6-[4-(2,2-Difluoro-3-hydroxypropoxy)-2-fluoro-3-methylphenyl]-5-methyl-4,5-dihydro-2H-pyridazin-3-one (Example 107, 130 mg) was optically-resolved by chiral column chromatography according to the following preparative condition, and then recrystallized from ethyl acetate/heptane to afford the title compound as a white solid (33 mg, 99% ee).

<Preparative Condition>
Column: Daicel CHIRALFLASH IA (3.0 cmφ×10 cm)
Eluent: hexane/ethanol=75/25
Flow rate: 12 ml/min
Detection: UV (254 nm).
<HPLC Conditions of Optical Purity Analysis>
Column: Daicel CHIRALPAK IA (0.46 cmφ×25 cm)
Eluent: hexane/ethanol=50/50
Flow rate: 1.0 ml/min
Detection: UV (254 nm).
Retention time: 5.7 min
Optical rotation: $[\alpha]_D^{27}$-101.5° (c=0.29, MeOH)
$^1$H-NMR (DMSO-d6) δ: 1.03 (3H, d, J=7.1 Hz), 2.11 (3H, d, J=2.2 Hz), 2.23 (1H, dd, J=16.7, 3.8 Hz), 2.67 (1H, dd, J=16.7, 6.7 Hz), 3.05-3.18 (1H, m), 3.79 (2H, td, J=13.7, 6.0 Hz), 4.39 (2H, t, J=12.6 Hz), 5.68 (1H, t, J=6.0 Hz), 6.97 (1H, d, J=8.8 Hz), 7.40 (1H, t, J=8.8 Hz), 10.95 (1H, s).

The following compounds were prepared from each appropriate starting material in a similar manner to Example 120.

Example 121

(5R)-(-)-6-[3,5-Difluoro-4-(3-hydroxypropoxy)phenyl]-5-methyl-4,5-dihydro-2H-pyridazin-3-one

[Chem. 376]

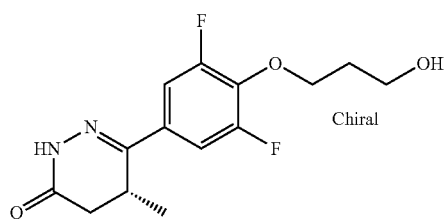

Optical purity: 95% ee
<HPLC Conditions of Optical Purity Analysis>
Column: Daicel CHIRALPAK IA (0.46 cmφ×25 cm)
Eluent: hexane/ethanol=60/40
Flow rate: 1.0 ml/min
Detection: UV (254 nm).
Retention time: 6.9 min
$[\alpha]_D^{24}$-293.5° (c=0.30, MeOH)
$^1$H-NMR (DMSO-d6) δ: 1.05 (3H, d, J=7.3 Hz), 1.76-1.90 (2H, m), 2.24 (1H, d, J=16.7 Hz), 2.68 (1H, dd, J=16.7, 7.0 Hz), 3.36-3.46 (1H, m), 3.52-3.60 (2H, m), 4.23 (2H, t, J=6.3 Hz), 4.53 (1H, t, J=5.1 Hz), 7.44-7.59 (2H, m), 11.05 (1H, s).

Example 122

(5R)-(-)-6-[3-Chloro-2-fluoro-4-(3-hydroxy-2,2-dimethylpropoxy)phenyl]-5-methyl-4,5-dihydro-2H-pyridazin-3-one

[Chem. 377]

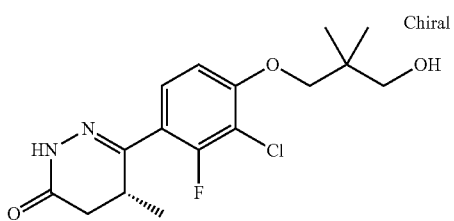

Optical purity: 96% ee
<HPLC Conditions of Optical Purity Analysis>
Column: Daicel CHIRALPAK IA (0.46 cmφ×25 cm)
Eluent: hexane/ethanol=60/40
Flow rate: 1.0 ml/min
Detection: UV (254 nm).
Retention time: 7.2 min
$[\alpha]_D^{24}$-114.2° (c=0.28, MeOH)
$^1$H-NMR (DMSO-d6) δ: 0.96 (6H, s), 1.04 (3H, d, J=7.2 Hz), 2.25 (1H, dd, J=16.8, 3.6 Hz), 2.70 (1H, dd, J=16.8, 6.7 Hz), 3.09-3.20 (1H, m), 3.29-3.34 (2H, m), 3.86 (2H, s), 4.66 (1H, t, J=5.4 Hz), 7.06 (1H, d, J=9.3 Hz), 7.49-7.58 (1H, m), 11.01 (1H, s).

Example 123

(5R)-(-)-6-[2,3-Difluoro-4-[(1-hydroxycyclopropyl)methoxy]phenyl]-5-methyl-4,5-dihydro-2H-pyridazin-3-one

[Chem. 378]

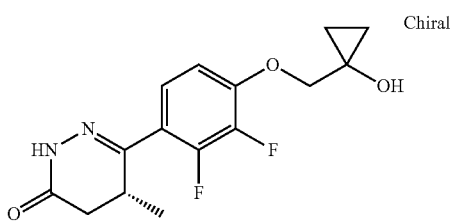

Optical purity: 99% ee
<HPLC Conditions of Optical Purity Analysis>
Column: Daicel CHIRALPAK IA (0.46 cmφ×25 cm)
Eluent: hexane/ethanol=60/40

Flow rate: 1.0 ml/min

Detection: UV (254 nm).

Retention time: 8.0 min $[\alpha]_D^{24}$ −138.7° (c=0.44, MeOH)

$^1$H-NMR (DMSO-d6) δ: 0.61-0.76 (4H, m), 1.05 (3H, d, J=7.2 Hz), 2.25 (1H, dd, J=16.8, 3.4 Hz), 2.70 (1H, dd, J=16.8, 6.8 Hz), 3.11-3.22 (1H, m), 4.12 (2H, s), 5.66 (1H, s), 7.05-7.14 (1H, m), 7.33-7.41 (1H, m), 11.03 (1H, s).

Example 124

Production of (5R)-(−)-6-[2,3-difluoro-4-(2-hydroxy-2-methylpropoxy)phenyl]-5-methyl-4,5-dihydro-2H-pyridazin-3-one

[Chem. 379]

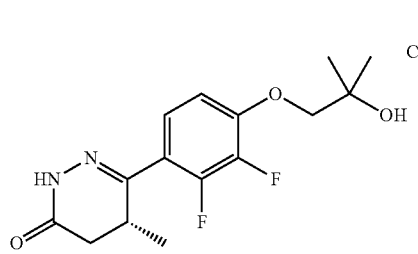

6-[2,3-Difluoro-4-(2-hydroxy-2-methylpropoxy)phenyl]-5-methyl-4,5-dihydro-2H-pyridazin-3-one (Example 27, 117 mg) was optically-resolved by chiral column chromatography according to the following preparative condition, and then recrystallized from ethanol/heptane to afford the title compound as a white solid (30 mg, 99% ee).

<Preparative Condition>

Column: Daicel CHIRALFLASH IA (3.0 cmφ×10 cm)

Eluent: hexane/ethanol=80/20

Flow rate: 12 ml/min

Detection: UV (254 nm).

<HPLC Conditions of Optical Purity Analysis>

Column: Daicel CHIRALPAK AS-RH (0.46 cmφ×15 cm)

Eluent: acetonitrile/water=40/60

Flow rate: 1.0 ml/min

Detection: UV (254 nm).

Retention time: 5.9 min

Optical rotation: $[\alpha]_D^{24}$ −137.6° (c=0.38, MeOH)

$^1$H-NMR (DMSO-d6) δ: 1.05 (3H, d, J=7.3 Hz), 1.21 (6H, s), 2.25 (1H, dd, J=16.7, 3.3 Hz), 2.70 (1H, dd, J=16.7, 6.7 Hz), 3.10-3.23 (1H, m), 3.87 (2H, s), 4.71 (1H, s), 7.05-7.14 (1H, m), 7.34-7.41 (1H, m), 11.02 (1H, s).

The following compounds were prepared from each appropriate starting material in a similar manner to Example 124.

Example 125

(5R)-(−)-6-[3-Fluoro-4-(3-hydroxy-2,2-dimethylpropoxy)-5-methylphenyl]-5-methyl-4,5-dihydro-2H-pyridazin-3-one

[Chem. 380]

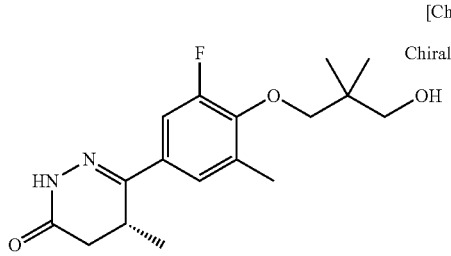

Optical purity: >99% ee

<HPLC Conditions of Optical Purity Analysis>

Column: Daicel CHIRALPAK IA (0.46 cmφ×25 cm)

Eluent: hexane/ethanol=50/50

Flow rate: 1.0 ml/min

Detection: UV (254 nm).

Retention time: 5.6 min $[\alpha]_D^{24}$ −249.7° (c=0.23, MeOH)

$^1$H-NMR (DMSO-d6) δ: 0.95 (6H, s), 1.05 (3H, d, J=7.3 Hz), 2.22 (1H, d, J=16.9 Hz), 2.28 (3H, s), 2.66 (1H, dd, J=16.9, 6.8 Hz), 3.27-3.42 (1H, m), 3.28-3.33 (2H, m), 3.79 (2H, d, J=1.7 Hz), 4.60 (1H, t, J=5.3 Hz), 7.38-7.49 (2H, m), 10.95 (1H, s).

Example 126

(5R)-(−)-6-[3-Chloro-2-fluoro-4-(2-hydroxyethoxy)phenyl]-5-methyl-4,5-dihydro-2H-pyridazin-3-one

[Chem. 381]

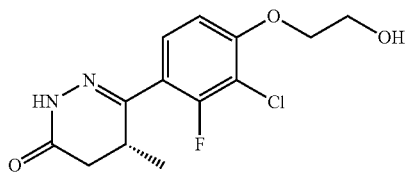

Optical purity: 98% ee

<HPLC Conditions of Optical Purity Analysis>

Column: Daicel CHIRALPAK IA (0.46 cmφ×25 cm)

Eluent: hexane/ethanol=60/40

Flow rate: 1.0 ml/min

Detection: UV (254 nm).

Retention time: 8.4 min $[\alpha]_D^{24}$ −137.2° (c=0.22, MeOH)

$^1$H-NMR (DMSO-d6) δ: 1.04 (3H, d, J=7.2 Hz), 2.25 (1H, dd, J=16.8, 3.7 Hz), 2.69 (1H, dd, J=16.8, 6.7 Hz), 3.09-3.20

(1H, m), 3.73-3.79 (2H, m), 4.17 (2H, t, J=4.9 Hz), 4.91 (1H, t, J=5.3 Hz), 7.10 (1H, dd, J=9.0, 1.3 Hz), 7.53 (1H, t, J=9.0 Hz), 11.01 (1H, s).

Example 127

(5R)-(−)-6-[3-Bromo-5-chloro-4-(3-hydroxy-2,2-dimethylpropoxy)phenyl]-5-methyl-4,5-dihydro-2H-pyridazin-3-one

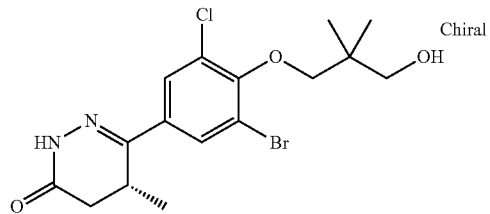

[Chem. 382]

Optical purity: 97% ee
<HPLC Conditions of Optical Purity Analysis>
Column: Daicel CHIRALPAK IA (0.46 cmφ×25 cm)
Eluent: hexane/ethanol=60/40
Flow rate: 1.0 ml/min
Detection: UV (254 nm).
Retention time: 5.5 min
$[\alpha]_D^{24}$ −231.9° (c=0.18, MeOH)
$^1$H-NMR (DMSO-d6) δ: 1.03 (6H, s), 1.04 (3H, d, J=6.8 Hz), 2.23 (1H, d, J=16.9 Hz), 2.69 (1H, dd, J=16.9, 6.8 Hz), 3.34 (2H, d, J=5.3 Hz), 3.37-3.47 (1H, m), 3.77 (2H, s), 4.58 (1H, t, J=5.3 Hz), 7.85 (1H, d, J=2.2 Hz), 7.95 (1H, d, J=2.2 Hz), 11.08 (1H, s).

Example 128

Production of 6-[3-chloro-2-hydroxy-4-(2-hydroxy-2-methylpropoxy)phenyl]-5-methyl-4,5-dihydro-2H-pyridazin-3-one

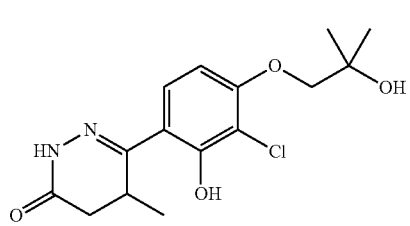

[Chem. 383]

To a mixture of 6-[3-chloro-4-(2-hydroxy-2-methylpropoxy)-2-(methoxymethyloxy)phenyl]-5-methyl-4,5-dihydro-2H-pyridazin-3-one (Reference example 212, 130 mg) in ethanol (2.0 mL) was added hydrogen chloride (2 M ethanol solution, 0.351 mL), and the mixture was stirred at room temperature overnight. The reaction mixture was concentrated, and the residue was washed by trituration with diethyl ether to afford the title compound as a white solid (100 mg).

$^1$H-NMR (DMSO-d6) δ: 1.11 (3H, d, J=7.3 Hz), 1.24 (6H, s), 2.25-2.34 (1H, m), 2.81 (1H, dd, J=17.0, 6.7 Hz), 3.48-3.60 (1H, m), 3.83 (2H, s), 4.67 (1H, brs), 6.73 (1H, d, J=9.3 Hz), 7.56 (1H, d, J=9.3 Hz), 11.13 (1H, s), 13.01 (1H, s).

The following compounds were prepared from each appropriate starting material in a similar manner to Example 128.

Example 129

6-[3-Chloro-2-hydroxy-4-(2-hydroxy-2-methylpropoxy)-5-methylphenyl]-5-methyl-4,5-dihydro-2H-pyridazin-3-one

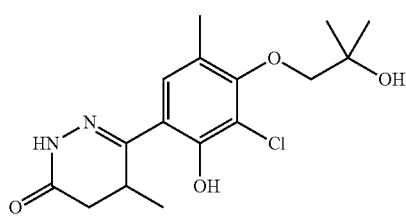

[Chem. 384]

$^1$H-NMR (DMSO-d6) δ: 1.12 (3H, d, J=7.3 Hz), 1.28 (6H, s), 2.24-2.34 (1H, m), 2.26 (3H, s), 2.80 (1H, dd, J=16.9, 6.6 Hz), 3.51-3.61 (1H, m), 3.64 (2H, s), 4.63 (1H, s), 7.46 (1H, s), 11.17 (1H, s), 12.78 (1H, s).

Example 130

6-[5-Chloro-2-hydroxy-4-(2-hydroxy-2-methylpropoxy)-3-methylphenyl]-5-methyl-4,5-dihydro-2H-pyridazin-3-one

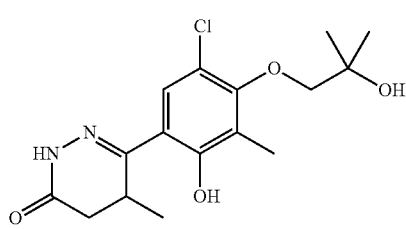

[Chem. 385]

$^1$H-NMR (DMSO-d6) δ: 1.10 (3H, d, J=7.3 Hz), 1.28 (6H, s), 2.15 (3H, s), 2.27 (1H, dd, J=16.8, 0.9 Hz), 2.78 (1H, dd, J=16.8, 6.7 Hz), 3.50-3.66 (3H, m), 4.66 (1H, s), 7.55 (1H, s), 11.18 (1H, s), 12.60 (1H, s).

The following compounds were prepared from each appropriate starting material in a similar manner to Example 1.

Example 131

6-[3-Chloro-2,5-difluoro-4-(2-hydroxy-2-methylpropoxy)phenyl]-5-methyl-4,5-dihydro-2H-pyridazin-3-one

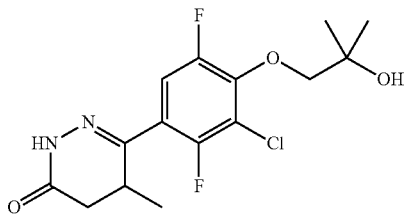

[Chem. 386]

$^1$H-NMR (DMSO-d6) δ: 1.06 (3H, d, J=7.2 Hz), 1.24 (6H, s), 2.26 (1H, dd, J=16.8, 3.5 Hz), 2.70 (1H, dd, J=16.8, 6.8 Hz), 3.12-3.23 (1H, m), 3.91-3.97 (2H, m), 4.66 (1H, s), 7.55 (1H, dd, J=12.3, 7.1 Hz), 11.13 (1H, s).

Example 132

6-[2-Fluoro-4-(2-hydroxy-2-methylpropoxy)-3,5-dimethylphenyl]-5-methyl-4,5-dihydro-2H-pyridazin-3-one

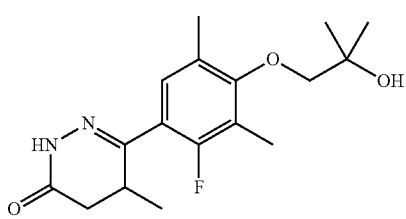

[Chem. 387]

$^1$H-NMR (DMSO-d6) δ: 1.04 (3H, d, J=7.3 Hz), 1.27 (6H, s), 2.17 (3H, d, J=2.3 Hz), 2.22 (3H, s), 2.23 (1H, dd, J=16.8, 3.8 Hz), 2.66 (1H, dd, J=16.8, 6.7 Hz), 3.07-3.17 (1H, m), 3.51 (2H, s), 4.65 (1H, s), 7.24 (1H, d, J=8.9 Hz), 10.96 (1H, s).

Example 133

6-[2-Fluoro-4-(2-hydroxy-2-methylpropoxy)-3-vinylphenyl]-5-methyl-4,5-dihydro-2H-pyridazin-3-one

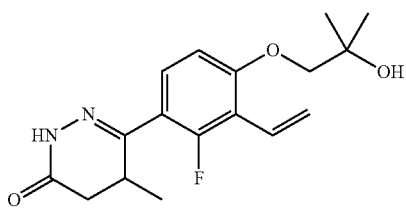

[Chem. 388]

$^1$H-NMR (DMSO-d6) δ: 1.03 (3H, d, J=7.6 Hz), 1.23 (6H, s), 2.23 (1H, dd, J=16.9, 4.2 Hz), 2.66 (1H, dd, J=16.9, 6.8 Hz), 3.06-3.18 (1H, m), 3.82 (2H, s), 4.71 (1H, s), 5.53-5.60 (1H, m), 6.03-6.11 (1H, m), 6.83 (1H, dd, J=18.1, 12.0 Hz), 6.93 (1H, d, J=8.8 Hz), 7.43 (1H, t, J=8.8 Hz), 10.96 (1H, s).

Example 134

6-[3-Ethyl-2-fluoro-4-(2-hydroxy-2-methylpropoxy)phenyl]-5-methyl-4,5-dihydro-2H-pyridazin-3-one

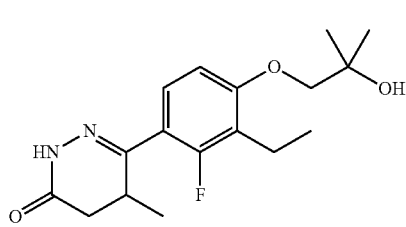

[Chem. 389]

$^1$H-NMR (DMSO-d6) δ: 1.03 (3H, d, J=7.3 Hz), 1.11 (3H, t, J=7.3 Hz), 1.24 (6H, s), 2.22 (1H, dd, J=16.9, 3.9 Hz), 2.61-2.71 (3H, m), 3.06-3.18 (1H, m), 3.76 (2H, s), 4.68 (1H, s), 6.84 (1H, d, J=9.0 Hz), 7.37 (1H, t, J=9.0 Hz), 10.92 (1H, s).

Example 135

6-[2-Fluoro-4-(2-hydroxyethoxy)-3-vinylphenyl]-5-methyl-4,5-dihydro-2H-pyridazin-3-one

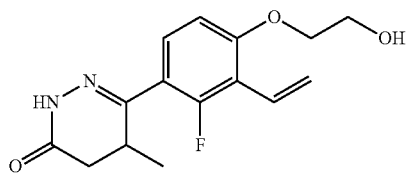

[Chem. 390]

$^1$H-NMR (DMSO-d6) δ: 1.03 (3H, d, J=7.1 Hz), 2.23 (1H, dd, J=16.9, 3.9 Hz), 2.66 (1H, dd, J=16.9, 6.8 Hz), 3.06-3.18 (1H, m), 3.72-3.80 (2H, m), 4.10 (2H, t, J=4.6 Hz), 4.91 (1H, t, J=5.6 Hz), 5.54 (1H, dt, J=12.2, 2.0 Hz), 6.06 (1H, dt, J=18.1, 2.0 Hz), 6.80 (1H, dd, J=18.1, 12.2 Hz), 6.95 (1H, d, J=8.8 Hz), 7.43 (1H, t, J=8.8 Hz), 10.95 (1H, s).

The following compounds were prepared from each appropriate starting material in a similar manner to Example 5.

Example 136

6-[5-Chloro-2-fluoro-4-(3-hydroxy-2,2-dimethyl-propoxy)-3-methylphenyl]-5-methyl-4,5-dihydro-2H-pyridazin-3-one

[Chem. 391]

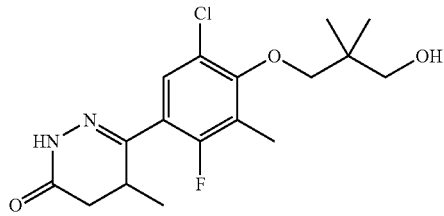

$^1$H-NMR (DMSO-d6) δ: 1.00 (6H, s), 1.04 (3H, d, J=7.2 Hz), 2.20-2.29 (4H, m), 2.68 (1H, dd, J=16.8, 6.8 Hz), 3.09-3.19 (1H, m), 3.34 (2H, d, J=5.2 Hz), 3.66 (2H, s), 4.64 (1H, t, J=5.2 Hz), 7.51 (1H, d, J=8.1 Hz), 11.06 (1H, s).

Example 137

6-[3-Chloro-2-fluoro-4-(3-hydroxy-2,2-dimethyl-propoxy)-5-methylphenyl]-5-methyl-4,5-dihydro-2H-pyridazin-3-one

[Chem. 392]

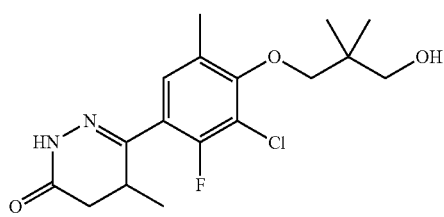

$^1$H-NMR (DMSO-d6) δ: 1.00 (6H, s), 1.04 (3H, d, J=7.2 Hz), 2.21-2.30 (4H, m), 2.69 (1H, dd, J=16.7, 6.7 Hz), 3.09-3.19 (1H, m), 3.34 (2H, d, J=5.2 Hz), 3.68 (2H, s), 4.62 (1H, t, J=5.2 Hz), 7.42 (1H, d, J=8.5 Hz), 11.07 (1H, s).

Example 138

6-[2-Fluoro-4-(3-hydroxy-2,2-dimethylpropoxy)-3,5-dimethylphenyl]-5-methyl-4,5-dihydro-2H-pyridazin-3-one

[Chem. 393]

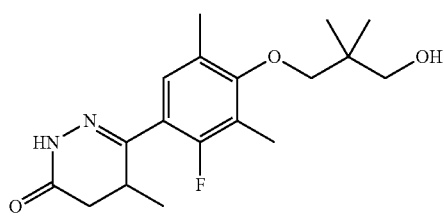

$^1$H-NMR (DMSO-d6) δ: 0.99 (6H, s), 1.03 (3H, d, J=7.2 Hz), 2.16 (3H, d, J=2.1 Hz), 2.18-2.27 (1H, m), 2.21 (3H, s), 2.66 (1H, dd, J=16.9, 6.6 Hz), 3.06-3.16 (1H, m), 3.35 (2H, d, J=5.1 Hz), 3.50 (2H, s), 4.62 (1H, t, J=5.1 Hz), 7.23 (1H, d, J=9.0 Hz), 10.96 (1H, s).

Example 139

6-[3-Chloro-2,5-difluoro-4-(3-hydroxy-2,2-dimethylpropoxy)phenyl]-5-methyl-4,5-dihydro-2H-pyridazin-3-one

[Chem. 394]

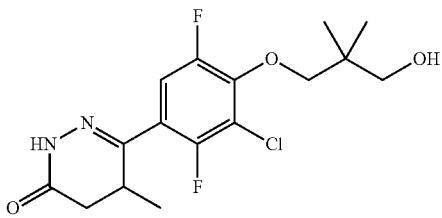

$^1$H-NMR (DMSO-d6) δ: 0.96 (6H, s), 1.05 (3H, d, J=7.2 Hz), 2.26 (1H, dd, J=16.9, 3.5 Hz), 2.70 (1H, dd, J=16.9, 6.8 Hz), 3.12-3.21 (1H, m), 3.29-3.33 (2H, m), 3.98-4.00 (2H, m), 4.63 (1H, t, J=5.3 Hz), 7.55 (1H, dd, J=12.5, 7.1 Hz), 11.13 (1H, s).

Example 140

6-[3-Chloro-2,5-difluoro-4-(3-hydroxypropoxy)phenyl]-5-methyl-4,5-dihydro-2H-pyridazin-3-one

[Chem. 395]

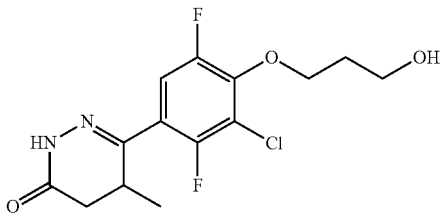

$^1$H-NMR (DMSO-d6) δ: 1.05 (3H, d, J=7.3 Hz), 1.82-1.92 (2H, m), 2.26 (1H, dd, J=16.9, 3.6 Hz), 2.70 (1H, dd, J=16.9, 6.8 Hz), 3.12-3.22 (1H, m), 3.55-3.63 (2H, m), 4.24-4.32 (2H, m), 4.55 (1H, t, J=5.1 Hz), 7.56 (1H, dd, J=12.1, 7.1 Hz), 11.14 (1H, s).

Example 141

6-[2-Fluoro-4-(3-hydroxypropoxy)-3,5-dimethylphenyl]-5-methyl-4,5-dihydro-2H-pyridazin-3-one

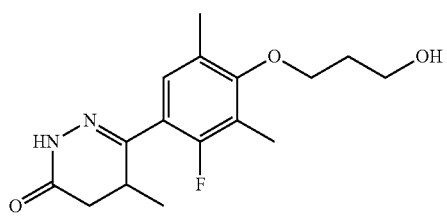

[Chem. 396]

¹H-NMR (DMSO-d6) δ: 1.04 (3H, d, J=7.1 Hz), 1.84-1.94 (2H, m), 2.15 (3H, d, J=2.3 Hz), 2.19-2.27 (1H, m), 2.21 (3H, s), 2.66 (1H, dd, J=16.7, 6.7 Hz), 3.06-3.17 (1H, m), 3.58-3.66 (2H, m), 3.85 (2H, t, J=6.3 Hz), 4.53 (1H, t, J=5.1 Hz), 7.24 (1H, d, J=8.9 Hz), 10.96 (1H, s).

Example 142

Production of 6-[3-chloro-4-(3-hydroxy-2-methylpropoxy)-5-methylphenyl]-5-methyl-4,5-dihydro-2H-pyridazin-3-one

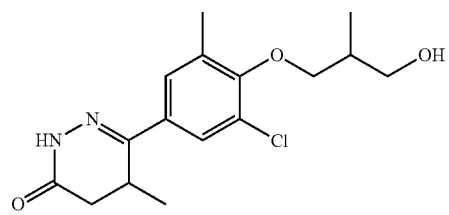

[Chem.397]

A suspension of 6-(3-chloro-4-hydroxy-5-methylphenyl)-5-methyl-4,5-dihydro-2H-pyridazin-3-one (Reference example 86, 251 mg), 3-hydroxy-2-methylpropyl 4-methylbenzenesulfonate (364 mg), and cesium carbonate (647 mg) in NMP (3.0 mL) was stirred at 150° C. under microwave irradiation for 30 minutes. To the reaction mixture was added water, and the mixture was extracted with ethyl acetate. The organic layer was washed with water and brine, dried over anhydrous sodium sulfate, and filtrated, and the solvent was removed. The obtained crude product was purified by silica gel column chromatography (heptane:ethyl acetate=50:50 to 0:100 to ethyl acetate:methanol=90:10), and the desired fractions were concentrated. The residue was crystallized from diisopropyl ether/2-propanol to afford the title compound as a white powder (224 mg).

¹H-NMR (DMSO-d6) δ: 1.03 (3H, d, J=6.6 Hz), 1.05 (3H, d, J=6.3 Hz), 2.01-2.07 (1H, m), 2.22 (1H, d, J=16.7 Hz), 2.31 (3H, s), 2.67 (1H, dd, J=16.7, 7.0 Hz), 3.35-3.54 (3H, m), 3.72-3.77 (1H, m), 3.85-3.91 (1H, m), 4.56 (1H, t, J=5.1 Hz), 7.60 (1H, d, J=2.2 Hz), 7.66 (1H, d, J=2.2 Hz), 10.99 (1H, s).

The following compound was prepared from the appropriate starting material in a similar manner to Example 142.

Example 143

6-[3-Chloro-4-(3-hydroxybutoxy)-5-methylphenyl]-5-methyl-4,5-dihydro-2H-pyridazin-3-one

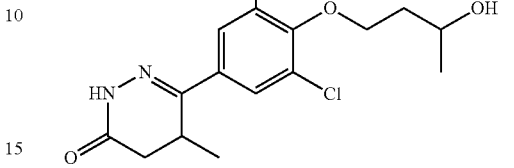

[Chem.398]

¹H-NMR (DMSO-d6) δ: 1.05 (3H, d, J=7.3 Hz), 1.13 (3H, d, J=6.1 Hz), 1.74-1.88 (2H, m), 2.23 (1H, d, J=16.7 Hz), 2.31 (3H, s), 2.67 (1H, dd, J=16.7, 7.0 Hz), 3.33-3.42 (1H, m), 3.82-4.03 (3H, m), 4.53 (1H, d, J=4.9 Hz), 7.60 (1H, d, J=2.2 Hz), 7.66 (1H, d, J=2.2 Hz), 10.99 (1H, s).

The following compounds were prepared from each appropriate starting material in a similar manner to Example 98.

Example 144

6-{3-Chloro-4-[1-(hydroxymethyl)cyclopropylmethoxy]-5-methylphenyl}-5-methyl-4,5-dihydro-2H-pyridazin-3-one

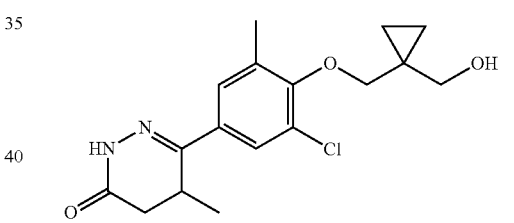

[Chem.399]

¹H-NMR (DMSO-d6) δ: 0.52-0.55 (4H, m), 1.05 (3H, d, J=7.3 Hz), 2.22 (1H, d, J=16.9 Hz), 2.32 (3H, s), 2.67 (1H, dd, J=16.9, 6.8 Hz), 3.32-3.42 (1H, m), 3.53 (2H, d, J=5.6 Hz), 3.80 (2H, s), 4.57 (1H, t, J=5.6 Hz), 7.59 (1H, d, J=2.2 Hz), 7.64 (1H, d, J=2.2 Hz), 10.97 (1H, s).

Example 145

6-{2,3-Difluoro-4-[1-(hydroxymethyl)cyclopropylmethoxy]phenyl}-5-methyl-4,5-dihydro-2H-pyridazin-3-one

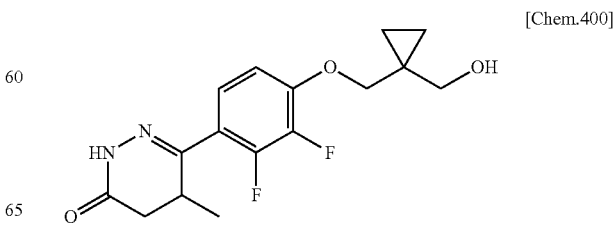

[Chem.400]

¹H-NMR (DMSO-d6) δ: 0.52-0.54 (4H, m), 1.05 (3H, d, J=7.1 Hz), 2.24 (1H, dd, J=16.9, 3.4 Hz), 2.70 (1H, dd, J=16.9, 6.8 Hz), 3.12-3.20 (1H, m), 3.39 (2H, d, J=5.6 Hz), 4.03 (2H, s), 4.67 (1H, t, J=5.6 Hz), 7.04-7.10 (1H, m), 7.37 (1H, td, J=8.8, 2.2 Hz), 11.02 (1H, s).

Example 146

Production of 6-[3-chloro-2-hydroxy-4-(4-hydroxy-2,2-dimethylbutoxy)phenyl]-5-methyl-4,5-dihydro-2H-pyridazin-3-one

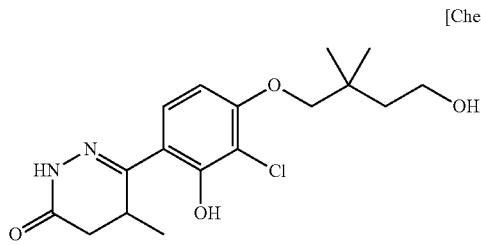
[Chem.401]

A mixture of 6-[3-chloro-4-hydroxy-2-(methoxymethyloxy)phenyl]-5-methyl-4,5-dihydro-2H-pyridazin-3-one (Reference example 99, 250 mg), 4-(tert-butyldimethylsilyloxy)-2,2-dimethylbutan-1-ol (214 mg), triphenylphosphine (285 mg), and bis(2-methoxyethyl) azodicarboxylate (255 mg) in THF (10 mL) was stirred at room temperature overnight. The solvent was removed, and the residue was purified by silica gel column chromatography (heptane:ethyl acetate=67:33 to 33:67) to afford a mixture containing the desired intermediate. To a mixture of the above intermediate in ethanol (2.0 mL) was added hydrogen chloride (2 M ethanol solution, 1.0 mL), and the mixture was stirred at room temperature overnight. The reaction mixture was filtrated, and the filtrate was concentrated, and the obtained solid was washed by trituration with ethyl acetate/heptane to afford the title compound as a colorless solid (28 mg).

¹H-NMR (DMSO-d6) δ: 1.02 (6H, s), 1.10 (3H, d, J=7.6 Hz), 1.57 (2H, t, J=7.6 Hz), 2.29 (1H, d, J=16.9 Hz), 2.80 (1H, dd, J=16.9, 6.8 Hz), 3.47-3.60 (3H, m), 3.79 (2H, s), 4.32 (1H, t, J=4.9 Hz), 6.70 (1H, d, J=9.0 Hz), 7.55 (1H, d, J=9.0 Hz), 11.12 (1H, s), 13.00 (1H, s).

The following compounds were prepared from each appropriate starting material in a similar manner to Example 48.

Example 147

6-[5-Chloro-2-fluoro-4-(2-hydroxypropoxy)-3-methylphenyl]-5-methyl-4,5-dihydro-2H-pyridazin-3-one

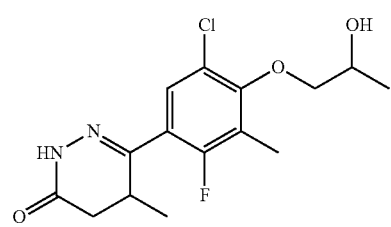
[Chem.402]

¹H-NMR (DMSO-d6) δ: 1.04 (3H, d, J=7.2 Hz), 1.19 (3H, d, J=6.2 Hz), 2.20-2.29 (4H, m), 2.68 (1H, dd, J=16.8, 6.8 Hz), 3.08-3.19 (1H, m), 3.74-3.84 (2H, m), 3.94-4.04 (1H, m), 4.90-4.95 (1H, m), 7.51 (1H, d, J=7.9 Hz), 11.06 (1H, s).

Example 148

6-[3-Chloro-2-fluoro-4-(2-hydroxypropoxy)-5-methylphenyl]-5-methyl-4,5-dihydro-2H-pyridazin-3-one

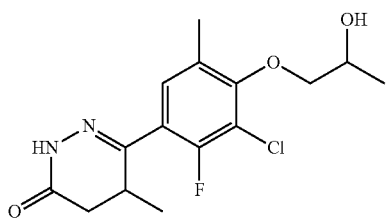
[Chem.403]

¹H-NMR (DMSO-d6) δ: 1.05 (3H, d, J=7.2 Hz), 1.19 (3H, d, J=6.3 Hz), 2.25 (1H, dd, J=16.8, 3.7 Hz), 2.29 (3H, s), 2.69 (1H, dd, J=16.8, 6.8 Hz), 3.09-3.20 (1H, m), 3.73-3.86 (2H, m), 3.93-4.05 (1H, m), 4.90 (1H, d, J=4.9 Hz), 7.43 (1H, d, J=8.3 Hz), 11.07 (1H, s).

Example 149

6-[3-Chloro-2,5-difluoro-4-(2-hydroxypropoxy)phenyl]-5-methyl-4,5-dihydro-2H-pyridazin-3-one

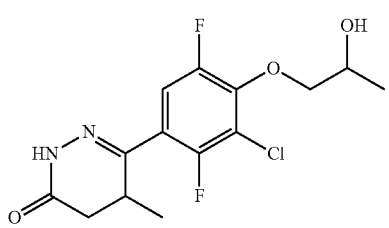
[Chem.404]

¹H-NMR (DMSO-d6) δ: 1.05 (3H, d, J=7.2 Hz), 1.18 (3H, d, J=6.2 Hz), 2.26 (1H, dd, J=16.9, 3.5 Hz), 2.70 (1H, dd, J=16.9, 6.8 Hz), 3.11-3.23 (1H, m), 3.89-4.12 (3H, m), 4.88 (1H, d, J=4.8 Hz), 7.55 (1H, dd, J=12.3, 7.1 Hz), 11.14 (1H, s).

The following compounds were prepared from each appropriate starting material in a similar manner to Example 76.

Example 150

6-{2-Fluoro-4-[(Z)-4-hydroxy-2-butenyloxy]-3,5-dimethylphenyl}-5-methyl-4,5-dihydro-2H-pyridazin-3-one

[Chem.405]

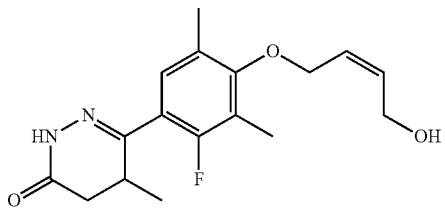

$^1$H-NMR (DMSO-d6) δ: 1.04 (3H, d, J=7.2 Hz), 2.16 (3H, d, J=2.3 Hz), 2.20-2.28 (1H, m), 2.22 (3H, s), 2.66 (1H, dd, J=16.7, 6.7 Hz), 3.06-3.16 (1H, m), 3.97-4.07 (2H, m), 4.39-4.46 (2H, m), 4.77 (1H, t, J=5.3 Hz), 5.68-5.79 (2H, m), 7.25 (1H, d, J=8.9 Hz), 10.97 (1H, s).

Example 151

6-{3-Chloro-2-fluoro-4-[(Z)-4-hydroxy-2-butenyloxy]-5-methylphenyl}-5-methyl-4,5-dihydro-2H-pyridazin-3-one

[Chem.406]

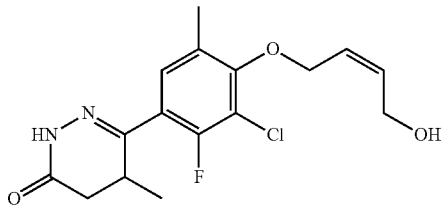

$^1$H-NMR (DMSO-d6) δ: 1.05 (3H, d, J=7.1 Hz), 2.22-2.32 (1H, m), 2.27 (3H, s), 2.70 (1H, dd, J=16.8, 6.8 Hz), 3.10-3.19 (1H, m), 3.97-4.07 (2H, m), 4.56-4.63 (2H, m), 4.78 (1H, t, J=5.4 Hz), 5.69-5.81 (2H, m), 7.44 (1H, d, J=8.7 Hz), 11.08 (1H, s).

Example 152

6-{3-Chloro-2,5-difluoro-4-[(Z)-4-hydroxy-2-butenyloxy]phenyl}-5-methyl-4,5-dihydro-2H-pyridazin-3-one

[Chem.407]

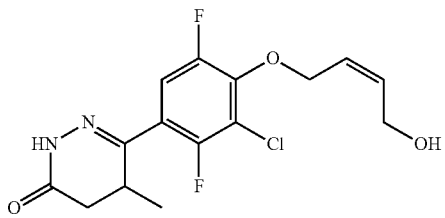

$^1$H-NMR (DMSO-d6) δ: 1.05 (3H, d, J=7.2 Hz), 2.26 (1H, dd, J=16.8, 3.6 Hz), 2.71 (1H, dd, J=16.8, 6.8 Hz), 3.12-3.23 (1H, m), 3.97-4.05 (2H, m), 4.76-4.86 (3H, m), 5.63-5.82 (2H, m), 7.56 (1H, dd, J=12.0, 7.1 Hz), 11.14 (1H, s).

Example 153

6-{2-Hydroxy-4-[(Z)-4-hydroxy-2-butenyloxy]-3-methylphenyl}-5-methyl-4,5-dihydro-2H-pyridazin-3-one

[Chem.408]

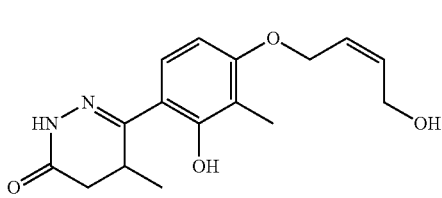

$^1$H-NMR (DMSO-d6) δ: 1.10 (3H, d, J=7.3 Hz), 2.01 (3H, s), 2.27 (1H, d, J=16.7 Hz), 2.76 (1H, dd, J=16.7, 6.7 Hz), 3.47-3.58 (1H, m), 4.05-4.14 (2H, m), 4.65-4.71 (2H, m), 4.81 (1H, t, J=5.3 Hz), 5.60-5.77 (2H, m), 6.60 (1H, d, J=8.8 Hz), 7.43 (1H, d, J=8.8 Hz), 11.04 (1H, s), 12.48 (1H, s).

Example 154

6-(3-Chloro-2-fluoro-4-{[(1S*,2R*)-2-(hydroxymethyl)cyclopropyl]methoxy}phenyl)-5-methyl-4,5-dihydro-2H-pyridazin-3-one

[Chem.409]

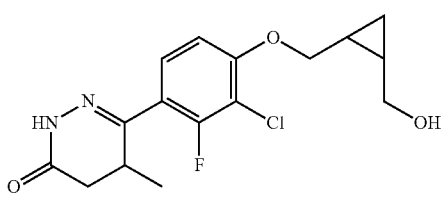

$^1$H-NMR (DMSO-d6) δ: 0.36-0.43 (1H, m), 0.77-0.85 (1H, m), 1.04 (3H, d, J=7.3 Hz), 1.14-1.26 (1H, m), 1.29-1.40 (1H, m), 2.25 (1H, dd, J=16.7, 3.5 Hz), 2.69 (1H, dd, J=16.7, 6.8 Hz), 3.09-3.21 (1H, m), 3.46-3.55 (2H, m), 4.20 (2H, d, J=7.6 Hz), 4.39-4.47 (1H, m), 7.04-7.10 (1H, m), 7.53 (1H, t, J=8.8 Hz), 11.02 (1H, s).

Example 155

6-(3-Chloro-4-{[(1 S*,2R*)-2-(hydroxymethyl)cyclopropyl]methoxy}-5-methylphenyl)-5-methyl-4,5-dihydro-2H-pyridazin-3-one

[Chem.410]

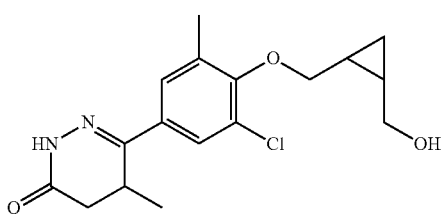

¹H-NMR (DMSO-d6) δ: 0.28-0.35 (1H, m), 0.74-0.83 (1H, m), 1.05 (3H, d, J=7.3 Hz), 1.11-1.23 (1H, m), 1.28-1.40 (1H, m), 2.19-2.27 (1H, m), 2.33 (3H, s), 2.67 (1H, dd, J=16.9, 6.8 Hz), 3.33-3.51 (3H, m), 3.82-3.92 (1H, m), 4.00-4.09 (1H, m), 4.41 (1H, t, J=5.3 Hz), 7.58-7.62 (1H, m), 7.64-7.68 (1H, m), 10.98 (1H, s).

Example 156

6-(3-Chloro-2-fluoro-4-{[(1S*,2S*)-2-(hydroxymethyl)cyclopropyl]methoxy}phenyl)-5-methyl-4,5-dihydro-2H-pyridazin-3-one

[Chem.411]

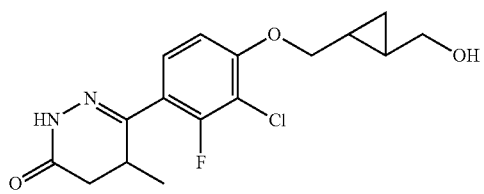

¹H-NMR (DMSO-d6) δ: 0.49-0.58 (2H, m), 0.99-1.20 (5H, m), 2.25 (1H, dd, J=16.9, 3.5 Hz), 2.69 (1H, dd, J=16.9, 6.8 Hz), 3.07-3.20 (1H, m), 3.25-3.41 (2H, m), 3.88-3.98 (1H, m), 4.11-4.20 (1H, m), 4.51 (1H, t, J=5.6 Hz), 7.02-7.11 (1H, m), 7.53 (1H, t, J=8.8 Hz), 11.02 (1H, s).

Example 157

6-{3-Chloro-2-hydroxy-4-[(Z)-4-hydroxy-2-butenyloxy]phenyl}-5-methyl-4,5-dihydro-2H-pyridazin-3-one

[Chem. 412]

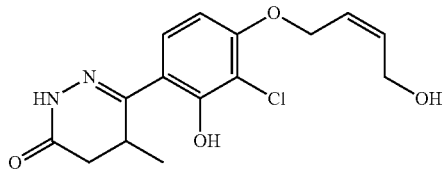

¹H-NMR (DMSO-d6) δ: 1.11 (3H, d, J=7.3 Hz), 2.26-2.32 (1H, m), 2.80 (1H, dd, J=16.9, 6.6 Hz), 3.49-3.61 (1H, m), 4.08-4.16 (2H, m), 4.75-4.86 (3H, m), 5.59-5.69 (1H, m), 5.70-5.80 (1H, m), 6.75 (1H, d, J=9.0 Hz), 7.57 (1H, d, J=9.0 Hz), 11.13 (1H, s), 13.02 (1H, s).

The following compounds were prepared from each appropriate starting material in a similar manner to Example 107.

Example 158

6-[5-Chloro-4-(2,2-difluoro-3-hydroxypropoxy)-2-fluoro-3-methylphenyl]-5-methyl-4,5-dihydro-2H-pyridazin-3-one

[Chem. 413]

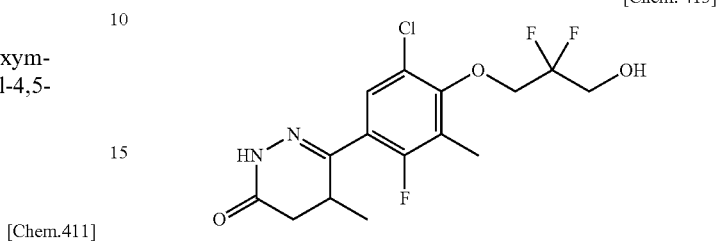

¹H-NMR (DMSO-d6) δ: 1.04 (3H, d, J=7.2 Hz), 2.21-2.31 (4H, m), 2.69 (1H, dd, J=16.7, 6.7 Hz), 3.08-3.18 (1H, m), 3.80 (2H, td, J=13.8, 6.1 Hz), 4.32 (2H, t, J=13.5 Hz), 5.68 (1H, t, J=6.1 Hz), 7.55 (1H, d, J=7.9 Hz), 11.08 (1H, s).

Example 159

6-[3-Chloro-4-(2,2-difluoro-3-hydroxypropoxy)-2-fluoro-5-methylphenyl]-5-methyl-4,5-dihydro-2H-pyridazin-3-one

[Chem. 414]

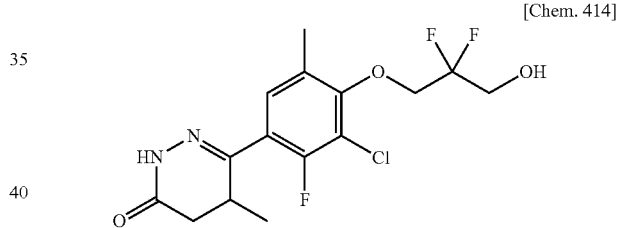

¹H-NMR (DMSO-d6) δ: 1.05 (3H, d, J=7.2 Hz), 2.26 (1H, dd, J=16.9, 3.8 Hz), 2.29 (3H, s), 2.70 (1H, dd, J=16.9, 6.8 Hz), 3.10-3.20 (1H, m), 3.81 (2H, td, J=13.9, 6.1 Hz), 4.32 (2H, t, J=13.4 Hz), 5.67 (1H, t, J=6.1 Hz), 7.46 (1H, d, J=8.5 Hz), 11.09 (1H, s).

Example 160

6-[4-(2,2-Difluoro-3-hydroxypropoxy)-2-fluoro-3,5-dimethylphenyl]-5-methyl-4,5-dihydro-2H-pyridazin-3-one

[Chem. 415]

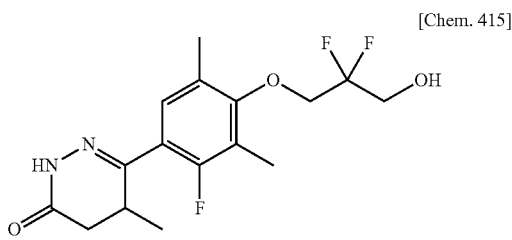 [SMILES: Cc1cc(C2=NNC(=O)CC2C)c(F)c(C)c1OCC(F)(F)CO]

¹H-NMR (DMSO-d6) δ: 1.04 (3H, d, J=7.1 Hz), 2.18 (3H, d, J=2.3 Hz), 2.237 (1H, dd, J=16.8, 3.7 Hz), 2.238 (3H, s), 2.66 (1H, dd, J=16.8, 6.8 Hz), 3.06-3.17 (1H, m), 3.80 (2H, td, J=13.8, 6.1 Hz), 4.14 (2H, t, J=13.3 Hz), 5.68 (1H, t, J=6.1 Hz), 7.27 (1H, d, J=8.8 Hz), 11.00 (1H, s).

Example 161

6-[3-Chloro-4-(2,2-difluoro-3-hydroxypropoxy)-2,5-difluorophenyl]-5-methyl-4,5-dihydro-2H-pyridazin-3-one

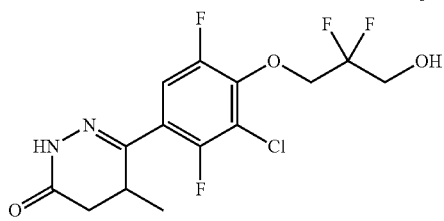

[Chem. 416]

¹H-NMR (DMSO-d6) δ: 1.05 (3H, d, J=7.2 Hz), 2.27 (1H, dd, J=16.9, 3.6 Hz), 2.71 (1H, dd, J=16.9, 6.8 Hz), 3.12-3.23 (1H, m), 3.79 (2H, td, J=13.8, 6.2 Hz), 4.55 (2H, t, J=13.1 Hz), 5.68 (1H, t, J=6.2 Hz), 7.61 (1H, dd, J=12.2, 7.1 Hz), 11.16 (1H, s).

Example 162

6-[3-Chloro-4-(2,2-difluoro-3-hydroxypropoxy)-2-hydroxyphenyl]-5-methyl-4,5-dihydro-2H-pyridazin-3-one

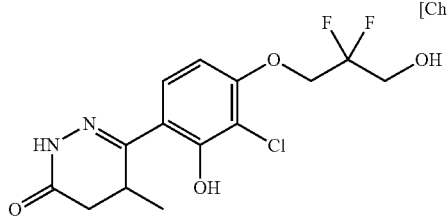

[Chem. 417]

¹H-NMR (DMSO-d6) δ: 1.10 (3H, d, J=7.3 Hz), 2.29 (1H, d, J=16.8 Hz), 2.80 (1H, dd, J=16.8, 6.8 Hz), 3.50-3.62 (1H, m), 3.80 (2H, td, J=13.9, 6.4 Hz), 4.46 (2H, t, J=12.5 Hz), 5.68 (1H, t, J=6.4 Hz), 6.83 (1H, d, J=9.3 Hz), 7.60 (1H, d, J=9.3 Hz), 11.16 (1H, s), 13.08 (1H, s).

The following compounds were prepared from each appropriate starting material in a similar manner to Example 74.

Example 163

6-[3-Chloro-2-hydroxy-4-(2-hydroxybutoxy)phenyl]-5-methyl-4,5-dihydro-2H-pyridazin-3-one

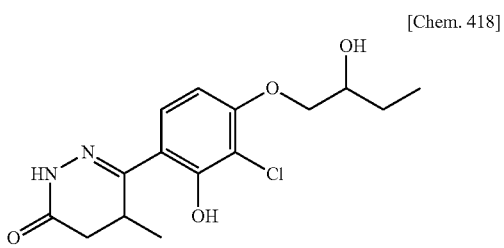 [SMILES: CCC(O)COc1ccc(C2=NNC(=O)CC2C)c(O)c1Cl]

[Chem. 418]

¹H-NMR (DMSO-d6) δ: 0.93 (3H, t, J=7.3 Hz), 1.11 (3H, d, J=7.3 Hz), 1.37-1.51 (1H, m), 1.56-1.70 (1H, m), 2.29 (1H, d, J=16.9 Hz), 2.79 (1H, dd, J=16.9, 6.8 Hz), 3.49-3.60 (1H, m), 3.68-3.79 (1H, m), 3.90-4.05 (2H, m), 4.85-4.90 (1H, m), 6.75 (1H, d, J=9.3 Hz), 7.55 (1H, d, J=9.3 Hz), 11.13 (1H, s), 13.00-13.03 (1H, m).

Example 164

6-[3-Chloro-2-hydroxy-4-(2-hydroxypropoxy)-5-methylphenyl]-5-methyl-4,5-dihydro-2H-pyridazin-3-one

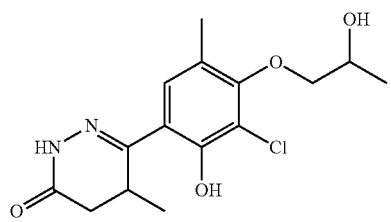

[Chem. 419]

¹H-NMR (DMSO-d6) δ: 1.11 (3H, d, J=7.3 Hz), 1.19 (3H, d, J=6.2 Hz), 2.25 (3H, s), 2.30 (1H, dd, J=16.8, 1.1 Hz), 2.79 (1H, dd, J=16.8, 6.7 Hz), 3.51-3.61 (1H, m), 3.68-3.81 (2H, m), 3.93-4.03 (1H, m), 4.84-4.90 (1H, m), 7.46 (1H, s), 11.17 (1H, s), 12.78 (1H, s).

Example 165

Production of 6-{3-bromo-5-chloro-4-[(1-hydroxycyclopropyl)methoxy]phenyl}-5-methyl-4,5-dihydro-2H-pyridazin-3-one

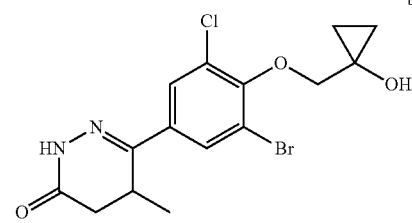

[Chem. 420]

To a mixture of 6-(3-bromo-5-chloro-4-hydroxyphenyl)-5-methyl-4,5-dihydro-2H-pyridazin-3-one (Reference example 87, 318 mg) and [1-(tetrahydro-2H-pyran-2-yloxy)cyclopropyl]methanol (207 mg) in THF (5.0 mL) were added triphenylphosphine (315 mg) and bis(2-methoxyethyl) azodicarboxylate (281 mg) at 0° C. The reaction mixture was stirred at room temperature for one hour, and then the solvent was removed. The residue was diluted with ethyl acetate, washed with 1 M aqueous sodium hydroxide and then brine, dried over anhydrous sodium sulfate, filtrated, and concentrated. The residue was purified by silica gel column chromatography (heptane:ethyl acetate=71:29 to 50:50 to 32:68) to afford a colorless amorphous. The amorphous was dissolved in ethanol (5.0 mL), pyridinium p-toluenesulfonate (23 mg) was added to the mixture, and the mixture was stirred at 60° C. for 30 minutes. The reaction mixture was allowed to cool to room temperature, water was added to the reaction mixture, and the mixture was extracted with ethyl acetate. The organic layer was washed with 1 M aqueous sodium hydroxide and then brine, dried over anhydrous sodium sulfate, filtrated, and then concentrated. The obtained solid was washed by trituration with diisopropyl ether to afford the title compound as a white solid (282 mg).

¹H-NMR (DMSO-d6) δ: 0.67-0.78 (4H, m), 1.04 (3H, d, J=7.3 Hz), 2.23 (1H, d, J=16.8 Hz), 2.69 (1H, dd, J=16.8, 6.9 Hz), 3.36-3.46 (1H, m), 3.97-4.03 (2H, m), 5.63 (1H, s), 7.85 (1H, d, J=2.2 Hz), 7.95 (1H, d, J=2.2 Hz), 11.08 (1H, s).

The following compounds were prepared from each appropriate starting material in a similar manner to Example 165.

Example 166

6-{2-Hydroxy-4-[(1-hydroxycyclopropyl)methoxy]-3-methylphenyl}-5-methyl-4,5-dihydro-2H-pyridazin-3-one

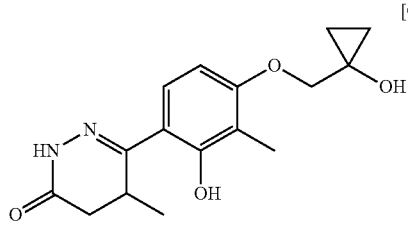

[Chem. 421]

¹H-NMR (DMSO-d6) δ: 0.60-0.73 (4H, m), 1.10 (3H, d, J=7.3 Hz), 2.05 (3H, s), 2.26 (1H, d, J=16.7 Hz), 2.76 (1H, dd, J=16.7, 6.7 Hz), 3.47-3.58 (1H, m), 3.96-4.05 (2H, m), 5.55 (1H, s), 6.57 (1H, d, J=9.0 Hz), 7.41 (1H, d, J=9.0 Hz), 11.02 (1H, s), 12.45 (1H, s).

Example 167

6-{3-Chloro-2-fluoro-4-[(1-hydroxycyclopropyl)methoxy]-5-methylphenyl}-5-methyl-4,5-dihydro-2H-pyridazin-3-one

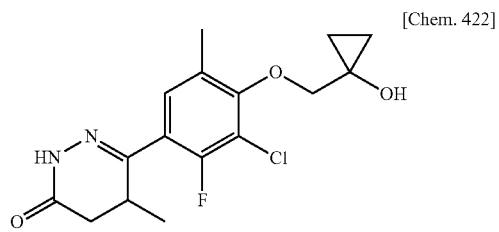 [SMILES: Cc1cc(C2=NNC(=O)CC2C)c(F)c(Cl)c1OCC1(O)CC1]

[Chem. 422]

¹H-NMR (DMSO-d6) δ: 0.61-0.74 (4H, m), 1.05 (3H, d, J=7.2 Hz), 2.25 (1H, dd, J=16.9, 3.7 Hz), 2.32 (3H, s), 2.69 (1H, dd, J=16.9, 6.8 Hz), 3.09-3.19 (1H, m), 3.95 (2H, s), 5.63 (1H, s), 7.39-7.45 (1H, m), 11.06 (1H, s).

Example 168

6-{3-Bromo-2-fluoro-4-[(1-hydroxycyclopropyl)methoxy]phenyl}-5-methyl-4,5-dihydro-2H-pyridazin-3-one

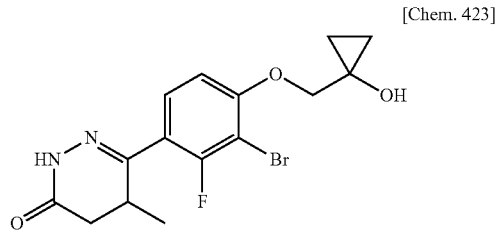 [SMILES: CC1CC(=O)NN=C1c1ccc(OCC2(O)CC2)c(Br)c1F]

[Chem. 423]

¹H-NMR (DMSO-d6) δ: 0.64-0.76 (4H, m), 1.04 (3H, d, J=7.2 Hz), 2.24 (1H, dd, J=16.8, 3.7 Hz), 2.69 (1H, dd, J=16.8, 6.8 Hz), 3.08-3.19 (1H, m), 4.15 (2H, s), 5.59 (1H, s), 7.06 (1H, dd, J=9.0, 1.0 Hz), 7.56 (1H, t, J=9.0 Hz), 11.01 (1H, s).

Example 169

6-{3-Bromo-5-fluoro-4-[(1-hydroxycyclopropyl)methoxy]phenyl}-5-methyl-4,5-dihydro-2H-pyridazin-3-one

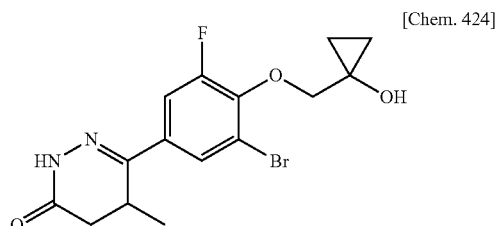

[Chem. 424]

¹H-NMR (DMSO-d6) δ: 0.65-0.72 (4H, m), 1.04 (3H, d, J=7.3 Hz), 2.23 (1H, d, J=16.8 Hz), 2.69 (1H, dd, J=16.8, 6.9

Hz), 3.35-3.45 (1H, m), 4.09 (2H, s), 5.55 (1H, s), 7.66 (1H, dd, J=12.5, 2.1 Hz), 7.81 (1H, t, J=2.1 Hz), 11.06 (1H, s).

Example 170

6-{3,5-Dichloro-4-[(1-hydroxycyclopropyl)methoxy]phenyl}-5-methyl-4,5-dihydro-2H-pyridazin-3-one

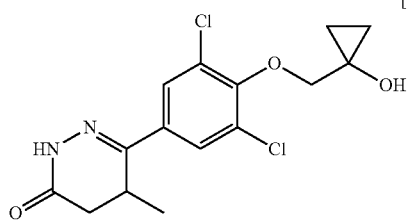

[Chem. 425]

¹H-NMR (DMSO-d6) δ: 0.66-0.75 (4H, m), 1.04 (3H, d, J=7.2 Hz), 2.24 (1H, d, J=16.9 Hz), 2.69 (1H, dd, J=16.9, 7.0 Hz), 3.36-3.47 (1H, m), 4.01 (2H, s), 5.61 (1H, s), 7.81 (2H, s), 11.08 (1H, s).

Example 171

6-{2-Fluoro-4-[(1-hydroxycyclopropyl)methoxy]-3,5-dimethylphenyl}-5-methyl-4,5-dihydro-2H-pyridazin-3-one

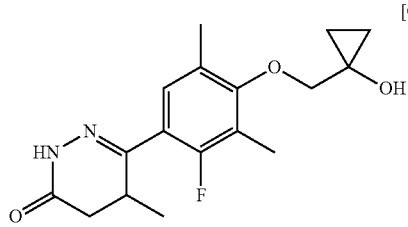

[Chem. 426]

¹H-NMR (DMSO-d6) δ: 0.59-0.71 (4H, m), 1.04 (3H, d, J=7.2 Hz), 2.19 (3H, d, J=2.4 Hz), 2.23 (1H, dd, J=16.8, 3.8 Hz), 2.24 (3H, s), 2.65 (1H, dd, J=16.8, 6.7 Hz), 3.06-3.17 (1H, m), 3.77 (2H, s), 5.65 (1H, s), 7.23 (1H, d, J=8.9 Hz), 10.96 (1H, s).

Example 172

6-{3-Chloro-2,5-difluoro-4-[(1-hydroxycyclopropyl)methoxy]phenyl}-5-methyl-4,5-dihydro-2H-pyridazin-3-one

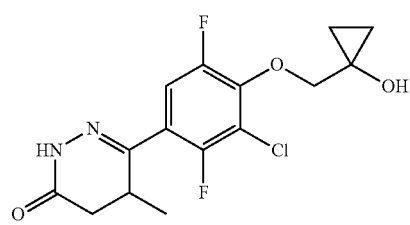

[Chem.427]

¹H-NMR (DMSO-d6) δ: 0.62-0.72 (4H, m), 1.05 (3H, d, J=7.2 Hz), 2.26 (1H, dd, J=16.8, 3.6 Hz), 2.70 (1H, dd, J=16.8, 6.8 Hz), 3.12-3.21 (1H, m), 4.17 (2H, s), 5.54 (1H, s), 7.54 (1H, dd, J=12.1, 7.1 Hz), 11.13 (1H, s).

Example 173

Production of 6-[3-chloro-2-hydroxy-4-(3-hydroxypropoxy)-5-methylphenyl]-5-methyl-4,5-dihydro-2H-pyridazin-3-one

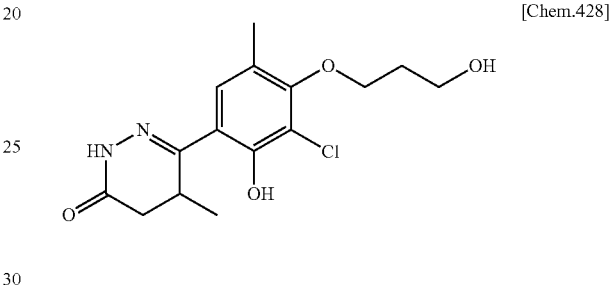

[Chem.428]

To a mixture of 6-[3-chloro-4-hydroxy-2-(methoxymethyloxy)-5-methylphenyl]-5-methyl-4,5-dihydro-2H-pyridazin-3-one (Reference example 203, 313 mg) and 3-(tetrahydro-2H-pyran-2-yloxy)propan-1-ol (208 mg) in THF (5.0 mL) were added triphenylphosphine (341 mg) and bis(2-methoxyethyl) azodicarboxylate (304 mg) at 0° C., and then the mixture was stirred at room temperature for one hour. The solvent was removed, and the residue was diluted with ethyl acetate. The solution was washed with 1 M aqueous sodium hydroxide and then brine, dried over anhydrous sodium sulfate, filtrated, and then concentrated. The obtained crude product was purified by silica gel column chromatography (heptane:ethyl acetate=61:39 to 40:60 to 33:67) to afford a colorless amorphous. The amorphous was dissolved in ethanol (5.0 mL), and hydrogen chloride (2 M ethanol solution, 1.0 mL) was added to the mixture. The mixture was stirred at room temperature for one hour. To the reaction mixture was added water, and the precipitates were collected on a filter, and dried to afford the title compound as a white solid (256 mg).

¹H-NMR (DMSO-d6) δ: 1.11 (3H, d, J=7.3 Hz), 1.85-1.96 (2H, m), 2.23 (3H, s), 2.30 (1H, d, J=16.8 Hz), 2.79 (1H, dd, J=16.8, 6.7 Hz), 3.50-3.67 (3H, m), 3.98 (2H, t, J=6.5 Hz), 4.51 (1H, t, J=5.1 Hz), 7.46 (1H, s), 11.17 (1H, s), 12.77 (1H, s).

The following compounds were prepared from each appropriate starting material in a similar manner to Example 173.

Example 174

6-{3-Chloro-2-hydroxy-4-[(1-hydroxycyclopropyl)methoxy]phenyl}-5-methyl-4,5-dihydro-2H-pyridazin-3-one

[Chem.429]

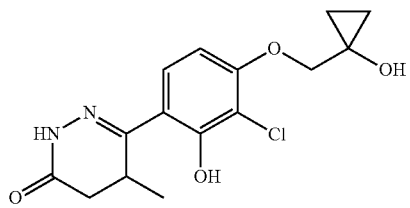

$^1$H-NMR (DMSO-d6) δ: 0.62-0.74 (4H, m), 1.11 (3H, d, J=7.3 Hz), 2.29 (1H, d, J=16.8 Hz), 2.80 (1H, dd, J=16.8, 6.8 Hz), 3.50-3.60 (1H, m), 4.07-4.15 (2H, m), 5.57 (1H, s), 6.76 (1H, d, J=9.2 Hz), 7.55 (1H, d, J=9.2 Hz), 11.12 (1H, s), 13.01 (1H, s).

Example 175

6-{3-Chloro-2-hydroxy-4-[(1-hydroxycyclopropyl)methoxy]-5-methylphenyl}-5-methyl-4,5-dihydro-2H-pyridazin-3-one

[Chem.430]

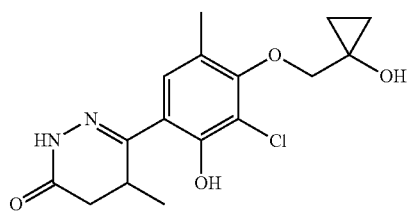

$^1$H-NMR (DMSO-d6) δ: 0.62-0.74 (4H, m), 1.12 (3H, d, J=7.3 Hz), 2.29 (3H, s), 2.30 (1H, dd, J=16.9, 1.3 Hz), 2.79 (1H, dd, J=16.9, 6.7 Hz), 3.51-3.62 (1H, m), 3.87-3.94 (2H, m), 5.61 (1H, s), 7.46 (1H, s), 11.16 (1H, s), 12.76 (1H, s).

Example 176

6-{5-Chloro-2-hydroxy-4-[(1-hydroxycyclopropyl)methoxy]-3-methylphenyl}-5-methyl-4,5-dihydro-2H-pyridazin-3-one

[Chem.431]

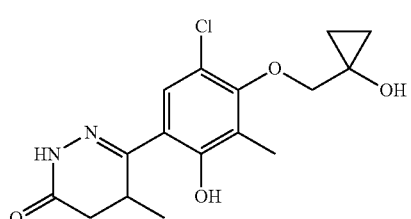

$^1$H-NMR (DMSO-d6) δ: 0.61-0.73 (4H, m), 1.10 (3H, d, J=7.3 Hz), 2.19 (3H, s), 2.27 (1H, dd, J=16.9, 1.2 Hz), 2.77 (1H, dd, J=16.9, 6.7 Hz), 3.50-3.60 (1H, m), 3.88 (2H, s), 5.64 (1H, s), 7.53 (1H, s), 11.17 (1H, s), 12.58 (1H, s).

Example 177

Production of 6-[4-(1,1-difluoro-2-hydroxyethoxy)-2-fluoro-5-methylphenyl]-5-methyl-4,5-dihydro-2H-pyridazin-3-one

[Chem.432]

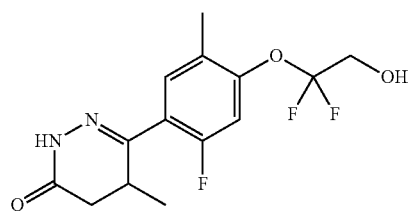

To a mixture of 6-(2-fluoro-4-hydroxy-5-methylphenyl)-5-methyl-4,5-dihydro-2H-pyridazin-3-one (Reference example 205, 472 mg) and ethyl bromodifluoroacetate (0.385 mL) in DMF (10 mL) was added potassium carbonate (415 mg) at 0° C. The mixture was gradually warmed to room temperature, and stirred overnight. To the reaction mixture was added water, and the mixture was extracted with ethyl acetate. The organic layer was washed with water and brine, dried over anhydrous sodium sulfate, filtrated, and then concentrated. The residue was purified by silica gel column chromatography (heptane:ethyl acetate=68:32 to 47:53 to 40:60) to afford a colorless amorphous. The amorphous was dissolved in THF (6.0 mL), and lithium borohydride (44 mg) was added to the mixture at 0° C. The reaction mixture was stirred at room temperature for one hour. To the reaction mixture was added water, and the mixture was extracted with ethyl acetate. The organic layer was washed with brine, dried over anhydrous sodium sulfate, filtrated, and then concentrated. The obtained crude product was purified by silica gel column chromatography (heptane:ethyl acetate=53:47 to 32:68 to 29:71), and the desired fractions were concentrated. The residue was washed by trituration with diisopropyl ether to afford the title compound as a white solid (44 mg).

$^1$H-NMR (DMSO-d6) δ: 1.06 (3H, d, J=7.2 Hz), 2.21-2.29 (1H, m), 2.22 (3H, s), 2.69 (1H, dd, J=16.8, 6.8 Hz), 3.11-3.21 (1H, m), 3.85-3.96 (2H, m), 5.94 (1H, t, J=6.7 Hz), 7.14 (1H, d, J=11.7 Hz), 7.54 (1H, d, J=8.5 Hz), 11.06 (1H, s).

Each absolute configuration of Examples 178-183 shown below was extrapolated by comparison with Example 116.

Example 178

Production of (5R)-(−)-6-[2-hydroxy-4-(3-hydroxypropoxy)-3-methylphenyl]-5-methyl-4,5-dihydro-2H-pyridazin-3-one

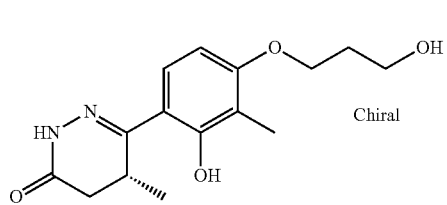

[Chem.433]

6-[4-(3-Hydroxypropoxy)-2-(methoxymethyloxy)-3-methylphenyl]-5-methyl-4,5-dihydro-2H-pyridazin-3-one (Reference example 228, 695 mg) was optically-resolved by chiral column chromatography according to the following preparative condition to afford chiral 6-[4-(3-hydroxypropoxy)-2-(methoxymethyloxy)-3-methylphenyl]-5-methyl-4,5-dihydro-2H-pyridazin-3-one as a colorless amorphous (322 mg, 99% ee).

<Preparative Condition>
Column: Daicel CHIRALFLASH IA (3.0 cmφ×10 cm)
Eluent: hexane/ethanol=80/20
Flow rate: 15 ml/min
Detection: UV (254 nm).
<HPLC Conditions of Optical Purity Analysis>
Column: Daicel CHIRALPAK IA (0.46 cmφ×25 cm)
Eluent: hexane/ethanol=40/60
Flow rate: 1.0 ml/min
Detection: UV (254 nm).
Retention time: 4.7 min
$^1$H-NMR (CDCl$_3$) δ: 1.06 (3H, d, J=7.3 Hz), 1.77-1.85 (1H, m), 2.09 (2H, quintet, J=6.0 Hz), 2.19 (3H, s), 2.41 (1H, dd, J=17.1, 4.6 Hz), 2.78 (1H, dd, J=17.1, 7.0 Hz), 3.28-3.37 (1H, m), 3.50 (3H, s), 3.87-3.91 (2H, m), 4.15 (2H, t, J=6.0 Hz), 4.88 (1H, d, J=5.6 Hz), 4.98 (1H, d, J=5.6 Hz), 6.70 (1H, d, J=8.5 Hz), 7.14 (1H, d, J=8.5 Hz), 8.56 (1H, brs).

To a mixture of the above-obtained chiral 6-[4-(3-hydroxypropoxy)-2-(methoxymethyloxy)-3-methylphenyl]-5-methyl-4,5-dihydro-2H-pyridazin-3-one (291 mg) in ethanol (1.5 mL) was added hydrogen chloride (2 M ethanol solution, 0.865 mL), and then the mixture was stirred at room temperature for one hour. The precipitated solid was collected on a filter, and then recrystallized from 2-propanol to afford the title compound as a white solid (182 mg, >99% ee).

<HPLC Conditions of Optical Purity Analysis>
Column: Daicel CHIRALPAK AS-RH (0.46 cmφ×15 cm)
Eluent: acetonitrile/water=40/60
Flow rate: 1.0 ml/min
Detection: UV (254 nm).
Retention time: 5.2 min
Optical rotation: $[α]_D^{31}$−332.1° (c=0.26, MeOH)
$^1$H-NMR (DMSO-d6) δ: 1.10 (3H, d, J=7.3 Hz), 1.84-1.92 (2H, m), 2.01 (3H, s), 2.27 (1H, dd, J=16.9, 1.3 Hz), 2.76 (1H, dd, J=16.9, 6.6 Hz), 3.48-3.61 (3H, m), 4.08 (2H, t, J=6.2 Hz), 4.55 (1H, t, J=5.1 Hz), 6.59 (1H, d, J=9.0 Hz), 7.43 (1H, d, J=9.0 Hz), 11.03 (1H, s), 12.46 (1H, s).

The following compounds were prepared from each appropriate starting material in a similar manner to Example 178.

Example 179

(5R)-(−)-6-[2-hydroxy-4-(2-hydroxy-2-methylpropoxy)-3-methylphenyl]-5-methyl-4,5-dihydro-2H-pyridazin-3-one

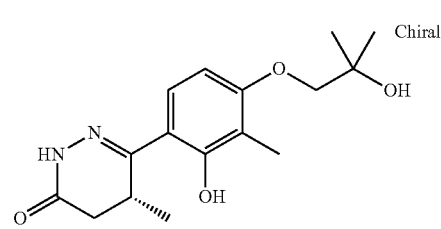

[Chem.434]

Chiral 6-[4-(2-hydroxy-2-methylpropoxy)-2-(methoxymethyloxy)-3-methylphenyl]-5-methyl-4,5-dihydro-2H-pyridazin-3-one
Optical purity: 98% ee
<HPLC Conditions of Optical Purity Analysis>
Column: Daicel CHIRALPAK IA (0.46 cmφ×25 cm)
Eluent: hexane/ethanol=50/50
Flow rate: 1.0 ml/min
Detection: UV (254 nm).
Retention time: 5.6 min
$^1$H-NMR (CDCl$_3$) δ: 1.07 (3H, d, J=7.3 Hz), 1.38 (6H, s), 2.16 (1H, s), 2.24 (3H, s), 2.41 (1H, dd, J=17.1, 4.6 Hz), 2.79 (1H, dd, J=17.1, 6.8 Hz), 3.28-3.38 (1H, m), 3.51 (3H, s), 3.82 (2H, s), 4.89 (1H, d, J=5.6 Hz), 5.00 (1H, d, J=5.6 Hz), 6.67 (1H, d, J=8.5 Hz), 7.14 (1H, d, J=8.5 Hz), 8.46 (1H, brs).

(5R)-(−)-6-[2-hydroxy-4-(2-hydroxy-2-methylpropoxy)-3-methylphenyl]-5-methyl-4, 5-dihydro-2H-pyridazin-3-one
Optical purity: 98% ee
<HPLC Conditions of Optical Purity Analysis>
Column: Daicel CHIRALPAK AS-RH (0.46 cmφ×15 cm)
Eluent: acetonitrile/water=35/75
Flow rate: 1.0 ml/min
Detection: UV (254 nm).
Retention time: 7.5 min
Optical rotation: $[α]_D^{31}$−312.2° (c=0.24, MeOH)
$^1$H-NMR (DMSO-d6) δ: 1.10 (3H, d, J=7.3 Hz), 1.23 (6H, s), 2.05 (3H, s), 2.23-2.31 (1H, m), 2.76 (1H, dd, J=16.7, 6.7 Hz), 3.47-3.57 (1H, m), 3.74 (2H, s), 4.65 (1H, s), 6.55 (1H, d, J=9.0 Hz), 7.42 (1H, d, J=9.0 Hz), 11.03 (1H, s), 12.46 (1H, s).

Example 180

(5R)-(−)-6-[3-chloro-2-hydroxy-4-(4-hydroxybutoxy)phenyl]-5-methyl-4,5-dihydro-2H-pyridazin-3-one

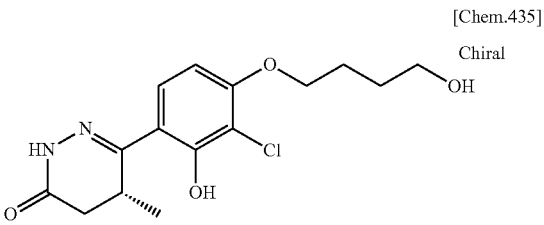 [SMILES: C[C@@H]1CC(=O)NN=C1c1ccc(OCCCCO)c(Cl)c1O]

[Chem.435]

Chiral 6-[3-chloro-4-(4-hydroxybutoxy)-2-(methoxymethyloxy)phenyl]-5-methyl-4,5-dihydro-2H-pyridazin-3-one Optical purity: >99% ee
<HPLC Conditions of Optical Purity Analysis>
Column: Daicel CHIRALPAK IA (0.46 cmφ×25 cm)
Eluent: hexane/ethanol=15/85
Flow rate: 1.0 ml/min
Detection: UV (254 nm).
Retention time: 4.6 min
$^1$H-NMR (CDCl$_3$) δ: 1.07 (3H, d, J=7.3 Hz), 1.50-1.54 (1H, m), 1.77-1.85 (2H, m), 1.94-2.01 (2H, m), 2.42 (1H, dd, J=17.0, 4.8 Hz), 2.80 (1H, dd, J=17.0, 7.0 Hz), 3.32-3.40 (1H, m), 3.53 (3H, s), 3.74-3.79 (2H, m), 4.11 (2H, t, J=6.1 Hz), 5.01 (1H, d, J=5.6 Hz), 5.16 (1H, d, J=5.6 Hz), 6.77 (1H, d, J=8.8 Hz), 7.21 (1H, d, J=8.8 Hz), 8.45 (1H, brs).

(5R)-(−)-6-[3-chloro-2-hydroxy-4-(4-hydroxybutoxy)phenyl]-5-methyl-4,5-dihydro-2H-pyridazin-3-one Optical purity: >99% ee
<HPLC Conditions of Optical Purity Analysis>
Column: Daicel CHIRALPAK AS-RH (0.46 cmφ×15 cm)
Eluent: acetonitrile/water=40/60
Flow rate: 1.0 ml/min
Detection: UV (254 nm).
Retention time: 4.7 min
Optical rotation: $[α]_D^{31}$−305.4° (c=0.24, MeOH)
$^1$H-NMR (DMSO-d6) δ: 1.11 (3H, d, J=7.3 Hz), 1.53-1.64 (2H, m), 1.73-1.84 (2H, m), 2.25-2.34 (1H, m), 2.79 (1H, dd, J=16.9, 6.8 Hz), 3.42-3.50 (2H, m), 3.50-3.60 (1H, m), 4.12 (2H, t, J=6.4 Hz), 4.46 (1H, t, J=5.1 Hz), 6.73 (1H, d, J=9.0 Hz), 7.56 (1H, d, J=9.0 Hz), 11.13 (1H, brs), 13.01 (1H, brs).

Example 181

(5R)-(−)-6-[3-chloro-2-hydroxy-4-(3-hydroxypropoxy)-5-methylphenyl]-5-methyl-4,5-dihydro-2H-pyridazin-3-one

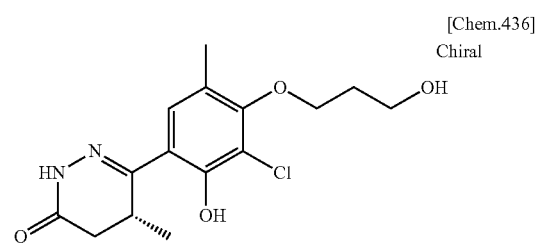 [SMILES: Cc1cc(C2=NNC(=O)C[C@H]2C)c(O)c(Cl)c1OCCCO]

[Chem.436]
Chiral

Chiral 6-[3-chloro-4-(3-hydroxypropoxy)-2-(methoxymethyloxy)-5-methylphenyl]-5-methyl-4,5-dihydro-2H-pyridazin-3-one Optical purity: >99% ee
<HPLC Conditions of Optical Purity Analysis>
Column: Daicel CHIRALPAK IA (0.46 cmφ×25 cm)
Eluent: hexane/ethanol=25/75
Flow rate: 1.0 ml/min
Detection: UV (254 nm).
Retention time: 3.9 min
$^1$H-NMR (CDCl$_3$) δ: 1.08 (3H, d, J=7.6 Hz), 1.90 (1H, t, J=5.5 Hz), 2.07-2.13 (2H, m), 2.30 (3H, d, J=0.7 Hz), 2.42 (1H, dd, J=17.0, 4.9 Hz), 2.80 (1H, dd, J=17.0, 7.0 Hz), 3.30-3.39 (1H, m), 3.52 (3H, s), 3.97 (2H, td, J=5.9, 5.5 Hz), 4.09 (2H, t, J=5.9 Hz), 4.98 (1H, d, J=5.4 Hz), 5.12 (1H, d, J=5.4 Hz), 7.08 (1H, d, J=0.7 Hz), 8.49 (1H, s).

(5R)-(−)-6-[3-chloro-2-hydroxy-4-(3-hydroxypropoxy)-5-methylphenyl]-5-methyl-4,5-dihydro-2H-pyridazin-3-one Optical purity: 96% ee
<HPLC Conditions of Optical Purity Analysis>
Column: Daicel CHIRALPAK AS-RH (0.46 cmφ×15 cm)
Eluent: acetonitrile/water=40/60
Flow rate: 1.0 ml/min
Detection: UV (254 nm).
Retention time: 4.7 min
Optical rotation: $[α]_D^{31}$−286.0° (c=0.23, MeOH)
$^1$H-NMR (DMSO-d6) δ: 1.11 (3H, d, J=7.3 Hz), 1.85-1.96 (2H, m), 2.23 (3H, s), 2.30 (1H, d, J=16.8 Hz), 2.79 (1H, dd, J=16.8, 6.7 Hz), 3.50-3.67 (3H, m), 3.98 (2H, t, J=6.5 Hz), 4.51 (1H, t, J=5.1 Hz), 7.46 (1H, s), 11.17 (1H, s), 12.77 (1H, s).

Example 182

Production of (5R)-(−)-6-[3-chloro-2-hydroxy-4-(2-hydroxy-2-methylpropoxy)phenyl]-5-methyl-4,5-dihydro-2H-pyridazin-3-one

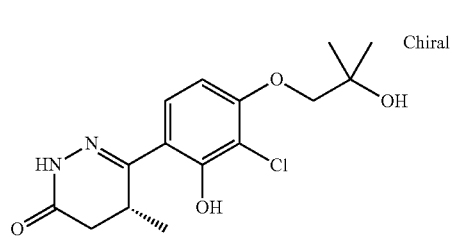

[Chem.437]
Chiral

6-[3-Chloro-4-(2-hydroxy-2-methylpropoxy)-2-(methoxymethyloxy)phenyl]-5-methyl-4,5-dihydro-2H-pyridazin-3-one (Reference example 212, 525 mg) was optically-resolved by chiral column chromatography according to the following preparative condition to afford chiral 6-[4-(3-hydroxypropoxy)-2-(methoxymethyloxy)-3-methylphenyl]-5-methyl-4,5-dihydro-2H-pyridazin-3-one as a colorless amorphous (220 mg, 99% ee).
<Preparative Condition>
Column: Daicel CHIRALFLASH IA (3.0 cmφ×10 cm)
Eluent: hexane/ethanol=75/25
Flow rate: 15 ml/min
Detection: UV (254 nm).
<HPLC Conditions of Optical Purity Analysis>
Column: Daicel CHIRALPAK IA (0.46 cmφ×25 cm)
Eluent: hexane/ethanol=40/60
Flow rate: 1.0 ml/min
Detection: UV (254 nm).
Retention time: 5.2 min
$^1$H-NMR (CDCl$_3$) δ: 1.07 (3H, d, J=7.3 Hz), 1.39 (6H, s), 2.42 (1H, dd, J=17.0, 4.8 Hz), 2.80 (1H, dd, J=17.0, 7.0 Hz), 3.30-3.41 (1H, m), 3.53 (3H, s), 3.87 (2H, s), 5.01-5.06 (1H, m), 5.14-5.20 (1H, m), 6.76 (1H, d, J=8.5 Hz), 7.22 (1H, d, J=8.5 Hz), 8.44 (1H, brs).

To a mixture of the above-obtained chiral 6-[4-(3-hydroxypropoxy)-2-(methoxymethyloxy)-3-methylphenyl]-5-methyl-4,5-dihydro-2H-pyridazin-3-one (164 mg) in ethanol (1.0 mL) was added hydrogen chloride (2 M ethanol solution, 0.442 mL), and then the mixture was stirred at room temperature for one hour. The precipitates were collected on a filter, and then recrystallized from 2-propanol to afford the title compound as a white solid (57 mg, 99% ee).
<HPLC Conditions of Optical Purity Analysis>
Column: Daicel CHIRALPAK AS-RH (0.46 cmφ×15 cm)
Eluent: acetonitrile/water=35/65
Flow rate: 1.0 ml/min
Detection: UV (254 nm).
Retention time: 6.5 min
Optical rotation: $[\alpha]_D^{30}$ −291.0° (c=0.26, MeOH)
$^1$H-NMR (DMSO-d6) δ: 1.11 (3H, d, J=7.3 Hz), 1.24 (6H, s), 2.25-2.34 (1H, m), 2.81 (1H, dd, J=17.0, 6.7 Hz), 3.48-3.60 (1H, m), 3.83 (2H, s), 4.67 (1H, brs), 6.73 (1H, d, J=9.3 Hz), 7.56 (1H, d, J=9.3 Hz), 11.13 (1H, s), 13.01 (1H, s).

Example 183

Production of (5R)-(−)-6-{3-chloro-2-hydroxy-4-[(Z)-4-hydroxy-2-butenyloxy]phenyl}-5-methyl-4,5-dihydro-2H-pyridazin-3-one

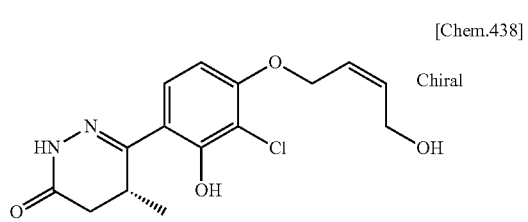 [SMILES: C[C@@H]1CC(=O)NN=C1c1ccc(OC/C=C\CO)c(Cl)c1O]

[Chem.438]

6-[3-Chloro-4-[(Z)-4-hydroxy-2-butenyloxy]-2-(methoxymethyloxy)phenyl]-5-methyl-4,5-dihydro-2H-pyridazin-3-one (Reference example 229, 497 mg) was optically-resolved by chiral column chromatography according to the following preparative condition to afford chiral 6-[3-chloro-4-[(Z)-4-hydroxy-2-butenyloxy]-2-(methoxymethyloxy)phenyl]-5-methyl-4,5-dihydro-2H-pyridazin-3-one as a colorless amorphous (232 mg, >99% ee).
<Preparative Condition>
Column: Daicel CHIRALFLASH IA (3.0 cmφ×10 cm)
Eluent: hexane/ethanol=70/30
Flow rate: 15 ml/min
Detection: UV (254 nm).
<HPLC Conditions of Optical Purity Analysis>
Column: Daicel CHIRALPAK IA (0.46 cmφ×25 cm)
Eluent: hexane/ethanol=20/80
Flow rate: 1.0 ml/min
Detection: UV (254 nm).
Retention time: 4.6 min
$^1$H-NMR (CDCl$_3$) δ: 1.07 (3H, d, J=7.3 Hz), 1.63-1.68 (1H, m), 2.42 (1H, dd, J=17.0, 4.8 Hz), 2.80 (1H, dd, J=17.0, 7.0 Hz), 3.31-3.40 (1H, m), 3.53 (3H, s), 4.29-4.35 (2H, m), 4.72-4.77 (2H, m), 5.02 (1H, d, J=5.6 Hz), 5.16 (1H, d, J=5.6 Hz), 5.83-5.96 (2H, m), 6.78 (1H, d, J=8.5 Hz), 7.22 (1H, d, J=8.5 Hz), 8.52 (1H, s).

To a mixture of the above-obtained chiral 6-[3-chloro-4-[(Z)-4-hydroxy-2-butenyloxy]-2-(methoxymethyloxy)phenyl]-5-methyl-4,5-dihydro-2H-pyridazin-3-one (204 mg) in ethanol (1.0 mL) was added hydrogen chloride (2 M ethanol solution, 0.442 mL), and then the mixture was stirred at room temperature for one hour. The precipitates were collected on a filter, and then recrystallized from hexane/2-propanol to afford the title compound as a white solid (54 mg, 93% ee).

<HPLC Conditions of Optical Purity Analysis>
Column: Daicel CHIRALPAK AS-RH (0.46 cmφ×15 cm)
Eluent: acetonitrile/water=35/65
Flow rate: 1.0 ml/min
Detection: UV (254 nm).
Retention time: 6.5 min
Optical rotation: $[\alpha]_D^{31}$ −274.0° (c=0.23, MeOH)
$^1$H-NMR (DMSO-d6) δ: 1.11 (3H, d, J=7.3 Hz), 2.26-2.32 (1H, m), 2.80 (1H, dd, J=16.9, 6.6 Hz), 3.49-3.61 (1H, m), 4.08-4.16 (2H, m), 4.75-4.86 (3H, m), 5.59-5.69 (1H, m), 5.70-5.80 (1H, m), 6.75 (1H, d, J=9.0 Hz), 7.57 (1H, d, J=9.0 Hz), 11.13 (1H, s), 13.02 (1H, s).

Example 184

Production of 6-[2-fluoro-4-(2-hydroxy-2-methyl-propoxy)-3-(trifluromethyl)phenyl]-5-methyl-4,5-dihydro-2H-pyridazin-3-one

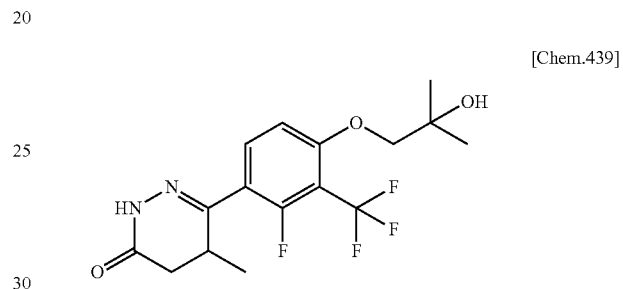

[Chem.439]

To a mixture of 6-[2-fluoro-4-hydroxy-3-(trifluoromethyl)phenyl]-5-methyl-4,5-dihydro-2H-pyridazin-3-one (Reference example 242, 290 mg) in DMF (5.0 mL) were added potassium carbonate (207 mg) and 3-chloro-2-methyl-1-propene (0.117 mL), and then the mixture was stirred at 80° C. for one hour. 3-Chloro-2-methyl-1-propene (0.029 mL) was added to the reaction mixture, and then the reaction mixture was stirred at 80° C. further for 30 minutes. The reaction mixture was allowed to cool to room temperature, water was added to the reaction mixture, and then the mixture was extracted with ethyl acetate. The organic layer was washed with 1 M aqueous sodium hydroxide and then brine, dried over anhydrous sodium sulfate, filtrated, and then concentrated. The obtained solid was washed by trituration with diisopropyl ether to afford a white solid (276 mg). The white solid (242 mg) was dissolved in methylene chloride (3.5 mL), m-chloroperbenzoic acid (280 mg) was added to the solution at 0° C. The reaction mixture was stirred at room temperature for 3 hours. Aqueous sodium thiosulfate was added to the reaction mixture at 0° C., and the mixture was extracted with ethyl acetate. The organic layer was washed with saturated aqueous sodium bicarbonate and then brine, dried over anhydrous sodium sulfate, filtrated, and then concentrated. The residue was purified by silica gel column chromatography (heptane:ethyl acetate=47:53 to 26:74 to 12:88), and the obtained solid was washed by trituration with diisopropyl ether to afford a white solid (163 mg). A mixture of the white solid (140 mg), ammonium formate (74 mg), and palladium-carbon (10% w/w, 14 mg) in ethanol (7.0 mL) was allowed to be under a hydrogen atmosphere, and the mixture was stirred at room temperature for 3 hours. The mixture was filtered through a Celite pad, and the filtrate was concentrated. The residual solid was washed by trituration with diisopropyl ether, and then collected on a filter to afford the title compound as a white solid (108 mg).

¹H-NMR (DMSO-d6) δ: 1.03 (3H, d, J=7.2 Hz), 1.21 (6H, s), 2.25 (1H, dd, J=16.8, 4.2 Hz), 2.69 (1H, dd, J=16.8, 6.7 Hz), 3.06-3.17 (1H, m), 3.88 (2H, s), 4.72 (1H, s), 7.17 (1H, d, J=9.0 Hz), 7.76-7.83 (1H, m), 11.05 (1H, s).

(Test)

The growth inhibitory activity against human childhood brain tumor cell lines (PFSK-1) was measured with WST-8 reagent [2-(2-methoxy-4-nitrophenyl)-3-(4-nitrophenyl)-5-(2,4-disulfophenyl)-2H-tetrazolium monosodium salt, Cell Counting Kit-8™], according to the method described in Tominaga, H. et al., Anal. Commun., 1999, 36, 47-50. Briefly, PFSK-1 was seeded in 96-well microplate at 100 μL/well with Roswell Park Memorial Institute (RPMI) 1640 medium containing 10% fetal bovine serum (FBS), and the cells were incubated in the presence of 5% carbon dioxide ($CO_2$) at 37° C. for 24 hours. 50 μL of each test compound diluted with the medium was added to each well, and then the cells were incubated further for 3 days. After the incubation, 15 μL of Cell Counting Kit-8™ was added to each well, and the cells were incubated for one and half hours. Then, optical density (OD) values at measurement wavelength 450 nm and reference wavelength 630 nm were measured and the difference thereof was calculated. From the calculated difference, the OD value difference (at measurement wavelength 450 nm and reference wavelength 630 nm) of the control well which includes no cell was subtracted to afford cell-growth activity in each well.

The cell growth inhibitory activity of each test compound was calculated by comparing the cell-growth activity with each test compound to the cell-growth activity without any test compound (control), and each IC50 (nM) which is the concentration inhibiting 50% of the cell growth was calculated. The results are shown in the table below.

| Example | IC50 (nM) |
| --- | --- |
| 1 | 1.1 |
| 2 | 1.0 |
| 6 | 3.8 |
| 7 | 1.0 |
| 8 | 7.9 |
| 9 | 4.2 |
| 10 | 3.7 |
| 11 | 3.0 |
| 12 | 1.9 |
| 14 | 8.0 |
| 15 | 4.0 |
| 16 | 3.6 |
| 17 | 2.9 |
| 18 | 4.0 |
| 19 | 1.3 |
| 20 | 4.2 |
| 21 | 4.0 |
| 22 | 1.9 |
| 23 | 8.0 |
| 24 | 1.7 |
| 25 | 2.6 |
| 26 | 2.0 |
| 28 | 6.3 |
| 31 | 1.1 |
| 32 | 4.0 |
| 33 | 5.1 |
| 34 | 5.2 |
| 35 | 6.3 |
| 36 | 1.0 |
| 37 | 8.8 |
| 38 | 5.2 |
| 39 | 2.8 |
| 40 | 1.6 |
| 43 | 4.3 |
| 44 | 1.0 |
| 45 | 7.2 |
| 46 | 3.9 |
| 47 | 2.4 |
| 48 | 0.9 |
| 49 | 2.8 |
| 50 | 2.9 |
| 51 | 5.5 |
| 52 | 3.8 |
| 53 | 1.9 |
| 54 | 0.5 |
| 55 | 1.9 |
| 56 | 7.6 |
| 57 | <1.0 |
| 58 | 2.8 |
| 59 | 2.2 |
| 60 | 4.7 |
| 61 | 4.7 |
| 62 | 8.9 |
| 63 | 5.0 |
| 64 | 2.1 |
| 65 | 4.3 |
| 66 | 4.1 |
| 67 | 3.6 |
| 69 | 1.2 |
| 70 | 5.3 |
| 71 | 3.9 |
| 72 | 0.9 |
| 74 | 4.1 |
| 75 | 3.2 |
| 76 | 2.7 |
| 77 | 5.3 |
| 78 | 6.6 |
| 79 | 5.6 |
| 80 | 5.1 |
| 81 | 4.7 |
| 82 | 6.0 |
| 83 | 6.6 |
| 84 | 3.3 |
| 85 | 4.0 |
| 86 | 4.6 |
| 87 | 9.8 |
| 88 | 9.5 |
| 89 | 4.9 |
| 90 | 3.9 |
| 91 | 6.0 |
| 92 | 4.9 |
| 93 | 3.1 |
| 94 | 3.0 |
| 95 | 3.0 |
| 96 | 3.9 |
| 97 | 8.6 |
| 98 | 3.6 |
| 99 | <1.0 |
| 100 | 1.6 |
| 101 | 7.5 |
| 102 | 3.4 |
| 103 | 2.6 |
| 104 | 5.2 |
| 105 | 9.0 |
| 106 | 6.4 |
| 108 | 4.1 |
| 109 | 1.6 |
| 110 | 7.9 |
| 111 | 3.0 |
| 112 | 2.3 |
| 113 | 1.1 |
| 114 | 3.3 |
| 115 | 5.9 |
| 116 | 4.3 |
| 117 | 3.0 |
| 118 | <1.0 |
| 119 | 2.9 |
| 120 | 2.4 |
| 121 | 3.8 |
| 122 | 4.1 |
| 123 | 3.3 |

-continued

| Example | IC50 (nM) |
|---|---|
| 124 | 2.3 |
| 125 | 1.5 |
| 126 | 2.9 |
| 127 | <1.0 |
| 129 | 3.6 |
| 130 | 7.0 |
| 131 | 1.0 |
| 132 | 3.0 |
| 133 | 3.4 |
| 134 | 7.1 |
| 135 | 6.8 |
| 136 | 5.2 |
| 137 | <1.0 |
| 138 | 3.9 |
| 139 | 2.7 |
| 140 | 2.0 |
| 141 | 4.6 |
| 142 | 1.0 |
| 143 | 6.9 |
| 144 | 4.2 |
| 145 | 7.1 |
| 146 | 6.8 |
| 147 | 7.6 |
| 148 | <1.0 |
| 149 | 3.6 |
| 150 | 3.7 |
| 151 | 1.3 |
| 152 | 3.4 |
| 153 | 5.3 |
| 154 | 2.9 |
| 155 | 2.2 |
| 156 | 2.9 |
| 158 | 4.3 |
| 159 | <1.0 |
| 160 | 1.9 |
| 161 | 2.7 |
| 162 | 6.4 |
| 163 | 5.2 |
| 164 | 4.9 |
| 165 | 2.6 |
| 166 | 4.7 |
| 167 | 1.3 |
| 168 | 2.3 |
| 169 | 4.0 |
| 170 | 2.5 |
| 171 | 6.3 |
| 172 | 5.2 |
| 174 | 4.2 |
| 175 | 4.1 |
| 176 | 9.2 |
| 177 | 4.0 |
| 178 | 4.6 |
| 179 | 3.3 |
| 180 | 6.5 |
| 181 | 3.9 |
| 182 | 2.9 |
| 183 | 4.5 |
| 184 | 2.2 |

The invention claimed is:
1. A compound of formula (1):

[Chem.1]

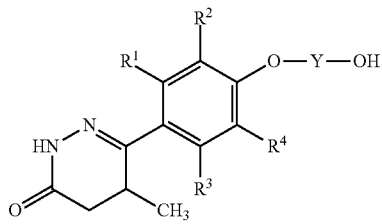

(1)

or a pharmaceutically acceptable salt thereof
wherein
$R^1$ to $R^4$ are independently hydrogen atom, halogen, OH, CN, $C_{1-6}$ alkyl group, halogenated $C_{1-6}$ alkyl group, $C_{2-6}$ alkenyl group, $C_{1-6}$ alkoxy group, or halogenated $C_{1-6}$ alkoxy group, provided that one or two of $R^1$ to $R^4$ are hydrogen atoms, but it is not that all of three or four thereof are hydrogen atoms, and
Y is $C_{1-6}$ alkylene or $C_{2-6}$ alkenylene group, wherein the alkylene or alkenylene group may be substituted with one or more substituents selected independently from the group consisting of $C_{1-6}$ alkyl group, halogen, and halogenated $C_{1-6}$ alkyl group, further wherein a substitutable carbon atom in the substituent bonding to the alkylene or alkenylene group and another substitutable carbon atom in the alkylene or alkenylene group, or two substitutable carbon atoms in the substituent bonding to the alkylene or alkenylene group may be combined together to form a 3- to 6-membered carbon ring.

2. The compound of claim 1 or a pharmaceutically acceptable salt thereof, wherein any two of $R^1$ to $R^4$ are hydrogen atoms.

3. The compound of claim 1 or a pharmaceutically acceptable salt thereof, wherein $R^1$ to $R^4$ are independently hydrogen atom, halogen, OH, CN, $C_{1-4}$ alkyl group, halogenated $C_{1-4}$ alkyl group, $C_{2-4}$ alkenyl group, $C_{1-4}$ alkoxy group, or halogenated $C_{1-4}$ alkoxy group.

4. The compound of claim 1 or a pharmaceutically acceptable salt thereof, wherein $R^1$ to $R^4$ are independently hydrogen atom, fluorine atom, chlorine atom, OH, CN, $C_{1-4}$ alkyl group, vinyl group, or $C_{1-4}$ alkoxy group.

5. The compound of claim 1 or a pharmaceutically acceptable salt thereof, wherein the alkylene or alkenylene group in Y is substituted with one or more substituents selected independently from the group consisting of
$C_{1-4}$ alkyl group, halogen, and halogenated $C_{1-4}$ alkyl group, further wherein a substitutable carbon atom in the substituent bonding to the alkylene or alkenylene group and another substitutable carbon atom in the alkylene or alkenylene group, or two substitutable carbon atoms in the substituent bonding to the alkylene or alkenylene group may be combined together to form a 3- to 6-membered carbon ring.

6. The compound of claim 1 or a pharmaceutically acceptable salt thereof, wherein a carbon atom of the alkylene or alkenylene group in Y is substituted with one or two substituents selected independently from the group consisting of $C_{1-4}$ alkyl group and halogenated $C_{1-4}$ alkyl group, further when the carbon atom is substituted with two substituents, each substitutable carbon atom in the two substituents may be combined together to form a 3- to 6-membered carbon ring.

7. The compound of claim 1 or a pharmaceutically acceptable salt thereof, wherein the alkylene or alkenylene group in Y has no substituent.

8. The compound of claim 1 or a pharmaceutically acceptable salt thereof, wherein the compound of formula (1) is represented in the following formula:

[Chem.2]

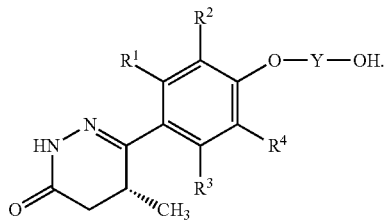

9. The compound of claim 1 or a pharmaceutically acceptable salt thereof, which is selected from the following compounds:

Example 1: 6-[3-bromo-5-chloro-4-(2-hydroxy-2-methylpropoxy)phenyl]-5-methyl-4,5-dihydro-2H-pyridazin-3-one, Example 2: 6-[3,5-dichloro-4-(2-hydroxy-2-methylpropoxy)phenyl]-5-methyl-4,5-dihydro-2H-pyridazin-3-one, Example 7: 6-[3-chloro-5-fluoro-4-(3-hydroxy-2,2-dimethylpropoxy)phenyl]-5-methyl-4,5-dihydro-2H-pyridazin-3-one, Example 12: 6-[3-bromo-2-fluoro-4-(3-hydroxypropoxy)phenyl]-5-methyl-4,5-dihydro-2H-pyridazin-3-one, Example 19: 6-[3-chloro-2-fluoro-4-(3-hydroxypropoxy)phenyl]-5-methyl-4,5-dihydro-2H-pyridazin-3-one, Example 22: 6-[3-chloro-2-fluoro-4-(3-hydroxypropoxy)-5-methylphenyl]-5-methyl-4,5-dihydro-2H-pyridazin-3-one, Example 24: 6-[3-bromo-2-fluoro-4-(2-hydroxy-2-methylpropoxy)phenyl]-5-methyl-4,5-dihydro-2H-pyridazin-3-one, Example 26: 6-[3-bromo-5-fluoro-4-(2-hydroxy-2-methylpropoxy)phenyl]-5-methyl-4,5-dihydro-2H-pyridazin-3-one, Example 31: 6-[3-chloro-4-(2-hydroxy-2-methylpropoxy)-5-methylphenyl]-5-methyl-4,5-dihydro-2H-pyridazin-3-one, Example 36: 6-[3-chloro-2-fluoro-4-(2-hydroxy-2-methylpropoxy)-5-methylphenyl]-5-methyl-4,5-dihydro-2H-pyridazin-3-one, Example 40: 6-{3-chloro-4-[(2R)-2-hydroxypropoxy]-5-methylphenyl}-5-methyl-4,5-dihydro-2H-pyridazin-3-one, Example 44: 6-{3-chloro-4-[(1-hydroxycyclopropyl)methoxy]-5-methylphenyl}-5-methyl-4,5-dihydro-2H-pyridazin-3-one, Example 46: 6-{2-fluoro-4[(1-hydroxycyclopropyl)methoxy]-3-methylphenyl{-5-methyl-4,5-dihydro-2H-pyridazin-3-one, Example 47: 6-{3-chloro-2-fluoro-4-[(1-hydroxycyclopropyl)methoxy]phenyl}-5-methyl-4,5-dihydro-2H-pyridazin-3-one, Example 48: 6-[3-bromo-2-fluoro-4-(2-hydroxypropoxy)phenyl]-5-methyl-4,5-dihydro-2H-pyridazin-3-one, Example 53: 6-[3,5-dichloro-4-(2-hydroxypropoxy)phenyl]-5-methyl-4,5-dihydro-2H-pyridazin-3-one, Example 54: 6-[3-chloro-2-fluoro-4-(2-hydroxypropoxy)phenyl]-5-methyl-4,5-dihydro-2H-pyridazin-3-one, Example 55: 6-[3-chloro-4-(2-hydroxypropoxy)-5-methylphenyl]-5-methyl-4,5-dihydro-2H-pyridazin-3-one, Example 57: 6-[3-bromo-5-chloro-4-(2-hydroxypropoxy)phenyl]-5-methyl-4,5-dihydro-2H-pyridazin-3-one, Example 59: 6-[2-fluoro-4-(2-hydroxypropoxy)-3-vinylphenyl]-5-methyl-4,5-dihydro-2H-pyridazin-3-one, Example 64: 6-[3-chloro-2-fluoro-4-(2-hydroxybutoxy)phenyl]-5-methyl-4,5-dihydro-2H-pyridazin-3-one, Example 69: 6-[3-bromo-5-fluoro-4-(3-hydroxy-2,2-dimethylpropoxy)phenyl]-5-methyl-4,5-dihydro-2H-pyridazin-3-one, Example 72: 6-[3-chloro-4-(3-hydroxy-2,2-dimethylpropoxy)-5-methylphenyl]-5-methyl-4,5-dihydro-2H-pyridazin-3-one, Example 99: 6-[3-chloro-5-fluoro-4-(4-hydroxy-2,2-dimethylbutoxy)phenyl]-5-methyl-4,5-dihydro-2H-pyridazin-3-one, Example 100: 6-[3,5-dichloro-4-(4-hydroxy-2,2-dimethylbutoxy)phenyl]-5-methyl-4,5-dihydro-2H-pyridazin-3-one, Example 104: 2-fluoro-6-(2-hydroxypropyl)-3-(4-methyl-6-oxo-4,5-dihydro-1H-pyridazin-3-yl)benzonitrile, Example 109: 6-[3,5-dichloro-4-(2,2-difluoro-3-hydroxypropoxy)phenyl]-5-methyl-4,5-dihydro-2H-pyridazin-3-one, Example 112: 6-[3-bromo-4-(2,2-difluoro-3-hydroxypropoxy)-2-fluorophenyl]-5-methyl-4,5-dihydro-2H-pyridazin-3-one, Example 113: 6-[3-chloro-4-(2,2-difluoro-3-hydroxypropoxy)-5-methylphenyl]-5-methyl-4,5-dihydro-2H-pyridazin-3-one, Example 118: (5R)-(−)-6-[3-chloro-2-fluoro-4-(2-hydroxy-2-methylpropoxy)phenyl]-5-methyl-4,5-dihydro-2H-pyridazin-3-one, Example 120: (5R)-(−)-6-[4-(2,2-difluoro-3-hydroxypropoxy)-2-fluoro-3-methylphenyl]-5-methyl-4,5-dihydro-2H-pyridazin-3-one, Example 124: (5R)-(−)-6-[2,3-difluoro-4-(2-hydroxy-2-methylpropoxy)phenyl]-5-methyl-4,5-dihydro-2H-pyridazin-3-one, Example 125: (5R)-(−)-6-[3-fluoro-4-(3-hydroxy-2,2-dimethylpropoxy)-5-methylphenyl]-5-methyl-4,5-dihydro-2H-pyridazin-3-one, Example 127: (5R)-(−)-6-[3-bromo-5-chloro-4-(3-hydroxy-2,2-dimethylpropoxy)phenyl]-5-methyl-4,5-dihydro-2H-pyridazin-3-one, Example 131: 6-[3-chloro-2,5-difluoro-4-(2-hydroxy-2-methylpropoxy)phenyl]-5-methyl-4,5-dihydro-2H-pyridazin-3-one, Example 137: 6-[3-chloro-2-fluoro-4-(3-hydroxy-2,2-dimethylpropoxy)-5-methylphenyl]-5-methyl-4,5-dihydro-2H-pyridazin-3-one, Example 140: 6-[3-chloro-2,5-difluoro-4-(3-hydroxypropoxy)phenyl]-5-methyl-4,5-dihydro-2H-pyridazin-3-one, Example 142: 6-[3-chloro-4-(3-hydroxy-2-methylpropoxy)-5-methylphenyl]-5-methyl-4,5-dihydro-2H-pyridazin-3-one, Example 148: 6-[3-chloro-2-fluoro-4-(2-hydroxypropoxy)-5-methylphenyl]-5-methyl-4,5-dihydro-2H-pyridazin-3-one,
Example 151: 6-{3-chloro-2-fluoro-4-[(Z)-4-hydroxy-2-butenyloxy]-5-methylphenyl}-5-methyl-4,5-dihydro-2H-pyridazin-3-one,
Example 155: 6-(3-chloro-4-{[(1S*,2R*)-2-(hydroxymethyl)cyclopropyl]methoxy}-5-methylphenyl)-5-methyl-4,5-dihydro-2H-pyridazin-3-one,
Example 159: 6-{3-chloro-4-(2,2-difluoro-3-hydroxypropoxy)-2-fluoro-5-methylphenyl}-5-methyl-4,5-dihydro-2H-pyridazin-3-one,
Example 160: 6-{4-(2,2-difluoro-3-hydroxypropoxy)-2-fluoro-3,5-dimethylphenyl}-5-methyl-4,5-dihydro-2H-pyridazin-3-one,
Example 167: 6-{3-chloro-2-fluoro-4-[(1-hydroxycyclopropyl)methoxy]-5-methylphenyl}-5-methyl-4,5-dihydro-2H-pyridazin-3-one,
Example 168: 6-{3-bromo-2-fluoro-4-[(1-hydroxycyclopropyl)methoxy]phenyl}-5-methyl-4,5-dihydro-2H-pyridazin-3-one,
Example 170: 6-{3,5-dichloro-4-[(1-hydroxycyclopropyl)methoxy]phenyl}-5-methyl-4,5-dihydro-2H-pyridazin-3-one,
Example 175: 6-{3-chloro-2-hydroxy-4-[(1-hydroxycyclopropyl)methoxy]-5-methylphenyl{-5-methyl-4,5-dihydro-2H-pyridazin-3-one,
Example 179: (5R)-(-)-6-[2-hydroxy-4-(2-hydroxy-2-methylpropoxy)-3-methylpheny]-5-methyl -4,5-dihydro-2H-pyridazin-3-one, and
Example 184: 6-[2-fluoro-4-(2-hydroxy-2-methylpropoxy)-3-(trifluoromethyl)phenyl]-5-methyl-4,5-dihydro-2H-pyridazin-3-one.

10. A pharmaceutical composition, comprising the compound of claim 1 or a pharmaceutically acceptable salt thereof.

11. The compound of claim 9 or a pharmaceutically acceptable salt thereof, which is 6-[3-bromo-5-chloro-4-(2-hydroxy-2-methylpropoxy)phenyl]-5-methyl-4,5-dihydro-2H-pyridazin-3-one.

12. The compound of claim 9 or a pharmaceutically acceptable salt thereof, which is a pharmaceutically acceptable salt of 6-[3-bromo-5-chloro-4-(2-hydroxy-2-methylpropoxy)phenyl]-5-methyl-4,5-dihydro-2H-pyridazin-3-one.

13. The compound of claim 9 or a pharmaceutically acceptable salt thereof, which is 6-[3-bromo-2-fluoro-4-(3-hydroxypropoxy)phenyl]-5-methyl-4,5-dihydro-2H-pyridazin-3-one.

14. The compound of claim 9 or a pharmaceutically acceptable salt thereof, which is a pharmaceutically acceptable salt of 6-[3-bromo-2-fluoro-4-(3-hydroxypropoxy)phenyl]-5-methyl-4,5-dihydro-2H-pyridazin-3-one.

15. The compound of claim 9 or a pharmaceutically acceptable salt thereof, which is 6-[3-bromo-2-fluoro-4-(2-hydroxy-2-methylpropoxy)phenyl]-5-methyl-4,5-dihydro-2H-pyridazin-3-one.

16. The compound of claim 9 or a pharmaceutically acceptable salt thereof, which is a pharmaceutically acceptable salt of 6-[3-bromo-2-fluoro-4-(2-hydroxy-2- methylpropoxy)phenyl]-5-methyl-4,5-dihydro-2H-pyridazin-3-one.

17. The compound of claim 9 or a pharmaceutically acceptable salt thereof, which is 6-[3-chloro-2-fluoro-4-(2-hydroxy-2-methylpropoxy)-5-methylphenyl]-5-methyl-4,5-dihydro-2H-pyridazin-3 -one.

18. The compound of claim 9 or a pharmaceutically acceptable salt thereof, which is a pharmaceutically acceptable salt of 6-[3-chloro-2-fluoro-4-(2-hydroxy-2-methylpropoxy)-5-methylphenyl]-5-methyl-4,5-dihydro-2H-pyridazin-3-one.

19. The compound of claim 9 or a pharmaceutically acceptable salt thereof, which is 6-{3-chloro-4- R2R)-2-hydroxypropoxyl-5-methylphenyl}-5 -methyl-4,5-dihydro-2H-pyridazin-3-one.

20. The compound of claim 9 or a pharmaceutically acceptable salt thereof, which is a pharmaceutically acceptable salt of 6-{3-chloro-4-R2R)-2-hydroxypropoxyl-5-methylphenyl }-5-methyl-4,5-dihydro-2H-pyridazin-3-one.

21. The compound of claim 9 or a pharmaceutically acceptable salt thereof, which is 6-{3 -chloro-4-[(2R-2-hydroxypropxyl}-5-methylphenyl }-5-methyl-4,5-dihydro-2H-pyridazin-3 -one.

22. The compound of claim 9 or a pharmaceutically acceptable salt thereof, which is a pharmaceutically acceptable salt of 6-{3-chloro-4-[(1-hydroxycyclopropyl)methoxyl -5-methylphenyl }-5-methyl-4,5-dihydro-2H-pyridazin-3-one.

23. The compound of claim 9 or a pharmaceutically acceptable salt thereof, which is 6{-2-fluoro-4-{(1-hydroxycyclopropyl)methoxy]-3-methylphenyl }-5-methyl-4,5-dihydro-2H-pyridazin-3 -one.

24. The compound of claim 9 or a pharmaceutically acceptable salt thereof, which is a pharmaceutically acceptable salt of 6-{2-fluoro-4-[(1-hydroxycyclopropyl)methoxy]-3-methylphenyl}-5-methyl-4,5-dihydro-2H-pyridazin-3-one.

25. The compound of claim 9 or a pharmaceutically acceptable salt thereof, which is 6-{3-chloro-4-(2-hydroxypropoxy)-5-methylphenyl]-5-methyl-4,5-dihydro-2H-pyridazin-3-one.

26. The compound of claim 9 or a pharmaceutically acceptable salt thereof, which is a pharmaceutically acceptable salt of 6-[3-chloro-4-(2-hydroxypropoxy)-5-methylphenyl]-5-methyl-4,5-dihydro-2H-pyridazin-3 -one.

27. The compound of claim 9 or a pharmaceutically acceptable salt thereof, which is 6-[2-fluoro-4-(2-hydroxypropoxy)-3-vinylphenyl]-5-methyl-4,5-dihydro-2H-pyridazin-3-one.

28. The compound of claim 9 or a pharmaceutically acceptable salt thereof, which is a pharmaceutically acceptable salt of 6-[2-fluoro-4-(2-hydroxypropoxy)-3-vinylphenyl]-5-methyl-4,5-dihydro-2H-pyridazin-3-one.

29. The compound of claim 9 or a pharmaceutically acceptable salt thereof, which is 6-[3-chloro-2-fluoro-4-(2-hydroxybutoxy)phenyl]-5-methyl-4,5-dihydro-2H-pyridazin-3-one.

30. The compound of claim 9 or a pharmaceutically acceptable salt thereof, which is a pharmaceutically acceptable salt of 6-[3-chloro-2-fluoro-4-(2-hydroxybutoxy)phenyl]-5-methyl-4,5-dihydro-2H-pyridazin-3-one.

31. The compound of claim 9 or a pharmaceutically acceptable salt thereof, which is 6-[3,5-dichloro-4-(4-hydroxy-2,2-dimethylbutoxy)phenyl]-5-methyl-4,5-dihydro-2H-pyridazin-3-one.

32. The compound of claim 9 or a pharmaceutically acceptable salt thereof, which is a pharmaceutically acceptable salt of 6[3,5-dichloro-4-(4-hydroxy-2,2-dimethylbutoxy)phenyl]-5-methyl-4,5-dihydro-2H-pyridazin-3-one.

33. The compound of claim 9 or a pharmaceutically acceptable salt thereof, which is 2-fluoro-6-(2-hydroxypropyl)-3-(4-methyl-6-oxo-4,5-dihydro-1H-pyridazin-3-yl)benzonitrile.

34. The compound of claim 9 or a pharmaceutically acceptable salt thereof, which is a pharmaceutically acceptable salt of 2-fluoro-6-(2-hydroxypropyl)-3-(4-methyl-6-oxo-4,5-dihydro-1H-pyridazin-3-yl)benzonitrile.

35. The compound of claim 9 or a pharmaceutically acceptable salt thereof, which is 6-[3-chloro-4-(2,2-difluoro-3-hydroxypropoxy)-5-methylphenyl]-5-methyl-4,5-dihydro-2H-pyridazin-3-one.

36. The compound of claim 9 or a pharmaceutically acceptable salt thereof, which is a pharmaceutically acceptable salt of 6-[3-chloro-4-(2,2-difluoro-3-hydroxypropoxy)-5-methylphenyl]-5-methyl-4,5-dihydro-2H-pyridazin-3-one.

37. The compound of claim 9 or a pharmaceutically acceptable salt thereof, which is (5R)-(-)-6-[3-chloro-2-fluoro-4-(2-hydroxy-2-methylpropoxy)phenyl]-5-methyl-4,5-dihydro-2H-pyridazin-3-one.

38. The compound of claim 9 or a pharmaceutically acceptable salt thereof, which is a pharmaceutically acceptable salt of (5R)-(-)-6-[3-chloro-2-fluoro-4-(2-hydroxy-2-methylpropoxy)phenyl]-5-methyl-4,5-dihydro-2H-pyridazin-3-one.

39. The compound of claim 9 or a pharmaceutically acceptable salt thereof, which is (5R)-(-)-6-[2,3-difluoro-4-(2-hydroxy-2-methylpropoxy)phenyl]-5-methyl-4,5-dihydro-2H-pyridazin-3-one.

40. The compound of claim 9 or a pharmaceutically acceptable salt thereof, which is a pharmaceutically acceptable salt of (5R)-(-)-6-[2,3-difluoro-4-(2-hydroxy-2-methylpropoxy)phenyl]-5-methyl-4,5-dihydro-2H-pyridazin-3-one.

41. The compound of claim 9 or a pharmaceutically acceptable salt thereof, which is (5R)-(-)-6-[3-bromo-5-chloro-4-(3-hydroxy-2,2-dimethylpropoxy)phenyl]-5-methyl-4,5-dihydro-2H-pyridazin-3-one.

42. The compound of claim 9 or a pharmaceutically acceptable salt thereof, which is a pharmaceutically acceptable salt of (5R)-(-)-6-[3-bromo-5-chloro-4-(3-hydroxy-2,2-dimethylpropoxy)phenyl]-5-methyl-4,5-dihydro-2H-pyridazin-3-one.

43. The compound of claim 9 or a pharmaceutically acceptable salt thereof, which is 6-[3-chloro-2-fluoro-4-(3-hydroxy-2,2-dimethylpropoxy)-5-methylphenyl]-5-methyl-4,5-dihydro-2H-pyridazin-3-one.

44. The compound of claim 9 or a pharmaceutically acceptable salt thereof, which is a pharmaceutically acceptable salt of 6-[3-chloro-2-fluoro-4-(3-hydroxy-2,2-dimethylpropoxy)-5-methylphenyl]-5-methyl-4,5-dihydro-2H-pyridazin-3-one.

45. The compound of claim 9 or a pharmaceutically acceptable salt thereof, which is 6-[3-chloro-2-fluoro-4-(2-hydroxypropoxy)-5-methylphenyl]-5-methyl-4,5-dihydro-2H-pyridazin-3-one.

46. The compound of claim 9 or a pharmaceutically acceptable salt thereof, which is a pharmaceutically acceptable salt of 6-[3-chloro-2-fluoro-4-(2-hydroxypropoxy)-5-methylphenyl[-5-methyl-4,5-dihydro-2H-pyridazin-3-one.

47. The compound of claim 9 or a pharmaceutically acceptable salt thereof, which is 6-{3-chloro-2-fluoro-4-[(Z)-4-hydroxy-2-butenyloxy]-5-methylphenyl}-5-methyl-4,5-dihydro-2H-pyridazin-3-one.

48. The compound of claim 9 or a pharmaceutically acceptable salt thereof, which is a pharmaceutically acceptable salt of 6-{3-chloro-2-fluoro-4-[(Z)-4-hydroxy-2-butenyloxyl-5-methylphenyl}-5-methyl-4,5-dihydro-2H-pyridazin-3-one.

49. The compound of claim 9 or a pharmaceutically acceptable salt thereof, which is 6-[4-(2,2-difluoro-3-hydroxypropoxy)-2-fluoro-3,5-dimethylphenyl]-5-methyl-4,5-dihydro-2H-pyridazin-3-one.

50. The compound of claim 9 or a pharmaceutically acceptable salt thereof, which is a pharmaceutically acceptable salt of 6-[4-(2,2-difluoro-3-hydroxypropoxy)-2-fluoro-3,5-dimethylphenyl]-5-methyl-4,5-dihydro-2H-pyridazin-3-one.

51. The compound of claim 9 or a pharmaceutically acceptable salt thereof, which is 6-{3-bromo-2-fluoro-4-[(1-hydroxycyclopropyl)methoxy]phenyl}-5-methyl-4,5-dihydro-2H-pyridazin-3-one.

52. The compound of claim 9 or a pharmaceutically acceptable salt thereof, which is a pharmaceutically acceptable salt of 6-{3-bromo-2-fluoro-4-[(1-hydroxycyclopropyl)methoxy]phenyl}-5-methyl-4,5-dihydro-2H-pyridazin-3-one.

53. The compound of claim 9 or a pharmaceutically acceptable salt thereof, which is 6-{3-chloro-2-hydroxy-4-[(1-hydroxycyclopropyl)methoxy]-5-methylphenyl}-5-methyl-4,5-dihydro-2H-pyridazin-3-one.

54. The compound of claim 9 or a pharmaceutically acceptable salt thereof, which is a pharmaceutically acceptable salt of 6-{3-chloro-2-hydroxy-4-[(1-hydroxycyclopropyl)methoxy]-5-methylphenyl}-5-methyl-4,5-dihydro-2H-pyridazin-3-one.

55. The compound of claim 9 or a pharmaceutically acceptable salt thereof, which is (5R)-(-)-6-[2-hydroxy-4-(2-hydroxy-2-methylpropoxy)-3-methylphenyl]-5-methyl-4,5-dihydro-2H-pyridazin-3-one.

56. The compound of claim 9 or a pharmaceutically acceptable salt thereof, which is a pharmaceutically acceptable salt of (5R)-(-)-6-[2hydroxy-4-(2-hydroxy-2-methylpropoxy)-3-methylphenyl]-5-methyl-4,5-dihydro-2H-pyridazin-3-one.

57. The compound of claim 9 or a pharmaceutically acceptable salt thereof, which is 6-[2-fluoro-4-(2-hydroxy-2-methylpropoxy)-3-(trifluoromethyl)phenyl]-5-methyl-4,5-dihydro-2H-pyridazin-3-one.

58. The compound of claim 9 or a pharmaceutically acceptable salt thereof, which is a pharmaceutically acceptable salt of 6-[2-fluoro-4-(2-hydroxy-2-methylpropoxy)-3-(trifluoromethyl)phenyl]-5-methyl-4,5-dihydro-2H-pyridazin-3-one.

* * * * *

UNITED STATES PATENT AND TRADEMARK OFFICE
CERTIFICATE OF CORRECTION

PATENT NO. : 10,611,731 B2
APPLICATION NO. : 16/081260
DATED : April 7, 2020
INVENTOR(S) : Takahiro Katoh et al.

It is certified that error appears in the above-identified patent and that said Letters Patent is hereby corrected as shown below:

In the Claims

Claim 9, Column 213, Line 63 should read:
methoxy]-3-methylphenyl}5-methyl-4,5-dihydro-2H-

Claim 9, Column 215, Lines 26-27 should read:
175: 6-{3-chloro-2-hydroxy-4-[(1-hydroxycy-
clopropyl)methoxy]-5-methylphenyl}-5-methyl-4,5-

Claim 9, Column 215, Line 30 should read:
methylpropoxy)-3-methylphenyl]-5-methyl-4,5-di- Claim 19, Column 216, Lines 7 and 8 should read:
acceptable salt thereof, which is 6-{3-chloro-4-[(2R)-2-
hydroxypropoxy]-5-methylphenyl}-5-methyl-4,5-dihydro- Claim 20, Column 216, Line 12 should read:
able salt of 6-{3-chloro-4-[(2R)-2-hydroxypropoxy]-5-

Claim 21, Column 216, Lines 15 to 17 should read:
acceptable salt thereof, which is 6-{3-chloro-4-[(1-hydroxycyclopropyl)-methoxy]-5-methylphenyl}-5-methyl-4,5-dihydro-2H-pyridazin-3-one.

Claim 22, Column 216, Line 21 should read:
methoxy]-5-methylphenyl}-5-methyl-4,5-dihydro-2H-

Claim 23, Column 216, Line 24 should read:
acceptable salt thereof, which is 6-{2-fluoro-4-[(1-hydroxy- Signed and Sealed this
Twenty-second Day of September, 2020

Andrei Iancu
*Director of the United States Patent and Trademark Office*

CERTIFICATE OF CORRECTION (continued)
U.S. Pat. No. 10,611,731 B2

Claim 25, Column 216, Line 33 should read:
acceptable salt thereof, which is 6-[3-chloro-4-(2-hydroxy- Claim 46, Column 217, Line 57 should read:
methylphenyl]-5-methyl-4,5-dihydro-2H-pyridazin-3-one.

Claim 48, Column 218, Lines 7-9 should read:
able salt of 6-{3-chloro-2-fluoro-4-[(Z)-4-hydroxy-2-butenyloxy]-5-methylphenyl}-5-methyl-4,5-dihydro-2H-pyridazin-3-one.

Claim 56, Column 218, Line 44 should read:
able salt of (5R)-(-)-6-[2-hydroxy-4-(2-hydroxy-2-methyl-